US008454972B2

(12) United States Patent
Nabel et al.

(10) Patent No.: US 8,454,972 B2
(45) Date of Patent: Jun. 4, 2013

(54) METHOD FOR INDUCING A MULTICLADE IMMUNE RESPONSE AGAINST HIV UTILIZING A MULTIGENE AND MULTICLADE IMMUNOGEN

(75) Inventors: Gary J. Nabel, Washington, DC (US); Yue Huang, Silver Spring, MD (US); Zengguang Wang, legal representative, Silver Spring, MD (US); Ling Xu, Potomac, MD (US); Bimal Chakrabarti, San Diego, CA (US); Lan Wu, Germantown, MD (US); Zhi-yong Yang, Potomac, MD (US); Jason G. D. Gall, Germantown, MD (US); C. Richter King, New York, NY (US)

(73) Assignees: The United States of America, as represented by the Secretary, Department of Health and Human Services, Washington, DC (US); GenVec, Inc., Gaithersburg, MD (US)

( * ) Notice: Subject to any disclaimer, the term of this patent is extended or adjusted under 35 U.S.C. 154(b) by 0 days.

(21) Appl. No.: 13/010,141

(22) Filed: Jan. 20, 2011

(65) Prior Publication Data
US 2011/0200636 A1    Aug. 18, 2011

Related U.S. Application Data

(62) Division of application No. 11/632,522, filed as application No. PCT/US2005/025219 on Jul. 15, 2005, now abandoned.

(60) Provisional application No. 60/588,378, filed on Jul. 16, 2004.

(51) Int. Cl.
*A61K 39/21* (2006.01)
*A61K 39/295* (2006.01)
*C07H 21/04* (2006.01)

(52) U.S. Cl.
USPC .................. 424/208.1; 424/202.1; 536/23.72

(58) Field of Classification Search
None
See application file for complete search history.

(56) References Cited

U.S. PATENT DOCUMENTS

| | | | |
|---|---|---|---|
| 7,094,598 B2 | 8/2006 | Nabel et al. | |
| 2003/0044421 A1 | 3/2003 | Emini et al. | |
| 2003/0064054 A1 | 4/2003 | Dong | |
| 2003/0143248 A1 | 7/2003 | Megede | |

FOREIGN PATENT DOCUMENTS

| | | |
|---|---|---|
| WO | WO 96/39178 A1 | 12/1996 |
| WO | WO 97/27311 A1 | 7/1997 |
| WO | WO 01/47955 A2 | 7/2001 |
| WO | WO 02/32943 A2 | 4/2002 |
| WO | WO 02/072754 A2 | 9/2002 |
| WO | WO 03/028632 A2 | 4/2003 |
| WO | WO 03/076591 A2 | 9/2003 |
| WO | WO 2005/034992 A2 | 4/2005 |

OTHER PUBLICATIONS

Kong, W.-P., et al., 2003, Immunogenicity of multiple gene and clade human immunodeficiency virus type 1 DNA vaccines, J. Virol. 77(23):12764-12772.*
Chakrabarti, B. K., et al., 2002, Modifications of the human immunodeficiency virus envelope glycoprotein enhance immunogenicity for genetic immunization, J. Virol. 76(11):5357-5368.*
Wang, L.-X., 2003, Bioorganic approaches towards HIV vaccine design, Curr. Pharm. Design 9:1771-1787.*
Gallo, R. C., 2005, The end or the beginning of the drive to an HIV-preventive vaccine: a view from over 20 years, The Lancet 366:1894-1898.*
Walker, B. D., and D. R. Burton, 2008, Toward an AIDS vaccine, Science 320:760-763.*
Levine, A. J., 2008, Why do we not have a human immunodeficiency virus vaccine? J. Virol. 82(24):11998-12000.*
Amara et al., *Science*, 292, 69-74 (2001).
Barouch et al., *Nature*, 415, 335-339 (2002).
Barouch et al., *Science*, 290:486-492, (2000).
Barouch et al., *J. of Virol.*, 79: 8828-8834 (2005).
Betts et al., *Journal of Virology*, 71(11), 8908-8911 (1997).
Bhardwaj et al., *Nat. Med.*, 9, 13-14 (2003).
Boaz, *IAVI Report*, (Dec. 2002/Jan. 2003).
Bojak et al., *Vaccine*, 20, 1975-1979 (2002).
Bonnet et al., *Immunol. Lett.*, 74, 11-25 (2000).
Borrow et al., *J. Virol.*, 68, 6103-6110 (1994).
Brander et al., *Curr. Opin. Immunol.*, 11, 451-459 (1999).
Cao et al., *Journal of Virology*, 71(11), 8615-8623 (1997).
Cao et al., *The Journal of Infectious Diseases*, 182, 1350-1356 (2000).
CDC, *MMWR Morb. Mortal Wkly. Rep.*, 52: 1145-1148 (2003).
Chakrabarti et al., *J. Viol.* 76, 5357-5368 (2002).
Chakrabarti et al., *Vaccine*, 23, 3434-3445 (2005).
Deml et al., *J. Viol.*, 75, 10991-11001 (2001).
Derosiers, *Nat. Med.* 10(3), 221-223 (2004).
Donnelly et al., *Nat. Med.*, 1:583-587, (1995).
Dorrell et al., *Eur. J. Immunol.*, 31, 1747-1756 (2001).
Dorrell et al., *Journal of Virology*, 73(2), 1708-1714 (1999).
Farina et al., *J. of Virology*, 75 (23): 11603-11613 (2001).
Ferrari et al., *Proc. Natl. Acad. Sci. USA*, 94, 1396-1401 (1997).
Finnefrock et al., *AIDS Research and Human Retroviruses*, 23(10), 1283-1292 (2007).
Gallo, *The Lancet*, 366: 1894-1898 (2005).
GENBANK® accession No. AF286227.
GENBANK® accession No. K03455.
GENBANK® accession No. M19921.
GENBANK® accession No. M68893.
GENBANK® accession No. U08794.

(Continued)

*Primary Examiner* — Jeffrey S. Parkin
(74) *Attorney, Agent, or Firm* — Leydig, Voit & Mayer, Ltd.

(57) ABSTRACT

The present disclosure provides compositions for eliciting an immune response, including a prophylactic immune response, against human immunodeficiency virus. The composition includes nucleic acid constructs encoding HIV antigenic polypeptides of multiple clades or strains. Methods for eliciting an immune response by administering the composition to a subject are also provided.

10 Claims, 13 Drawing Sheets

OTHER PUBLICATIONS

Goepfert, *J. Virol.*, 74, 10249-10255 (2000).
Graham, B.S., *Annu. Rev. Med.*, 53:207-221, (2002).
Halbert et al., *J. of Virology* 56(1): 250-257 (1985).
HIV Immunology and HIV/SIV Vaccine Databases, vol. 1, Division of AIDS, National Institute of Allergy and Infectious Diseases, (2003).
Huang et al., *J. Virol.*, 75, 4947-4951 (2001).
Jin et al., *J. Exp. Med.*, 189, 991-998 (1999).
Kantakamalakul et al., *Asian Pacific Journal of Allergy and Immunology*, 19(1), 17-22 (2001).
Keating et al., *AIDS Res. Hum. Retroviruses*, 18, 1067-1079 (2002).
Kim et al., *Virology*, 285, 204-217 (2001).
Kjerrstrom et al., *Virology*, 284, 46-61 (2001).
Klein et al., *J. Exp. Med.*, 181, 1365-1372 (1995).
Kong et al., *J. Viol.*, 77, 12764-12772 (2003).
Koup et al., *J. Virol.*, 68, 4650-4655 (1994).
Larke et al., *European Journal of Immunology*, 37, 566-577 (2007).
Lemiale et al., *J. Virol.*, 77 (18): 10078-10087 (2003).
Letvin et al., *J. Clin. Investig.*, 110, 15-20 (2002).
Letvin et al., *Nat. Med.*, 9, 864-866, (2003).
Luo et al., *Virus Research*, 92 (91): 75-82, (2003).
MacGregor et al., *AIDS*, 16:2137-2143, (2002).
MacGregor et al., *J. Infect. Dis.*, 178:92-100, (1998).
MacGregor et al., *J. Infect. Dis.*, 181:406, (2000).
Maecker et al., *J. Immunol. Methods*, 225, 27-40 (2001).
Mascola et al., *Curr. Opin. Immunol.*, 13:489-494, (2001).
Mascola et al., *J. Virol.*, 79:771-779, (2005).
McKay et al., *J. Immunol.*, 168, 332-337 (2002).
McMichael et al., *Nat. Med.*, 9(7): 874-880 (2003).
Migueles et al., *Immunol. Lett.*, 79, 141-150 (2001).
Mortara et al., *J. Virol.*, 72, 1403-1410 (1998).
Moss et al., *Clinical and Diagnostic Laboratory Immunology*, 7(5), 724-727 (2000).
Moss et al., *PNAS USA*, 92, 5773-5777 (1995).
Moss, *PNAS USA*, 93, 11341-11348 (1996).
Musey et al., *N. Engl. J. Med.*, 337, 1267-1274 (1997).
Muthumani et al., *Vaccine*, 20, 1999-2003 (2002).
Nabel, G.J., *Nature*, 410:1002-1007, (2001).
Natuk et al., *AIDS Res. Hum. Retroviruses*, 9 (5): 395-404, (1993).
NIAID News, Retrieved from the World Wide Web at http://www2.niaid.nih.gov/newsroom/releases/phase3hiv.htm, NIAID Phase III HIV vaccine trial to determine correlates of protection will not proceed. (Feb. 25, 2002).
Novitsky et al., *J. Viol.*, 75, 9210-9228 (2001).
Nwanegbo et al., *Clinical and Diag. Lab. Immunol.*, 11(2), 351-357 (2004).
Ogg et al., *Science*, 279, 2103-2106 (1998).
Ramsay et al., *Immunol. Cell Biol.*, 75, 382-388 (1997).
Rencher et al., *Vaccine*, 15(3), 265-272 (1997).
Rerks-Ngarm et al., *AIDS*, 20, 1471-1479 (2006).
Rollman et al., *Gene Ther.*, 11:1146-1154, (2004).
Rowland-Jones et al., *J. Clin. Investig.*, 102, 1758-1765 (1998).
Rowland-Jones et al., *Lancet*, 341, 860-861 (1993).
Rowland-Jones et al., *Nat. Med.* 1, 59-64 (1995).
Roy et al., *Vaccine*, 19:764-778, (2000).
Rubinstein et al., *J. Acquir. Immune Defic., Syndr.* 22, 467-476 (1999).
Schmitz et al., *Science*, 283, 857-860 (1999).
Seaman et al., *J. Virology*, 79(5): 2956-2963, (2005).
Seiki et al., *Proc. Natl. Acad. Sci. USA* 80: 3618-3622, (1983).
Shiver et al., *Annu. Rev. Med.*, 55: 355-372, (2004).
Shiver et al., *Nature*, 415, 331-335 (2002).
Slobod et al., *AIDS Research and Therapy*, 2(3), 1-3 (2005).
Srivastava et al., *J. Virol.*, 77, 2310-2320 (2003).
Stamatatos et al., *Journal of Virology*, 72(10), 7840-7845 (1998).
Subbramanian et al., *J. Virol.*, 77:10113-10118, (2003).
Tramont et al., *Expert Opin. Emerging Drugs*, 8(1), 37-45 (2002).
UNAIDS, AIDS Epidemic Update (2003).
Van Der Groen et al., *AIDS Res. Hum. Retrovir.*, 14(Suppl. 3), S211-S221 (1998).
Vogels et al., *Journal of Virology*, 77 (15), 8263-8271 (2003).
Walker et al., *Science*, 320: 760-764 (2008).
Wang et al., *Science*, 282:476-480, (1998).
Yang et al., *J. Virol.*, 78, 4029-4036 (2004).
Yang et al., *Science*, 279, 1034-1037 (1998).
Yew et al., *Mol. Ther.* 4:75-82, (2001).
Zur Megede et al., *J. Virol.*, 77, 6197-6207 (2003).
GENBANK® accession No. AF286227, Apr. 10, 2010.
GENBANK® accession No. K03455, Oct. 21, 2002.
GENBANK® accession No. M19921, May 24, 2010.
GENBANK® accession No. M68893, Aug. 2, 1993.
GENBANK® accession No. U08794, May 10, 2002.

\* cited by examiner

METHOD FOR INDUCING A MULTICLADE IMMUNE RESPONSE AGAINST HIV UTILIZING A MULTIGENE AND MULTICLADE IMMUNOGEN

CROSS REFERENCE TO RELATED APPLICATION

This patent application is a divisional of copending U.S. patent application Ser. No. 11/532,622, filed Oct. 29, 2008, which claims the benefit of U.S. Provisional Patent Application No. 60/588,378, filed Jul. 16, 2004. The disclosures of each of these applications are incorporated herein in its their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 336,113 Byte ASCII (Text) file named "707503_ST25.txt," created on Jan. 18, 2011.

ACKNOWLEDGMENT OF GOVERNMENT SUPPORT

Aspects of this disclosure were made with Government support. The Government has certain rights in this invention.

FIELD

This application relates to the field of vaccines. More specifically, this application relates to a multi-plasmid vaccine for the prevention of human immunodeficiency virus (HIV).

BACKGROUND

More than 40 million people are infected worldwide with HIV-1 and an estimated 14,000 new infections occur every day. Over 25 million people have died of HIV/AIDS since the first cases of AIDS were identified in 1981 (CDC, *MMWR Morb. Mortal Wkly. Rep.*, 52:1145-1148, 2003; UNAIDS, 2003 Report on the Global AIDS Epidemic Executive Summary, 2004). Development of a globally relevant HIV-1 vaccine is critical for controlling the HIV/AIDS pandemic.

The combination of a high transcriptional error rate and frequent recombination results in a remarkable amount of genetic diversity among HIV-1 strains and presents a challenge for selecting viral antigens. The other potential impact of HIV genetic variation is the high rate of mutation within each individual, which creates the opportunity for viral escape from epitope-specific immune responses and poses particular challenges for T cell based vaccine approaches (Altfield et al., *J. Virol.*, 77:12764-12772, 2002; Bhardwaj et al., *Nat. Med.*, 9:13-14, 2003; Brander et al., *Curr. Opin. Immunol.*, 11:451-459, 1999; Letvin et al., *Nat. Med.*, 9:861-866, 2003). A variety of vaccine strategies to elicit effective immunity to HIV-1 have been explored. Among them, immunization by plasmid DNA encoding genes for HIV protein antigens is a promising vaccine approach (Mascola et al., *Curr. Opin. Immunol.*, 13:489-494, 2001; Nabel, G. J., *Nature*, 410:1002-1007, 2001). Gene-based immunization promotes host cell synthesis and expression of the viral antigen and physiologic post-translational processing and folding in the cell cytoplasm. Therefore, DNA immunization elicits both $CD4^+$ and $CD8^+$ T lymphocyte responses with a variety of immunogens in animal models (Graham, B. S., *Annu. Rev. Med.*, 53:207-221, 2002; Rollman et al., *Gene Ther.*, 11:1146-1154, 2004; Barouch et al., *Science*, 290:486-492, 2000; Subbramanian et al., *J. Virol.*, 77:10113-10118, 2003; Mascola et al., *J. Virol.*, 79:771-779, 2005).

Delivering viral antigens by DNA plasmid vaccine vectors has potential advantages over other vector delivery systems, notably the lack of anti-vector immunity. However, DNA immunization has shown only limited immunogenicity in humans, despite many examples of vaccine-induced protection in mice and nonhuman primates (Rollman et al., *Gene Ther.*, 11:1146-1154, 2004; Donnelly et al., *Nat. Med.*, 1:583-587, 1995). The first DNA vaccine demonstrated to be immunogenic in antigen-naïve humans was a construct expressing the circumsporozoite antigen from *Plasmodium falciparum* delivered by Biojector®. In this study, $CD8^+$ CTL responses were detected only after in vitro expansion of effectors (Wang et al., *Science*, 282:476-480, 1998). Another report described a DNA plasmid expressing the Hepatitis B surface antigen delivered by a different needleless injection device, Powderject™, induced antibody as well as vaccine-specific T cell responses in antigen-naïve humans (Roy et al., *Vaccine*, 19:764-778, 2000). A DNA plasmid vaccine expressing the HIV-1 Env and Rev proteins tested in both HIV-infected and HIV-uninfected subjects (MacGregor et al., *J. Infect. Dis.*, 178:92-100, 1998) was not associated with adverse events, but only sporadic lymphoproliferative and antibody responses were observed (MacGregor et al., *J. Infect. Dis.*, 181:406, 2000; MacGregor et al., *AIDS*, 16:2137-2143, 2002).

This disclosure describes vaccine compositions that elicit broad spectrum immunity against HIV, by providing robust expression of HIV antigens corresponding to important immunogenic epitopes of multiple clades and strains of human immunodeficiency virus 1. The foregoing and other objects, features, and advantages of the invention will become more apparent from the following detailed description, which proceeds with reference to the accompanying figures.

SUMMARY

This disclosure relates to nucleic acid constructs that encode HIV antigens. These nucleic acid constructs are capable of eliciting an immune response against multiple variants of HIV, and are suitable for therapeutic (for example, prophylactic) administration. In the context of an immunogenic composition, multiple nucleic acids are combined, each of which encodes an HIV antigenic polypeptide, for example different HIV antigenic polypeptides (such as Gag, Pol, and Nef). A single immunogenic composition includes nucleic acid constructs that encode antigenic polypeptides of multiple clades or strains of HIV for example multiple clades or strains of Gag, Pol or Nef, or multiple clades or strains on Gag, Pol and Nef. Thus, when administered to a subject, the composition elicits an immune response against multiple clades or strains prevalent in human populations.

Methods of using the compositions are also described. Such methods involve administering compositions including the disclosed nucleic acid constructs to a subject, for example, for the purpose of eliciting an immune response against multiple clades or strains of HIV. The compositions can be administered alone or in combination with additional immunogenic compositions.

The foregoing and other objects, features, and advantages of the invention will become more apparent from the following detailed description, which proceeds with reference to the accompanying figures.

BRIEF DESCRIPTION OF THE SEQUENCE LISTING

SEQ ID NOs:1-6 represent the VRC-HIVDNA016-00-VP plasmids 4401, 4409, 4404, 5736, 5737, and 5738, respectively. Each of these plasmids is a nucleic acid construct for expressing a single HIV antigenic polypeptide.

SEQ ID NOs:7-15 represent chimeric Env plasmids.

SEQ ID NOs:16-19 represent adenovirus vectors

SEQ ID NOs:20-25 represent exemplary Gag, Pol, Nef, clade A Env, clade B Env and clade C Env polypeptides, respectively.

SEQ ID NO:26 represents the CMV/R transcription regulatory sequence.

DETAILED DESCRIPTION

The present disclosure relates to a nucleic acid constructs suitable for use as a preventive vaccine for HIV-1. Specific examples of compositions disclosed herein provide two significant advances with respect to prior HIV vaccine candidates. Such compositions exhibit increased expression and immunogenicity, and are capable of eliciting an immune response against multiple divergent strains of HIV. The vaccine includes a mixture of different nucleic acid constructs, and is designed to produce Gag, Pol, Nef and Env HIV-1 proteins to elicit broad immune responses against multiple HIV-1 subtypes isolated in human infections. Most typically, the nucleic acids are incorporated into a plasmid vector. An exemplary clinical embodiment of the multi-plasmid vaccine is designated VRC-HIVDNA016-00-VP.

The rationale in development of the exemplary vaccine disclosed herein is to separate the gag, pol and nef genes into separate nucleic acid constructs, such as, plasmids, rather than having one construct that produces a fusion protein immunogen, as was the case with previously developed HIV vaccines. In exemplary embodiments, the nucleic acid construct has been modified to increase production of immunogenic protein products in vivo. The modifications include: 1) a change in the promoter incorporated into these plasmids and/or 2) a 68 amino acid addition to the gag gene (for example, in the VRC 4401 (Gag protein only) plasmid). Whereas previous HIV vaccine plasmids have most commonly utilized the cytomegalovirus (CMV) immediate early promoter to regulate transcription of the polynucleotide sequence encoding the antigenic polypeptide, in the nucleic acid constructs disclosed herein, the polynucleotide sequence encoding the immunogenic HIV polypeptides is operably linked to a promoter designated CMV/R. The CMV/R promoter was previously described in published US patent application no. 20040259825, the disclosure of which is incorporated herein in its entirety.

Figure 1:
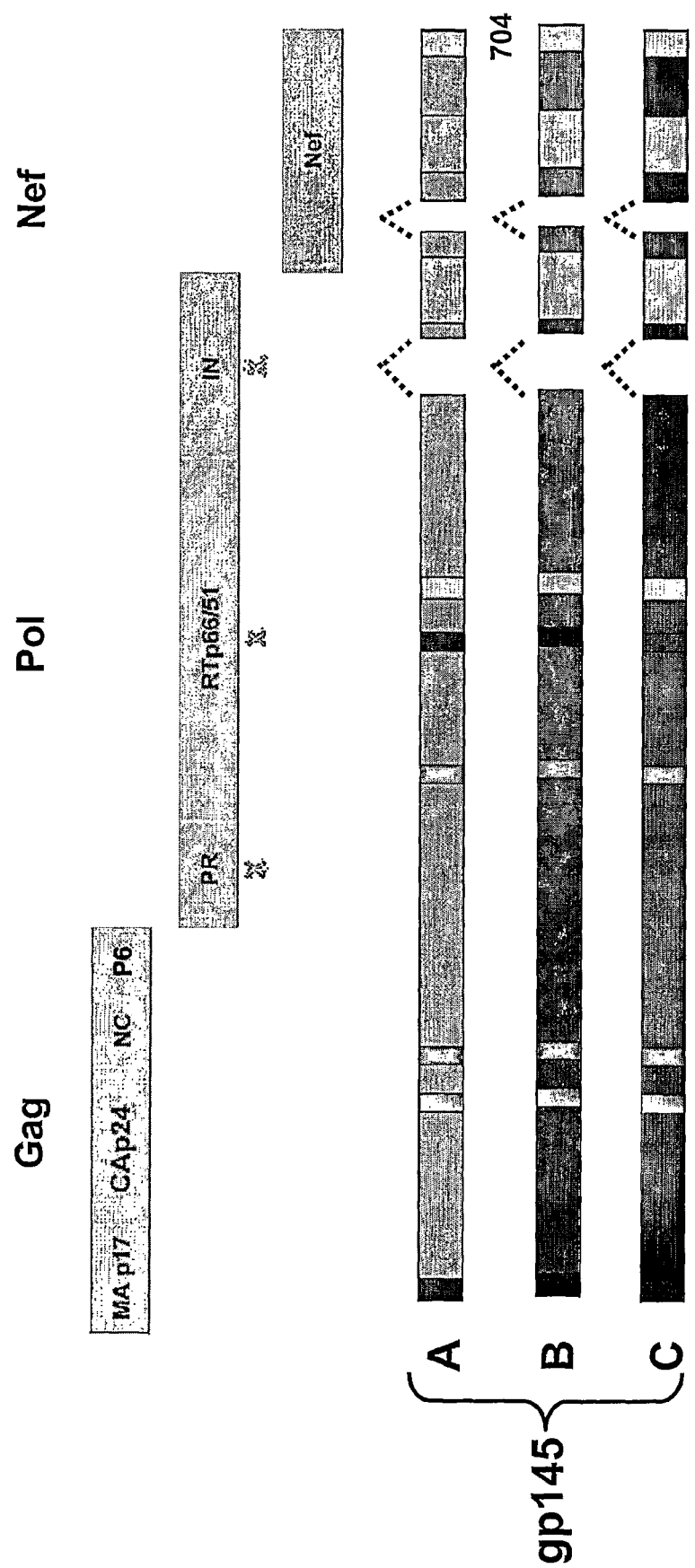
FIG. 1 is a schematic representation of a multi-clade, multi-valent HIV vaccine composition.

The nucleic acid constructs disclosed herein can incorporate polynucleotide sequences encoding essentially any HIV antigenic polypeptide, so long as antigens corresponding to multiple clades and/or strains are included. The compositions are described in detail with respect to a specific example of the nucleic acid constructs collectively designated the VRC-HIVDNA016-00-VP vaccine composition. This exemplary embodiment is illustrated in FIG. 1.

The vaccine composition VRC-HIVDNA016-00-VP includes six closed circular plasmid DNA macromolecules, VRC 4401, VRC 4409, VRC 4404, VRC 5736, VRC 5737 and VRC 5738, which can, for example, be combined in equal concentrations (mg/mL). VRC 4401 encodes the clade B HIV-1 Gag structural core protein that encapsidates the viral RNA and exhibits highly conserved domains. VRC 4409 encodes for clade B polymerase (Pol), which is also highly conserved, and VRC 4404 encodes for clade B Nef, an accessory protein against which a vigorous T-cell response is mounted in natural infection. The DNA plasmid expressing HIV-1 Pol has been modified to reduce potential toxicity through the incorporation of changes in the regions affecting the protease, reverse transcriptase, and integrase activities. Two amino acids in the myristoylation site in the HIV-1 nef gene were deleted to abrogate MHC class I and CD4+ down-regulation by the Nef protein. No modifications were made to the amino acid sequence of Gag. The other three plasmids express synthetic versions of modified, truncated envelope glycoproteins (gp145) from three strains of HIV-1: VRC 5736 (clade A), VRC 5737 (clade B) and VRC 5738 (clade C). The sequences used to create the DNA plasmids encoding Env are derived from three HIV-1 CCR5-tropic strains of virus. These genes have been modified to improve immunogenicity, which has been demonstrated in mice and monkeys. The vaccine is designed to elicit immune responses to a broad range of HIV-1 strains.

In particular examples, plasmids containing Gag, Pol, Nef and Env complementary DNAs (cDNAs) were used to subclone the relevant inserts into plasmid DNA expression vectors that use the CMV/R promoter and the bovine growth hormone polyadenylation sequence. All the plasmids expressing the HIV-1 genes were made synthetically with sequences designed to disrupt viral RNA structures that limit protein expression by using codons typically found in humans, thereby increasing gene expression. The translational enhancer region of the CMV immediate early region 1 enhancer was substituted with the 5'-untranslated HTLV-1 R-U5 region of the human T-cell leukemia virus type 1 (HTLV-1) long terminal repeat (LTR) to further optimize gene expression.

The DNA plasmids are typically produced in bacterial cell cultures containing a kanamycin selection medium. In all such cases, bacterial cell growth is dependent upon the cellular expression of the kanamycin resistance protein encoded by a portion of the plasmid DNA. Following growth of bacterial cells harboring the plasmid, the plasmid DNA is purified from cellular components. In a particular example, the Gag plasmid (VRC 4401) is 5886 nucleotide pairs in length and has an approximate molecular weight of 3.9 MDa; the Pol plasmid (VRC 4409) is 7344 nucleotide pairs in length and has an approximate molecular weight of 4.8 MDa; the Nef plasmid (VRC 4404) is 5039 nucleotide pairs in length and has an approximate molecular weight of 3.3 MDa; the clade A, B, and C Env plasmids (VRC 5736, 5737, and 5738) are 6305, 6338 and 6298 nucleotides in length, respectively, and have an approximate molecular weight of 4.2 MDa.

Thus, one aspect of the present disclosure relates to compositions capable of eliciting an immune response against HIV. For example, the compositions can be capable of eliciting a protective immune response against HIV when administered alone or in combination with at least one additional immunogenic compositions. It will be understood by those of skill in the art, the ability to produce an immune response after exposure to an antigen is a function of complex cellular and humoral processes, and that different subjects have varying capacity to respond to an immunological stimulus. Accordingly, the compositions disclosed herein are capable of eliciting an immune response in an immunocompetent subject, that is a subject that is physiologically capable of responding to an immunological stimulus by the production of a substantially normal immune response, e.g., including the production of antibodies that specifically interact with the immunological stimulus, and/or the production of functional T cells ($CD4^+$ and/or $CD8^+$ T cells) that bear receptors that specifically interact with the immunological stimulus. It will further be understood, that a particular effect of infection with HIV is to render a previously immunocompetent subject immunodeficient. Thus, with respect to therapeutic methods discussed below, it is generally desirable to administer the compositions to a subject prior to exposure to HIV (that is, prophylactically, e.g., as a vaccine) or therapeutically at a time following exposure to HIV during which the subject is nonetheless capable of developing an immune response to a stimulus, such as an antigenic polypeptide.

The compositions include a plurality of (that is two, three, four, five, six or even more) different nucleic acid constructs. Multiple copies of each of the different nucleic acid constructs are typically present. Each of the different nucleic acid constructs includes a polynucleotide sequence encoding an HIV antigenic polypeptide operably linked to a transcription regulatory sequence capable of directing its expression in the cells of a subject following systemic or localized administration. Included among the nucleic acid constructs are polynucleotide sequences that encode antigenic polypeptides of more than one (multiple) clades or strains of HIV. Thus, the composition includes multiple nucleic acid constructs, at least two of which incorporate polynucleotide sequences that encode HIV antigenic polypeptides from different clades or strains. Frequently, the composition includes nucleic acid constructs that encode HIV antigenic polypeptides from at least three different clades or strains.

In one embodiment, the composition includes multiple separate nucleic acid constructs, each of which includes a polynucleotide sequence encoding an HIV antigenic polypeptide operably linked to a CMV/R transcription control sequence. In one example, the CMV/R transcription control sequence has the sequence of SEQ ID NO:26. In another embodiment, the composition includes multiple separate nucleic acid constructs, each of which includes a polynucleotide sequence encoding a single HIV antigenic polypeptide. In certain embodiments, the nucleic acid constructs are plasmids.

The compositions typically include a first nucleic acid construct that includes a polynucleotide sequence that encodes an HIV Gag polypeptide, a second nucleic acid construct that includes a polynucleotide sequence that encodes an HIV Pol polypeptide, a third nucleic acid construct comprising a polynucleotide sequence that encodes an HIV Nef polypeptide, and at least one additional nucleic acid construct that includes a polynucleotide sequence that encodes an HIV Env polypeptide. The composition can also include one or more additional nucleic acid constructs that include a polynucleotide sequence that encodes an Env polypeptide of a different HIV clade or strain.

For example, the first nucleic acid construct can include a polynucleotide sequence that encodes a clade B Gag polypeptide, the second nucleic acid construct can include a polynucleotide sequence that encodes a clade B Pol polypeptide, and the third nucleic acid construct can include a polynucleotide sequence that encodes a clade B Nef polypeptide. Alternatively, the first, second and third nucleic acid constructs can include polynucleotide sequences that encode Gag, Pol and Nef polypeptides of a different clade, such as clade A or clade C, etc. For example, the composition can include a nucleic acid construct that include a polynucleotide sequence that encodes a Gag polypeptide with at least about 95% sequence identity to SEQ ID NO:20; a nucleic acid construct that includes a polynucleotide sequence that encodes a Pol polypeptide with at least about 95% sequence identity to SEQ ID NO:21 and/or a nucleic acid construct that includes a polynucleotide sequence that encodes a Nef polypeptide with at least about 95% sequence identity to SEQ ID NO:22. In one embodiment, the immunogenic composition includes a first nucleic acid construct with a polynucleotide sequence that encodes the Gag polypeptide of SEQ ID NO:20, a second nucleic acid construct with a polynucleotide sequence that encodes the Pol polypeptide of SEQ ID NO:21; and a third nucleic acid construct with a polynucleotide sequence that encodes the Nef polypeptide of SEQ ID NO:22. For example, the composition can include a nucleic acid construct that include a polynucleotide sequence with at least 95% sequence identity to positions 1375-2883 of SEQ ID NO:1; a nucleic acid construct that include a polynucleotide sequence with at least 95% sequence identity to positions 1349-4357 of SEQ ID NO:2 and/or a nucleic acid construct that include a polynucleotide sequence with at least 95% sequence identity to positions 1392-2006 of SEQ ID NO:3, or differing from the reference sequence by the substitution of one or more degenerate condons. In one embodiment, the composition includes the nucleic acid constructs represented by SEQ ID NO:1, SEQ ID NO:2 and SEQ ID NO:3 (plasmids VRC 4401, VRC 4409 and VRC 4404), or constructs having at least 95% sequence identity thereto.

Additionally, the composition can include multiple nucleic acid constructs that encode Env polypeptides from different clades or strains. For example, the composition can include a first additional nucleic acid construct including a polynucleotide sequence that encodes a clade A Env polypeptide, a second additional nucleic acid construct including a polynucleotide sequence that encodes a clade B Env polypeptide, and a third additional nucleic acid construct including a polynucleotide sequence that encodes a clade C Env polypeptide. Generally, clade A, clade B and clade C Env polypeptides will be utilized as clades A, B and C collectively account for the highest proportion of HIV infections worldwide. However, one of skill in the art will recognize that compositions can be produced that include Env polypeptides from any combination of HIV clades or strains. In certain embodiments, the immunogenic compositions include a first additional nucleic acid construct that includes a polynucleotide sequence that encodes a clade A Env polypeptide with at least 95% sequence identity to SEQ ID NO:23; a second additional nucleic acid construct that includes a polynucleotide sequence that encodes a clade B Env polypeptide with at least 95% sequence identity to SEQ ID NO:24; and/or a third additional nucleic acid construct that includes a polynucleotide sequence that encodes a clade C Env polypeptide with at least 95% sequence identity to SEQ ID NO:25. In one embodiment, the composition includes a first additional nucleic acid construct with a polynucleotide sequence that encodes the clade A Env polypeptide of SEQ ID NO:23; a second additional nucleic acid construct with a polynucleotide sequence that encodes the clade B Env polypeptide of SEQ ID NO:24; and a third additional nucleic acid construct with a polynucleotide sequence that encodes the clade C Env polypeptide of SEQ ID NO:25. For example, the immunogenic composition can include a nucleic acid construct with a polynucleotide sequence that is at least about 95% identical to positions 1392-3272 of SEQ ID NO:4; a nucleic acid construct with a polynucleotide sequence that is at least about 95% identical to positions 1384-3312 of SEQ ID NO:5 and/or a nucleic acid construct with a polynucleotide sequence that is at least about 95% identical to positions 1392-3272 of SEQ ID NO:6. In an embodiment, the immunogenic compositions includes nucleic acid constructs represented by SEQ ID NO:4; SEQ ID NO:5 and SEQ ID NO:6 (plasmids VRC 5736, 5737 and 5738, respectively), or constructs having at least 95% sequence identity thereto, or constructs differing from the reference sequence by the substitution of degenerate codons.

Thus, in certain embodiments, the immunogenic composition includes a first nucleic construct with a polynucleotide sequence encoding a Gag polypeptide, a second nucleic acid construct with polynucleotide sequence encoding a Pol polypeptide, a third nucleic acid construct with a polynucleotide sequence encoding a Nef polypeptide, a fourth nucleic acid construct with a polynucleotide sequence encoding a clade A Env polypeptide, a fifth nucleic acid construct with a polynucleotide sequence encoding a clade B Env polypeptide, and a sixth nucleic acid construct with a polynucleotide sequence encoding a clade C Env polypeptide. In one such an embodiment, the first nucleic acid construct encodes a polypeptide with at least 95% sequence identity to SEQ ID NO:20, the second nucleic acid construct encodes a polypeptide with at least 95% sequence identity to SEQ ID NO:21; the third nucleic acid construct encodes a polypeptide with at least 95% sequence identity to SEQ ID NO:22; the fourth nucleic acid construct encodes a polypeptide with at least 95% sequence identity to SEQ ID NO:23; the fifth nucleic acid construct encodes a polypeptide with at least 95% sequence identity to SEQ ID NO:24 and the sixth nucleic acid construct encodes a polypeptide with at least 95% sequence identity to SEQ ID NO:25. In an embodiment, the immunogenic composition includes six nucleic acid constructs, of which one or more are at least 95% identical to positions 1375-2883 of SEQ ID NO:1; positions 1349-4357 of SEQ ID NO:2; positions 1392-2006 of SEQ ID NO:3; positions 1392-3272 of SEQ ID NO:4; positions 1384-3312 of SEQ ID NO:5 and positions 1392-3272 of SEQ ID NO:6. For example, the composition can include six nucleic acid constructs with the polynucleotide sequences represented by SEQ ID NO:1, SEQ ID NO:2, SEQ ID NO:3, SEQ ID NO:4, SEQ ID NO:5 and SEQ ID NO:6 (plasmids VRC 4401, VRC 4409, VRC 4404, VRC 5736, VRC 5737 and VRC 5738, respectively), or constructs having at least 95% sequence identity thereto, or constructs differing from the reference sequences by the substitution of degenerate codons. When combined in an immunogenic composition, the nucleic acid constructs can be combined in a substantially equal ratio by weight (that is an approximately 1:1:1:1:1:1 ratio).

In some cases, the compositions include nucleic acid constructs that each encode an HIV antigenic polypeptide of a single clade or strain. In other cases, it can be useful to include nucleic acid constructs that incorporate polynucleotide sequences that encode a chimeric Env polypeptide. Thus, in certain embodiments, the nucleic acid construct can encode a chimeric Env polypeptide with at least 95% identity to a polypeptide encoded by one of SEQ ID NOs:7-15.

Typically, when formulated for administration to a subject, the compositions also include a pharmaceutically acceptable carrier or excipient, for example, an aqueous carrier, such as phosphate buffered saline (PBS) or another neutral physiological salt solution. The composition can also include an adjuvant or other immunostimulatory molecule. The composition can be administered one or more times to a subject to elicit an immune response. For example, the composition can be administered multiple times at intervals of at least about 28 days, or at different intervals as dictated by logistical or therapeutic concerns.

Thus, a feature of the disclosure includes pharmaceutical compositions or medicaments for the therapeutic or prophylactic treatment of an HIV infection. The use of the compositions disclosed herein in the production of medicament for the therapeutic or prophylactic treatment of HIV is also expressly contemplated. Any of the limitations or formulations disclosed above with respect to compositions are applicable to their use in or as medicaments for the treatment of an HIV infection.

Another aspect of the disclosure relates to methods for eliciting an immune response against HIV by administering the compositions described above to a human subject. When administered to an immunocompetent subject, the composition is capable of eliciting an immune response against multiple clades or strains of HIV. For example, in one embodiment the method involves administering a composition that includes multiple different nucleic acid constructs, each of which includes a polynucleotide sequence encoding an HIV antigenic polypeptide operably linked to a CMV/R transcription control sequence. In another embodiment, the method involves administering a composition that includes multiple different nucleic acid constructs, each of which includes a polynucleotide sequence encoding a single HIV antigenic polypeptide. In certain embodiments, the administered nucleic acid constructs are plasmids. Indeed, any of the above described compositions are suitable for administration to human subjects in the methods disclosed herein.

One dose or multiple doses of the composition can be administered to a subject to elicit an immune response with desired characteristics, including the production of HIV specific antibodies, or the production of functional T cells that react with HIV. In certain embodiments, the composition is administered intramuscularly, for example, using a needleless delivery device. Alternatively, the composition is administered by other routes, such as intravenous, transdermal, intranasal, oral (or via another mucosa).

In some embodiments, the methods also involve administering viral vectors that encode HIV antigenic polypeptides, instead of, or in combination with one or more of the nucleic acid constructs already described. In some cases, the viral vectors are adenoviral vectors (for example a replication deficient adenoviral vectors). For example, one or more doses of a "primer" composition, such as those disclosed above, can be administered to a subject, followed by administration of one or more doses of a "booster" composition including multiple adenoviral vectors encoding HIV antigenic polypeptides. In certain embodiments, the adenoviral vectors encode one or more HIV antigenic polypeptide that is identical to an HIV antigenic polypeptide previously administered in the primer composition. Exemplary recombinant adenoviral vectors are represented by SEQ ID NO:16, SEQ ID NO:17, SEQ ID NO:18 and SEQ ID NO:19. Of course, alternative adenoviral vectors, for example, that encode polypeptides with at least about 95% sequence identity to a polypeptide encoded by one of these sequences, or that share at least about 95% sequence identity to one of these sequences, can also be used.

In another aspect, the disclosure concerns isolated or recombinant nuclei acids that include a polynucleotide sequence that encodes an HIV antigenic polypeptide operably linked to a CMV/R transcription regulatory sequence. For example, such a nucleic acid can be a plasmid or a viral vector. The polynucleotide sequence can encode an HIV Gag polypeptide, an HIV Pol polypeptide, an HIV Nef polypeptide or an HIV Env polypeptide. In some examples, the HIV polypeptide encoded by the nucleic acid construct is the only HIV antigen encoded by the isolated or recombinant nucleic acid. Exemplary polypeptides encoded by these nucleic acids are represented by SEQ ID NOs:20-25, and include sequences that are at least 95% identical to the amino acid sequences of SEQ ID NOs:20-25. For example, such a nucleic acid can include a polynucleotide sequence that is at least 95% identical to: positions 1375-2883 of SEQ ID NO:1; positions 1349-4357 of SEQ ID NO:2; positions 1392-2006 of SEQ ID NO:3; positions 1392-3272 of SEQ ID NO:4; positions 1384-3312 of SEQ ID NO:5 or positions 1392-3272 of SEQ ID NO:6, any of which can be operably linked to a CMV/R transcription regulatory sequence. For example, the CMV/R transcription control sequence can be a polynucleotide sequence with at least 95% sequence identity to SEQ ID NO:26. Exemplary embodiments of such nucleic acids include the plasmids VRC 4401, VRC 4409, VRC 4404, VRC 5736, VRC 5737 and VRC 5738 represented by SEQ ID NOs:1-6, respectively.

In other embodiments, the nucleic acids include a polynucleotide sequence that encodes a chimeric HIV polypeptide that incorporates at least a subsequence of multiple HIV clades or strains. For example, the chimeric HIV polypeptide can be a chimeric Env polypeptide that includes subsequences of different HIV clades or strains. Examples of such nucleic acids include SEQ ID NOs:7-15, as well as substantially similar polynucleotide sequences, such as those having at least about 95% sequence identity to one of SEQ ID NOs: 7-15, or polynucleotide sequences in which one or more degenerate codons have been substituted for each other. Alternatively, the nucleic acids can include a polynucleotide sequence that encodes a chimeric HIV Env polypeptide operably linked to a transcription regulatory sequence other than the CMV/R transcription regulatory region (for example, the CMV immediate early promoter enhance or other promoter and/or enhancer as discussed below). Chimeric Env polypeptides are also a feature of this disclosure.

Additional technical details are provided under the specific topic headings below. In order to facilitate review of the various embodiments of this disclosure, the following explanations of specific terms are provided:

Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

Adjuvant: A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides.

Antigen: A compound, composition, or substance that can stimulate the production of antibodies or a T cell response in an animal, including compositions that are injected, absorbed or otherwise introduced into an animal. The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids or noncontiguous amino acids juxtaposed by tertiary folding of an antigenic polypeptide. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and multi-dimensional nuclear magnetic resonance spectroscopy.

Antibody: Immunoglobulin molecules and immunologically active portions of immunoglobulin molecules, that is, molecules that contain an antigen binding site that specifically binds (immunoreacts with) an antigen. A naturally occurring antibody (for example, IgG, IgM, IgD) includes four polypeptide chains, two heavy (H) chains and two light (L) chains interconnected by disulfide bonds. The phrase "antibody response" refers to an immunological response against an antigen involving the secretion of antibodies specific for the antigen. An antibody response is a B cell mediated immune response initiated through the interaction of an antigen (or epitope) with a B cell receptor (membrane bound IgD) on the surface of a B cell. Following binding of the stimulation of the B cell receptor by its cognate antigen, the B cell differentiates into a plasma cell that secretes antigen specific immunoglobulin to produce an antibody response. "Neutralizing antibodies" are antibodies that bind to an epitope on a virus inhibiting infection and/or replication as measured, for example, in a plaque neutralization assay.

cDNA (complementary DNA): A piece of DNA lacking internal, non-coding segments (introns) and regulatory sequences that determine transcription. cDNA is typically synthesized in the laboratory by reverse transcription from messenger RNA extracted from cells. In the context of preparing nucleic acid constructs including polynucleotide sequences that encode an HIV antigenic polypeptide, a cDNA can be prepared, for example by reverse transcription or amplification (e.g., by the polymerase chain reaction, PCR) from an HIV RNA genome (or genome segment).

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, the nucleic acid constructs described herein can be introduced into host cells where their polynucleotide sequences (including those encoding HIV antigenic polypeptides) can be expressed.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. A "protective immune response" is an immune response that inhibits a detrimental function or activity of a pathogen (such as HIV), reduces infection by the pathogen, or decreases symptoms (including death) that result from infection by the pathogen. A protective immune response can be measured, for example, by the inhibition of viral replication or plaque formation in a plaque reduction assay or ELISA-neutralization assay (NELISA), or by measuring resistance to viral challenge in vivo in an experimental system.

Immunogenic composition: A composition comprising at least one epitope of a pathogenic organism, that induces a measurable CTL response, or induces a measurable B cell response (for example, production of antibodies that specifically bind the epitope), or both, when administered to an immunocompetent subject. Thus, an immunogenic composition is a composition capable of eliciting an immune response in an immunocompetent subject. For example, an immunogenic composition can include isolated nucleic acid constructs (such as plasmids or viral vectors) that encode one or more immunogenic epitopes of an HIV antigenic polypeptide that can be used to express the epitope(s) (and thus be used to elicit an immune response against this polypeptide or a related polypeptide expressed by the pathogen). For in vitro use, the immunogenic composition can consist of the isolated nucleic acid, protein or peptide. For in vivo use, the immunogenic composition will typically include the nucleic acid or virus that expresses the immunogenic epitope in pharmaceutically acceptable carriers or excipients, and/or other agents, for example, adjuvants. An immunogenic polypeptide (such as an HIV antigen), or nucleic acid encoding the polypeptide, can be readily tested for its ability to induce a CTL or antibody response by art-recognized assays.

Pharmaceutically acceptable carriers and/or pharmaceutically acceptable excipients: The pharmaceutically acceptable carriers or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides and polynucleotides disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition used to achieve a desired effect in a subject. For instance, this can be the amount of the composition necessary to inhibit viral (or other pathogen) replication or to prevent or measurably alter outward symptoms of viral (or other pathogenic) infection. When administered to a subject, a dosage will generally be used that will achieve target tissue concentrations (for example, in lymphocytes) that has been shown to achieve an in vitro effect.

Inhibiting or treating a disease: Inhibiting infection by HIV refers to inhibiting the full development of disease caused by exposure to human immunodeficiency virus. For example, inhibiting an HIV infection refers to lessening symptoms resulting from infection by the virus, such as preventing the development of symptoms in a person who is known to have been exposed to the virus, or to reducing virus load or infectivity of a virus in a subject exposed to the virus. "Treatment" refers to a therapeutic or prophylactic intervention that ameliorates or inhibits or otherwise avoids a sign or symptom of a disease or pathological condition related to infection of a subject with a virus.

Subject: Living multi-cellular vertebrate organisms, a category that includes both human and veterinary subjects, including human and non-human mammals. In a clinical setting with respect to HIV, a subject is usually a human subject. An immunocompetent subject is a subject that is able to produce a substantially normal immune response against an antigenic stimulus.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as CD4, for example, a "helper" T cell. These cells, also known as helper T cells, help orchestrate the immune response, including antibody responses as well as killer T cell responses. $CD8^+$ T cells carry the CD8 marker, and include T cells with cytotoxic or "killer" effector function.

Transduced or Transfected: A transduced cell is a cell into which a nucleic acid molecule has been introduced, for example, by molecular biology techniques. As used herein, the term introduction or transduction encompasses all techniques by which a nucleic acid molecule might be introduced into such a cell, including transformation with plasmid vectors, transfection with viral vectors, and introduction of naked DNA by electroporation, lipofection, and particle gun acceleration.

Vaccine: A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen. In the context of this disclosure, the vaccines elicit an immune response against HIV. The vaccines described herein include nucleic acid constructs, for example, plasmids or viral vectors, encoding HIV antigens.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. The term vector includes plasmids, linear nucleic acid molecules, and viral vectors, such as adenovirus vectors and adenoviruses. The term adenovirus vector is utilized herein to refer to nucleic acids including one or more components of an adenovirus that generate viral particles in host cells. Such particles may be capable of one or more rounds of infection and replication, or can be replication deficient, e.g., due to a mutation. An adenovirus includes nucleic acids that encode at least a portion of the assembled virus. Thus, in many circumstances, the terms can be used interchangeably.

Nucleic Acid Constructs Encoding HIV Antigens

The present disclosure concerns nucleic acid constructs including polynucleotide sequences that encode antigenic polypeptides of human immunodeficiency virus-1 ("HIV-1" or simply, "HIV"). The term polynucleotide or nucleic acid sequence refers to a polymeric form of nucleotide at least 10 bases in length. The nucleotides can be ribonucleotides, deoxyribonucleotides, or modified forms of either nucleotide. The term includes single- and double-stranded forms of DNA. In the context of this disclosure, the nucleic acid constructs are "recombinant" nucleic acids. A recombinant nucleic acid is a nucleic acid that has a sequence that is not naturally occurring or has a sequence that is made by an artificial combination of two otherwise separated segments of sequence, for example, a heterologous sequence that is not immediately contiguous with both of the coding sequences with which it is immediately contiguous (one on the 5' end and one on the 3' end) in the naturally occurring genome of the organism from which it is derived. This artificial combination is often accomplished by chemical synthesis or, more commonly, by the artificial manipulation of isolated segments of nucleic acids, e.g., by genetic engineering techniques.

In some cases, the nucleic acids are "isolated" nucleic acids. An "isolated" nucleic acid (and similarly, an isolated protein) has been substantially separated or purified away from other biological components in the cell of the organism in which the nucleic acid naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

An "HIV antigenic polypeptide" or "HIV antigen" can include any proteinaceous HIV molecule or portion thereof that is capable of provoking an immune response in an immunocompetent mammal. An "HIV molecule" is a molecule that is a part of a human immunodeficiency virus, is encoded by a nucleic acid sequence of a human immunodeficiency virus, or is derived from or synthetically based upon any such molecule. Administration of a nucleic acid that encodes an HIV antigen that provokes an immune response preferably leads to protective immunity against HIV. In this regard, an "immune response" to HIV is an immune response to any one or more HIV antigens.

Examples of suitable HIV antigens include as all or part of the HIV Gag, Pol, Nef or Env proteins. In the virus, Gag proteins are components of the viral capsid. The Pol polyprotein provides reverse transcriptase (RT); integrase (IN) and protease(PR) functions, which reverse transcribe the viral RNA into double stranded DNA, integrated into the chromosome of a host cell, and cleave the gag-pol derived proteins into functional polypeptides, respectively. The Nef polypeptide is a negative regulatory factor involved in determining pathogenicity of the virus following infection. Env proteins are envelope proteins involved in viral attachment and fusion to target cells. One of skill in the art will recognize that functional attributes of the polypeptides can be altered (for example, deleted) without altering antigenic properties of the polypeptides. Immunogenic variants or fragments of each of Gag, Pol, Nef or Env are also HIV antigenic polypeptides that can included in the immunogenic compositions disclosed herein. Immunogenic variants include those, for example, having at least 90%, 95%, or 98% sequence identity to SEQ ID NOs:20-25, or immunogenic fragments thereof. The nucleic acid vaccines disclosed herein can include SEQ ID NOs:1-19 or sequences that encode HIV antigens, such as those represented by SEQ ID NOS:20-25, or HIV antigens that have at least 90%, 95% or 98% sequence identity to SEQ ID NOs:20-25.

Suitable Env proteins are known in the art and include, for example, gp160, gp120, gp41, and gp140. Any clade of HIV is appropriate for antigen selection, including HIV clades A, B, C, and the like. Thus, it will be appreciated that any one, or a combination, of the following HIV antigens can be used in the inventive method: HIV clade A gp140, Gag, Pol, Nef and/or Env; HIV clade B gp140, Gag, Pol, Nef and/or Env proteins; and HIV clade C gp140, Gag, Pol, Nef and/or Env proteins. While the compositions and methods are described in detail with respect to Gag, Pol, Nef and/or Env proteins, any HIV protein or portion thereof capable of inducing an immune response in a mammal can be used in connection with the inventive method. HIV Gag, Pol, Nef and/or Env proteins from HIV clades A, B, C, as well as nucleic acid sequences encoding such proteins and methods for the manipulation and insertion of such nucleic acid sequences into vectors, are known (see, for example, HIV Sequence Compendium, Division of AIDS, National Institute of Allergy and Infectious Diseases, 2003, HIV Sequence Database (on the world wide web at hiv-web.lan1.gov/content/ hiv-db/mainpage.html), Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

Gag, Pol, Nef and Env polypeptide sequences are known in the art, and numerous amino acid sequences are available from publicly accessible databases, such as GENBANK®. For example, a Gag polypeptide corresponding to the amino acid sequence of the strain HXB2 is represented by the sequence of GENBANK® accession number K03455. Pol and Nef polypeptides corresponding to the amino acid sequence of the strain NL4-3 is represented by the sequence of GENBANK® accession number M19921. Exemplary Env polypeptides, for example, corresponding to clades A, B and C are represented by the sequences of GENBANK® accession numbers U08794, K03455 and AF286227, respectively. Particular exemplary sequences encoded by the nucleic acid constructs disclosed herein are represented by SEQ ID NOs: 20-25, corresponding to Gag, Pol, Nef, clade A Env, clade B Env, and clade C Env, respectively. Certain of these exemplary polypeptides have been modified functionally (as indicated in further detail in the Examples) but nonetheless retain important antigenic characteristics of the naturally occurring proteins.

An entire, intact HIV protein is not required to produce an immune response. Indeed, most antigenic epitopes of HIV proteins are relatively small in size. Thus, fragments (for example, epitopes or other antigenic fragments) of an HIV protein, such as any of the HIV proteins described herein, can be used as an HIV antigen. Antigenic fragments and epitopes of the HIV Gag, Pol, Nef and/or Env proteins, as well as nucleic acid sequences encoding such antigenic fragments and epitopes, are known (see, for example, HIV Immunology and HIV/SIV Vaccine Databases, Vol. 1, Division of AIDS, National Institute of Allergy and Infectious Diseases, 2003).

A nucleic acid construct is said to "encode" an antigen when a polynucleotide sequence incorporated into the construct includes one or more open reading frames that upon recognition and activity by cellular transcriptional and translational processes gives rise to a sequence of amino acids constituting the antigen.

HIV antigens are "different" if they comprise a different antigenic amino acid sequence. When referring to a plurality of different HIV antigens, the two or more different HIV antigens can be any HIV antigens, such as two or more (or three, or four, or five, or six, or more) of the HIV antigens described herein. Different HIV antigenic polypeptides can be two or more antigenic polypeptides from different HIV proteins, that is proteins encoded by different genes in the HIV genome (for example, an HIV Gag polypeptide is different from an HIV Pol polypeptide, which is different from an HIV Nef polypeptide, which again is different from an HIV Env polypeptide). Thus, Gag, Pol, Nef and Env are different HIV proteins or antigenic polypeptides. Alternatively, different HIV antigenic polypeptides are different if they are encoded by a homologous genomic segment (or gene) from different strains or clades of HIV. Thus, a clade A Env polypeptide is different from a clade B Env polypeptide, which is different from a clade C Env polypeptide, and the like. In the context of immunogenic (for example, vaccine) compositions described herein, the two or more different HIV antigens include HIV antigens from two or more different HIV clades or strains, such as from three or more different HIV clades (such as clades A, B and C) or from two or more variant HIV strains of the same clade. Exposing the immune system of a mammal to a "cocktail" of different HIV antigens can elicit a broader and more effective immune response than exposing the immune system to only a single HIV antigen.

Thus, a plurality of separate nucleic acid constructs each including a polynucleotide sequence encoding a single HIV antigenic polypeptide, wherein the plurality of nucleic acid constructs encode a plurality of antigenic polypeptides or a plurality of HIV clades or strains, can include a plurality of encoded polypeptides of the same clade or strain (for example all clade B) or encoded polypeptides of different clades or strains (for example some of clade A and others of clade B).

In some particularly disclosed embodiments the composition includes a plurality of different nucleic acid constructs. The nucleic acid constructs include a polynucleotide sequence encoding a single (no more than once) HIV antigen operably linked to a transcription control sequence, and the single HIV antigen is different for the different nucleic acid constructs. In particular examples, the different single HIV antigens of the different nucleic acid constructs, are different encoded polypeptides of the same clade or strain, but may further include different encoded polypeptides, expressed from different constructs, of clades or strains that differ from the encoded polypeptides that share the same clade or strain. For example, the different nucleic acid constructs that encode HIV antigens of the same clade or strain can be three separate constructs that respectively encode Gag, Pol, and Nef as the only HIV antigen expressed from each of the constructs, and each of Gag, Pol, and Nef are of the same clade or strain (for example, all clade B). In addition, in some embodiments the composition can further include separate nucleic acid constructs that encode Env antigens of different clades or strains. For example, at least three separate constructs independently encode clade A Env, clade B Env and clade C Env as their only encoded HIV antigen.

For example, a nucleic acid construct can include a polynucleotide sequence that encodes a single HIV antigenic polypeptide. In specific examples provided herein, the nucleic acid construct encodes a single Gag polypeptide, a single Pol polypeptide, a single Nef polypeptide or a single Env polypeptide. For example, the nucleic acid construct can include a polynucleotide sequence that encodes a single Gag polypeptide, such as a clade B Gag polypeptide (e.g., the amino acid sequence of SEQ ID NO:20); a polynucleotide sequence that encodes a single Pol polypeptide, such as a clade B Pol polypeptide (e.g., SEQ ID NO:21); a polynucleotide sequence that encodes a single Nef polypeptide, such as a clade B Nef polypeptide (e.g., SEQ ID NO:22), or a polynucleotide sequence that encodes a single Env polypeptide, such as a clade A, a clade B or a clade C Env polypeptide (for examples, SEQ ID NO:23, SEQ ID NO:24 and SEQ ID NO:25). Exemplary nucleic acid constructs encoding these polypeptides are represented by SEQ ID NOs:1-6, respectively.

Alternatively, a nucleic acid construct can include a polynucleotide sequence that encodes an HIV antigenic polypeptide that includes subsequences of multiple clades or strains, that is, a "chimeric" HIV polypeptide. A chimeric HIV antigenic polypeptide can include subsequences of two or more clades or strains, such as three or more different clades or strains. For example, a chimeric HIV Env polypeptide can include one or more subsequence of a clade A Env polypeptide in combination with one or more subsequence of a clade B Env polypeptide and/or one or more subsequence of a clade C Env polypeptide, or in combination with one or more subsequences of a different clade A strain (or strains) of HIV with a different amino acid sequence. Similarly, subsequences of clade B and C Env polypeptides can be combined with subsequences of other clades and/or strains. Nucleic acid constructs including chimeric Env polypeptides are represented by SEQ ID NOs:7-15.

Typically, the nucleic acid constructs encoding the HIV antigenic polypeptides are plasmids. However, other vectors (for example, viral vectors, phage, cosmids, etc.) can be utilized to replicate the nucleic acids. In the context of this disclosure, the nucleic acid constructs typically are expression vectors that contain a promoter sequence which facilitates the efficient transcription of the inserted genetic sequence of the host. The expression vector typically contains an origin of replication, a promoter, as well as specific nucleic acid sequences that allow phenotypic selection of the transformed cells. In exemplary nucleic acid constructs, the coding sequence is operably linked under the transcriptional control of a human cytomegalovirus (CMV) immediate early (IE) enhancer/promoter that has been modified to include a regulatory sequence from the R region of the long terminal repeat (LTR) of human T-cell leukemia virus type 1 (HTLV-1). This transcription regulatory sequence is designated "CMV/R" or "CMV/R promoter." The CMV/R transcription regulatory sequence (alternatively referred to as a "transcription control sequence") contains, in a 5' to 3' direction: the CMV IE enhancer/promoter; the HTLV-1 R region; and a 123 base pair (bp) fragment of the CMV IE 3' intron. The CMV/R transcription regulatory region confers substantially increased expression and improved cellular immune responses to HIV antigens operably linked under its control. An exemplary CMV/R is represented by SEQ ID NO:26. However, transcription control sequences that retain the regulatory properties or have been modified to enhance expression, including transcription regulatory regions that are at least about 90%, or 95% or 98% identical to SEQ ID NO:26, can also be used.

More generally, polynucleotide sequences encoding HIV antigenic polypeptides can be operably linked to any promoter and/or enhancer that is capable of driving expression of the nucleic acid following introduction into a host cell. A promoter is an array of nucleic acid control sequences that directs transcription of a nucleic acid. A promoter includes necessary nucleic acid sequences (which can be) near the start site of transcription, such as in the case of a polymerase II type promoter (a TATA element). A promoter also can include distal enhancer or repressor elements which can be located as much as several thousand base pairs from the start site of transcription. Both constitutive and inducible promoters are included (see, for example, Bitter et al., *Methods in Enzymology* 153:516-544, 1987). Specific, non-limiting examples of promoters include promoters derived from the genome of mammalian cells (e.g., metallothionein promoter) or from mammalian viruses (e.g., the cytomegalovirus immediate early gene promoter, the retrovirus long terminal repeat; the adenovirus late promoter; the vaccinia virus 7.5K promoter) may be used. Promoters produced by recombinant DNA or synthetic techniques may also be used. A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

To produce such nucleic acid constructs, polynucleotide sequences encoding HIV antigenic polypeptides are inserted into a suitable expression vector, such as a plasmid expression vector that use the CMV/R promoter and the bovine growth hormone polyadenylation sequence to regulate expression. The CMV/R promoter consists of a translational enhancer region of the CMV immediate early region 1 enhancer (CMV-IE) substituted with the 5'-untranslated HTLV-1 R-U5 region of the human T-cell leukemia virus type 1 (HTLV-1) long terminal repeat (LTR) to optimize gene expression. The HIV-1 polynucleotide sequences are typically modified to optimize expression in human cells. The plasmid expression vectors are introduced into bacterial cells, such as, *E. coli*, which are grown in culture in kanamycin selection medium. In all cases, bacterial cell growth is dependent upon the cellular expression of the kanamycin resistance protein encoded by a portion of the plasmid DNA. Following growth of bacterial cells harboring the plasmid, the plasmid DNA is purified from cellular components. Procedures for producing polynucleotide sequences encoding HIV antigenic polypeptides and for manipulating them in vitro are well known to those of skill in the art, and can be found, e.g., in Sambrook and Ausubel, supra.

In addition to the polynucleotide sequences encoding the polypeptides represented by SEQ ID NOs:20-25 disclosed herein, such as SEQ ID NOs:1-6 (as well as nucleic acids encoding chimeric Env polypeptides represented by SEQ ID NOs:7-15 and nucleic acids encoding adenoviral vectors represented by SEQ ID NOs:16-19) as disclosed herein, the nucleic acid constructs can include variant polynucleotide sequences that encode polypeptides that are substantially similar to SEQ ID NOs:20-25 (for example, are substantially similar to SEQ ID NOs:1-6 and/or SEQ ID NOs:16-19). Similarly, the nucleic acid constructs can include polynucleotides that encode chimeric polypeptides that are substantially similar to those encoded by SEQ ID NOs:7-15. The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. Variants of an HIV antigenic polypeptide (for example, of a particular clade) can have one or a small number of amino acid deletions, additions or substitutions but will nonetheless share a very high percentage of their amino acid (and generally their polynucleotide sequence). To the extent that variants of a subtype differ from each other, their overall antigenic characteristics are maintained. In contrast, HIV antigens of different clades share less sequence identity and/or differ from each other such that their antigenic characteristics are no longer identical. Thus, the nucleic acid constructs can include polynucleotides that encode polypeptides that are at least about 90%, or 95%, or 98% identical to one of SEQ ID NOs:20-25 with respect to amino acid sequence, or that have at least about 90%, 95%, or 98% sequence identity to one or more of SEQ ID NOs; 1-19 and/or that differ from one of these sequences by the substitution of degenerate codons.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, NY, 1993 and Ausubel et al. *Short Protocols in Molecular Biology*, 4$^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid. For example, a nucleic acid construct can include a polynucleotide sequence that hybridizes under high stringency or very high stringency, or even higher stringency conditions to a polynucleotide sequence that encodes any one of SEQ ID NOs:20-25. Similarly, the nucleic acid constructs can hybridize under such conditions to any one of SEQ ID NOs:1-19.

Thus, in addition to polynucleotides encoding the particular amino acid sequences represented by SEQ ID NOs:20-25, for example those polynucleotides represented by the codon optimized constructs of SEQ ID NO:s1-19, the nucleic acid constructs used in the vaccine compositions can include polynucleotide sequences having a high percentage of sequence identity, for example, that hybridize under high stringency, or very high stringency (or even higher stringency) to one of these sequences. A codon composition at one or more positions that is found in a naturally occurring or mutant strain of HIV are also encompassed within the nucleic acid constructs disclosed herein. One of skill in the art can easily identify numerous HIV polynucleotide sequences, and determine which nucleotides can be varied without substantially altering the amino acid content of the encoded polypeptide. In addition, polynucleotide sequences that encode variants with a small number of amino acid additions, deletions or substitution are also encompassed within the nucleic acid constructs described herein. Typically, any amino acid additions, deletions and/or substitutions are located in positions that do not alter the antigenic epitopes and that do not interfere with folding, or other translational or post-translational processing. Most commonly, any amino acid substitutions are conservative amino acid substitutions. For example, a variant polynucleotide sequence can encode an HIV antigenic polypeptide with one or two or three or four or five, or more amino acid additions, deletions or substitutions.

Conservative variants of particular amino acids are well known in the art, and can be selected, for example from groupings set forth in Table 1.

TABLE 1

Conservative amino acid substitutions

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Immunogenic Compositions

Used in combination, the nucleic acid constructs, such as those exemplified by SEQ ID NOs:1-6, can be used to provide immunogenic compositions that elicit a broad spectrum immune response against HIV. This specific combination of nucleic acid constructs is referred to herein as VRC-HIVDNA016-00-VP, and includes the plasmidsVRC-4401, VRC-4409, VRC-4404, VRC-5736, VRC 5737, and VRC-5738, corresponding respectively to SEQ ID NOs:1-6).

The composition including two or more nucleic acid construct encoding different HIV antigens is typically provided by a composition including multiple nucleic acid constructs, each of which encodes a single HIV antigen. Collectively, the two or more nucleic acid constructs encode antigens from more than one clade or strain, for example, from two or more clades or strains, or from three or more clades or strains. In some cases, the composition includes polynucleotide sequences that encode a chimeric HIV antigen, with subsequences of more than one clade or strain.

For clinical purposes, all nucleic acid constructs, such as plasmids and host *E. coli* strains used in the production of the vaccine are characterized in accordance with the relevant sections of the "Points to Consider in the Production and Testing of New Drugs and Biologicals Produced by Recombinant DNA Technology" (1985), the "Supplement: Nucleic Acid Characterization and Genetic Stability" (1992), and "Points to Consider in Human Somatic Cell Therapy and Gene Therapy" (1991, 1998), "Points to Consider on Plasmid DNA Vaccines for Preventive Infectious Disease Indications" (1996). In addition for clinical testing and use, all compositions are produced in compliance with current Good Manufacturing Practices (cGMP).

Thus, in one embodiment, the immunogenic composition is VRC-HIVDNA016-00-VP, a six-component multiclade plasmid DNA vaccine, expressing Gag, Pol and Nef proteins from clade B HIV-1 and Env glycoproteins from clades A, B and C. This composition is suitable for the prophylactic treatment of HIV, that is, as a preventive HIV-1 vaccine. The vaccine has been designed to elicit immune responses against several proteins from a variety of HIV-1 strains. This vaccine differs from previous multiclade vaccine compositions in two significant ways. First, previous compositions have relied on a single plasmid encoding a Gag-Pol-Nef fusion protein. In the particular examples described herein, these three proteins are separated into three different plasmids, encoding Gag (VRC 4401), Pol (VRC 4409), and Nef (VRC 4404) individually. Additionally, there is a 68 amino acid addition in the gag gene as compared to the previous fusion protein composition. Second, the promoter is modified to include the 5'-untranslated HTLV-1 R-U5 region of the human T-cell leukemia virus type 1 (HTLV-1) long terminal repeat (LTR) rather than a portion of the translational enhancer region of the CMV immediate early region 1 enhancer used in previous constructs. Vaccination, for example, of non-human primates, with plasmids containing CMV/R transcription regulatory region elicited higher and more consistent HIV-1 specific cellular immune responses than vaccination with plasmids constructed with the unmodified CVM IE promoter/enhancer sequence.

VRC-HIVDNA016-00-VP is designed to elicit immune responses against several proteins from a variety of HIV-1 strains. This vaccine product has evolved from the initial HIV-1 DNA plasmid product (VRC-4302; BB-IND 9782) that encoded for an HIV-1 clade B Gag-Pol fusion protein. Preclinical studies demonstrated expression of immunogenic protein in small animals, and an ongoing Phase I clinical trial has revealed no safety concerns at the doses tested to date. The VRC-HIVDNA009-00-VP vaccine (BB-IND 10681) expanded upon the product concept to include proteins from multiple subtypes (clades) of HIV-1 and increased the number of vaccine components to include a highly immunogenic regulatory protein (Nef), as well as modified Envelope glycoproteins that have been able to generate immune responses in rhesus macaques.

The four plasmid product, VRC-HIVDNA009-00-VP, was chosen to advance to clinical testing based upon preclinical immunogenicity studies conducted in rhesus macaques and mice, as well as preclinical safety studies of a vaccine product (VRC-HIVDNA006-00-VP) consisting of the same four plasmids and two additional Gag-Pol-Nef expressing plasmids. Based on biological safety testing of these plasmid products, and the high degree of homology between the candidate vaccines VRC-HIVDNA009-00-VP (BB-IND 10681) and VRC-HIVDNA016-00-VP, it was determined that the six plasmid vaccine was safe for human clinical trials.

Therapeutic Methods

The nucleic acid constructs encoding HIV antigenic polypeptides described herein are used, for example, in combination, as pharmaceutical compositions (medicaments) for use in therapeutic, for example, prophylactic regimens (e.g., vaccines) and administered to subjects (e.g., human subjects) to elicit an immune response against one or more clade or strain of HIV. For example, the compositions described herein can be administered to a human (or non-human) subject prior to infection with HIV to inhibit infection by or replication of the virus. Thus, the pharmaceutical compositions described above can be administered to a subject to elicit a protective immune response against HIV. To elicit an immune response, a therapeutically effective (e.g., immunologically effective) amount of the nucleic acid constructs are administered to a subject, such as a human (or non-human) subject.

A "therapeutically effective amount" is a quantity of a chemical composition (such as a nucleic acid construct or vector) used to achieve a desired effect in a subject being treated. For instance, this can be the amount necessary to express an adequate amount of antigen to elicit an antibody or T cell response, or to inhibit or prevent infection by or replication of the virus, or to prevent, lessen or ameliorate symptoms caused by infection with the virus. When administered to a subject, a dosage will generally be used that will achieve target tissue or systemic concentrations that are empirically determined to achieve an in vitro effect. Such dosages can be determined without undue experimentation by those of ordinary skill in the art. Exemplary dosages are described in detail in the Examples.

A pharmaceutical composition including an HIV encoding nucleic acid construct can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995; *DNA Vaccines: Methods and Protocols* (Methods in Molecular Medicine) by Douglas B. Lowrie and Robert G. Whalen (Eds.), Humana Press, 2000) such as by intramuscular, subcutaneous, or intravenous injection, but even oral, nasal, or anal administration is contemplated. In one embodiment, administration is by subcutaneous or intramuscular injection. Actual methods for preparing administrable compositions will be known or apparent to those skilled in the art and are described in more detail in such publications as *Remingtons Phamaceutical Sciences*, $19^{th}$ Ed., Mack Publishing Company, Easton, Pa., 1995.

Suitable formulations for the nucleic acid constructs, for example, the primer or booster compositions disclosed herein, include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the composition for use in the inventive method is formulated to protect the nucleic acid constructs from damage prior to administration. For example, the composition can be formulated to reduce loss of the adenoviral vectors on devices used to prepare, store, or administer the expression vector, such as glassware, syringes, or needles. The compositions can be formulated to decrease the light sensitivity and/or temperature sensitivity of the components. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such an adenoviral vector composition will extend the shelf life of the vector, facilitate administration, and increase the efficiency of the inventive method. Formulations for adenoviral vector-containing compositions are further described in, for example, U.S. Pat. Nos. 6,225,289, 6,514,943, U.S. Patent Application Publication No. 2003/0153065 A1, and International Patent Application Publication WO 00/34444. An adenoviral vector composition also can be formulated to enhance transduction efficiency. In addition, one of ordinary skill in the art will appreciate that the composition can comprise other therapeutic or biologically-active agents. For example, factors that control inflammation, such as ibuprofen or steroids, can be part of the adenoviral vector composition to reduce swelling and inflammation associated with in vivo administration of the adenoviral vectors. As discussed herein, immune system stimulators can be administered to enhance any immune response to the antigens. Antibiotics, i.e., microbicides and fungicides, can be present to treat existing infection and/or reduce the risk of future infection, such as infection associated with gene transfer procedures.

The compositions can be administered for therapeutic treatments. In therapeutic applications, a therapeutically effective amount of the composition is administered to a subject prior to or following exposure to or infection by HIV. When administered prior to exposure, the therapeutic application can be referred to as a prophylactic administration (e.g., a vaccine). Single or multiple administrations of the compositions are administered depending on the dosage and frequency as required and tolerated by the subject. In one embodiment, the dosage is administered once as a bolus, but in another embodiment can be applied periodically until a therapeutic result, such as a protective immune response, is achieved. Generally, the dose is sufficient to treat or ameliorate symptoms or signs of disease without producing unacceptable toxicity to the subject. Systemic or local administration can be utilized.

Controlled release parenteral formulations can be made as implants, oily injections, or as particulate systems. Particulate systems include microspheres, microparticles, microcapsules, nanocapsules, nanospheres, and nanoparticles. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see, Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

In certain embodiments, the pharmaceutical composition includes an adjuvant. An adjuvant can be a suspension of minerals, such as alum, aluminum hydroxide, aluminum phosphate, on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). In the context of nucleic acid vaccines, naturally occurring or synthetic immunostimulatory compositions that bind to and stimulate receptors involved in innate immunity can be administered along with nucleic acid constructs encoding the HIV antigenic polypeptides. For example, agents that stimulate certain Toll-like receptors (such as TLR7, TLR8 and TLR9) can be administered in combination with the nucleic acid constructs encoding HIV antigenic polypeptides. In some embodiments, the nucleic acid construct is administered in combination with immunostimulatory CpG oligonucleotides.

Nucleic acid constructs encoding HIV antigenic polypeptides can be introduced in vivo as naked DNA plasmids. DNA vectors can be introduced into the desired host cells by methods known in the art, including but not limited to transfection, electroporation (e.g., transcutaneous electroporation), microinjection, transduction, cell fusion, DEAE dextran, calcium phosphate precipitation, use of a gene gun, or use of a DNA vector transporter (See e.g., Wu et al. *J. Biol. Chem.*, 267:963-967, 1992; Wu and Wu *J. Biol. Chem.*, 263:14621-14624, 1988; and Williams et al. *Proc. Natl. Acad. Sci. USA* 88:2726-2730, 1991). As described in detail in the Examples, a needle-less delivery device, such as a BIOJECTOR® needleless injection device can be utilized to introduce the therapeutic nucleic acid constructs in vivo. Receptor-mediated DNA delivery approaches can also be used (Curiel et al. *Hum. Gene Ther.*, 3:147-154, 1992; and Wu and Wu, *J. Biol. Chem.*, 262:4429-4432, 1987). Methods for formulating and administering naked DNA to mammalian muscle tissue are disclosed in U.S. Pat. Nos. 5,580,859 and 5,589,466, both of which are herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

Alternatively, electroporation can be utilized conveniently to introduce nucleic acid constructs encoding HIV antigens into cells. Electroporation is well known by those of ordinary skill in the art (see, for example: Lohr et al. *Cancer Res.* 61:3281-3284, 2001; Nakano et al. *Hum Gene Ther.* 12:1289-1297, 2001; Kim et al. *Gene Ther.* 10:1216-1224, 2003; Dean et al. *Gene Ther.* 10:1608-1615, 2003; and Young et al. *Gene Ther* 10:1465-1470, 2003). For example, in electroporation, a high concentration of vector DNA is added to a suspension of host cell (such as isolated autologous peripheral blood or bone marrow cells) and the mixture shocked with an electrical field. Transcutaneous electroporation can be utilized in animals and humans to introduce heterologous nucleic acids into cells of solid tissues (such as muscle) in vivo. Typically, the nucleic acid constructs are introduced into tissues in vivo by introducing a solution containing the DNA into a target tissue, for example, using a needle or trochar in conjunction with electrodes for delivering one or more electrical pulses. For example, a series of electrical pulses can be utilized to optimize transfection, for example, between 3 and ten pulses of 100V and 50 msec. In some cases, multiple sessions or administrations are performed.

Another well known method that can be used to introduce nucleic acid constructs encoding HIV antigens into host cells is particle bombardment (also know as biolistic transformation). Biolistic transformation is commonly accomplished in one of several ways. One common method involves propelling inert or biologically active particles at cells. This technique is disclosed in, e.g., U.S. Pat. Nos. 4,945,050, 5,036,006; and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al. *Proc. Natl. Acad. Sci. USA* 84:7413-7417, 1987; Mackey, et al. *Proc. Natl. Acad. Sci. USA* 85:8027-8031, 1988; Ulmer et al. *Science* 259:1745-1748, 1993). The use of cationic lipids can promote encapsulation of negatively charged nucleic acids, and also promote fusion with negatively charged cell membranes (Felgner and Ringold *Science* 337:387-388, 1989). Particularly useful lipid compounds and compositions for transfer of nucleic acids are described in WO95/18863 and WO96/17823, and in U.S. Pat. No. 5,459,127, herein incorporated by reference.

In other embodiments, the nucleic acid constructs are viral vectors. Methods for constructing and using viral vectors are known in the art (See e.g., Miller and Rosman, *BioTech.*, 7:980-990, 1992). Preferably, the viral vectors are replication defective, that is, they are unable to replicate autonomously in the target cell. In general, the genome of the replication defective viral vectors that are used within the scope of the present disclosure lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques can be performed in vitro (for example, on the isolated DNA).

In some cases, the replication defective virus retains the sequences of its genome that are necessary for encapsidating the viral particles. DNA viral vectors commonly include attenuated or defective DNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV) and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al. *Mol. Cell. Neurosci.*, 2:320-330, 1991), defective herpes virus vector lacking a glycoprotein L gene (See for example, Patent Publication RD 371005 A), or other defective herpes virus vectors (See e.g., WO 94/21807; and WO 92/05263); an attenuated adenovirus vector, such as the vector described by Stratford-Perricaudet et al. (*J. Clin. Invest.*, 90:626-630 1992; La Salle et al., *Science* 259:988-990, 1993); and a defective adeno-associated virus vector (Samulski et al., *J. Virol.*, 61:3096-3101, 1987; Samulski et al., *J. Virol.*, 63:3822-3828, 1989; and Lebkowski et al., *Mol. Cell. Biol.*, 8:3988-3996, 1988).

In one embodiment, the vector is an adenovirus vector. Adenoviruses are eukaryotic DNA viruses that can be modified to efficiently deliver a nucleic acid of the disclosure to a variety of cell types. Various serotypes of adenovirus exist. Of these serotypes, preference is given, within the scope of the present disclosure, to type 2 or type 5 human adenoviruses (Ad 2 or Ad 5), or adenoviruses of animal origin (See e.g., WO94/26914). Those adenoviruses of animal origin that can be used within the scope of the present disclosure include adenoviruses of canine, bovine, murine (e.g., Mav1, Beard et al. *Virol.*, 75-81, 1990), ovine, porcine, avian, and simian (e.g., SAV) origin. In some embodiments, the adenovirus of animal origin is a canine adenovirus, such as a CAV2 adenovirus (e.g. Manhattan or A26/61 strain (ATCC VR-800)).

The replication defective adenoviral vectors described herein include the ITRs, an encapsidation sequence and the polynucleotide sequence of interest. In some embodiments, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions can also be modified, in particular the E3 region (e.g., WO95/02697), the E2 region (e.g., WO94/28938), the E4 region (e.g., WO94/28152, WO94/12649 and WO95/02697), or in any of the late genes L1-L5.

In other embodiments, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO95/02697 and WO96/22378.

The replication defective recombinant adenoviruses according to this disclosure can be prepared by any technique known to the person skilled in the art (See e.g., Levrero et al. *Gene* 101:195, 1991; EP 185 573; and Graham *EMBO J.*, 3:2917, 1984). In particular, they can be prepared by homologous recombination between an adenovirus and a plasmid, which includes, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that can be used are the human embryonic kidney cell line 293 (Graham et al. *J. Gen. Virol.* 36:59, 1977), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques that are well known to one of ordinary skill in the art. Nucleic acids encoding HIV antigens can also be introduced using other viral vectors, such as retroviral vectors, for example, lentivirus vectors or adenovirus-associated viral (AAV) vectors.

As described in detail in the Examples, in one embodiment, a pharmaceutical composition including nucleic acid constructs encoding HIV antigens that correspond to antigenic polypeptides of multiple clades or strains of HIV are introduced into a subject prior to exposure to HIV to elicit a protective immune response. Typically, the nucleic acid constructs are plasmids. For example, several plasmids including polynucleotide sequences that encode different HIV antigens can be included in a pharmaceutical composition. For example, a set of plasmids that encodes antigenic polypeptides of different HIV clades or strains can be included in the composition to elicit immunity that protects against infection by HIV of multiple clades or strains. In an exemplary embodiment, the composition includes six plasmids. Each of the plasmids includes a polynucleotide sequence encoding a different HIV antigen operably linked to a transcription regulatory sequence that promotes expression of the antigenic polypeptide in vivo. For example, the composition can include different plasmids that encode a Gag polypeptide, a Pol polypeptide, a Nef polypeptide, and optionally, Env polypeptides of different clades or strains (for example, a clade A Env polypeptide, a clade B Env polypeptide and/or a clade C polypeptide. In one specific embodiment, the vaccine composition includes the six plasmids (VRC 4409, VRC 4401, VRC-4404, VRC 5736, VRC 5737 and VRC 5738 represented by SEQ ID NOs:1-6, respectively. This particular embodiment is designated VRC-HIVDNA016-00-VP, and is described in further detail in the Examples.

Typically, the multi-plasmid composition includes the six plasmids in substantially equal ratio (e.g., approximately 1:1:1:1:1:1). The pharmaceutical composition can be administered to a subject in a single or multiple doses. The dose range can be varied according to the physical, metabolic and immunological characteristics of the subject, however, a dose of at least about 1 mg and no more than about 12 mg is typically administered. For example, a single dose can be at least about 2 mg, or at least about 3 mg, or at least about 4 mg of combined DNA. Typically, a single dose does not exceed about 6 mg, or about 8 mg or about 10 mg of combined DNA. As described in the Examples, a dose of about 4 mg combined plasmid weight is typically effective to elicit a protective immune response in an immunocompetent adult.

A single dose, or multiple doses separated by a time interval can be administered to elicit an immune response against HIV. For example, two doses, or three doses, or four doses, or five doses, or six doses or more can be administered to a subject over a period of several weeks, several months or even several years, to optimize the immune response.

In some cases the pharmaceutical composition including the nucleic acid constructs, for example the multi-plasmid vaccine VRC-HIVDNA016-00-VP is included in combination modality regimens using it as a DNA vaccine prime followed by an adenoviral vector boost. Prime-boost regimens have shown promise in non-human primate models of HIV infection. Such regimens have the potential for raising high levels of immune responses. For example, a "primer" composition including one or more nucleic acid constructs that encode at least one HIV antigen that is the same as an HIV antigen encoded by an adenoviral vector of an adenoviral vector composition can be administered to a subject. For example, the primer composition can be administered at least about one week before the administration of the "booster" composition including one or more adenoviral vectors. The one or more nucleic acid sequences of the primer composition (such as VRC-HIVDNA016-00-VP) can be administered as part of a gene transfer vector or as naked DNA. Any gene transfer vector can be employed in the primer composition, including, but not limited to, a plasmid, a retrovirus, an adeno-associated virus, a vaccine virus, a herpesvirus, or an adenovirus. In an exemplary embodiment, the transfer vector is a plasmid.

Thus, the multi-plasmid composition described above can be used to prime an immune response against HIV, in combination with administration of a composition including one or more adenovirus vectors encoding HIV antigens. For example, the adenoviral vector composition can include (i) a single adenoviral vector that encodes two or more HIV antigens, for example, as a polyprotein or fusion protein, such as a fusion protein encoding a Gag-Pol-Nef polypepetide. Alternatively, the adenoviral vector composition can include (ii) multiple adenoviral vectors each of which encodes a single HIV antigen, such as, two or more, such as three, or four, or more, adenovirus vectors that each encode one HIV antigen, such as an Env polypeptide. Consistent with configuration (i), it is within the scope of the invention to use an adenoviral vector comprising a nucleic acid sequence that encodes more than two different HIV antigens (e.g., three or more, four or more, or even five or more different HIV antigens) or encodes multiple copies of the same antigen, provided that it encodes at least two or more different HIV antigens. Likewise, consistent with configuration (ii), it is within the scope of the invention to use an adenoviral vector comprising several nucleic acid sequences (e.g., three or more, four or more, or even five or more different nucleic acid sequences) each encoding different HIV antigens or multiple copies of the same antigen, provided that the adenoviral vector encodes at least two different HIV antigens. Whether by configuration (i) or (ii), the adenoviral vector composition preferably comprises one or more adenoviral vectors encoding three or more, or even four or more, different HIV antigens (e.g., wherein each vector comprises a nucleic acid sequence that encodes three or more, or four or more different HIV antigens, or wherein each vector comprises three or more, or four or more nucleic acid sequences, and each nucleic acid sequence encodes a different HIV antigen). In certain embodiments, the two or more, three or more, or four or more different HIV antigens are from two or more, three or more, or four or more different HIV clades. There is no upper limit to the number of adenoviral vectors used or the number of different HIV antigens encoded thereby.

Of course, a combination of the above configurations of adenoviral vectors can be used in a single composition. For example, the adenoviral vector composition used in accordance with the invention can comprise a first adenoviral vector encoding a single HIV antigen and a second adenoviral vector encoding two or more HIV antigens that are different from the HIV antigen encoded by the first adenoviral vector. Other similar combinations and permutations of the adenoviral vector configurations disclosed herein can be readily determined by one of skill in the art.

In certain embodiments, the booster composition includes multiple adenoviral vectors. For example, the booster can include multiple adenoviral vectors each of which encodes an HIV Env polypeptide, such as Env polypeptide of different clades or strains. In addition, the booster composition can include an adenoviral vector that encodes Gag, Pol and/or Nef polypeptides. In one specific embodiment, designated VRC-HIVDNA014-00VP, the booster composition includes four adenoviral vectors, three of which encode Env polypeptides of different clades (that is, clade A, clade B and clade C), and an adenoviral vector that encodes Gag and Pol antigens (of clade B). Of course, numerous variants can easily be designed by one of skill in the art, incorporating fewer or more adenoviral vectors, and/or encoding antigens of the same or different HIV clades or strains.

While the HIV antigen encoded by the one or more nucleic acid sequences of the boost composition often is the same as an HIV antigen encoded by the nucleic acid constructs of the primer composition, in some embodiments it may be appropriate to use a primer composition comprising one or more nucleic acid sequences encoding an HIV antigen that is different from the antigen(s) encoded by the adenoviral vector composition. For example, Gag and/or Pol and/or Nef antigens of a different clade or strain, or Env antigens of a different clade or strain.

The primer composition is administered to the mammal to prime the immune response to HIV. More than one dose of primer composition can be provided in any suitable timeframe (e.g., at least about 1 week, 2 weeks, 4 weeks, 8 weeks, 12 weeks, 16 weeks, or more prior to boosting). Preferably, the primer composition is administered to the mammal at least three months (e.g., three, six, nine, twelve, or more months) before administration of the booster composition. Most preferably, the primer composition is administered to the mammal at least about six months to about nine months before administration of the booster composition. More than one dose of booster composition can be provided in any suitable timeframe to maintain immunity.

Any route of administration can be used to deliver the adenoviral vector composition and/or the primer composition to the mammal. Indeed, although more than one route can be used to administer the adenoviral vector composition and/or the primer composition, a particular route can provide a more immediate and more effective reaction than another route. Most commonly, the adenoviral vector composition and/or the primer composition is administered via intramuscular injection. The adenoviral vector composition and/or the primer composition also can be applied or instilled into body cavities, absorbed through the skin (for example, via a transdermal patch), inhaled, ingested, topically applied to tissue, or administered parenterally via, for instance, intravenous, peritoneal, or intraarterial administration.

The adenoviral primer composition and/or the booster composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the composition. The adenoviral vector composition and/or the primer composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

A booster composition can include a single dose of adenoviral vector comprising at least about $1\times10^5$ particles (which also is referred to as particle units) of adenoviral vector. The dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^9$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ particles). In other words, the adenoviral vector composition can comprise a single dose of adenoviral vector comprising, for example, about $1\times10^6$ particle units (pu), $2\times10^6$ pu, $4\times10^6$ pu, $1\times10^7$ pu, $2\times10^7$ pu, $4\times10^7$ pu, $1\times10^8$ pu, $2\times10^8$ pu, $4\times10^8$ pu, $1\times10^9$ pu, $2\times10^9$ pu, $4\times10^9$ pu, $1\times10^{10}$ pu, $2\times10^{10}$ pu, $4\times10^{10}$ pu, $1\times10^{11}$ pu, $2\times10^{11}$ pu, $4\times10^{11}$ pu, $1\times10^{12}$ pu, $2\times10^{12}$ pu, or $4\times10^{12}$ pu of adenoviral vector.

EXAMPLES

Example 1

Construction of Plasmids

The nucleic acid constructs were derived from parental 1012 DNA vaccine plasmid containing the human CMV immediate early (IE) enhancer, promoter, and intron. To construct the CMV/R regulatory element, a SacII/HpaI fragment of the 1012 plasmid containing the majority of the CMV IE intron was replaced with a 227 bp EcoRV/HpaI fragment of the HTLV-1 R region (Seiki et al., Proc. Natl. Acad. Sci. USA 80: 3618-3622, 1983). The resulting CMV/R plasmid thus contains the human CMV IE enhancer/promoter, followed by the HTLV-1 R region and a 123 bp fragment of CMV IE 3' intron. The splice donor in the R region and the splice acceptor in the CMV IE 3' intron serve as the pair of splicing signals. RSV/R and mUB/R plasmids were similarly constructed by replacing the CMV enhancer/promoter region of the CMV/R plasmid with a 381 bp AflIII/HindIII fragment of the Rous sarcoma virus (RSV) enhancer/promoter or an 842 bp SpeI/EcoRV fragment of the mouse ubiquitin B(mUB) enhancer/promoter respectively. The mUB enhancer/promoter has been described previously (Yew et al., Mol. Ther. 4:75-82, 2001).

Construction of CMV/R Clade B Gag/h (VRC-4401)

To construct DNA plasmid VRC-4401, diagrammed in FIG. 1, the protein sequence of the gag polyprotein (Pr55, amino acids 1-432) from HXB2 (GENBANK® accession number K03455) was used to create a synthetic version of the gag gene using codons optimized for expression in human cells. The nucleotide sequence of the synthetic gag gene shows little homology to the HXB2 gene, but the protein encoded is the same. A SalI/BamHI fragment including the synthetic gene encoding Gag (B) was excised from plasmid VRC 3900, which contained the same insert in a pVR1012 backbone, and cloned into the SalI/BamHI sites of the CMV/R backbone described above. A summary of predicted VRC-4401 domains is provided in Table 2. The plasmid is 5886 nucleotide base pairs (bp) in length and has an approximate molecular weight of 3.9 MDa. The sequence of VRC-4401 is provided in SEQ ID NO:1.

TABLE 2

Description of plasmid VRC-4401

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 31 | 1344-1374 |
| HIV-1 Gag (Clade B) | 1509 | 1375-2883 |
| Synthetic Linker | 23 | 2884-2906 |
| Bovine Growth Hormone Poly A | 548 | 2907-3454 |
| pUC18 plasmid-derived | 1311 | 3455-4765 |
| Kanamycin Resistance Gene | 816 | 4766-5581 |
| pUC18 plasmid-derived | 305 | 5582-5886 |

Construction of CMV/R Clade B Pol/h (VRC-4409)

Figure 2:
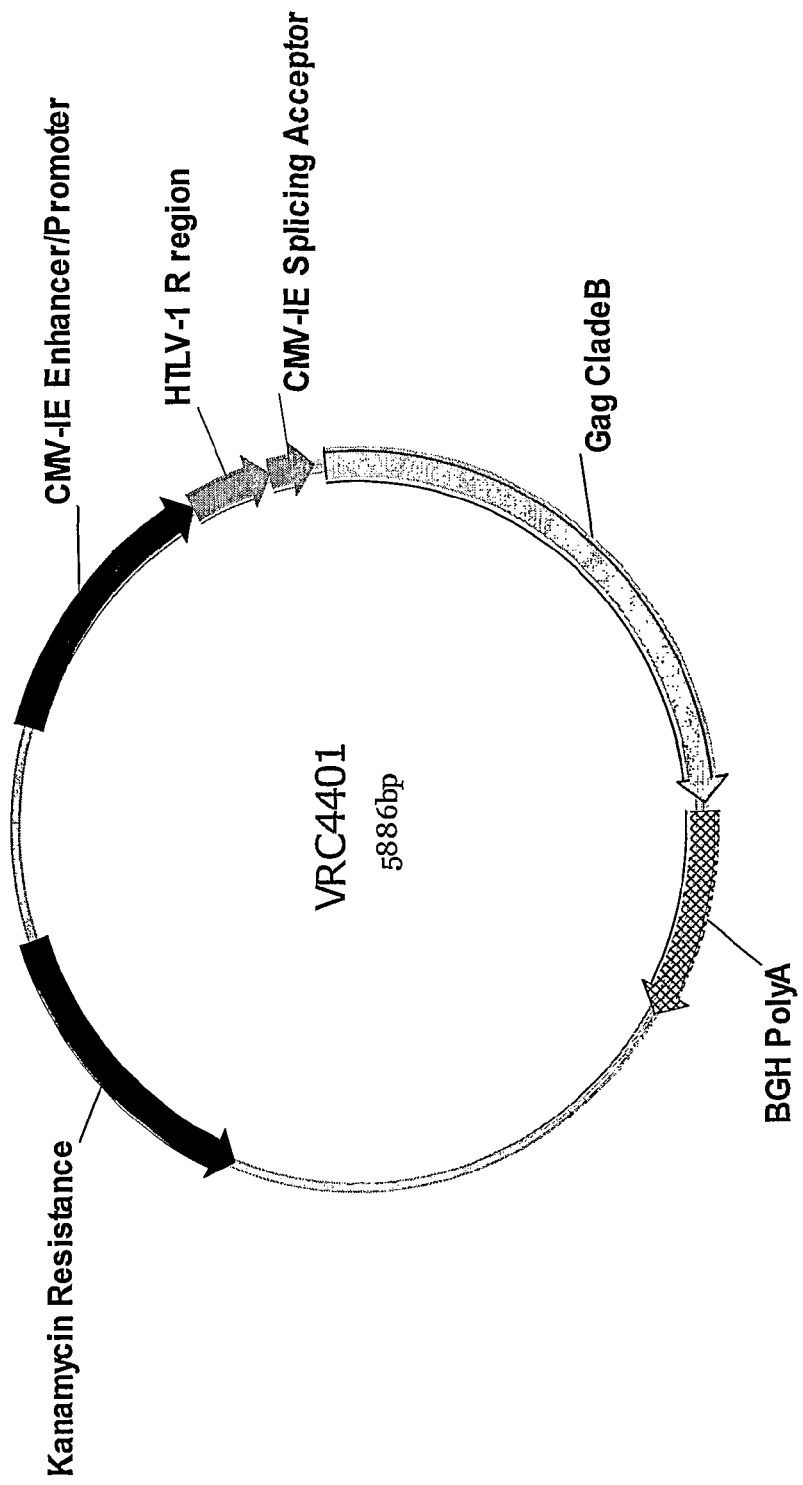
FIG. 2 is a schematic representation of the plasmid VRC 4401.

To construct DNA plasmid VRC-4409 diagrammed in FIG. 2, the protein sequence of the Pol polyprotein (amino acids 3-1003) from NL4-3 (GENBANK® accession number M19921) was used to create a synthetic version of the pol gene using codons optimized for expression in human cells. To initiate translation at the beginning of Pol, a methionine codon was added to the 5'-end of the synthetic polymerase gene to create the Pol/h gene. Additionally, a Protease (PR) mutation was introduced at amino acid 553 (AGG→GGC or amino acids R→G), a Reverse Transcriptase (RT) mutation was introduced at amino acid 771 (GAC→CAC or amino acids D→H), and an Integrase (IN) mutation was introduced at amino acid 1209 (ACT→CAT or amino acids D→A). The gene expressing Pol was inserted into the CMV/R backbone described above. A summary of predicted VRC-4409 domains is provided in Table 3. The plasmid is 7344 nucleotide base pairs (bp) in length and has an approximate molecular weight of 4.8 MDa. The sequence of VRC-4409 is provided in SEQ ID NO:2.

TABLE 3

Description of Plasmid VRC-4409

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 5 | 1344-1348 |
| HIV-1 Pol (Clade B) (Pr−, RT−, IN−) | 3009 | 1349-4357 |
| Synthetic Linker | 7 | 4358-4364 |
| Bovine Growth Hormone Poly A | 548 | 4365-4912 |
| pUC18 plasmid-derived | 1311 | 4913-6223 |
| Kanamycin Resistance Gene | 816 | 6224-7039 |
| pUC18 plasmid-derived | 305 | 7040-7344 |

Construction of CMV/R HIV-1 Nef/h (VRC-4404)

Figure 3:
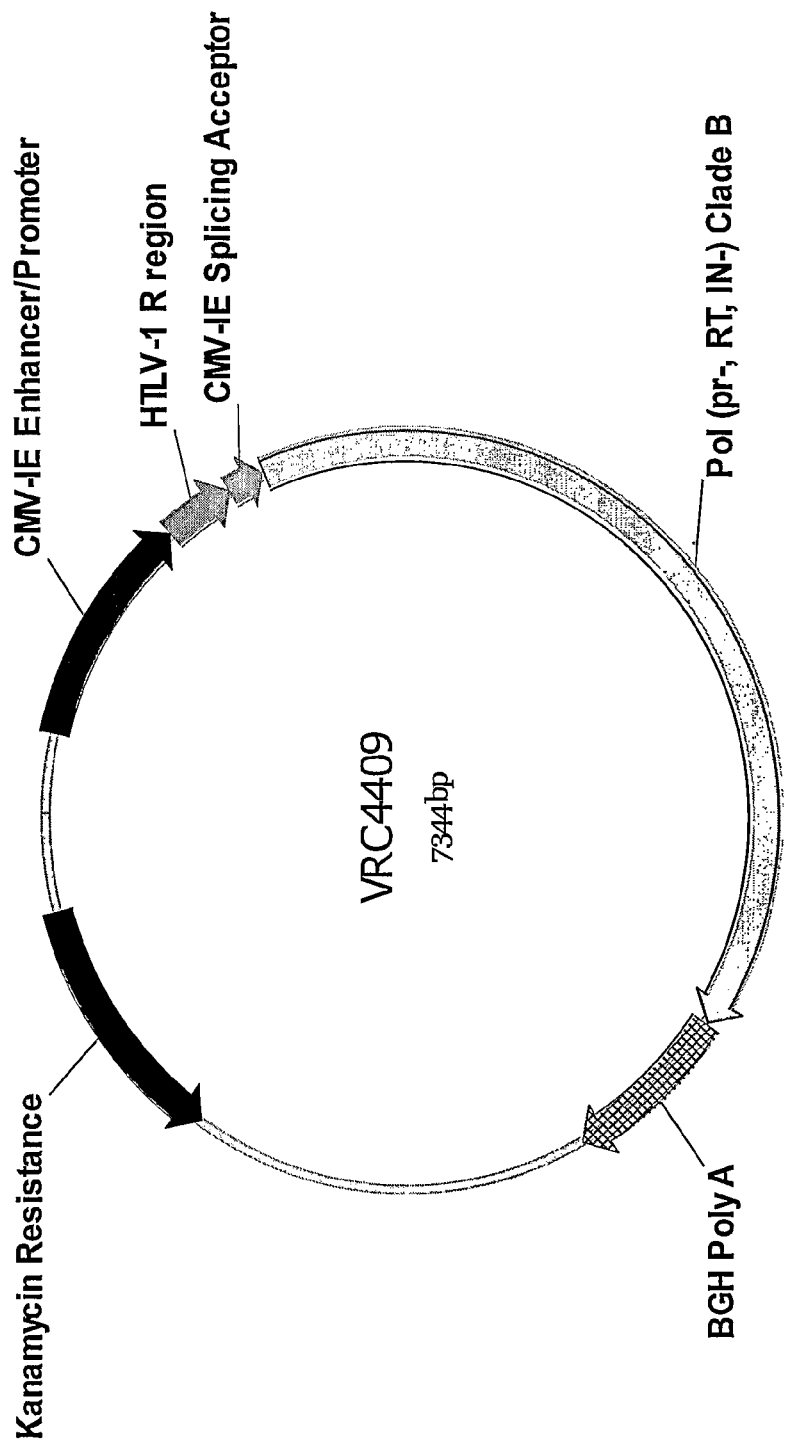
FIG. 3 is a schematic representation of the plasmid VRC 4409.

To construct DNA plasmid VRC-4404, diagrammed in FIG. 3, the protein sequence of the Nef protein from HIV-1 NY5/BRU (LAV-1) clone pNL4-3 (GENBANK® accession number M19921) was used to create a synthetic version of the Nef gene (Nef/h) using codons optimized for expression in human cells. The nucleotide sequence Nef/h shows little homology to the viral gene, but the protein encoded is the same. The Myristol site (GGC-Gly, amino acid 2-3) was deleted. The fragment encoding Nef was digested from the pVR1012 backbone in which it was originally inserted, with XbaI/BamHI, and then cloned into the XbaI/BamHI site of the CMV/R backbone described above. A summary of predicted VRC-4404 domains is provided in Table 4. The plasmid is 5039 nucleotide base pairs (bp) in length and has an approximate molecular weight of 3.3 MDa. The sequence of VRC-4404 is provided in SEQ ID NO:3.

TABLE 4

Description of plasmid VRC-4404

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 48 | 1344-1391 |
| HIV-1 Nef (Clade B) (Delta Myr) | 615 | 1392-2006 |
| Synthetic Linker | 19 | 2007-2025 |
| Bovine Growth Hormone Poly A | 548 | 2026-2573 |
| pUC18 plasmid-derived | 1345 | 2574-3918 |
| Kanamycin Resistance Gene | 816 | 3919-4734 |
| pUC18 plasmid-derived | 305 | 4735-5039 |

CMV/R-HIV-1 Clade A Env/h (VRC-5736)

Figure 4:
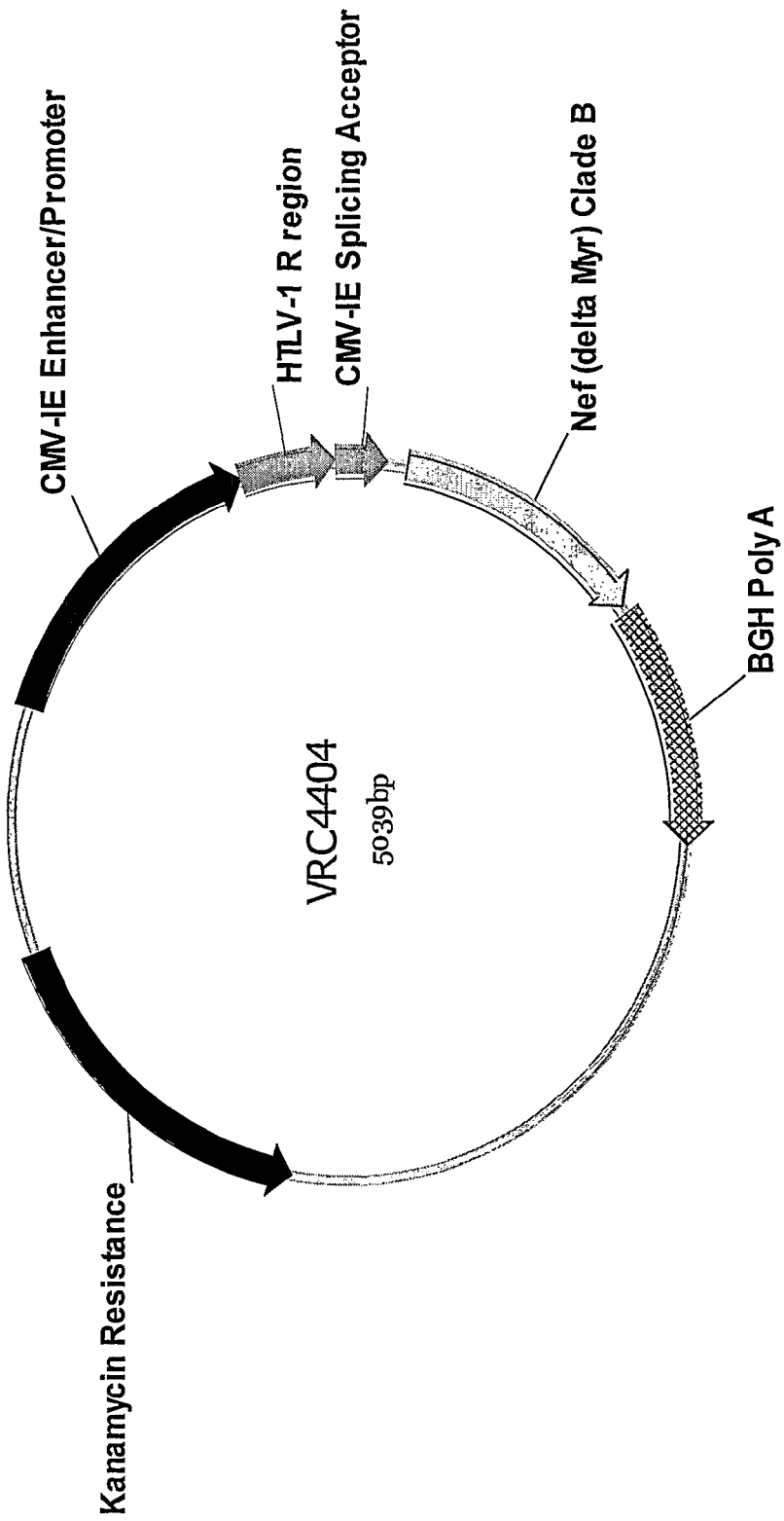
FIG. 4 is a schematic representation of the plasmid VRC 4404.

To construct DNA plasmid VRC-5736, diagrammed in FIG. 4, the protein sequence of the envelope polyprotein (gp160) from 92rw020 (R5-tropic, GENBANK® accession number U08794) was used to create a synthetic version of the gene (Glade-A gp145delCFI) using codons altered for expression in human cells. Plasmids expressing the HIV-1 genes were made synthetically with sequences designed to disrupt viral RNA structures that limit protein expression by using codons typically found in human cells. The nucleotide sequence R5gp145delCFI shows little homology to the 92rw020 gene, but the protein encoded is the same. The truncated envelope polyprotein contains the entire SU protein and the TM domain, but lacks the fusion domain and cytoplasmic domain. Heptad (H) 1, Heptad 2 and their Interspace (IS) are involved in oligomerization. The Fusion and Cleavage (F/CL) domains, from amino acids 486-519, have been deleted. The Interspace (IS) between Heptad (H) 1 and 2, from amino acids 576-604, has been deleted. The XbaI (18nt up-stream from ATG) to BamH1 (1912 nt down-stream from ATG) fragment, which contains a polylinker at the 5' end, a Kozak sequence and ATG, was cloned into the XbaI to BamH1 sites of the CMV/R backbone described above. EnvA summary of predicted VRC-5736 domains is provided in Table 5. The plasmid is 6305 nucleotide base pairs (bp) in length and has an approximate molecular weight of 4.2 MDa. The sequence of VRC-5736 is provided in SEQ ID NO:4.

TABLE 5

Description of plasmid VRC-5736

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 48 | 1344-1391 |
| HIV-1 Env (Clade A), gp145 (delCFI)/h | 1881 | 1392-3272 |
| Synthetic Linker | 19 | 3273-3291 |
| Bovine Growth Hormone Poly A | 548 | 3292-3839 |
| pUC18 plasmid-derived | 1345 | 3840-5184 |
| Kanamycin Resistance Gene | 816 | 5185-6000 |
| pUC18 plasmid-derived | 305 | 6001-6305 |

Construction of CMV/R Clade B Env/h (VRC-5737)

Figure 5:
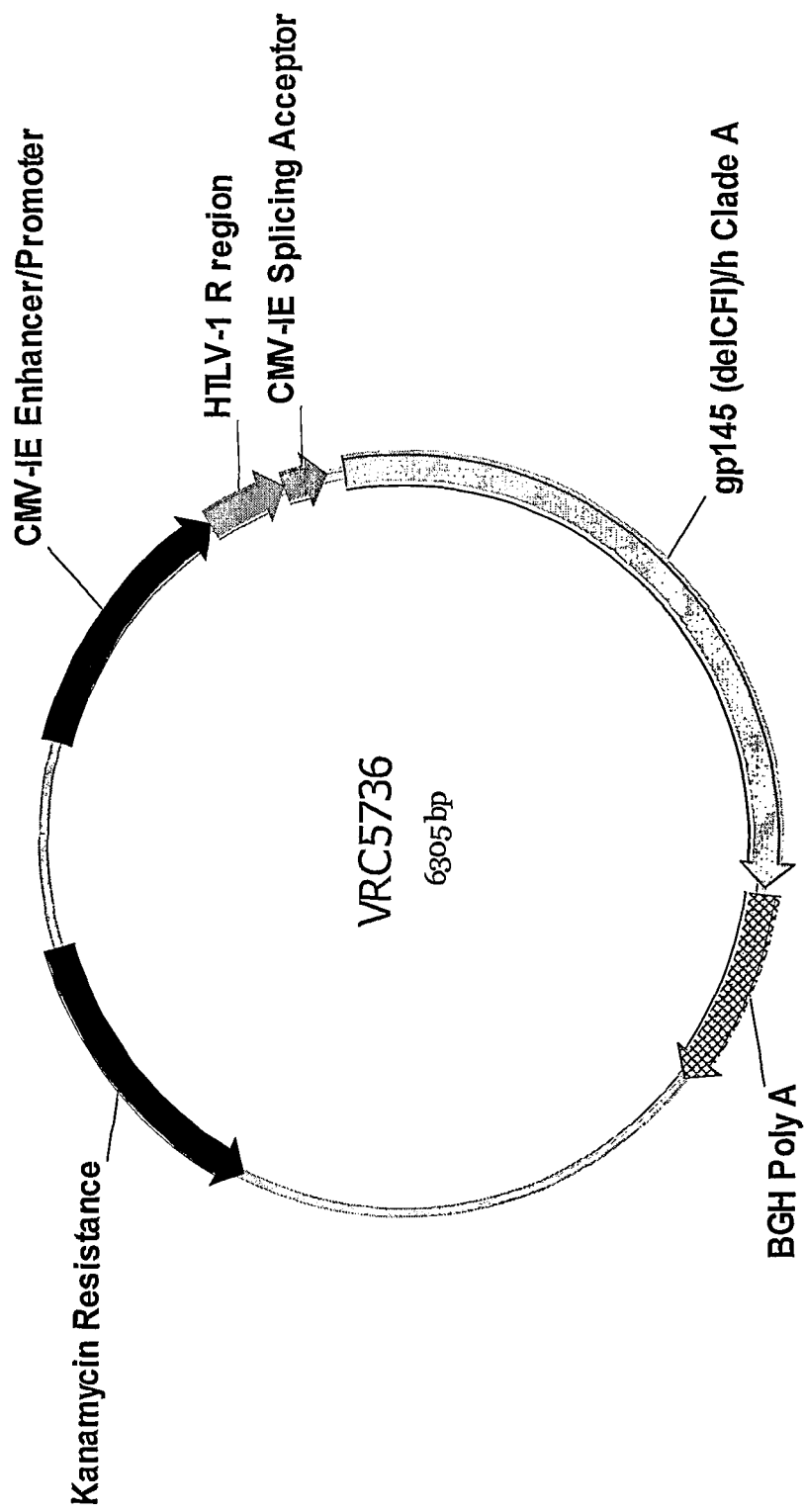
FIG. 5 is a schematic representation of the plasmid VRC 5736.

To construct DNA plasmid VRC-5737 diagrammed in FIG. 5, the protein sequence of the envelope polyprotein (gp160) from HXB2 (X4-tropic, GENBANK® accession number K03455) was used to create a synthetic version of the gene (X4gp160/h) using codons optimized for expression in human cells. The nucleotide sequence X4gp160/h shows little homology to the HXB2 gene, but the protein encoded is the same with the following amino acid substitutions: F53L, N94D, K192S, I215N, A224T, A346D, and P470L. To produce an R5-tropic version of the envelope protein (R5gp160/h), the region encoding HIV-1 envelope polyprotein amino acids 275 to 361 from X4gp160/h (VRC3300) were replaced with the corresponding region from the BaL strain of HIV-1 (GENBANK® accession number M68893, again using human preferred codons). The full-length R5-tropic version of the envelope protein gene from pR5gp160/h (VRC3000) was terminated after the codon for amino acid 704. The truncated envelope polyprotein (gp145) contains the entire SU protein and a portion of the TM protein including the fusion domain, the transmembrane domain, and regions important for oligomer formation. Heptad(H) 1, Heptad 2 and their Interspace(IS) are involved in oligomerization. The Fusion and Cleavage (F/CL) domains, from amino acids 503-536, have been deleted. The Interspace (IS) between Heptad (H) 1 and 2, from amino acids 593-620, has been deleted. The expression vector backbone is CMV/R, described above. A summary of predicted VRC-5737 domains is provided in Table 6. The plasmid is 6338 nucleotide base pairs (bp) in length and has an approximate molecular weight of 4.2 MDa. The sequence of VRC-5737 is provided in SEQ ID NO:5.

TABLE 6

Description of plasmid VRC-5737

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 40 | 1344-1383 |
| HIV-1 Env (Clade B), gp145 (delCFI)/h | 1929 | 1384-3312 |
| Synthetic Linker | 12 | 3313-3324 |
| Bovine Growth Hormone Poly A | 548 | 3325-3872 |
| pUC18 plasmid-derived | 1345 | 3873-5217 |
| Kanamycin Resistance Gene | 816 | 5218-6033 |
| pUC18 plasmid-derived | 305 | 6034-6338 |

Construction of CMV/R HIV-1 Clade C Env/h (VRC-5738)

Figure 6:
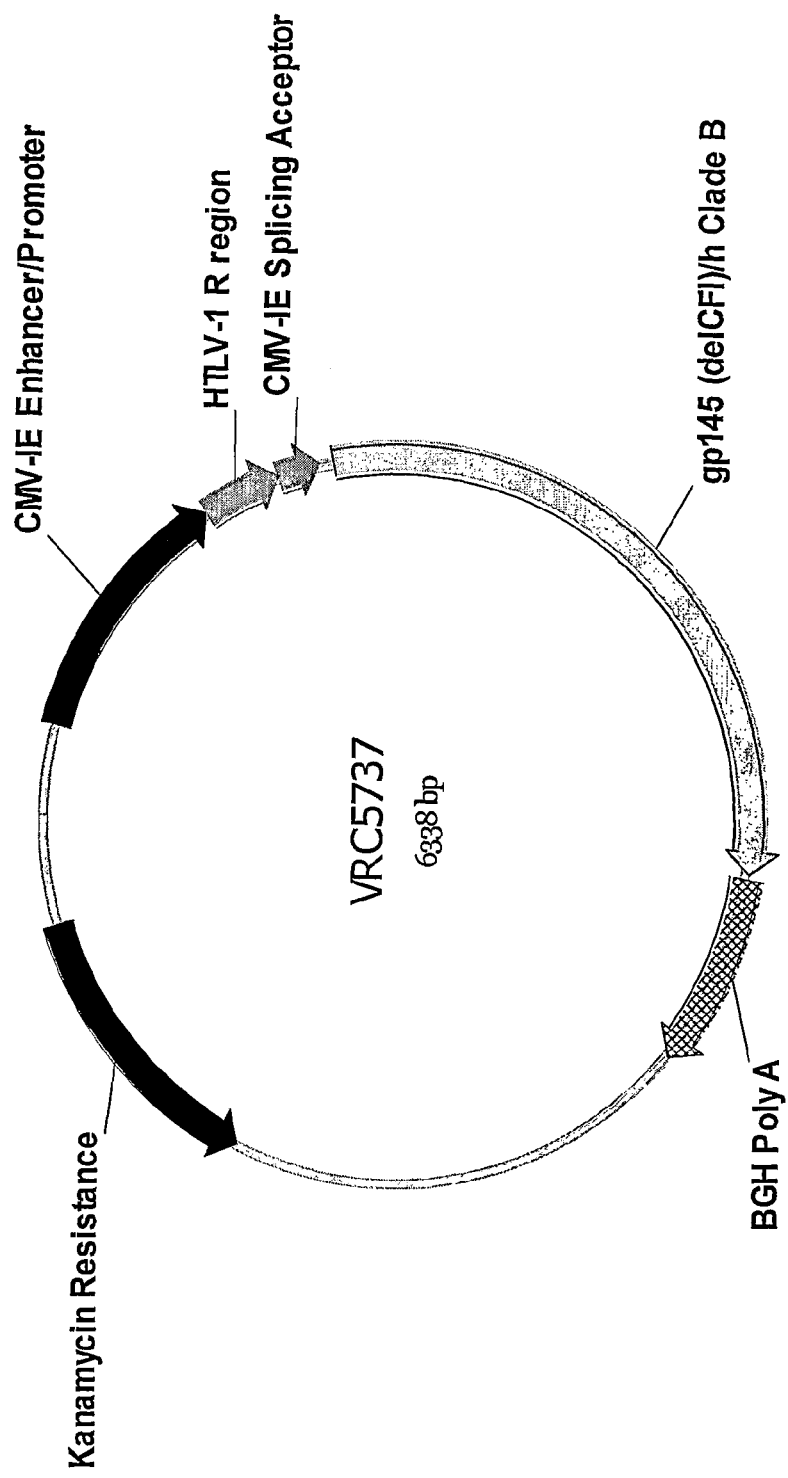
FIG. 6 is a schematic representation of the plasmid VRC 5737.
Figure 7:
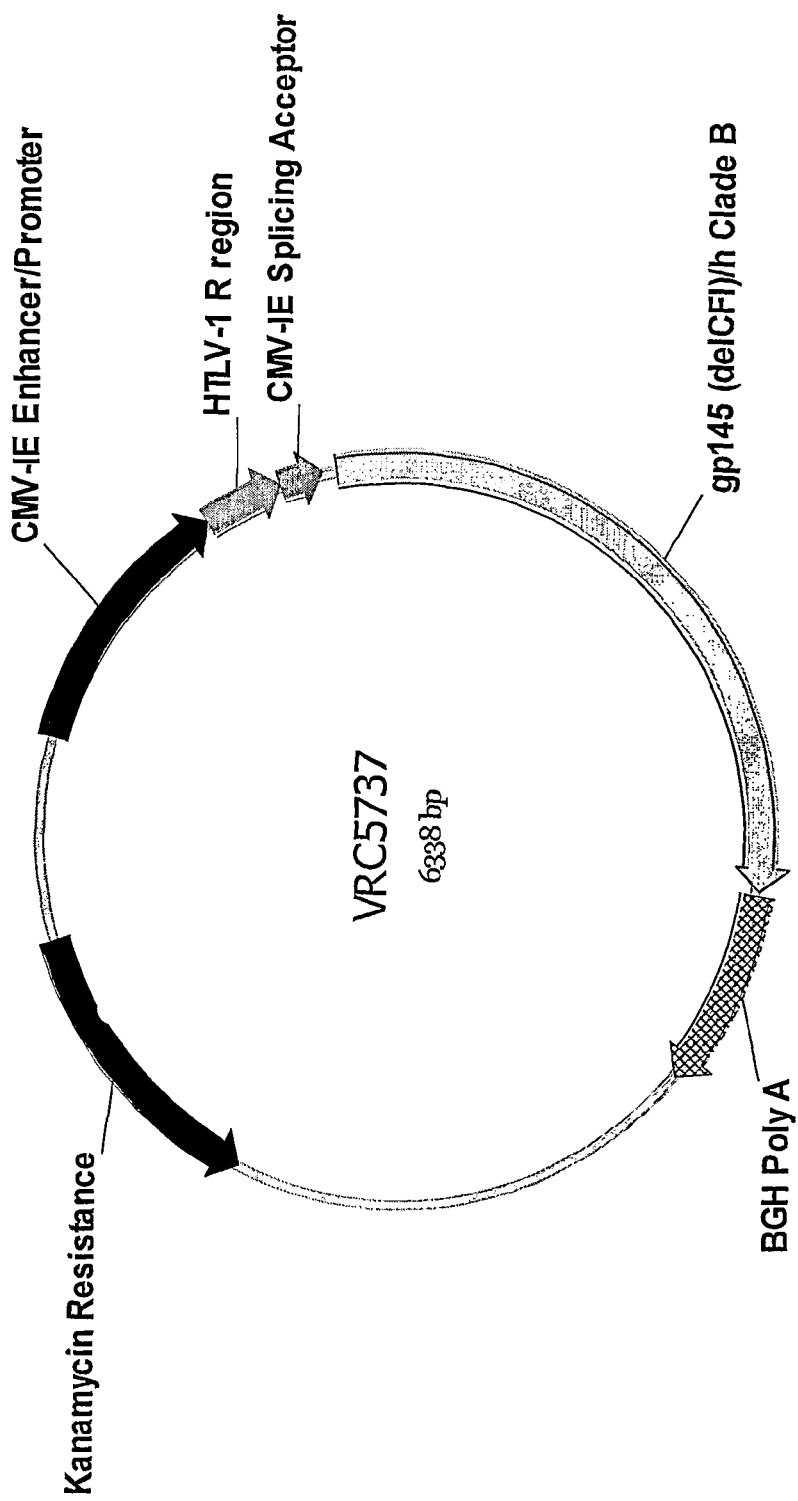
FIG. 7 is a schematic representation of the plasmid VRC 5738.

To construct DNA plasmid VRC-5738, diagrammed in FIG. 6, the protein sequence of the envelope polyprotein (gp145delCFI) from 97ZA012 (R5-tropic, GENBANK® accession number AF286227) was used to create a synthetic version of the gene (Clade-C gp145delCFI) using codons optimized for expression in human cells. The nucleotide sequence R5gp145delCFI shows little homology to the gene 97ZA012, but the protein encoded is the same. The truncated envelope polyprotein contains the entire SU protein and the TM domain, but lacks the fusion domain and cytoplasmic domain. Heptad(H) 1, Heptad 2 and their Interspace (IS) are involved in oligomerization. The Fusion and Cleavage (F/CL) domains, from amino acids 487-520, have been deleted. The Interspace (IS) between Heptad (H) 1 and 2, from amino acids 577-605, has been deleted. The XbaI (18nt up-stream from ATG) to BamHl (1914 nt down-stream from ATG) fragment, which contains polylinker at the 5' end, Kozak sequence and ATG, was cloned into the XbaI to BamHl sites of the CMV/R backbone. A summary of predicted VRC-5738 domains is provided in Table 7. The plasmid is 6298 nucleotide base pairs (bp) in length and has an approximate molecular weight of 4.2 MDa. The sequence of VRC-5738 is provided in SEQ ID NO:6.

TABLE 7

Description of plasmid VRC-5738

| Fragment Name or Protein Domain | Fragment Size (bp) | Predicted Fragment |
|---|---|---|
| pUC18 plasmid-derived | 247 | 1-247 |
| CMV-IE Enhancer/Promoter | 742 | 248-989 |
| HTLV-1 R region | 231 | 990-1220 |
| CMV IE Splicing Acceptor | 123 | 1221-1343 |
| Synthetic Linker | 48 | 1344-1391 |
| HIV-1 Env (Clade C), gp145 (delCFI)/h | 1881 | 1392-3272 |
| Synthetic Linker | 12 | 3273-3284 |
| Bovine Growth Hormone Poly A | 548 | 3285-3832 |
| pUC18 plasmid-derived | 1345 | 3833-5177 |
| Kanamycin Resistance Gene | 816 | 5178-5993 |
| pUC18 plasmid-derived | 305 | 5994-6298 |

Example 2

Increased Expression of HIV Antigenic Polypeptides by CMV/R Transcription Regulatory Sequence To assess antigen expression from plasmids containing the CMV/R transcriptional regulatory elements, 3T3 cells were transfected with the above described expression vectors and gp145ΔCFI expression was measured by Western blots. Murine fibroblast 3T3 cells were transfected with 0.5 μg parental 1012 (CMV), CMV/R, RSV, RSV/R, mUB, and mUB/R DNA vaccines expressing HIV-1 Env gp145 ΔCFI (9) in 6-well plates using calcium phosphate. 24 h after transfection, cells were harvested and lysed in 50 mM HEPES, 150 mM NaCl, 1% NP-40 with protease inhibitors. 10 μg total protein was electrophoresed by SDS-PAGE, and gp145 expression was assessed by Western blot analysis. A 1:5000 dilution of human HIV-IgG was utilized as the primary antibody, and a 1:5000 dilution of HRP-conjugated goat anti-human IgG was utilized as the secondary antibody. The blots were developed with the ECL Western blot developing system (Amersham Biosciences, Piscataway, N.J.).

Figure 8:
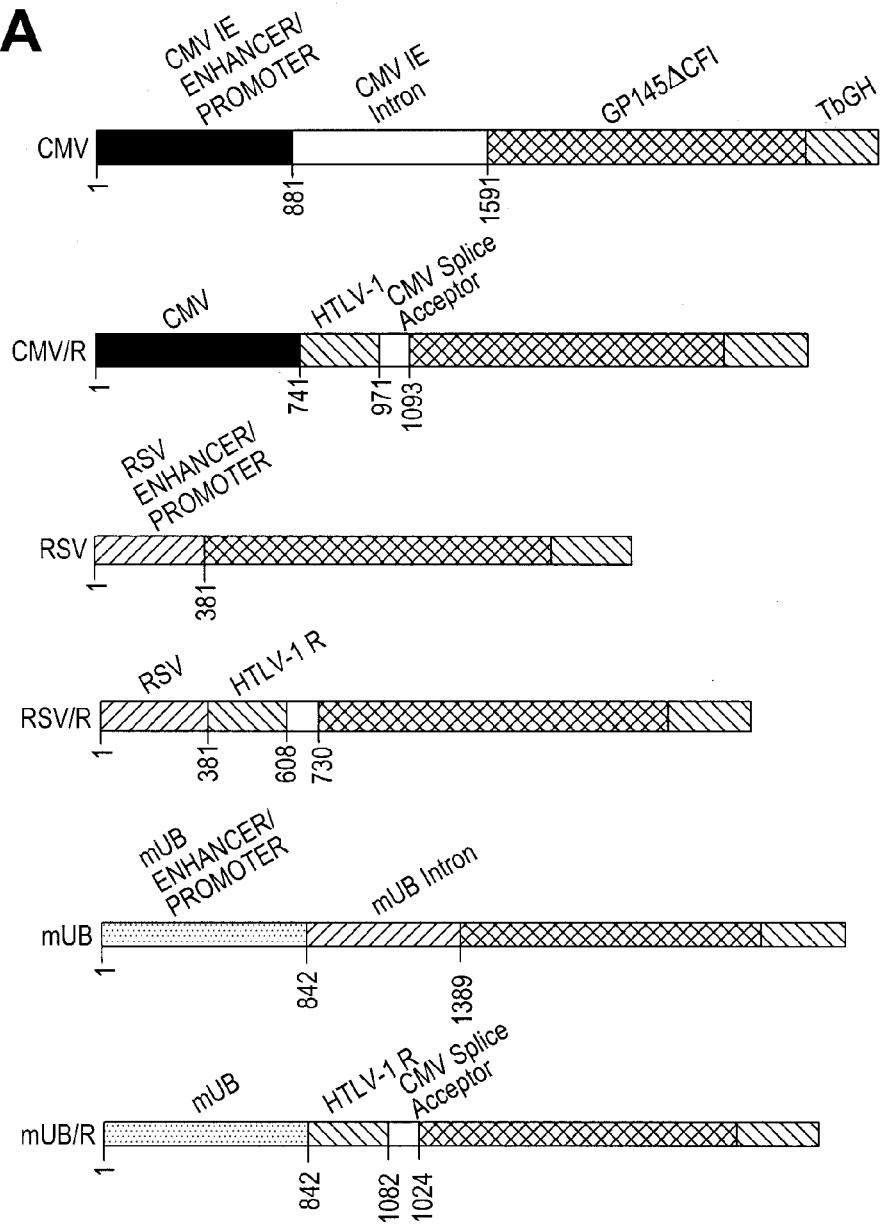
FIG. 8A schematically represents antigenic expression constructs with different transcription regulatory sequences.
FIG. 8B is an image of a Western blot showing relative expression of the various constructs.
Figure 8:
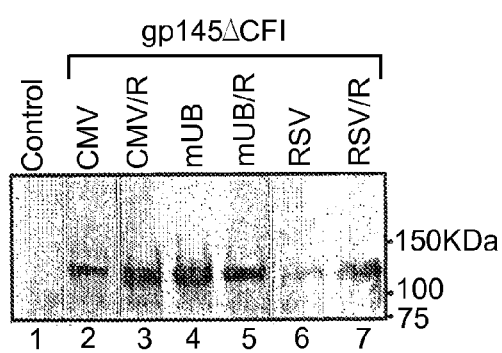

The expression of gp145ΔCFI from the CMV/R plasmid was 5- to 10-fold higher than expression from the parental 1012 plasmid (FIG. 8). Thus, addition of the HTLV-1 R element substantially increased antigen expression driven by the CMV promoter. Baseline expression from the mUB plasmid was higher than from the 1012 plasmid but was not further enhanced by addition of the R element (FIG. 8), demonstrating that the effects of adding the R element were promoter-dependent. An increase in expression was observed in the RSV/R compared to RSV plasmid (FIG. 8). Expression from RSV plasmids is routinely lower than from the 1012 plasmid.

Example 3

Immunogenicity of CMV/R Multiclade HIV Vaccine

Non-clinical immunogenicity studies were conducted with plasmid constructs comprising the DNA plasmid vaccine VRC-HIVDNA016-00-VP as well as with DNA plasmid prime/adenoviral vector boost regimens using the recombinant adenoviral vector vaccine VRC-HIVADV014-00-VP in mice and non-human primates. Cellular immune responses were tested in these non-clinical immunogenicity studies by the interferon gamma (IFN-γ) ELISPOT assay which quantitatively measures the production of IFN-γ by peripheral blood mononuclear cells (PBMC) from immunized animals. The cells are exposed in vitro to HIV-1 antigens (a series of short, overlapping peptides that span the length of the protein expressed in the vaccine). The IFN-γ produced by antigen sensitized T-lymphocytes are bound to antibody coating an assay plate and may be counted colorimetrically as spot forming cells (SFC) by using an alkaline phosphatase conjugated read-out system. The results are expressed as SFCs per million PBMC.

DNA plasmid prime regimens are performed using plasmids expressing HIV-1 genes, identical in composition to clinical grade vaccine VRC-HIVDNA009-00-VP (4 plasmid vaccine, PCT Publication No. WO/05034992) or VRC-HIVDNA016-00-VP. The recombinant adenoviral vector vaccines used in preclinical immunology studies consisted of GMP grade VRC-HIVADV014-00-VP (Lot#026-03017, PCT Application No. PCT/US2005/12291, filed Apr. 12, 2005), composed of four adenoviral vectors that encode clade B gag/pol and clade A, B and C Env, supplied by GenVec, Inc. Gaithersburg, Md.). Table 8 provides a summary of the plasmids.

A tabulated summary of the immunology studies performed in mice and in non-human primates are summarized in Table 9.

TABLE 8

Summary of preclinical and clinical studies of VRC DNA vaccines

| | Plasmid | Gag | Pol | Nef | Env (A) | Env (B) | Env (C) | Safety Testing | Clinical Trial |
|---|---|---|---|---|---|---|---|---|---|
| VRC-4302 (1-plasmid) | p1012w/ CMV promoter | Gag-Pol (B) Nef not included | | | Not included | Not included | Not included | + | + |
| VRC-HIVDNA006-00-VP (6-plasmids) | p1012w/ CMV promoter | Gag-Pol-Nef (A) (4413) Gag-Pol-Nef (B) (4306) Gag-Pol-Nef (C) (4311) | | | 5305 | 2805 | 5309 | + | N/A |
| VRC-HIVDNA009-00-VP (4-plasmids) | p1012w/ CMV promoter | Gag-Pol-Nef (B) (4306) | | | 5305 | 2805 | 5309 | + | + |
| VRC-EBODNA012-00-VP (3-plasmids) | p1012w/ CMV/R promoter | | | | Ebola GP's and NP | | | + | + |
| VRC-HIVDNA016-00-VP (6-plasmids) | p1012w/ CMV/R promoter | 4401 | 4409 | 4404 | 5736 | 5737 | 5738 | * | In progress |

TABLE 9

Summary of Vaccine Immunogenicity Studies in Mice and Non-Human Primates

| Test System | Mouse | Cynomolgus macaques |
|---|---|---|
| Study Design | Immunogenicity | Immunogenicity |
| Route | i.m.[1] | i.m.[2] |
| Dose | DNA: 50 μg | DNA: 8 mg<br>rAd: 1 × 10$^{11}$ PU |
| Treatments per Animal | 1 DNA | 3 DNA<br>1 rAd |
| Treatment Period | 0 day | 38 Wks |
| Study Duration | 21 days | 58 Wks |
| Conclusions | Vaccination with gag-pol-nef (CMV/R) elicits higher HIV-1-specific cellular responses in mice than plasmids constructed with the 1012 backbone. | Cynomolgus macaques receiving DNA prime/rAd boost immunization with the 6-plasmid DNA vaccine that expresses HIV-1 Gag, Pol, Nef and clade A, B and C Env (VRC-HIVDNA016-00-VP), and boosted with rAd expressing HIV-1 Gag/Pol and 3 Env, elicited cellular immune responses to all viral antigens. |
| References | Item (8) Section 2.3.1 | Item (8) Section 2.3.2<br>Study VRC-02-035 |

PU = Particle Unit
[1]DNA plasmid administered intramuscularly (i.m.) by needle and syringe
[2]DNA Plasmid administered i.m. by Biojector; recombinant adenoviral vector vaccine (rAd) VRC-HIVADV014-00-VP (Lot # 026-03024) delivered i.m. by needle and syringe.

Vaccination with the CMV/R Plasmid Encoding the Gag-Pol-Nef Fusion Protein Elicits Higher HIV-1-Specific Cellular Responses in Mice than the Unmodified 1012 Plasmid Encoding the Same Fusion Protein.

Figure 9:
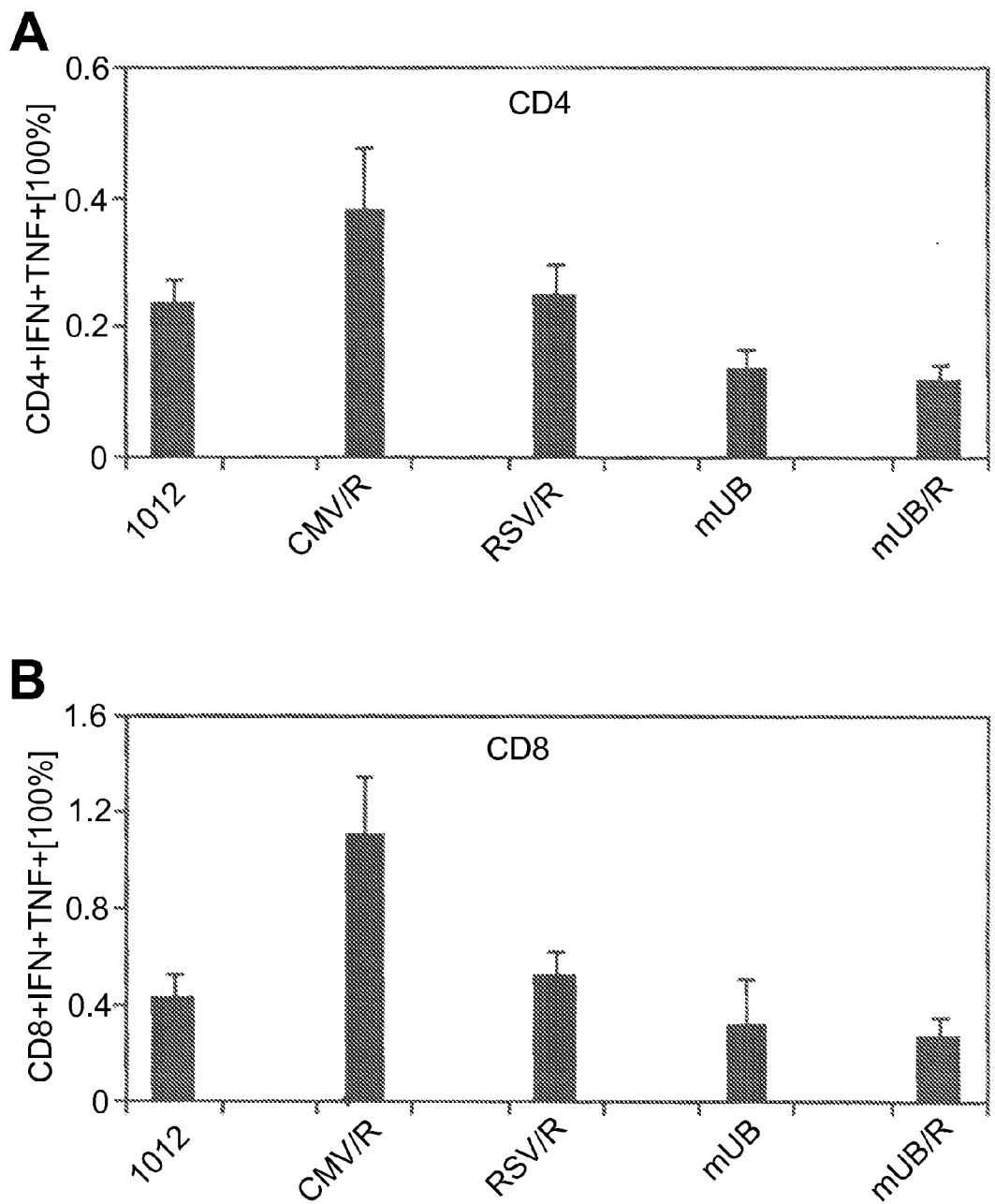
FIGS. 9A and B are bar graphs illustrating $CD4^+$ and $CD8^+$ T cell responses in mice immunized with expression plasmids with different transcription regulatory sequences.

To explore the possibility that enhanced antigen expression results in improved immunogenicity of these novel DNA vaccines in vivo, Balb/c mice (N=5/group) were immunized with 50 μg of the parental 1012 DNA vaccine or the CMV/R, RSV/R, mUB, or mUB/R DNA vaccines expressing HIV-1 Env gp145 ΔCFI. Mice were immunized three times at weeks 0, 2, and 6. On day 10 following the final immunization, splenocytes were assessed for Env-specific cellular immune responses by IFN-γ and TNF-α intracellular cytokine staining (ICS) assays. The CMV/R DNA vaccine elicited approximately 2-fold higher CD4$^+$ (p=0.15) and CD8$^+$ (p=0.043) T lymphocyte responses as compared with the parental 1012 DNA vaccine expressing the same antigen (FIG. 9). In contrast, the RSV/R, mUB, and mUB/R DNA vaccines did not elicit enhanced CD8$^+$ immune responses, suggesting that the HTLV-1 R element selectively improved immunogenicity in the context of the CMV promoter.

Immunogenicity of the parental 1012 DNA vaccines and the CMV/R DNA vaccines expressing other antigens were then compared. Mice (N=8/group) were immunized with sham plasmids or with these DNA vaccines expressing the HIV-1 Gag-Pol-Nef fusion protein. Mice were immunized twice at weeks 0 and 6, and cellular immune responses were assessed by IFN-γ ELISPOT assays using splenocytes harvested 3 weeks after the initial or boost immunization. Groups of BALB/c female mice (8 mice per group) were immunized with the following regimens of plasmids diluted in normal saline:

clade B g-p-n (1012): VRC-4306 (50 μg/animal); this plasmid expresses Gag-Pol-Nef as a fusion protein, and is contained in the four-plasmid vaccine VRC-HIVDNA009-00-VP (BB-IND 10681);

clade B g-p-n (CMV/R): VRC-4400 (50 μg/animal); this plasmid expresses Gag-Pol-Nef as a fusion protein.

Mice were injected with a single intramuscular (i.m.) immunization of 50 μl total DNA in the quadriceps muscles using on day 0. On day 21 following immunization, mice were sacrificed for immunologic assays.

ICS assays. CD4+ and CD8+ T lymphocyte responses were evaluated by intracellular cytokine staining (ICS) for interferon-gamma (IFN-γ) and tumor necrosis factor-alpha (TNF-α). Briefly, splenocytes from immunized mice were harvested and incubated with pools of 15 amino acid peptides overlapping by 11 amino acids (2.5 μg/ml each) covering the entire HIV-1 Env protein, followed by treatment with 10 μg/ml brefeldin A (Sigma, St. Louis, Mo.). Cells were then fixed, permeabilized, and stained using rat anti-mouse CD3, CD4, CD8, IFN-γ and TNF-α monoclonal antibodies (BD Pharmingen, San Diego, Calif.). The IFN-γ and TNF-α positive cells in the CD4+ and CD8+ cell populations were analyzed with the program FlowJo (Tree Star, Ashland, Oreg.).

Splenocytes were removed aseptically and homogenized to create a single-cell suspension. IFN-γ ELISPOT assays were then performed using splenocytes from vaccinated mice to assess the magnitude of vaccine-elicited cellular immune responses. Ninety-six-well multiscreen plates (Millipore, Bedford, Mass.) coated overnight with 100 μl/well of 10 μg/ml rat anti-mouse IFN-γ (Pharmingen, San Diego, Calif.) in PBS were washed with endotoxin-free Dulbecco's PBS (Life Technologies, Gaithersburg, Md.) containing 0.25% Tween-20 and blocked with PBS containing 5% FBS for 2 h at 37° C. The plates were washed three times with Dulbecco's PBS containing 0.25% Tween-20, rinsed with RPMI 1640 containing 10% FBS, and incubated in triplicate with $5 \times 10^5$ splenocytes per well in a 100 μl reaction volume containing pooled peptides. Responses were measured using the HIV-1 Gag, Pol, and Nef peptide pools (VRC, Bethesda, Md.). Following an 18 h incubation, the plates were washed nine times with Dulbecco's PBS containing 0.25% Tween-20 and once with distilled water. The plates were then incubated for 2 h with 75 μl/well of 5 μg/ml biotinylated rat anti-mouse IFN-γ (Pharmingen, San Diego, Calif.), washed six times with Coulter Wash (Coulter Corporation, Miami, Fla.), and incubated for 2 h with a 1:500 dilution of streptavidin-AP (Southern Biotechnology Associates, Birmingham, Ala.). Following five washes with Coulter Wash and one with PBS, the plates were developed with NBT/BCIP chromogen (Pierce, Rockford, Ill.), stopped by washing with tap water, air dried, and read using an ELISPOT reader (Hitech Instruments, Edgemont, Pa.).

Immunologic data are presented as means with standard errors. Statistical analyses were performed with GraphPad Prism version 4.01 (GraphPad Software, Inc., 2004). Comparisons of mean cellular immune responses between groups of animals were performed by two-tailed nonparametric Mann-Whitney tests. In all cases, p-values of less than 0.05 were considered significant.

Figure 10:
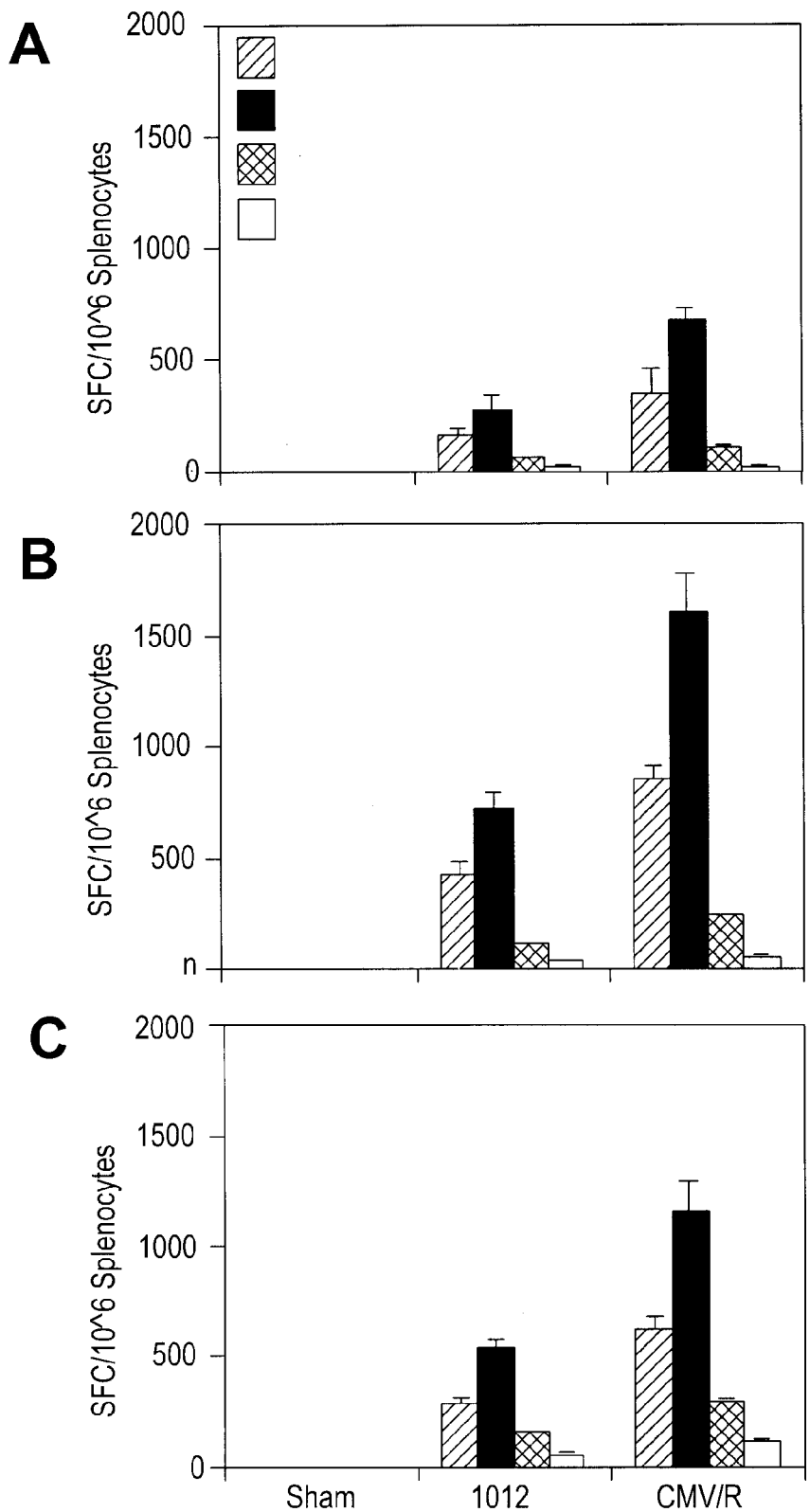
FIGS. 10A, B and C are bar graphs illustrating relative immune responses against HIV Gag, Pol and Nef antigens in mice immunized with nucleic acid constructs having either a CMV/R transcription control sequence or a CMV IE transcription control sequence.

Consistent with the prior experiment, we observed approximately 2-fold higher Gag-(p=0.038) and Pol-specific (p=0.020) responses elicited by the CMV/R DNA vaccine compared to the parental 1012 DNA vaccine following the initial immunization (FIG. 10A). Following the boost immunization, responses elicited by the CMV/R DNA vaccine remained approximately 2-fold higher than responses elicited by the parental DNA vaccine using both unfractionated splenocytes (FIG. 10B) and CD8-depleted splenocytes (FIG. 10C).

Immunogenicity of DNA Prime/Recombinant Adenoviral Vector Boost Immunization of

Cynomolgus Macaques

Immunogenicity of the parental 1012 DNA vaccines was compared with CMV/R DNA vaccines expressing multiple HIV-1 antigens in cynomolgus monkeys. Two groups of adult cynomolgus monkeys (N=6/group) were immunized with 4-plasmid mixtures of 1012 or CMV/R DNA vaccines expressing HIV-1 Env gp145 ΔCFI from clades A, B, and C and the Gag-Pol-Nef fusion protein from clade B in a 1:1:1:3 ratio. This multiclade, multivalent DNA vaccine has been previously described and is currently being evaluated in clinical trials (VRC-HIVDNA009-00-VP; PCT Publication No. WO/05034992). A third group of monkeys was included to investigate whether separating the Gag-Pol-Nef fusion protein into separate genes encoded on separate plasmids would further increase immune responses to these antigens (VRC-HIVDNA016-00-VP). This third group of monkeys received a 6-plasmid mixture of CMV/R DNA vaccines encoding HIV-1 Env gp145 from clades A, B, and C and separate Gag, Pol, and Nef proteins from clade B in a 1:1:1:1:1:1 ratio. All monkeys received three immunizations of 8 mg total DNA vaccine at weeks 0, 4, and 8.

Plasmid DNA vectors (Althea Technologies, Inc., San Diego Calif.) expressing HIV-1 Gag, Pol, Nef proteins or Gag-Pol-Nef fusion protein and Clade A, B and C Env were used for the DNA prime immunization. The plasmids expressed the same proteins as those contained in 4-plasmid vaccine VRC-HIVDNA009-00-VP and 6-plasmid vaccine VRC-HIVDNA016-00-VP.

The 4-plasmid combination was formulated using 1012 plasmids VRC 4306 (clade B Gag-Pol-Nef), VRC 5305 (clade A Env), VRC 2805 (clade B Env), and VRC 5309 (clade C Env). To achieve the required volumes for the three scheduled injections in the animal study, three lots of formulated material were prepared. The three lots were combined in a 50 mL conical tube. Following inversion of the tube several times to mix, 15.6-15.7 mL of the mixture was aliquotted into each of three 50 mL conical tubes. Tubes were labeled with study number, lot number, plasmid numbers, tube number, and date of preparation. Tubes were stored at −20° C. until distributed.

The 6-plasmid combination was formulated using CMV/R plasmids VRC 4401 (clade B Gag), VRC 4409 (clade B Pol), VRC 4404 (clade B Nef), VRC 5736 (clade A Env), VRC 5737 (clade B Env) and VRC 5738 (clade C Env). To achieve the required volumes for the three scheduled injections of the animal study, three lots of formulated material were prepared. The three lots were combined in a sterile container. Following inversion of the container several times to mix, 16.8 mL of the mixture was aliquotted into each of three 50 mL conical tubes. Tubes were labeled with study number, lot number, plasmid numbers, tube number and date of preparation and stored at −20° C. until distributed.

VRC-HIVADV014-00-VP (Lot #026-03024) was used as the rAd boost.

Outbred adult Cynomolgus macaques (6 monkeys per group) were vaccinated with DNA vaccine prime, delivered i.m. at weeks 0, 4, and 8 by Biojector. In each case, plasmid vaccine was delivered as two 0.5 ml injections in the quadriceps muscles using a No. 3 Biojector syringe (BIOJECT). A rAd vaccine boost was delivered i.m. by needle and syringe at week 38 (Group 1) and week 24 (Group 2). The following vaccination regimens were administered:

Group 1: 1012 plasmid DNA prime (4-plasmid combination): 8 mg total dose delivered as a combination of clade B Gag-Pol-Nef fusion protein (4 mg), clade A Env (1.3 mg), clade B Env (1.3 mg) and clade C Env (1.3 mg). This is a non-GMP version of the VRC-HIVDNA009-00-VP clinical product (BB-IND 10681). rAd vaccine boost: VRC-HIVADV014-00-VP ($10^{11}$ PU total dose; GMP lot #026-03024).

Group 2: CMV/R plasmid DNA (6-plasmid combination): 8 mg total dose delivered as a combination of clade B Gag (1.3 mg), clade B Pol (1.3 mg), clade B Nef (1.3 mg), clade A Env (1.3 mg), clade B Env (1.3 mg) and clade C Env (1.3 mg). This is a non-GMP version of the VRC-HIVDNA016-00-VP clinical product (the subject of this IND submission). rAd vaccine boost: VRC-HIVADV014-00-VP (GMP lot #026-03024).

Group 3: CMV/R plasmid DNA (4 plasmid combination): 8 mg total dose delivered as a combination of clade B Gag-Pol-Nef fusion protein (4 mg), clade A Env (1.3 mg), clade B Env (1.3 mg) and clade C Env (1.3 mg). rAd vaccine boost: VRC-HIVADV014-00-VP (GMP lot #026-03024).

Group 4: 1012 plasmid DNA (6 plasmid combination): 8 mg total dose delivered as a combination of clade B Gag (1.3 mg), clade B Pol (1.3 mg), clade B Nef (1.3 mg), clade A Env (1.3 mg), clade B Env (1.3 mg) and clade C Env (1.3 mg). rAd vaccine boost: VRC-HIVADV014-00-VP (GMP lot #026-03024).

Monkeys were bled at various intervals through week 42 post-immunization.

ELISPOT assays were utilized to monitor the emergence of vaccine-elicited T cell immune responses to multiple viral antigens. Separate assays were performed for each animal using pools of 15 amino acid peptides overlapping by 11 amino acids spanning the HIV-1 Gag, Pol, Nef, clade A Env, clade B Env and clade C Env proteins matching the sequences of the vaccine immunogens. 96-well multiscreen plates were coated overnight with 100 μl/well of 5 μg/ml anti-human IFN-γ (B27; BD Pharmingen) in endotoxin-free Dulbecco's PBS (D-PBS). The plates were then washed three times with D-PBS containing 0.25% Tween-20 (D-PBS/Tween), blocked for 2 h with D-PBS containing 5% FBS at 37° C., washed three times with D-PBS/Tween, rinsed with RPMI 1640 containing 10% FBS to remove the Tween-20, and incubated with peptide pools and $2 \times 10^5$ PBMC in triplicate in 100 μl reaction volumes. Following an 18 h incubation at 37° C., the plates were washed nine times with D-PBS/Tween and once with distilled water. The plates were then incubated with 2 μg/ml biotinylated rabbit anti-human IFN-γ (Biosource) for 2 h at room temperature, washed six times with Coulter Wash (Beckman-Coulter), and incubated for 2.5 h with a 1:500 dilution of streptavidin-AP (Southern Biotechnology). Following five washes with Coulter Wash and one with PBS, the plates were developed with NBT/BCIP chromogen (Pierce), stopped by washing with tap water, air dried, and read using an ELISPOT reader (Hitech Instruments). Spot-forming cells (SFC) per $10^6$ PBMC were calculated. Media backgrounds were consistently <15 spot-forming cells per $10^6$ PBMC.

Cellular immune responses against Env clade A, Env clade B, Env clade C, and Gag, Pol, and Nef from clade B were compared in monkeys that received the 4-plasmid mixtures under the control of CMV (1012) (Group 1) or CMV/R regulatory elements (Group 3). Monkeys immunized with the parental 1012 DNA vaccines developed low and sporadic IFN-γ ELISPOT responses to Env two weeks following the second immunization at week 6, and no clear responses above background were detected to Gag, Pol, and Nef (FIG. 11A). In contrast, monkeys immunized with the analogous CMV/R DNA vaccines exhibited significantly higher responses to all antigens (FIG. 11B). Compared to the parental 1012 DNA vaccines, the CMV/R DNA vaccines elicited >10-fold higher ELISPOT responses to Gag (p=0.0022), Pol (p=0.0043), and Nef (p=0.041) and 7- to 9-fold higher responses to Env clade A (p=0.026), B (p=0.0087), and C (p=0.030) at this time point. These results demonstrate that the CMV/R DNA vaccines were markedly more immunogenic than the parental 1012 DNA vaccines for multiple HIV-1 antigens in nonhuman primates.

Separating the Gag-Pol-Nef fusion protein into individual genes encoded on different plasmids further improved these responses. In particular, monkeys that received the 6-plasmid mixture of CMV/R DNA vaccines (Group 2) developed 4-fold higher responses to Gag (p=0.0022), a trend towards 2-fold higher responses to Pol (p=0.19), and 4-fold higher responses to Nef (p=0.049) (FIG. 11C), as compared to animals that received the 4-plasmid mixture of CMV/R DNA vaccines that included the Gag-Pol-Nef fusion protein (FIG. 11B). Env-specific responses between these two groups of monkeys that received the 4-plasmid and 6-plasmid mixtures of CMV/R DNA vaccines were comparable (p=0.48).

Figure 12:
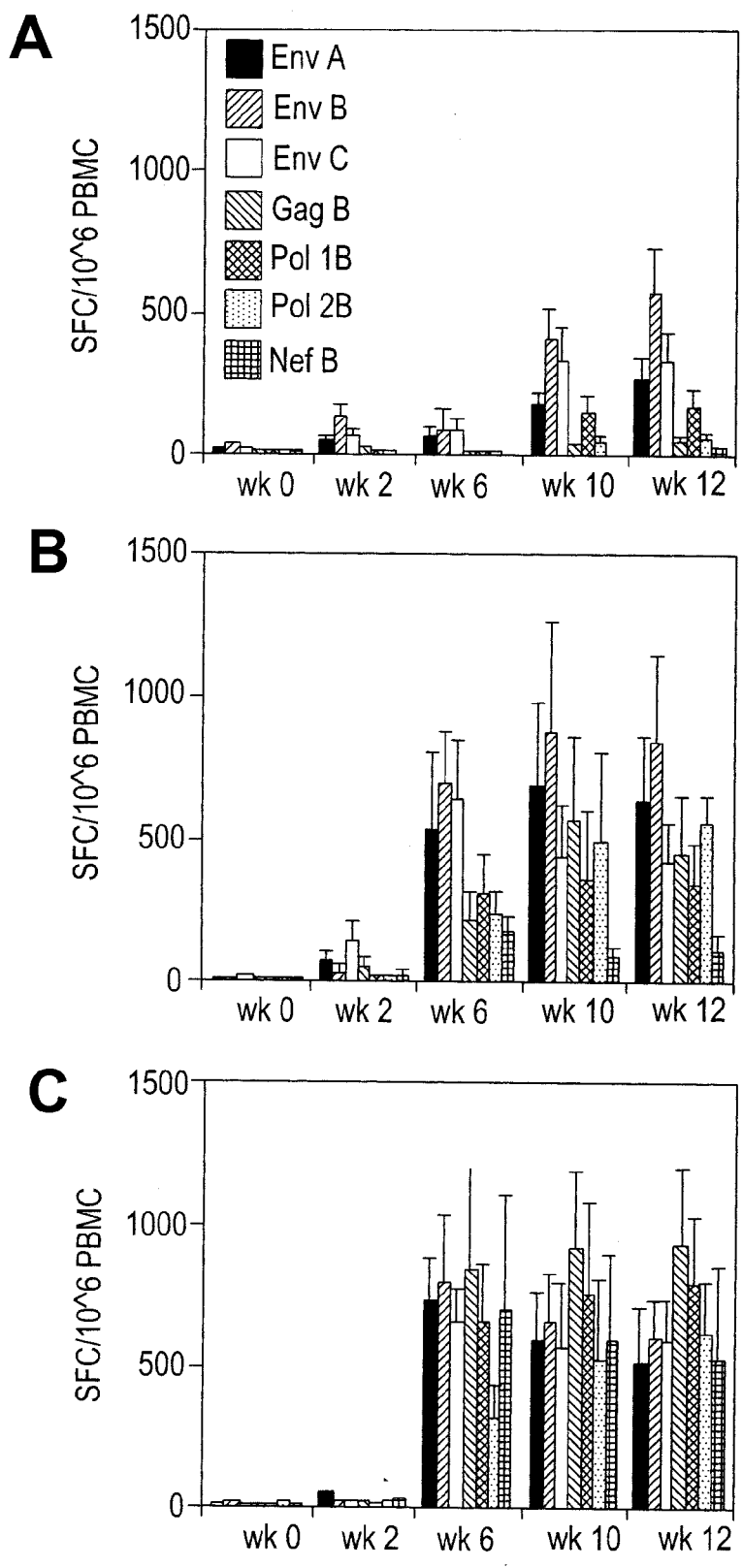
FIGS. 12A, B and C are bar graphs illustrate the time course of development of the immune response against HIV antigens following immunization of cynomolgous macaques with different vaccine compositions.

The evolution of mean IFN-γ ELISPOT responses in these groups of monkeys was evaluated at weeks 0, 2, 6, 10, and 12. Following the third DNA immunization at week 8, responses increased in all groups of monkeys (FIG. 12). At week 10, the parental 1012 DNA vaccines elicited Env- and Pol-specific responses in the majority of animals, although Gag- and Nef-specific responses remained low (FIG. 12A). In contrast, the CMV/R DNA vaccines elicited potent and broad responses to all antigens (FIG. 12B-C). At week 10, the 4-plasmid CMV/R DNA vaccines (FIG. 12B) elicited >10-fold higher ELISPOT responses to Gag (p=0.0022) and Nef (p=0.0022), 4-fold higher ELISPOT responses to Pol (p=0.043), and trends toward 1.5- to 4-fold higher responses to Env clade A, B, and C (FIG. 12B), as compared with the 4-plasmid parental 1012 DNA vaccines (FIG. 12A). Gag-, Pol- and Nef-specific responses remained highest in the animals that received the 6-plasmid CMV/R DNA vaccines with these genes encoded on separate plasmids (FIG. 12C). All responses boosted well with rAd. These studies confirm that the CMV/R DNA vaccines elicited substantially higher magnitude and broader cellular immune responses to multiple antigens as compared with the parental 1012 DNA vaccines. Thus, including the HTLV-1 R element and separating the Gag, Pol, and Nef genes significantly enhanced the immunogenicity of HIV-1 DNA vaccines in nonhuman primates.

Figure 11:
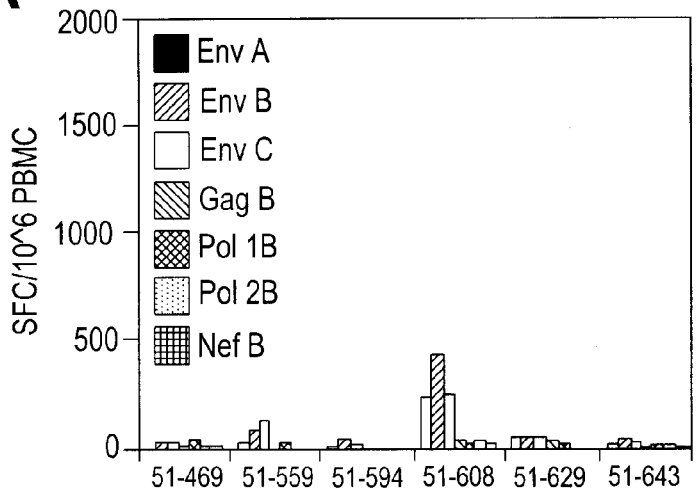
FIGS. 11A, B and C are bar graphs illustrating relative immune responses against HIV Gag, Pol, Nef and Env antigens in cynomolgous macaques immunized with different vaccine compositions.
Figure 11:
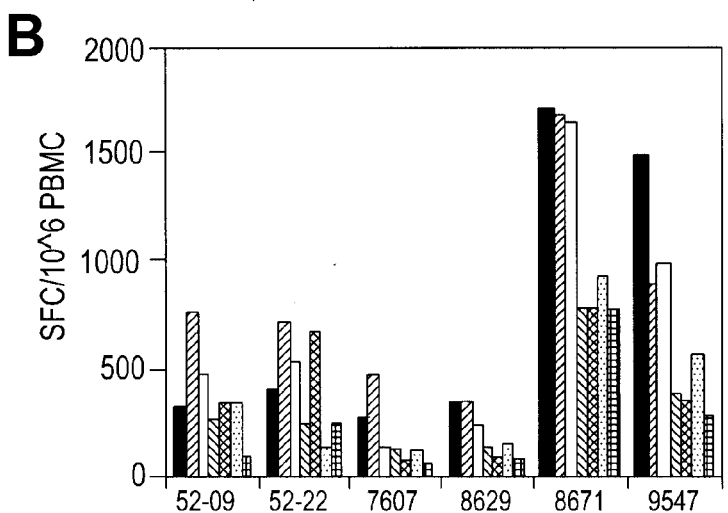
Figure 11:
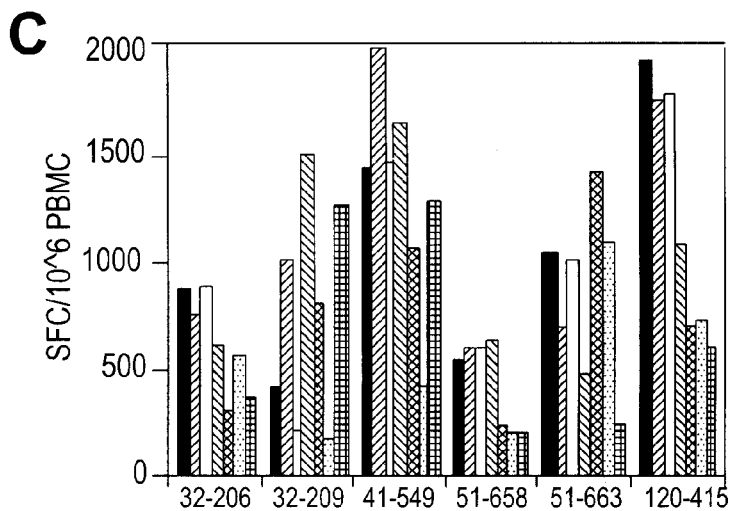

In both mice and cynomolgus monkeys, CMV/R DNA vaccines expressing HIV-1 antigens elicited higher cellular immune responses than the parental 1012 DNA vaccines expressing the same antigens. However, the magnitude of the observed effects differed substantially between the two species. While the CMV/R DNA vaccines elicited only 2-fold higher responses in mice (FIG. 10), the CMV/R DNA vaccines elicited >10-fold higher cellular immune responses to Gag, Pol, and Nef and 7- to 9-fold higher responses to Env after two immunizations in cynomolgus monkeys (FIGS. 11,12). This difference reflects the lower baseline immunogenicity of the parental 1012 DNA vaccines in nonhuman primates and indicates that the beneficial effects of the R element is more apparent in limiting situations. Consistent with this observation, the R element had the greatest effect at enhancing the weakest responses elicited by the parental 1012 DNA vaccine against Gag and Nef. However, Env- and Pol-specific cellular immune were also significantly higher when induced by CMV/R DNA vaccines as compared with the parental 1012 DNA vaccines.

The 6-plasmid mixture of CMV/R DNA vaccines that included Gag, Pol, and Nef on separate plasmids elicited significantly higher cellular immune responses to these antigens as compared to the 4-plasmid mixture of CMV/R DNA vaccines that included the Gag-Pol-Nef fusion protein. These effects are particularly notable since the separate Gag, Pol, and Nef plasmids were each utilized at one-third the dose of the plasmid encoding the Gag-Pol-Nef fusion protein. Without being bound by theory, this increased immunogenicity may reflect enhanced translation or mRNA stability of the shorter genes as compared with the fusion gene, which might potentially affect antigen processing and presentation.

Accumulating data has confirmed the importance of cellular immune responses in controlling HIV-1 replication in humans and SIV replication in rhesus monkeys. Moreover, vaccines aimed at eliciting virus-specific cellular immune responses have afforded partial control of SHIV and SIV challenges in rhesus monkeys. Thus, the markedly increased magnitude and breadth of HIV-1-specific cellular immune responses afforded by the CMV/R DNA vaccines in nonhuman primates in the present study is believed to be beneficial in the development of second-generation DNA vaccines for both HIV-1 and other pathogens. In particular, incorporating the HTLV-1 R element and utilizing separate genes in place of fusion genes represent simple and practical strategies to improve DNA vaccines, making these vaccines suitable for clinical applications.

Example 4

Preparation of Material for Clinical Use

The process for manufacturing, filling, and packaging the VRC-HIVDNA016-00-VP drug product involves *E. coli* fermentation, purification, and formulation as a sterile liquid injectable dosage form for intramuscular injection. This naked DNA product involves no lipid, viral, or cellular vector components.

The vaccine, VRC-HIVDNA016-00-VP, is composed of a combination of six closed circular plasmid DNA macromolecules (VRC-4401, 4409, 4404, 5736, 5737 and 5738). For preparation of plasmids for clinical use, a master cell band (MCB) was prepared for each source plasmid (VRC-4401, 4409, 4404, 5736, 5737 and 5738). Identity and composition of plasmid DNA samples from each of these MCBs was confirmed by sequence analysis. Restriction enzyme analysis and microbial analysis (including mold and yeast) were also performed to confirm identity and sterility.

Bulk plasmid preparations are prepared from bacterial cell cultures containing a kanamycin selection medium. In all cases, bacterial cell growth is dependent upon the cellular expression of the kanamycin resistance protein encoded by a portion of the plasmid DNA. Following growth of bacterial cells harboring the plasmid, the plasmid DNA is purified from cellular components.

Clinical trial vaccines are prepared under cGMP conditions. The vaccines meet lot release specifications prior to administration. The DNA vaccine is manufactured at a 4.0 mg dose in phosphate buffered saline (PBS). Vials are aseptically filled to a volume of 1.2 mL at a ratio of 1:1:1:1:1:1 of the six plasmids. The 4.0 mg plasmid DNA vaccine vials is shipped, unblinded, to the study pharmacist on dry ice, and is stored at or below −20° C. until use. Placebo control vials of 2.4 mL PBS, pH 7.2 ±0.2, are obtained from Bell-More Labs, Incorporated (Hampstead, Md.).

Expression testing of the individual plasmids and the final formulated drug product are conducted prior to release of the vaccine product. Qualitative expression of the plasmid proteins is verified by comparing the reactive protein bands on the Western blot with the standards run under the same conditions. Once the plasmids are combined, expression is verified using the same assay procedures. Expression is determined by detecting proteins expressed by transfected 293 human embryonic kidney (HEK) cells. For transfection, $10^5$ to $10^6$ cells are transfected with 1-5 µg of plasmid DNA using the calcium phosphate method. Cells are incubated for 14-20 hours to allow for DNA uptake. Following a medium change, cells are grown for an additional 24-48 hours before harvesting. Transfection efficiency is monitored using a known similar vector in the same backbone. After cell lysis, 10 µg of an appropriate amount of total cellular protein is loaded onto an SDS-PAGE gel to separate the crude lysate proteins.

Following electrophoresis for approximately 1.5 hours, the proteins are transferred to a nitrocellulose membrane (0.45 µm) for Western blot analysis. The membrane is blocked with skim milk to prevent non-specific binding interaction prior to incubation with the primary antibody for 60 minutes. Following washing, the membrane is incubated for 45 minutes with HRP conjugated second antibody. Visualization of the protein bands is achieved by incubating the membrane with chemiluminescent substrates and exposing to X-ray film for 2 minutes or an appropriate time. Expression of protein produced by transfected cells is determined by observing the intensity of expressed protein on the Western blot. The assay is being further developed to allow for semi-quantitative analysis of protein expression by the vaccine plasmids.

Example 5

Clinical Safety in Humans

For clinical use, VRC-HIVDNA016-00-VP is composed of 6 closed, circular DNA plasmids that are each 16.67% (by weight) of the vaccine. Each of the 6 plasmids in this vaccine expresses a single gene product. Plasmids VRC 4401, VRC 4409 and VRC 4404 are designed to express clade B HIV-1 Gag, Pol and Nef, respectively. VRC 5736, VRC 5737, and VRC 5738 are designed to express HIV-1 Env glycoprotein from clade A, clade B, and clade C, respectively. Vaccine vials are supplied at 4 mg/mL. Each DNA administration is 1 mL of the vaccine composition delivered intramuscularly (in deltoid muscle) using the Biojector 2000® Needle-Free Injection Management System™.

Evaluation of the safety of this vaccine includes laboratory studies, medical history, physical assessment by clinicians, and subject self-assessment recorded on a diary card. Potential adverse reactions are further evaluated prior to continuing the immunization schedule. Day 0 is defined as the day of enrollment and first injection. Day 0 evaluations prior to the first injection are the baseline for subsequent safety assessments. The schedule of vaccination is Day 0, Day 28±7, Day 56±7 (with at least 21 days between injection days). All study injections are given by an intramuscular administration of VRC-HIVDNA016-00-VP at a 4 mg dose using a Biojector 2000® needle-free injection system. Study injections are administered into deltoid muscle.

Following study injections, subjects are observed for a minimum of 30 minutes. Vital signs (temperature, blood pressure, pulse and respiratory rate) are taken at 30-45 minutes post-immunization. The injection site is inspected for evidence of local reaction. Subjects will be given a "Diary Card" on which to record temperature and symptoms daily for 5 days. Follow-up on subject well-being will be performed by telephone on the first or second day following each injection. A clinic visit will occur if indicated by the telephone inter-view. On each injection day (prior to injection) and at 14±3 days after each injection, study subjects are evaluated by clinical exam and laboratory tests. Long-term follow-up visits are at Week 12±7 days, Week 24±14 days and Week 32±14 days. At intervals throughout the study subjects have blood drawn for immunologic assays. Any cells, serum or plasma not used will be stored for future virological and immunological assays. Subjects are also interviewed at the final clinical visit (Week 32) regarding social harms, including problems with employment, travel, immigration, access to insurance, medical or dental care, and negative reactions from family, friends, and co-workers.

Assessment of product safety includes clinical observation and monitoring of hematological and chemical parameters. The following parameters will be assessed: local reactogenicity signs and symptoms; systemic reactogenicity signs and symptoms; laboratory measures of safety; and adverse and serious adverse experiences.

The principal immunogenicity endpoints are measured at Week 0 (baseline) and Weeks 6, 8, 10 and 12 (for cellular immune responses) and consist of HIV-1-specific T cell responses, as measured by intracellular cytokine staining (ICS) assays. ICS at other study timepoints, as well as HIV-1-specific humoral immune responses as measured by HIV-specific antibody assays will be completed as exploratory evaluations.

Administration of the vaccine composition is performed using a BIOJECTOR 2000® NEEDLE-FREE INJECTION MANAGEMENT SYSTEM® as directed by the company. Neither the material being injected nor the deltoid injection site skin preparation require deviation from standard procedures. In brief, the injection site is disinfected and the area allowed to dry completely. The skin around the injection site is held firmly while the syringe is placed against the injection site at a 90° angle. The actuator is pressed and the material is released into the muscle. Continue to hold firmly for 3 seconds. After the injection, the site is covered with a sterile covering and pressure applied with 3 fingers for 1 minute. BIOJECTOR 2000® utilizes sterile, single-use syringes for variable dose, up to 1.0 mL, medication administration. The study agent is delivered under pressure by a compressed $CO_2$ gas cartridge that is stored inside the BIOJECTOR®. When the BIOJECTOR®'s actuator is depressed, $CO_2$ is released, causing the plunger to push the study agent out of the sterile syringe through the skin and into the underlying tissue. The study agent is expelled through a micro-orifice at high velocity in a fraction of a second to pierce the skin. The $CO_2$ does not come in contact with the injectate and the syringe design prevents any back splatter or contamination of the device by tissue from the subject.

Fifteen subjects received three 1 mL doses at 4 mg/mL on a 0, 1, 2 month schedule. Vaccinations were administered intramuscularly using the BIOJECTOR 2000®. Fourteen of the 15 subjects received 3 intramuscular injections of a 4 mg dose of vaccine administered by BIOJECTOR 2000®; one subject was lost to follow-up after two vaccinations. No subjects reported fever following vaccination. Reactogenicity was none to mild except that two subjects reported moderate injection site pain and one subject reported moderate nausea and malaise. The only adverse event requiring expedited reporting to the IND sponsor was a grade 3 generalized urticaria. The subject had reported starting an antihistamine about 2 weeks after first vaccination but reported at that time that the reason was latex allergy. While being screened for the rollover booster study, VRC 010, it was learned that the subject had experienced generalized urticaria around the time of the second vaccination when the supply of antihistamine ran out. The subject has chronic urticaria that are well controlled by antihistamine. Evaluation is ongoing. The etiology is unknown but at this time the chronic urticaria is assessed as possibly related to study vaccine. To date, there have been two moderate (grade 2) adverse events possibly attributed to vaccine. These were intermittent dizziness of 2 days duration beginning 13 days after the second vaccination in one subject (this subject received the third vaccination without recurrence of symptoms) and asymptomatic hypoglycemia in another subject, first noted at the follow-up visit that was 14 days after the third vaccination. The last safety evaluation of the subject lost to follow-up was by telephone one day after the second vaccination; at that time the subject reported no side effects from the vaccination.

An unexpected local injection site reaction for this DNA vaccine has been observed. Mild cutaneous lesions (0.5-1.0 cm diameter) at the vaccination site occurred after 4 of 44 (9%) vaccinations administered; these occurred in 3 of 15 (20%) subjects. Subjects were routinely asked to call if they experience any unusual problem after study vaccinations. The vaccination site cutaneous lesions did not alarm subjects enough to prompt them to contact the VRC Clinic prior to their next regularly-scheduled visit. In retrospect, three subjects reported that they experienced skin lesions that started as a small papule or vesicle within 3 days after vaccination. After a few days the papule or vesicle unroofed and a scab formed. There was surrounding mild erythema and mild induration. After the scab came off, the skin healed without treatment. None of the cutaneous lesions were associated with pustular exudates, fever, rash or urticaria. They did not appear to be either a local infection or an allergic reaction.

The first three cutaneous lesions were discovered at the first post-vaccination clinic visit (days 14±3 Day); at that time they were largely resolved. The fourth cutaneous lesion was examined in the clinic while still in an active stage and it was biopsied at post-vaccination day 6. This biopsy demonstrated a microscopic subcutaneous and dermal perivascular lymphocytic infiltrate. The infiltrate was composed almost exclusively of CD3 positive cells, including both $CD4^+$ and $CD8^+$. There were rare eosinophils present and rare giant cells noted. The process appeared to be primarily a subcutaneous and dermal response to vaccination with cutaneous manifestations.

Whether these reactions correlate with the strength of the vaccine-induced immune response is also not yet known. Eight of the 14 subjects who remained in follow-up have had a vaccine-induced positive HIV ELISA by a commercial test at one or more timepoints; this includes all three subjects who had a cutaneous lesion. Preliminary immunogenicity data with the 6-plasmid DNA indicate that the Env-specific T cell responses are similar to those seen in the 4-plasmid DNA, and the Gag- and Nef-specific responses are also present.

Figure 13:
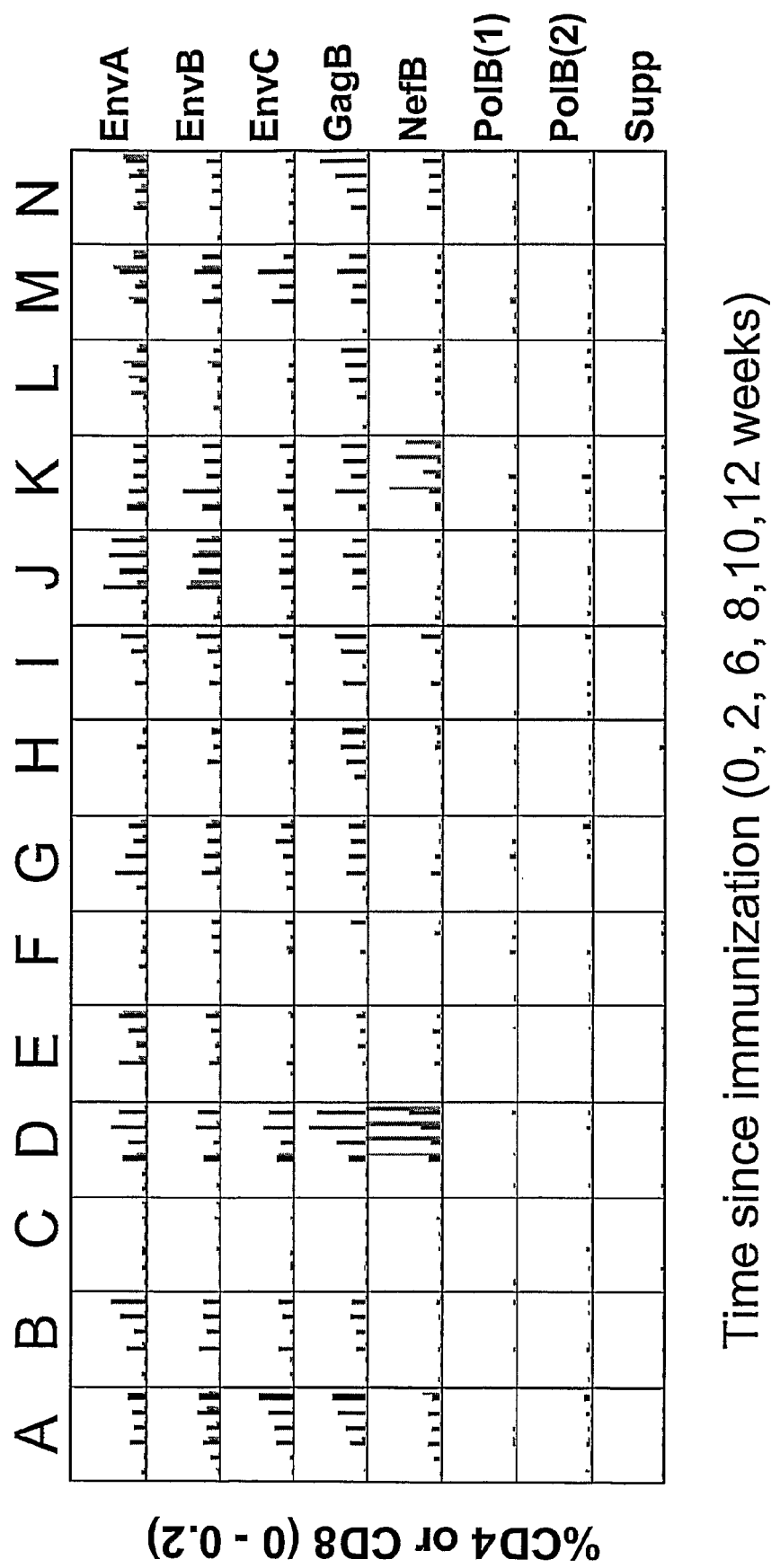
FIG. 13 is a series of bar graphs illustrating the cellular immune response measured by intracellular cytokine staining (ICS) in humans immunized with VRC-HIVDNA016-00-VP.

Cellular responses in subjects were measured by intracellular cytokine staining (ICS) and flow cytometry to detect IFN-γ or IL-2 in both CD4+ and CD8+ T lymphocytes after stimulation with peptide pools representing the viral antigens (FIG. 13). Data for each individual subject is shown in columns. Responses to each peptide pools are shown in rows. Each box represents the entire time course from prevaccination to 12 weeks (4 weeks after the last immunization). The scale for each box is 0-0.2% of the total CD4+ or CD8+ population tested. CD4+ responses are shown in red and CD8+ responses shown in green. Nearly all subject have detectable responses to Env peptides. In contrast to the 4-plasmid product, the majority of subjects have detectable responses to Gag and there are also Nef responders.

Example 6

Immunogenicity of Chimeric Env Proteins

To demonstrate the role of different genetic sequences in the induction of neutralizing antibodies, nucleic acid constructs expressing chimeric antigenic polypeptides having different regions of the viral envelope from two different clades were produced. Nucleic acid constructs encoding different portions of the clade C Env polypeptide and clade B Env polypeptide were analyzed and compared to the clade C Env polypeptide. The transposition of the proximal 25% of clade C onto the clade B background showed an increase in the potency and breadth of neutralization against a variety of clade B isolates and improved the neutralization of clade C isolates. Replacement of the distal region of clade B Env with the clade C Env resulted in improved neutralization against clade B isolates, demonstrating that the region containing $V_3$ in clade B isolates contributes to its ability to inhibit a variety of diverse viral isolates. These nucleic acid constructs are represented by SEQ ID NOs:7-15. Thus, certain embodiments of the disclosed compositions can include constructs encoding chimeric Env polypeptides combining multiple clades.

To demonstrate the roles of V regions in alternative clades, mutations were made both in the $V_1V_2$ as well as the $V_3$ regions of clades A, B and C. To demonstrate the role of $V_1V_2$ in clade A, a clade A prototype was compared to that containing deletions of the $V_1$ and $V_2$ regions. Removal of $V_1V_2$ and/or $V_3$ enhanced the ability of the clade A Env polypeptide to elicit an immune response that neutralized a variety of clade B isolates, demonstrating that deletion of these regions increases the ability of the antigenic polypeptide to elicit broadly neutralizing antibodies (for example, by increasing accessibility to specific epitopes that elicit cross-reactive antibodies). Accordingly, in certain embodiments disclosed herein, the nucleic acid constructs include deletions of a $V_1$, $V_2$ and/or $V_3$ region.

To demonstrate the role of $V_1V_2$ in clade B against a heterologous $V_3$ from clade C, the $V_3$ from a South African clade C isolate was inserted in place of the $V_3$ from a clade B and compared to a stem-shortened version that has been shown to enhance neutralization using clade B $V_3$ loops. The ability of these plasmid DNA vectors in combination with a recombinant adenovirus boost to elicit neutralizing antibodies was evaluated against the indicated strains. Immunization with both $V_3$ substitutions allowed neutralization of viral isolates from clades A, B and C, although the magnitude of the response was greater with the stem-shortened 1AB $V_3$. In addition, the peptide inhibition revealed that the neutralizing antibodies elicited in this response were of greater breadth and intereacted with $V_3$ regions from diverse clades, A, B and C. Thus, the clade C $V_3$ loop appeared to elicit broadly reactive $V_3$ neutralizing antibodies.

Deletion of the $V_1$ and $V_2$ regions of these envelopes improves their ability to elicit neutralizing antibody responses. These responses are directed largely against the $V_3$ regions in diverse clades. The use of alternative V regions derived from different clades demonstrates that these V regions also display differences in their ability to elicit strain-specific responses. For example, the inclusion of $V_3$ regions from clade C allowed neutralization of a variety of clade B isolates and greater breadth of neutralization by $V_3$ peptides from diverse strains. Thus, the elimination of both the $V_1$ and $V_2$ regions as well as the presentation of more broadly reactive $V_3$s can enhance the breadth of neutralization mediated by an Env antigenic polypeptide.

In addition to the $V_3$-mediated neutralization, other variable regions contribute to virus neutralization when $V_3$ is not exposed. Among these, a highly exposed region in $V_1$ was identified. Although this region is highly likely to show strain-specific variation, there are also conserved subregions within the $V_1$ that contribute to increased breadth of the immune response to this variable loop.

The ability to define improved immunogens using genetic information based on viral diversity can improve the ability to design effective HIV vaccines. The results described above demonstrate that genotypic sequence variation can result in neutralization sensitivities that are independent of clade. This finding has important implications for the design of improved HIV immunogens based on genetic sequence.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of inducing an immune response against HIV in a human, which method comprises (1) administering a first composition to a human, wherein the first composition comprises (a) a plasmid comprising a nucleic acid sequence encoding an HIV Env protein from Glade A, (b) a plasmid comprising a nucleic acid sequence encoding an HIV Env protein from Glade B, (c) a plasmid comprising a nucleic acid sequence encoding an HIV Env protein from Glade C, (d) a plasmid comprising a nucleic acid sequence encoding an HIV Gag protein from Glade B, (e) a plasmid comprising a nucleic acid sequence encoding an HIV Pol protein from Glade B, (f) a plasmid comprising a nucleic acid sequence encoding an HIV Nef protein from Glade B, and (g) a pharmaceutically acceptable carrier, and (2) administering a second composition to the human after the administration of the first composition to the human, wherein the second composition comprises (a) an adenoviral vector comprising a nucleic acid sequence encoding an HIV Env protein from Glade A, (b) an adenoviral vector comprising a nucleic acid sequence encoding an HIV Env protein from Glade B, (c) an adenoviral vector comprising a nucleic acid sequence encoding an HIV Env protein from Glade C, (d) an adenoviral vector comprising a nucleic acid sequence encoding an HIV Gag-Pol fusion protein from Glade B, and (e) a pharmaceutically acceptable carrier, whereupon an immune response against HIV is induced in the human.

2. The method of claim 1, wherein each of the Env proteins from Glade A, B, and C encoded by a plasmid of the first composition is a gp145 protein which lacks (a) the fusion and cleavage domains and (b) the interspace between heptad (H) 1 and 2.

3. The method of claim 1, wherein each of the Env proteins from Glade A, B, and C encoded by an adenoviral vector of the second composition is HIV gp140 or gp140dv12.

4. The method of claim 1, wherein the nucleic acid sequences encoding the HIV Env, Gag, Pol, Nef, and/or Gag-Pol proteins comprise codons optimized for expression in a human.

5. The method of claim 1, wherein the first composition is administered to the human at least one week prior to administration of the second composition to the human.

6. The method of claim 5, wherein the first composition is administered to the human three months prior to administration of the second composition to the human.

7. The method of claim 5, wherein the first composition is administered to the human nine months prior to administration of the second composition to the human.

8. The method of claim 5, wherein the first composition is administered to the human two or more times prior to administration of the second composition to the human.

9. The method of claim 1, wherein the first composition and the second composition are administered to the human intramuscularly or via a needleless delivery device.

10. The method of claim 1, wherein each of the adenoviral vectors of the second composition is replication-deficient.

* * * * *

SEQUENCE LISTING

```
<160> NUMBER OF SEQ ID NOS: 26

<210> SEQ ID NO 1
<211> LENGTH: 5886
<212> TYPE: DNA
<213> ORGANISM: Artificial Sequence
<220> FEATURE:
<223> OTHER INFORMATION: plasmid VRC4401

<400> SEQUENCE: 1
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accatatgcg gtgtgaaata ccgcacagat gcgtaaggag aaaataccgc atcagattgg       240
```

```
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tcacgccggg ttgagtcgcg ttctgccgcc tcccgctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtctttttct gcagtcaccg tcgtcgacac gtgtgatcag ataaacttaa gcttatgggc   1380
gcccgcgcca gcgtgctgag cggcggcgag ctggaccgct gggagaagat ccgcctgcgc   1440
cccggcggca agaagaagta caagctgaag cacatcgtgt gggccagccg cgagctggag   1500
cgcttcgccg tgaaccccgg cctgctggag accagcgagg gctgccgcca gatcctgggc   1560
cagctgcagc ccagcctgca gaccggcagc gaggagctgc gcagcctgta caacaccgtg   1620
gccaccctgt actgcgtgca ccagcgcatc gagatcaagg acaccaagga ggccctggac   1680
aagatcgagg aggagcagaa caagagcaag aagaaggccc agcaggccgc cgccgacacc   1740
ggccacagca accaggtgag ccagaactac cccatcgtgc agaacatcca gggccagatg   1800
gtgcaccagg ccatcagccc ccgcaccctg aacgcctggg tgaaggtggt ggaggagaag   1860
gccttcagcc ccgaggtgat ccccatgttc agcgccctga gcgagggcgc caccccccag   1920
gacctgaaca ccatgctgaa caccgtgggc ggccaccagg ccgccatgca gatgctgaag   1980
gagaccatca acgaggaggc cgccgagtgg gaccgcgtgc accccgtgca cgccggcccc   2040
atcgcccccg gccagatgcg cgagcccgc ggcagcgaca tcgccggcac caccagcacc   2100
ctgcaggagc agatcggctg gatgaccaac aaccccccca tccccgtggg cgagatctac   2160
aagcgctgga tcatcctggg cctgaacaag atcgtgcgca tgtacagccc caccagcatc   2220
ctggacatcc gccagggccc caaggagccc ttccgcgact acgtggaccg cttctacaag   2280
accctgcgcg ccgagcaggc cagccaggag gtgaagaact ggatgaccga ccctgctg   2340
gtgcagaacg ccaacccga ctgcaagacc atcctgaagg ccctgggccc cgccgccacc   2400
ctggaggaga tgatgaccgc ctgccaggc gtggcggcc ccggccacaa ggcccgcgtg   2460
ctggccgagg ccatgagcca ggtgaccaac agcgccacca tcatgatgca gcgcggcaac   2520
ttccgcaacc agcgcaagat cgtgaagtgc ttcaactgcg gcaaggaggg ccacaccgcc   2580
cgcaactgcc gcgccccccg caagaagggc tgctggaagt gcggcaagga gggccaccag   2640
```

```
atgaaggact gcaccgagcg acaggctaat ttttagggga agatctggcc ttcccacaag    2700
ggaaggccag ggaatttct tcagagcaga ccagagccaa cagccccacc agaagagagc    2760
ttcaggtttg gggaagagac aacaactccc tctcagaagc aggagccgat agacaaggaa    2820
ctgtatcctt tagcttccct cagatcactc tttggcagcg accctcgtc acaataaaga     2880 taggtaccga gctcggatcc agatctgctg tgccttctag ttgccagcca tctgttgttt    2940 gccctcccc cgtgccttcc ttgacccctgg aaggtgccac tcccactgtc ctttcctaat   3000
aaaatgagga aattgcatcg cattgtctga gtaggtgtca ttctattctg ggggtgggg    3060 tgggcagga cagcaagggg gaggattggg aagacaatag caggcatgct ggggatgcgg     3120
tgggctctat gggtacccag gtgctgaaga attgacccgg ttcctcctgg ccagaaaga    3180 agcaggcaca tccccttctc tgtgacacac cctgtccacg cccctggttc ttagttccag    3240
ccccactcat aggacactca tagctcagga gggctccgcc ttcaatccca cccgctaaag    3300
tacttggagc ggtctctccc tccctcatca gcccaccaaa ccaaacctag cctccaagag    3360
tgggaagaaa ttaaagcaag ataggctatt aagtgcagag ggagagaaaa tgcctccaac    3420
atgtgaggaa gtaatgagag aaatcataga atttcttccg cttcctcgct cactgactcg    3480
ctgcgctcgg tcgttcggct gcggcgagcg gtatcagctc actcaaaggc ggtaatacgg    3540
ttatccacag aatcagggga taacgcagga agaacatgt gagcaaaagg ccagcaaaag   3600
gccaggaacc gtaaaaaggc cgcgttgctg gcgttttcc ataggctccg cccccctgac     3660
gagcatcaca aaaatcgacg ctcaagtcag aggtggcgaa acccgacagg actataaaga    3720
taccaggcgt ttccccctgg aagctccctc gtgcgctctc ctgttccgac cctgccgctt    3780
accggatacc tgtccgcctt tctcccttcg ggaagcgtgg cgctttctca tagctcacgc    3840
tgtaggtatc tcagttcggt gtaggtcgtt cgctccaagc tgggctgtgt gcacgaaccc    3900
cccgttcagc ccgaccgctg cgccttatcc ggtaactatc gtcttgagtc caacccggta    3960
agacacgact tatcgccact ggcagcagcc actggtaaca ggattagcag agcgaggtat    4020
gtaggcggtg ctacagagtt cttgaagtgg tggcctaact acggctacac tagaagaaca    4080
gtatttggta tctgcgctct gctgaagcca gttaccttcg gaaaaagagt ggtagctct    4140 tgatccggca aacaaaccac cgctggtagc ggtggttttt ttgtttgcaa gcagcagatt    4200
acgcgcagaa aaaaaggatc tcaagaagat cctttgatct tttctacggg gtctgacgct    4260
cagtggaacg aaaactcacg ttaagggatt ttggtcatga gattatcaaa aaggatcttc    4320
acctagatcc ttttaaatta aaaatgaagt tttaaatcaa tctaaagtat atatgagtaa    4380
acttggtctg acagttacca atgcttaatc agtgaggcac ctatctcagc gatctgtcta    4440
tttcgttcat ccatagttgc ctgactcggg ggggggggc gctgaggtct gcctcgtgaa    4500
gaaggtgttg ctgactcata ccaggcctga atcgccccat catccagcca gaaagtgagg    4560
gagccacggt tgatgagagc tttgttgtag gtggaccagt tggtgatttt gaactttgc     4620 tttgccacgg aacggtctgc gttgtcggga agatgcgtga tctgatcctt caactcagca    4680
aaagttcgat ttattcaaca aagccgccgt cccgtcaagt cagcgtaatg ctctgccagt    4740
gttacaacca attaaccaat tctgattaga aaaactcatc gagcatcaaa tgaaactgca    4800
atttattcat atcaggatta tcaataccat attttgaaa aagccgtttc tgtaatgaag    4860
gagaaaactc accgaggcag ttccatagga tggcaagatc ctggtatcgg tctgcgattc    4920
cgactcgtcc aacatcaata caacctatta atttccctc gtcaaaaata aggttatcaa    4980
gtgagaaatc accatgagtg acgactgaat ccggtgagaa tggcaaaagc ttatgcattt    5040
```

-continued

| | |
|---|---|
| cttccagac ttgttcaaca ggccagccat tacgctcgtc atcaaaatca ctcgcatcaa | 5100 |
| ccaaaccgtt attcattcgt gattgcgcct gagcgagacg aaatacgcga tcgctgttaa | 5160 |
| aaggacaatt acaaacagga atcgaatgca accggcgcag gaacactgcc agcgcatcaa | 5220 |
| caatattttc acctgaatca ggatattctt ctaatacctg gaatgctgtt ttcccgggga | 5280 |
| tcgcagtggt gagtaaccat gcatcatcag gagtacggat aaaatgcttg atggtcggaa | 5340 |
| gaggcataaa ttccgtcagc cagtttagtc tgaccatctc atctgtaaca tcattggcaa | 5400 |
| cgctaccttt gccatgtttc agaaacaact ctggcgcatc gggcttccca tacaatcgat | 5460 |
| agattgtcgc acctgattgc ccgacattat cgcgagccca tttataccca tataaatcag | 5520 |
| catccatgtt ggaatttaat cgcggcctcg agcaagacgt ttcccgttga atatggctca | 5580 |
| taacacccct tgtattactg tttatgtaag cagacagttt tattgttcat gatgatatat | 5640 |
| ttttatcttg tgcaatgtaa catcagagat tttgagacac aacgtggctt tccccccccc | 5700 |
| cccattattg aagcatttat cagggttatt gtctcatgag cggatacata tttgaatgta | 5760 |
| tttagaaaaa taaacaaata ggggttccgc gcacatttcc ccgaaaagtg ccacctgacg | 5820 |
| tctaagaaac cattattatc atgacattaa cctataaaaa taggcgtatc acgaggccct | 5880 |
| ttcgtc | 5886 |

<210> SEQ ID NO 2
<211> LENGTH: 7344
<212> TYPE: DNA
<213> ORGANISM: Artificial Sequence
<220> FEATURE:
<223> OTHER INFORMATION: plasmid VRC4409

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggA ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |

-continued

```
accctgcttg ctcaactcta gttaacggtg gagggcagtg tagtctgagc agtactcgtt      1260
gctgccgcgc gcgccaccag acataatagc tgacagacta acagactgtt cctttccatg      1320
ggtctttttct gcagtcaccg tcgtcgacat gagggaagat ctggccttcc cacaagggaa     1380
ggccagggaa ttttcttcag agcagaccag agccaacagc cccaccagaa gagagcttca      1440
ggtttgggga agagacaaca actccctctc agaagcagga gccgatagac aaggaactgt      1500
atcctttagc ttccctcaga tcactctttg gcagcgaccc ctcgtcacaa taaagatagg      1560
gggccagctg aaggaggccc tgctggacac cggcgccgac gacaccgtgc tggaggagat      1620
gaacctgccc ggccgctgga agcccaagat gatcggcggc atcggcggct tcatcaaggt      1680
gggccagtac gaccagatcc tgatcgagat ctgcggccac aaggccatcg gcaccgtgct      1740
ggtgggcccc acccccgtga acatcatcgg ccgcaacctg ctgacccaga tcggctgcac      1800
cctgaacttc cccatcagcc ccatcgagac cgtgcccgtg aagctgaagc ccggcatgga      1860
cggccccaag gtgaagcagt ggcccctgac cgaggagaag atcaaggccc tggtggagat      1920
ctgcaccgag atggagaagg agggcaagat cagcaagatc ggccccgaga cccctacaa       1980
cacccccgtg ttcgccatca agaagaagga cagcaccaag tggcgcaagc tggtggactt      2040
ccgcgagctg aacaagcgca cccaggactt ctgggaggtg cagctgggca tccccacccc      2100
cgccggcctg aagcagaaga gagcgtgac cgtgctggac gtgggcgacg cctacttcag       2160
cgtgcccctg gacaaggact ccgcaagta caccgccttc accatcccca gcatcaacaa       2220
cgagaccccc ggcatccgct accagtacaa cgtgctgccc cagggctgga agggcagccc      2280
cgccatcttc cagtgcagca tgaccaagat cctggagccc ttccgcaagc agaacccga       2340
catcgtgatc taccagtaca tggaccaccct gtacgtgggc agcgacctgg agatcggcca     2400
gcaccgcacc aagatcgagg agctgcgcca gcacctgctg cgctgggct tcaccacccc       2460
cgacaagaag caccagaagg agcccccctt cctgtggatg ggctacgagc tgcaccccga     2520
caagtggacc gtgcagccca tcgtgctgcc cgagaaggac agctggaccg tgaacgacat      2580
ccagaagctg gtgggcaagc tgaactgggc cagccagatc tacgccggca tcaaggtgcg      2640
ccagctgtgc aagctgctgc gcggcaccaa ggccctgacc gaggtggtgc ccctgaccga      2700
ggaggccgag ctggagctgg ccgagaaccg cgagatcctg aaggagcccg tgcacggcgt      2760
gtactacgac cccagcaagg acctgatcgc cgagatccag aagcagggcc agggccagtg      2820
gacctaccag atctaccagg agcccttcaa gaacctgaag accggcaagt acgcccgcat      2880
gaagggcgcc cacaccaacg acgtgaagca gctgaccgag gccgtgcaga gatcgccac       2940
cgagagcatc gtgatctggg gcaagacccc caagttcaag ctgcccatcc agaaggagac      3000
ctgggaggcc tggtggaccg agtactgcag gccacctgg atccccgagt gggagttcgt       3060
gaacaccccc cccctggtga agctgtggta ccagctggag aaggagccca tcatcggcgc      3120
cgagaccttc tacgtggacg gcgccgccaa ccgcgagacc aagctgggca aggccggcta      3180
cgtgaccgac cgcggccgcc agaaggtggt gccctgacc gacaccacca accagaagac       3240
cgagctgcag gccatccacc tggccctgca ggacagcggc ctggaggtga catcgtgac       3300
cgacagccag tacgccctgg gcatcatcca ggcccagccc gacaagagcg agagcgagct      3360
ggtgagccag atcatcgagc agctgatcaa gaaggagaag gtgtacctgg cctgggtgcc      3420
cgcccacaag ggcatcggcg gcaacgagca ggtggacggc ctggtgagcg ccggcatccg      3480
caaggtgctt ttcctggacg gcatcgacaa ggcccaggag gagcacgaga gtaccacag      3540
caactggcgc gccatggcca gcgacttcaa cctgccccc gtggtggcca aggagatcgt        3600
```

```
ggccagctgc gacaagtgcc agctgaaggg cgaggccatg cacggccagg tggactgcag    3660
ccccggcatc tggcagctgg catgcaccca cctggagggc aaggtgatcc tggtggccgt    3720
gcacgtggcc agcggctaca tcgaggccga ggtgatcccc gccgagaccg gccaggagac    3780
cgcctacttc ctgctgaagc tggcggccg ctggcccgtg aagaccgtgc acaccgacaa    3840
cggcagcaac ttcaccagca ccaccgtgaa ggccgcctgc tggtgggccg gcatcaagca    3900
ggagttcggg atcccctaca accccccgag ccagggcgtg atcgagagca tgaacaagga    3960
gctgaagaag atcatcggcc aggtgcgcga ccaggccgag cacctgaaga ccgccgtgca    4020
gatggccgtg ttcatccaca acttcaagcg caagggcggc atcggcggct acagcgccgg    4080
cgagcgcatc gtggacatca tcgccaccga catccagacc aaggagctgc agaagcagat    4140
caccaagatc cagaacttcc gcgtgtacta ccgcgacagc cgcgacccg tgtgaaggg    4200
ccccgccaag ctgctgtgga agggcgaggg cgccgtggtg atccaggaca cagcgacat    4260
caaggtggtg ccccgccgca aggccaagat catccgcgac tacggcaagc agatggccgg    4320
cgacgactgc gtggccagcc gccaggacga ggactaggaa ttctgctgtg ccttctagtt    4380
gccagccatc tgttgtttgc ccctccccg tgccttcctt gaccctggaa ggtgccactc    4440
ccactgtcct ttcctaataa aatgaggaaa ttgcatcgca ttgtctgagt aggtgtcatt    4500
ctattctggg gggtggggtg gggcaggaca gcaaggggga ggattgggaa gacaatagca    4560
ggcatgctgg ggatgcggtg ggctctatgg gtacccaggt gctgaagaat tgacccggtt    4620
cctcctgggc cagaaagaag caggcacatc cccttctctg tgacacaccc tgtccacgcc    4680
cctggttctt agttccagcc ccactcatag gacactcata gctcaggagg gctccgcctt    4740
caatcccacc cgctaaagta cttggagcgg tctctccctc cctcatcagc ccaccaaacc    4800
aaacctagcc tccaagagtg ggaagaaatt aaagcaagat aggctattaa gtgcagaggg    4860
agagaaaatg cctccaacat gtgaggaagt aatgagagaa atcatagaat tcttccgct    4920
tcctcgctca ctgactcgct gcgctcggtc gttcggctgc ggcgagcggt atcagctcac    4980
tcaaaggcgg taatacggtt atccacagaa tcagggata acgcaggaaa gaacatgtga    5040
gcaaaaggcc agcaaaaggc caggaaccgt aaaaaggccg cgttgctggc gttttcat    5100
aggctccgcc cccctgacga gcatcacaaa atcgacgct caagtcagag gtggcgaaac    5160
ccgacaggac tataaagata ccaggcgttt cccctggaa gctccctcgt gcgctctcct    5220
gttccgaccc tgccgcttac cggatacctg tccgcctttc tcccttcggg aagcgtggcg    5280
ctttctcata gctcacgctg taggtatctc agttcggtgt aggtcgttcg ctccaagctg    5340
ggctgtgtgc acgaaccccc cgttcagccc gaccgctgcg ccttatccgg taactatcgt    5400
cttgagtcca acccggtaag acacgactta tcgccactgg cagcagccac tggtaacagg    5460
attagcagag cgaggtatgt aggcggtgct acagagttct tgaagtggtg gcctaactac    5520
ggctacacta gaagaacagt atttggtatc tgcgctctgc tgaagccagt taccttcgga    5580
aaaagagttg gtagctcttg atccggcaaa caaaccaccg ctggtagcgg tggttttttt    5640
gtttgcaagc agcagattac gcgcagaaaa aaaggatctc aagaagatcc tttgatcttt    5700
tctacggggt ctgacgctca gtggaacgaa aactcacgtt aagggatttt ggtcatgaga    5760
ttatcaaaaa ggatcttcac ctagatcctt ttaaattaaa aatgaagttt taaatcaatc    5820
taaagtatat atgagtaaac ttggtctgac agttaccaat gcttaatcag tgaggcacct    5880
atctcagcga tctgtctatt tcgttcatcc atagttgcct gactcggggg gggggggcgc    5940
tgaggtctgc ctcgtgaaga aggtgttgct gactcatacc aggcctgaat cgccccatca    6000
```

-continued

| | |
|---|---|
| tccagccaga aagtgaggga gccacggttg atgagagctt tgttgtaggt ggaccagttg | 6060 |
| gtgattttga acttttgctt tgccacggaa cggtctgcgt tgtcgggaag atgcgtgatc | 6120 |
| tgatccttca actcagcaaa agttcgattt attcaacaaa gccgccgtcc cgtcaagtca | 6180 |
| gcgtaatgct ctgccagtgt tacaaccaat taaccaattc tgattagaaa aactcatcga | 6240 |
| gcatcaaatg aaactgcaat ttattcatat caggattatc aataccatat ttttgaaaaa | 6300 |
| gccgtttctg taatgaagga gaaaactcac cgaggcagtt ccataggatg caagatcct | 6360 |
| ggtatcggtc tgcgattccg actcgtccaa catcaataca acctattaat ttcccctcgt | 6420 |
| caaaaataag gttatcaagt gagaaatcac catgagtgac gactgaatcc ggtgagaatg | 6480 |
| gcaaaagctt atgcatttct ttccagactt gttcaacagg ccagccatta cgctcgtcat | 6540 |
| caaaatcact cgcatcaacc aaaccgttat tcattcgtga ttgcgcctga gcgagacgaa | 6600 |
| atacgcgatc gctgttaaaa ggacaattac aaacaggaat cgaatgcaac cggcgcagga | 6660 |
| acactgccag cgcatcaaca atattttcac ctgaatcagg atattcttct aatacctgga | 6720 |
| atgctgtttt cccggggatc gcagtggtga gtaaccatgc atcatcagga gtacggataa | 6780 |
| aatgcttgat ggtcggaaga ggcataaatt ccgtcagcca gtttagtctg accatctcat | 6840 |
| ctgtaacatc attggcaacg ctacctttgc catgtttcag aaacaactct ggcgcatcgg | 6900 |
| gcttcccata caatcgatag attgtcgcac ctgattgccc gacattatcg cgagcccatt | 6960 |
| tatacccata taaatcagca tccatgttgg aatttaatcg cggcctcgag caagacgttt | 7020 |
| cccgttgaat atggctcata caccccttg tattactgtt tatgtaagca gacagtttta | 7080 |
| ttgttcatga tgatatattt ttatcttgtg caatgtaaca tcagagattt tgagacacaa | 7140 |
| cgtggctttc ccccccccc cattattgaa gcatttatca gggttattgt ctcatgagcg | 7200 |
| gatacatatt tgaatgtatt tagaaaaata acaaataggg gttccgcgc acatttcccc | 7260 |
| gaaaagtgcc acctgacgtc taagaaacca ttattatcat gacattaacc tataaaaata | 7320 |
| ggcgtatcac gaggcccttt cgtc | 7344 |

<210> SEQ ID NO 3
<211> LENGTH: 5039
<212> TYPE: DNA
<213> ORGANISM: Artificial Sequence
<220> FEATURE:
<223> OTHER INFORMATION: plasmid VRC4404

<400> SEQUENCE: 3

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg agcctacct agactcagcc ggctctccac gctttgcctg    1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagag   1380
atatcgccgc catgaagtgg agcaagagca cgtgatcgg ctggcccgcc gtgcgcgagc    1440
gcatgcgccg cgccgagccc gccgccgacg gcgtgggcgc cgtgagccgc gacctggaga   1500
agcacgcgc catcaccagc agcaacaccg ccgccaacaa cgccgcctgc gcctggctgg    1560
aggcccagga ggaggaggag gtgggcttcc ccgtgacccc ccaggtgccc ctgcgcccca   1620
tgacctacaa ggccgccgtg gacctgagcc acttcctgaa ggagaagggc ggcctggagg   1680
gcctgatcca cagccagcgc cgccaggaca tcctggacct gtggatctac cacacccagg   1740
gctacttccc cgactggcag aactacaccc ccggccccgg cgtgcgctac cccctgacct   1800
tcggctggtg ctacaagctg gtgcccgtgg agcccgacaa ggtggaggag gccaacaagg   1860
gcgagaacac cagcctgctg cacccccgtga gcctgcacgg catggacgac cccgagcgcg   1920
aggtgctgga gtggcgcttc gacagccgcc tggccttcca ccacgtggcc cgcgagctgc   1980
accccgagta cttcaagaac tgctgaacac gtgggatcca gatctgctgt gccttctagt   2040
tgccagccat ctgttgtttg cccctccccc gtgccttcct tgaccctgga aggtgccact   2100
cccactgtcc tttcctaata aaatgaggaa attgcatcgc attgtctgag taggtgtcat   2160
tctattctgg ggggtgggt ggggcaggac agcaagggg aggattggga agacaatagc     2220
aggcatgctg gggatgcggt gggctctatg ggtacccagg tgctgaagaa ttgacccggt   2280
tcctcctggg ccagaaagaa gcaggcacat ccccttctct gtgacacacc ctgtccacgc   2340
ccctggttct tagttccagc cccactcata ggacactcat agctcaggag gctccgcct    2400
tcaatcccac ccgctaaagt acttggagcg gtctctccct ccctcatcag cccaccaaac   2460
caaacctagc ctccaagagt gggaagaaat taaagcaaga taggctatta agtgcagagg   2520
gagagaaaat gcctccaaca tgtgaggaag taatgagaga aatcatagaa ttttaaggcc   2580
atgatttaag gccatcatgg ccttaatctt ccgcttcctc gctcactgac tcgctgcgct   2640
cggtcgttcg gctgcggcga gcggtatcag ctcactcaaa ggcggtaata cggttatcca   2700
cagaatcagg ggataacgca ggaaagaaca tgtgagcaaa aggccagcaa aaggccagga   2760
accgtaaaaa ggccgcgttg ctggcgtttt tccataggct ccgcccccct gacgagcatc   2820
acaaaaatcg acgctcaagt cagaggtggc gaaacccgac aggactataa agataccagg   2880
cgtttccccc tggaagctcc ctcgtgcgct ctcctgttcc gaccctgccg cttaccggat   2940
acctgtccgc ctttctccct tcgggaagcg tggcgctttc tcatagctca cgctgtaggt   3000
atctcagttc ggtgtaggtc gttcgctcca agctgggctg tgtgcacgaa ccccccgttc   3060
agcccgaccg ctgcgcctta tccggtaact atcgtcttga gtccaacccg gtaagacacg   3120
```

```
acttatcgcc actggcagca gccactggta acaggattag cagagcgagg tatgtaggcg   3180
gtgctacaga gttcttgaag tggtggccta actacggcta cactagaaga acagtatttg   3240
gtatctgcgc tctgctgaag ccagttacct tcggaaaaag agttggtagc tcttgatccg   3300
gcaaacaaac caccgctggt agcggtggtt ttttgtttg caagcagcag attacgcgca    3360
gaaaaaagg atctcaagaa gatcctttga tctttctac ggggtctgac gctcagtgga     3420
acgaaaactc acgttaaggg attttggtca tgagattatc aaaaggatc ttcacctaga    3480
tccttttaaa ttaaaaatga agttttaaat caatctaaag tatatatgag taaacttggt   3540
ctgacagtta ccaatgctta atcagtgagg cacctatctc agcgatctgt ctatttcgtt   3600
catccatagt tgcctgactc ggggggggg ggcgctgagg tctgcctcgt gaagaaggtg    3660
ttgctgactc ataccaggcc tgaatcgccc catcatccag ccagaaagtg agggagccac   3720
ggttgatgag agctttgttg taggtggacc agttggtgat tttgaacttt tgctttgcca   3780
cggaacggtc tgcgttgtcg ggaagatgcg tgatctgatc cttcaactca gcaaaagttc   3840
gatttattca acaaagccgc cgtcccgtca agtcagcgta atgctctgcc agtgttacaa   3900
ccaattaacc aattctgatt agaaaaactc atcgagcatc aaatgaaact gcaatttatt   3960
catatcagga ttatcaatac catattttg aaaaagccgt ttctgtaatg aaggagaaaa    4020
ctcaccgagg cagttccata ggatggcaag atcctggtat cggtctgcga ttccgactcg   4080
tccaacatca atacaaccta ttaatttccc ctcgtcaaaa ataaggttat caagtgagaa   4140
atcaccatga gtgacgactg aatccggtga gaatggcaaa agcttatgca tttctttcca   4200
gacttgttca acaggccagc cattacgctc gtcatcaaaa tcactcgcat caaccaaacc   4260
gttattcatt cgtgattgcg cctgagcgag acgaaatacg cgatcgctgt taaaaggaca   4320
attacaaaca ggaatcgaat gcaaccggcg caggaacact gccagcgcat caacaatatt   4380
ttcacctgaa tcaggatatt cttctaaatac ctggaatgct gttttcccgg ggatcgcagt   4440
ggtgagtaac catgcatcat caggagtacg dataaaatgc ttgatggtcg gaagaggcat   4500
aaattccgtc agccagttta gtctgaccat ctcatctgta acatcattgg caacgctacc   4560
tttgccatgt ttcagaaaca actctggcgc atcgggcttc ccatacaatc gatagattgt   4620
cgcacctgat tgcccgacat tatcgcgagc ccatttatac ccatataaat cagcatccat   4680
gttggaattt aatcgcggcc tcgagcaaga cgtttcccgt tgaatatggc tcataacacc   4740
ccttgtatta ctgtttatgt aagcagacag ttttattgtt catgatgata tatttttatc   4800
ttgtgcaatg taacatcaga gattttgaga cacaacgtgg ctttcccccc cccccatta    4860
ttgaagcatt tatcagggtt attgtctcat gagcggatac atatttgaat gtatttagaa   4920
aaataaacaa atagggttc cgcgcacatt tccccgaaaa gtgccacctg acgtctaaga    4980
aaccattatt atcatgacat taacctataa aaataggcgt atcacgaggc cctttcgtc    5039
```

<210> SEQ ID NO 4
<211> LENGTH: 6305
<212> TYPE: DNA
<213> ORGANISM: Artificial Sequence
<220> FEATURE:
<223> OTHER INFORMATION: plasmid VRC5736

<400> SEQUENCE: 4

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
```

```
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgaccccg cccattgacg tcaataatga cgtatgttcc       480
catagtaacg ccaataggga ctttccattg acgtcaatgg gtggagtatt tacggtaaac      540
tgcccacttg gcagtacatc aagtgtatca tatgccaagt acgcccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctcca tcggctcgca tctctccttc acgcgcccgc     1020
cgccctacct gaggccgcca tccacgccgg ttgagtcgcg ttctgccgcc tcccgcctgt     1080
ggtgcctcct gaactgcgtc cgccgtctag gtaagtttaa agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacac gtgtgatcag atatcgcggc cgctctagag     1380
atatcgccac catgcgcgtg cgcggcatcc agaccagctg gcagaacctg tggcgctggg     1440
gcaccatgat cctgggcatg ctggtgatct acagcgccgc cgagaacctg tgggtggccg     1500
tgtactacgg cgtgccgtg tggaaggacg ccgagaccac cctgttctgc gccagcgacg      1560
ccaaggccta cgacaccgag gtgcacaacg tgtgggagac ccacgcctgc gtgcccaccg     1620
accccaaccc ccaggagatc cacctggaga acgtgaccga ggcttcaac atgtggcgca      1680 acaacatggt ggagcagatg cacaccgaca tcatcagcct gtgggaccag agcctgaagc     1740
cctgcgtgaa gctgacccc ctgtgcgtga ccctggactg caacgccacc gccagcaacg      1800
tgaccaacga gatgcgcaac tgtagcttca acatcaccac cgagctgaag gacaagaagc     1860
agcaggtgta cagcctgttc tacaagctgg acgtggtgca gatcaacgag aagaacgaga     1920
ccgacaagta ccgcctgatc aactgcaaca ccagcgccat cacccaggcc tgccccaagg     1980
tgagcttcga gcccatcccc atccactact gcgccccgc cggcttcgcc atcctgaagt      2040
gcaaggacac cgagttcaac ggtaccggcc cctgcaagaa cgtgagcacc gtgcagtgca     2100
cccacggcat ccgaccggtg atcagcaccc agctgctgct gaacggcagc ctggccgagg     2160
agggcatcca gatccgcagc gagaacatca ccaacaacgc caagaccatc atcgtgcagc     2220
tggataaggc cgtgaagatc aactgcaccc gccccaacaa caacacccgc aagggcgtgc     2280
gcatcggccc cggccaggcc ttctacgcca ccggcggcat catcggcgac atccgccagg     2340
cccactgcca cgtgagccgc gccaagtgga acgacaccct cgcggcgtg gccaagaagc      2400 tgcgcgagca cttcaagaac aagaccatca tcttcgagaa gagcagcggc ggcgacatcg     2460
agatcaccac ccacagcttc atctgcgggcg gcgagttctt ctactgcaac accagcggcc     2520
tgttcaacag cacctgggag agcaacagca ccgagagcaa caacaccacc agcaacgaca     2580
```

```
ccatcaccct gacctgccgc atcaagcaga tcatcaacat gtggcagaag gtgggccagg      2640
ccatgtaccc cccccccatc cagggcgtga tccgctgcga gagcaacatc accggcctgc      2700
tgctgacccg cgacggcggc aacaacagca ccaacgagat cttccgcccc ggcggcggca      2760
acatgcgcga caactggcgc agcgagctgt acaagtacaa ggtggtgaag atcgagcccc      2820
tgggcgtggc ccccagccgc gccaagctta ccgcccaggc ccgccagctg ctgagcggca      2880
tcgtgcagca gcagagcaac ctgctgcgcg ccatcgaggc ccagcagcac atgctgaagc      2940
tgaccgtgtg gggcatcaag cagctgcagg cccgcgtgct ggccgtggag cgctacctga      3000
aggaccagca gctcgagatc tgggacaaca tgacctggct gcagtgggac aaggagatca      3060
gcaactacac ccagatcatc tacaacctga tcgaggagag ccagaaccag caggagaaga      3120
acgagcagga cctgctggcc ctggacaagt gggccagcct gtggaactgg ttcgacatca      3180
gccgctggct gtggtacatc aagatcttca tcatgatcgt gggcggcctg atcggcctgc      3240
gcatcgtgtt cgccgtgctg agcgtgatct gaacacgtgg gatccagatc tgctgtgcct      3300
tctagttgcc agccatctgt tgtttgcccc tcccccgtgc cttccttgac cctggaaggt      3360
gccactccca ctgtcctttc ctaataaaat gaggaaattg catcgcattg tctgagtagg      3420
tgtcattcta ttctgggggg tggggtgggg caggacagca agggggagga ttgggaagac      3480
aatagcaggc atgctgggga tgcggtgggc tctatgggta cccaggtgct gaagaattga      3540
cccggttcct cctgggccag aaagaagcag gcacatcccc ttctctgtga cacaccctgt      3600
ccacgccccc ggttcttagt tccagcccca ctcataggac actcatagct caggagggct      3660
ccgccttcaa tcccacccgc taaagtactt ggagcggtct ctccctccct catcagccca      3720
ccaaaccaaa cctagcctcc aagagtggga agaaattaaa gcaagatagg ctattaagtg      3780
cagagggaga gaaaatgcct ccaacatgtg aggaagtaat gagagaaatc atagaatttt      3840
aaggccatga tttaaggcca tcatggcctt aatcttccgc ttcctcgctc actgactcgc      3900
tgcgctcggt cgttcggctg cggcgagcgg tatcagctca ctcaaaggcg gtaatacggt      3960
tatccacaga atcaggggat aacgcaggaa agaacatgtg agcaaaaggc cagcaaaagg      4020
ccaggaaccg taaaaaggcc gcgttgctgg cgttttccca taggctccgc cccctgacg      4080 agcatcacaa aaatcgacgc tcaagtcaga ggtggcgaaa cccgacagga ctataaagat      4140
accaggcgtt tccccctgga agctccctcg tgcgctctcc tgttccgacc ctgccgctta      4200
ccggatacct gtccgccttt ctcccttcgg gaagcgtggc gctttctcat agctcacgct      4260
gtaggtatct cagttcggtg taggtcgttc gctccaagct gggctgtgtg cacgaacccc      4320
ccgttcagcc cgaccgctgc gccttatccg gtaactatcg tcttgagtcc aacccggtaa      4380
gacacgactt atcgccactg gcagcagcca ctggtaacag gattagcaga gcgaggtatg      4440
taggcggtgc tacagagttc ttgaagtggt ggcctaacta cggctacact agaagaacag      4500
tatttggtat ctgcgctctg ctgaagccag ttaccttcgg aaaaagagtt ggtagctctt      4560
gatccggcaa acaaaccacc gctggtagcg tggttttttt gtttgcaag cagcagatta      4620 cgcgcagaaa aaaaggatct caagaagatc ctttgatctt ttctacgggg tctgacgctc      4680
agtggaacga aaactcacgt taagggattt tggtcatgag attatcaaaa aggatcttca      4740
cctagatccc tttaaattaa aaatgaagtt ttaaatcaat ctaaagtata tatgagtaaa      4800
cttggtctga cagttaccaa tgcttaatca gtgaggcacc tatctcagcg atctgtctat      4860
ttcgttcatc catagttgcc tgactcgggg gggggggcg ctgaggtctg cctcgtgaag      4920
aaggtgttgc tgactcatac caggcctgaa tcgccccatc atccagccag aaagtgaggg      4980
```

```
agccacggtt gatgagagct tgttgtagg tggaccagtt ggtgattttg aacttttgct      5040
ttgccacgga acggtctgcg ttgtcgggaa gatgcgtgat ctgatccttc aactcagcaa      5100
aagttcgatt tattcaacaa agccgccgtc ccgtcaagtc agcgtaatgc tctgccagtg      5160
ttacaaccaa ttaaccaatt ctgattagaa aaactcatcg agcatcaaat gaaactgcaa      5220
tttattcata tcaggattat caataccata tttttgaaaa agccgtttct gtaatgaagg      5280
agaaaactca ccgaggcagt tccataggat ggcaagatcc tggtatcggt ctgcgattcc      5340
gactcgtcca acatcaatac aacctattaa tttcccctcg tcaaaaataa ggttatcaag      5400
tgagaaatca ccatgagtga cgactgaatc cggtgagaat ggcaaaagct tatgcatttc      5460
tttccagact tgttcaacag gccagccatt acgctcgtca tcaaaatcac tcgcatcaac      5520
caaaccgtta ttcattcgtg attgcgcctg agcgagacga atacgcgat cgctgttaaa       5580 aggacaatta caaacaggaa tcgaatgcaa ccggcgcagg aacactgcca gcgcatcaac      5640
aatattttca cctgaatcag gatattcttc taatacctgg aatgctgttt tcccggggat      5700
cgcagtggtg agtaaccatg catcatcagg agtacggata aaatgcttga tggtcggaag      5760
aggcataaat tccgtcagcc agtttagtct gaccatctca tctgtaacat cattggcaac      5820
gctacctttg ccatgtttca gaaacaactc tggcgcatcg gcttcccat acaatcgata       5880 gattgtcgca cctgattgcc cgacattatc gcgagcccat ttatacccat ataaatcagc      5940
atccatgttg gaatttaatc gcggcctcga gcaagacgtt cccgttgaa tatggctcat       6000 aacacccctt gtattactgt ttatgtaagc agacagtttt attgttcatg atgatatatt      6060
tttatcttgt gcaatgtaac atcagagatt ttgagacaca acgtggcttt ccccccccc       6120 ccattattga agcatttatc agggttattg tctcatgagc ggatacatat ttgaatgtat      6180
ttagaaaaat aaacaaatag gggttccgcg cacatttccc cgaaaagtgc cacctgacgt      6240
ctaagaaacc attattatca tgacattaac ctataaaaat aggcgtatca cgaggccctt      6300
tcgtc                                                                   6305
```

<210> SEQ ID NO 5
<211> LENGTH: 6338
<212> TYPE: DNA
<213> ORGANISM: Artificial Sequence
<220> FEATURE:
<223> OTHER INFORMATION: plasmid VRC5737

<400> SEQUENCE: 5

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
catagtaacg ccaataggga ctttccattg acgtcaatgg gtggagtatt tacggtaaac       540
tgcccacttg gcagtacatc aagtgtatca tatgccaagt acgcccccta ttgacgtcaa       600
tgacggtaaa tggcccgcct ggcattatgc ccagtacatg accttatggg actttcctac       660
ttggcagtac atctacgtat tagtcatcgc tattaccatg gtgatgcggt tttggcagta       720
```

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatgcgcg tgaaggagaa gtaccagcac ctgtggcgct ggggctggcg ctggggcacc   1440
atgctgctgg gcatgctgat gatctgcagc gccaccgaga agctgtgggt gaccgtgtac   1500
tacgccgtgc ccgtgtggaa ggaggccacc accaccctgc tctgcgccag cgacgccaag   1560
gcctacgaca ccgaggtgca acgtgtgtgg gccacccacg cctgcgtgcc caccgacccc   1620
aaccccagg aggtggtgct ggtgaacgtg accgagaact tcgacatgtg gaagaacgac   1680
atggtggagc agatgcacga ggacatcatc agcctgtggg accagagcct gaagccctgc   1740
gtgaagctga ccccccctgtg cgtgagcctg aagtgcaccg acctgaagaa cgacaccaac   1800
accaacagca gcagcggccg catgatcatg gagaagggcg agatcaagaa ctgcagcttc   1860
aacatcagca ccagcatccg cggcaaggtg cagaaggagt acgccttctt ctacaagctg   1920
gacatcatcc ccatcgacaa cgacaccacc agctacagcc tgaccagctg caacaccagc   1980
gtgatcaccc aggcctgccc caaggtgagc ttcgagccca tccccaacca ctactgcgcc   2040
cccgccggct cgccatcct gaagtgcaag gacaagaagt tcaacggcaa gggccccctgc   2100
accaacgtga gcaccgtgca gtgcacccac ggcatccgcc cgtggtgag cacccagctg   2160
ctggttacgg gtaacctggc cgaggaggag gtggtgatcc gcagcgctaa cttcgccgac   2220
aacgccaagg tgatcatcgt gcagctgaac gagagcgtgg agatcaactg cacccgcccc   2280
aacaacaaca cccgcaagag catccacatc ggccccggcc gcgccttcta caccaccggc   2340
gagatcatcg gcgacatccg ccaggcccac tgcaacctga gccgcgccaa gtggaacgac   2400
accctgaaca agatcgtgat caagctgcgc gagcagttcg gcaacaagac catcgtgttc   2460
aagcacagca gcggcggcga ccccgagatc gtgacccaca gcttcaactg cggcggcgag   2520
ttcttctact gcaacagcac ccagctgttc aacagcacct ggttcaacag cacctggagc   2580
accgagggca gcaacaacac cgagggcagc gacaccatca ccctgccctg ccgcatcaag   2640
cagatcatca catgtggca aaggtgggc aaggccatgt acgccccccc catcagcggc   2700
cagatccgct gcagcagcaa catcaccggc ctgctgctga cccgcgacgg cggcaacagc   2760
aacaacgaga gcgagatctt ccgcctgggc ggcggcgaca tgcgcgacaa ctggcgcagc   2820
gagctgtaca gtacaaggt ggtgaagatc gagcccctgg gcgtggcccc caccaaggcc   2880
aagcttaccg tccaggcccg ccagctgctg agcggcatcg tgcagcagca gaacaacctg   2940
ctgcgcgcca tcgaggccca gcagcacctg ctgcagctga ccgtgtgggg catcaagcag   3000
ctgcaggccc gcaccctggc cgtggagcgc tacctgaagg accagcagct gctcgagcag   3060
atctggaacc acaccacctg gatggagtgg gaccgcgaga tcaacaacta caccagcctg   3120
```

```
atccacagcc tgatcgagga gagccagaac cagcacgaga agaacgagca ggagctgctg    3180
gagctggaca agtgggccag cctgtggaac tggttcaaca tcaccaactg gctgtggtac    3240
atcaagctgt tcatcatgat cgtgggcggc ctggtgggcc tgcgcatcgt gttcgccgtg    3300
ctgagcatct gaggatccag atctgctgtg ccttctagtt gccagccatc tgttgtttgc    3360
ccctcccccg tgccttcctt gaccctggaa ggtgccactc ccactgtcct ttcctaataa    3420
aatgaggaaa ttgcatcgca ttgtctgagt aggtgtcatt ctattctggg gggtggggtg    3480
gggcaggaca gcaaggggga ggattgggaa gacaatagca ggcatgctgg ggatgcggtg    3540
ggctctatgg gtacccaggt gctgaagaat tgacccggtt cctcctgggc cagaaagaag    3600
caggcacatc cccttctctg tgacacaccc tgtccacgcc cctggttctt agttccagcc    3660
ccactcatag gacactcata gctcaggagg gctccgcctt caatcccacc cgctaaagta    3720
cttggagcgg tctctccctc cctcatcagc ccaccaaacc aaacctagcc tccaagagtg    3780
ggaagaaatt aaagcaagat aggctattaa gtgcagaggg agagaaaatg cctccaacat    3840
gtgaggaagt aatgagagaa atcatagaat tttaaggcca tgatttaagg ccatcatggc    3900
cttaatcttc cgcttcctcg ctcactgact cgctgcgctc ggtcgttcgg ctgcggcgag    3960
cggtatcagc tcactcaaag gcggtaatac ggttatccac agaatcaggg gataacgcag    4020
gaaagaacat gtgagcaaaa ggccagcaaa aggccaggaa ccgtaaaaag gccgcgttgc    4080
tggcgttttt ccataggctc cgcccccctg acgagcatca caaaaatcga cgctcaagtc    4140
agaggtggcg aaacccgaca ggactataaa gataccaggc gtttccccct ggaagctccc    4200
tcgtgcgctc tcctgttccg accctgccgc ttaccggata cctgtccgcc tttctccctt    4260
cgggaagcgt ggcgctttct catagctcac gctgtaggta tctcagttcg gtgtaggtcg    4320
ttcgctccaa gctgggctgt gtgcacgaac cccccgttca gcccgaccgc tgcgccttat    4380
ccggtaacta tcgtcttgag tccaacccgg taagacacga cttatcgcca ctggcagcag    4440
ccactggtaa caggattagc agagcgaggt atgtaggcgg tgctacagag ttcttgaagt    4500
ggtggcctaa ctacggctac actagaagaa cagtatttgg tatctgcgct ctgctgaagc    4560
cagttacctt cggaaaaaga gttggtagct cttgatccgg caaacaaacc accgctggta    4620
gcggtggttt ttttgtttgc aagcagcaga ttacgcgcag aaaaaaagga tctcaagaag    4680
atcctttgat cttttctacg gggtctgacg ctcagtggaa cgaaaactca cgttaaggga    4740
ttttggtcat gagattatca aaaaggatct tcacctagat ccttttaaat taaaaatgaa    4800
gttttaaatc aatctaaagt atatatgagt aaacttggtc tgacagttac caatgcttaa    4860
tcagtgaggc acctatctca gcgatctgtc tatttcgttc atccatagtt gcctgactcg    4920
ggggggggggg gcgctgaggt ctgcctcgtg aagaaggtgt tgctgactca taccaggcct    4980
gaatcgcccc atcatccagc cagaaagtga gggagccacg gttgatgaga gctttgttgt    5040
aggtggacca gttggtgatt ttgaactttt gctttgccac ggaacggtct gcgttgtcgg    5100
gaagatgcgt gatctgatcc ttcaactcag caaaagttcg atttattcaa caaagccgcc    5160
gtcccgtcaa gtcagcgtaa tgctctgcca gtgttacaac caattaacca attctgatta    5220
gaaaaactca tcgagcatca atgaaactgc aatttattca tatcaggat tatcaatacc    5280
atatttttga aaagccgttt ctgtaatga aggagaaaac tcaccgaggc agttccatag    5340
gatggcaaga tcctggtatc ggtctgcgat tccgactcgt ccaacatcaa tacaacctat    5400
taatttcccc tcgtcaaaaa taaggttatc aagtgagaaa tcaccatgag tgacgactga    5460
atccggtgag aatggcaaaa gcttatgcat ttctttccag acttgttcaa caggccagcc    5520
```

```
attacgctcg tcatcaaaat cactcgcatc aaccaaaccg ttattcattc gtgattgcgc    5580
ctgagcgaga cgaaatacgc gatcgctgtt aaaaggacaa ttacaaacag gaatcgaatg    5640
caaccggcgc aggaacactg ccagcgcatc aacaatattt tcacctgaat caggatattc    5700
ttctaatacc tggaatgctg ttttcccggg gatcgcagtg gtgagtaacc atgcatcatc    5760
aggagtacgg ataaaatgct tgatggtcgg aagaggcata aattccgtca gccagtttag    5820
tctgaccatc tcatctgtaa catcattggc aacgctacct ttgccatgtt tcagaaacaa    5880
ctctggcgca tcgggcttcc catacaatcg atagattgtc gcacctgatt gcccgacatt    5940
atcgcgagcc catttatacc catataaatc agcatccatg ttggaattta atcgcggcct    6000
cgagcaagac gtttcccgtt gaatatggct cataacaccc cttgtattac tgtttatgta    6060
agcagacagt tttattgttc atgatgatat attttatct tgtgcaatgt aacatcagag    6120
attttgagac acaacgtggc tttcccccccc ccccattat tgaagcattt atcagggtta    6180
ttgtctcatg agcggataca tatttgaatg tatttagaaa aataaacaaa tagggggttcc    6240 gcgcacattt ccccgaaaag tgccacctga cgtctaagaa accattatta tcatgacatt    6300
aacctataaa aataggcgta tcacgaggcc ctttcgtc                             6338

<210> SEQ ID NO 6
<211> LENGTH: 6298
<212> TYPE: DNA
<213> ORGANISM: Artificial Sequence
<220> FEATURE:
<223> OTHER INFORMATION: plasmid VRC5738

<400> SEQUENCE: 6
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc gccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg agggcagtg tagtctgagc agtactcgtt    1260
```

-continued

```
gctgccgcgc gcgccaccag acataatagc tgacagacta acagactgtt cctttccatg      1320
ggtcttttct gcagtcaccg tcgtcgacac gtgtgatcag atatcgcggc cgctctagag      1380
atatcgccac catgcgtgtt cgtggtatcc cgcgtaactg gccgcagtgg tggatgtggg      1440
gtatcctggg tttctggatg atcatcatct gccgtgttgt tggtaacatg tgggttaccg      1500
tttactacgg tgttccggtt tggaccgacg ctaaaaccac cctgttctgc gcttccgaca      1560
ccaaagccta cgaccgtgaa gttcacaacg tttgggctac ccacgcttgc gttccgaccg      1620
acccgaaccc gcaggaaatc gttctggaaa cgttaccga aaacttcaac atgtggaaaa      1680
acgacatggt tgaccagatg cacgaagaca tcatctccct gtgggaccag tccctgaaac      1740
cgtgcgttaa actgaccccg ctgtgcgtta ccctgcactg caccaacgct accttcaaaa      1800
acaacgttac caacgacatg aacaaagaaa tccgtaactg ctccttcaac accaccaccg      1860
aaatccgtga caaaaaacag cagggttacg ctctgttcta ccgtccggac atcgttctgc      1920
tgaaagaaaa ccgtaacaac tccaacaact ccgaatacat cctgatcaac tgcaacgctt      1980
ccaccatcac ccaggcttgc cgaaagtta acttcgaccc gatcccgatc cactactgcg      2040
ctccggctgg ttacgctatc ctgaaatgca acaacaaaac cttctccggt aaaggtccgt      2100
gcaacaacgt ttccaccgtt cagtgcaccc atggtatcaa accggttgtt tccacccagc      2160
tgctgctgaa cggttccctg ctgaaaaag aaatcatcat ccgttccgaa acctgaccg      2220 acaacgttaa aaccatcatc gttcacctga acaaatccgt tgaaatcgtt tgcacccgtc      2280
cgaacaacaa cacccgtaaa tccatgcgta tcggtccggg tcagaccttc tacgctaccg      2340
gtgacatcat cggtgacatc cgtcaggctt actgcaacat ctccggttcc aaatggaacg      2400
aaaccctgaa acgtgttaaa gaaaactgc aggaaaacta caacaacaac aaaaccatca      2460
aattcgctcc gtcctccggt ggtgacctgg aaatcaccac ccactccttc aactgccgtg      2520
gtgaattctt ctactgcaac accacccgtc tgttcaacaa caacgctacc gaagacgaaa      2580
ccatcaccct gccgtgccgt atcaaacaga tcatcaacat gtggcagggt gttggtcgtg      2640
ctatgtacgc tccgccgatc gctggtaaca tcacctgcaa atccaacatc accggtctgc      2700
tgctggttcg tgacggtggt gaagacaaca aaaccgaaga atcttccgt ccgggtggtg      2760 gtaacatgaa agacaactgg cgttccgaac tgtacaaata caagttatc gaactgaaac      2820 cgctgggtat cgctccgacc ggtgctaagc ttaccgttca ggctcgtcag ctgctgtcct      2880
ccatcgttca gcagcagtcc aacctgctgc gtgctatcga agctcagcag cacatgctgc      2940
agctgaccgt ttggggtatc aaacagctgc agacccgtgt tctggctatc gaacgttacc      3000
tgaaagacca gcagctcgag atctggaaca acatgacctg gatggaatgg gaccgtgaaa      3060
tctccaacta caccgacacc atctaccgtc tgctggaaga ctcccagacc cagcaggaaa      3120
aaaacgaaaa agacctgctg ctctggact cctggaaaaa cctgtggtcc tggttcgaca      3180
tctccaactg gctgtggtac atcaaaatct tcatcatgat cgttggtggt ctgatcggtc      3240
tgcgtatcat cttcgctgtt ctgtccatct gaggatccag atctgctgtg ccttctagtt      3300
gccagccatc tgttgtttgc ccctcccccg tgccttcctt gaccctggaa ggtgccactc      3360
ccactgtcct ttcctaataa aatgaggaaa ttgcatcgca ttgtctgagt aggtgtcatt      3420
ctattctggg gggtggggtg ggcaggaca gcaggggga ggattgggaa gacaatagca      3480
ggcatgctgg ggatgcggtg ggctctatgg gtacccaggt gctgaagaat tgaccggtt      3540 cctcctgggc cagaaagaag caggcacatc cccttctctg tgcacaccc tgtcacgcc      3600 cctggttctt agttccagcc ccactcatag gacactcata gctcaggagg gctccgcctt      3660
```

```
caatcccacc cgctaaagta cttggagcgg tctctccctc cctcatcagc ccaccaaacc   3720
aaacctagcc tccaagagtg ggaagaaatt aaagcaagat aggctattaa gtgcagaggg   3780
agagaaaatg cctccaacat gtgaggaagt aatgagagaa atcatagaat tttaaggcca   3840
tgatttaagg ccatcatggc cttaatcttc cgcttcctcg ctcactgact cgctgcgctc   3900
ggtcgttcgg ctgcggcgag cggtatcagc tcactcaaag gcggtaatac ggttatccac   3960
agaatcaggg gataacgcag gaaagaacat gtgagcaaaa ggccagcaaa aggccaggaa   4020
ccgtaaaaag gccgcgttgc tggcgttttt ccataggctc cgcccccctg acgagcatca   4080
caaaaatcga cgctcaagtc agaggtggcg aaacccgaca ggactataaa gataccaggc   4140
gtttccccct ggaagctccc tcgtgcgctc tcctgttccg accctgccgc ttaccggata   4200
cctgtccgcc tttctccctt cgggaagcgt ggcgctttct catagctcac gctgtaggta   4260
tctcagttcg gtgtaggtcg ttcgctccaa gctgggctgt gtgcacgaac cccccgttca   4320
gcccgaccgc tgcgccttat ccggtaacta tcgtcttgag tccaacccgg taagacacga   4380
cttatcgcca ctggcagcag ccactggtaa caggattagc agagcgaggt atgtaggcgg   4440
tgctacagag ttcttgaagt ggtggcctaa ctacggctac actagaagaa cagtatttgg   4500
tatctgcgct ctgctgaagc cagttacctt cggaaaaaga gttggtagct cttgatccgg   4560
caaacaaacc accgctggta gcggtggttt ttttgtttgc aagcagcaga ttacgcgcag   4620
aaaaaaagga tctcaagaag atcctttgat cttttctacg gggtctgacg ctcagtggaa   4680
cgaaaactca cgttaaggga ttttggtcat gagattatca aaaaggatct tcacctagat   4740
ccttttaaat taaaaatgaa gttttaaatc aatctaaagt atatatgagt aaacttggtc   4800
tgacagttac caatgcttaa tcagtgaggc acctatctca gcgatctgtc tatttcgttc   4860
atccatagtt gcctgactcg gggggggggg gcgctgaggt ctgcctcgtg aagaaggtgt   4920
tgctgactca taccaggcct gaatcgcccc atcatccagc cagaaagtga gggagccacg   4980
gttgatgaga gctttgttgt aggtggacca gttggtgatt tgaacttttt gctttgccac   5040
ggaacggtct gcgttgtcgg gaagatgcgt gatctgatcc ttcaactcag caaaagttcg   5100
atttattcaa caaagccgcc gtcccgtcaa gtcagcgtaa tgctctgcca gtgttacaac   5160
caattaacca attctgatta gaaaaactca tcgagcatca aatgaaactg caatttattc   5220
atatcaggat tatcaatacc atattttga aaaagccgtt tctgtaatga aggagaaaac   5280
tcaccgaggc agttccatag gatggcaaga tcctggtatc ggtctgcgat tccgactcgt   5340
ccaacatcaa tacaacctat taatttcccc tcgtcaaaaa taaggttatc aagtgagaaa   5400
tcaccatgag tgacgactga atccggtgag aatggcaaaa gcttatgcat ttctttccag   5460
acttgttcaa caggccagcc attacgctcg tcatcaaaat cactcgcatc aaccaaaccg   5520
ttattcattc gtgattgcgc ctgagcgaga cgaaatacgc gatcgctgtt aaaaggacaa   5580
ttacaaacag gaatcgaatg caaccggcgc aggaacactg ccagcgcatc aacaatattt   5640
tcacctgaat caggatattc ttctaatacc tggaatgctg ttttcccggg gatcgcagtg   5700
gtgagtaacc atgcatcatc aggagtacgg ataaaatgct tgatggtcgg aagaggcata   5760
aattccgtca gccagtttag tctgaccatc tcatctgtaa catcattggc aacgctacct   5820
ttgccatgtt tcagaaacaa ctctggcgca tcgggcttcc catacaatcg atagattgtc   5880
gcacctgatt gcccgacatt atcgcgagcc catttatacc catataaatc agcatccatg   5940
ttggaattta atcgcggcct cgagcaagac gtttcccgtt gaatatggct cataacaccc   6000
cttgtattac tgtttatgta agcagacagt tttattgttc atgatgatat atttttatct   6060
```

-continued

| | |
|---|---|
| tgtgcaatgt aacatcagag attttgagac acaacgtggc tttcccccccc ccccccattat | 6120 |
| tgaagcattt atcagggtta ttgtctcatg agcggataca tatttgaatg tatttagaaa | 6180 |
| aataaacaaa taggggttcc gcgcacattt ccccgaaaag tgccacctga cgtctaagaa | 6240 |
| accattatta tcatgacatt aacctataaa aataggcgta tcacgaggcc ctttcgtc | 6298 |

<210> SEQ ID NO 7
<211> LENGTH: 6298
<212> TYPE: DNA
<213> ORGANISM: Artificial Sequence
<220> FEATURE:
<223> OTHER INFORMATION: plasmid CMV/R-gp145dCFI(CCCC)

<400> SEQUENCE: 7

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctggg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg agggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgctctagag | 1380 |
| atatcgccac catgcgtgtt cgtggtatcc gcgtaactg gccgcagtgg tggatgtggg | 1440 |
| gtatcctggg tttctggatg atcatcatct gccgtgttgt tggtaacatg tgggttaccg | 1500 |
| tttactacgg tgttccggtt tggaccgacg ctaaaaccac cctgttctgc gcttccgaca | 1560 |
| ccaaagccta cgaccgtgaa gttcacaacg tttgggctac ccacgcttgc gttccgaccg | 1620 |
| acccgaaccc gcaggaaatc gttctggaaa acgttaccga aaacttcaac atgtggaaaa | 1680 |
| acgacatggt tgaccagatg cacgaagaca tcatctccct gtgggaccag tccctgaaac | 1740 |
| cgtgcgttaa actgaccccg ctgtgcgtta cctgcactg caccaacgct accttcaaaa | 1800 |
| acaacgttac caacgacatg aacaaagaaa tccgtaactg ctccttcaac accaccaccg | 1860 |

```
aaatccgtga caaaaaacag cagggttacg ctctgttcta ccgtccggac atcgttctgc    1920
tgaaagaaaa ccgtaacaac tccaacaact ccgaatacat cctgatcaat tgcaacgctt    1980
ccaccatcac ccaggcttgc ccgaaagtta acttcgaccc gatcccgatc cactactgcg    2040
ctccggctgg ttacgctatc ctgaaatgca acaacaaaac cttctccggt aaaggtccgt    2100
gcaacaacgt ttccaccgtt cagtgcaccc atggtatcaa accggttgtt tccacccagc    2160
tgctgctgaa cggttccctg ctgaaaaag aaatcatcat ccgttccgaa aacctgaccg    2220
acaacgttaa aaccatcatc gttcacctga caaatccgt tgaaatcgtt tgcacccgtc    2280
cgaacaacaa caccccgtaaa tccatgcgta tcggtccggg tcagaccttc tacgctaccg    2340
gtgacatcat cggtgacatc cgtcaggctt actgcaacat ctccggttcc aaatggaacg    2400
aaaccctgaa acgtgttaaa gaaaaactgc aggaaaacta caacaacaac aaaaccatca    2460
aattcgctcc gtcctccggt ggtgacctgg aaatcaccac ccactccttc aactgccgtg    2520
gtgaattctt ctactgcaac accacccgtc tgttcaacaa caacgctacc gaagacgaaa    2580
ccatcaccct gccgtgccgt atcaaacaga tcatcaacat gtggcagggt gttggtcgtg    2640
ctatgtacgc tccgccgatc gctggtaaca tcacctgcaa atccaacatc accggtctgc    2700
tgctggttcg tgacggtggt gaagacaaca aaaccgaaga atcttccgt ccgggtggtg    2760 gtaacatgaa agacaactgg cgttccgaac tgtacaaata caaagttatc gaactgaaac    2820
cgctgggtat cgctccgacc ggtgctaagc ttaccgttca ggctcgtcag ctgctgtcct    2880
ccatcgttca gcagcagtcc aacctgctgc gtgctatcga agctcagcag cacatgctgc    2940
agctgaccgt ttggggtatc aaacagctgc agacccgtgt tctggctatc gaacgttacc    3000
tgaaagacca gcagctcgag atctggaaca acatgacctg gatggaatgg gaccgtgaaa    3060
tctccaacta caccgacacc atctaccgtc tgctggaaga ctcccagacc cagcaggaaa    3120
aaaacgaaaa agacctgctg gctctggact cctggaaaaa cctgtggtcc tggttcgaca    3180
tctccaactg gctgtggtac atcaaaatct tcatcatgat cgttggtggt ctgatcggtc    3240
tgcgtatcat cttcgctgtt ctgtccatct gaggatccag atctgctgtg ccttctagtt    3300
gccagccatc tgttgtttgc ccctcccccg tgccttcctt gaccctggaa ggtgccactc    3360
ccactgtcct ttcctaataa aatgaggaaa ttgcatcgca ttgtctgagt aggtgtcatt    3420
ctattctggg gggtggggtg gggcaggaca gcaaggggga ggattgggaa gacaatagca    3480
ggcatgctgg ggatgcggtg ggctctatgg gtacccaggt gctgaagaat tgacccggtt    3540
cctcctgggc cagaaagaag caggcacatc cccttctctg tgacacaccc tgtccacgcc    3600
cctggttctt agttccagcc ccactcatag gacactcata gctcaggagg ctccgccttt    3660
caatcccacc cgctaaagta cttggagcgg tctctccctc cctcatcagc ccaccaaacc    3720
aaacctagcc tccaagagtg ggaagaaatt aaagcaagat aggctattaa gtgcagaggg    3780
agagaaaatg cctccaacat gtgaggaagt aatgagagaa atcatagaat tttaaggcca    3840
tgatttaagg ccatcatggc cttaatcttc cgcttcctcg ctcactgact cgctgcgctc    3900
ggtcgttcgc ctgcggcgag cggtatcagc tcactcaaag gcggtaatac ggttatccac    3960
agaatcaggg gataacgcag gaaagaacat gtgagcaaaa ggccagcaaa aggccaggaa    4020
ccgtaaaaag gccgcgttgc tggcgttttt ccataggctc cgcccccctg acgagcatca    4080
caaaaatcga cgctcaagtc agaggtggcg aaacccgaca ggactataaa gataccaggc    4140
gtttccccct ggaagctccc tcgtgcgctc tcctgttccg accctgccgc ttaccggata    4200
cctgtccgcc tttctccctt cgggaagcgt ggcgctttct catagctcac gctgtaggta    4260
```

```
tctcagttcg gtgtaggtcg ttcgctccaa gctgggctgt gtgcacgaac ccccgttca    4320 gcccgaccgc tgcgccttat ccggtaacta tcgtcttgag tccaacccgg taagacacga    4380
cttatcgcca ctggcagcag ccactggtaa caggattagc agagcgaggt atgtaggcgg    4440
tgctacagag ttcttgaagt ggtggcctaa ctacggctac actagaagaa cagtatttgg    4500
tatctgcgct ctgctgaagc cagttacctt cggaaaaaga gttggtagct cttgatccgg    4560
caaacaaacc accgctggta gcggtggttt ttttgtttgc aagcagcaga ttacgcgcag    4620
aaaaaaagga tctcaagaag atcctttgat cttttctacg gggtctgacg ctcagtggaa    4680
cgaaaactca cgttaaggga ttttggtcat gagattatca aaaaggatct tcacctagat    4740
ccttttaaat taaaaatgaa gttttaaatc aatctaaagt atatatgagt aaacttggtc    4800
tgacagttac caatgcttaa tcagtgaggc acctatctca gcgatctgtc tatttcgttc    4860
atccatagtt gcctgactcg ggggggggg gcgctgaggt ctgcctcgtg aagaaggtgt    4920
tgctgactca taccaggcct gaatcgcccc atcatccagc cagaaagtga gggagccacg    4980
gttgatgaga gctttgttgt aggtggacca gttggtgatt ttgaactttt gctttgccac    5040
ggaacggtct gcgttgtcgg aagatgcgt gatctgatcc ttcaactcag caaaagttcg    5100
atttattcaa caaagccgcc gtcccgtcaa gtcagcgtaa tgctctgcca gtgttacaac    5160
caattaacca attctgatta gaaaaactca tcgagcatca aatgaaactg caatttattc    5220
atatcaggat tatcaatacc atattttga aaaagccgtt tctgtaatga aggagaaaac    5280
tcaccgaggc agttccatag gatggcaaga tcctggtatc ggtctgcgat tccgactcgt    5340
ccaacatcaa tacaacctat taatttcccc tcgtcaaaaa taaggttatc aagtgagaaa    5400
tcaccatgag tgacgactga atccggtgag aatggcaaaa gcttatgcat ttctttccag    5460
acttgttcaa caggccagcc attacgctcg tcatcaaaat cactcgcatc aaccaaaccg    5520
ttattcattc gtgattgcgc ctgagcgaga cgaaatacgc gatcgctgtt aaaaggacaa    5580
ttacaaacag gaatcgaatg caaccggcgc aggaacactg ccagcgcatc aacaatattt    5640
tcacctgaat caggatattc ttctaatacc tggaatgctg ttttcccggg gatcgcagtg    5700
gtgagtaacc atgcatcatc aggagtacgg ataaaatgct tgatggtcgg aagaggcata    5760
aattccgtca gccagtttag tctgaccatc tcatctgtaa catcattggc aacgctacct    5820
ttgccatgtt tcagaaacaa ctctggcgca tcgggcttcc catacaatcg atagattgtc    5880
gcacctgatt gcccgacatt atcgcgagcc catttatacc catataaatc agcatccatg    5940
ttggaattta atcgcggcct cgagcaagac gtttcccgtt gaatatggct cataacaccc    6000
cttgtattac tgtttatgta agcagacagt tttattgttc atgatgatat atttttatct    6060
tgtgcaatgt aacatcagag attttgagac acaacgtggc tttcccccccc ccccattat    6120 tgaagcattt atcagggtta ttgtctcatg agcggataca tatttgaatg tatttagaaa    6180
aataaacaaa taggggttcc gcgcacattt ccccgaaaag tgccacctga cgtctaagaa    6240
accattatta tcatgacatt aacctataaa aataggcgta tcacgaggcc ctttcgtc     6298
```

<210> SEQ ID NO 8
<211> LENGTH: 6325
<212> TYPE: DNA
<213> ORGANISM: Artificial Sequence
<220> FEATURE:
<223> OTHER INFORMATION: plasmid CMV/R-gp145dCFI(BBBB)

<400> SEQUENCE: 8

```
tcgcgcgttt cggtgatgac ggtgaaaacc tctgacacat gcagctcccg gagacggtca       60
```

```
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcagattgg      240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagga cttttccattg acgtcaatgg gtggagtatt tacggtaaac      540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140 cttttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
accatgcgcg tgaaggagaa gtaccagcac ctgtggcgct ggggctggcg ctggggcacc    1440
atgctgctgg gcatcctgat gatctgcaac gccgaggaga agctgtgggt gaccgtgtac    1500
tacggcgtgc ccgtgtggaa ggaggccacc accaccctgt tctgcgccag cgaccgcaag    1560
gcctacgaca ccgaggtgca caacgtgtgg gccacccacg cctgcgtgcc caccgacccc    1620
aacccccagg aggtggagct gaagaacgtg accgagaact tcaacatgtg gaagaacaac    1680
atggtggagc agatgcacga ggacatcatc agcctgtggg accagagcct gaagccctgc    1740
gtgaagctga cccccctgtg cgtgaccctg aactgcaccg acctgcgcaa cgccaccaac    1800
ggaaacgaca caaacacaac aagcagcagc agaggaatgg tgggaggagg cgagatgaag    1860
aactgcagct tcaacatcac caccaacatc cgcggcaagg tgcagaagga gtacgccctg    1920
ttctacaagc tggacatcgc ccccatcgac aacaactcca caacagata tagactgatt     1980 agctgcaaca ccagcgtgat cacccaggcc tgccccaagg tgagcttcga gcccatcccc    2040
atccactact gcgcccccgc cggcttcgcc atcctgaagt gcaaggacaa gaagttcaac    2100
ggcaagggcc cctgcaccaa cgtgagcacc gtgcagtgca cccacggcat ccgcccgtg     2160 gtgagcaccc agctgctgct gaacggtagc ctggccgagg aggaggtggt gatccgcagc    2220
gctaacttcg ccgacaacgc caaggtgatc atcgtgcagc tgaacgagag cgtggagatc    2280
aactgcaccc gccccaacaa caacacccgc aagagcatcc acatcggccc cggccgcgcc    2340
ttctacacca ccgcgagat catcggcgac atccgccagg cccactgcaa cctgagccgc    2400
gccaagtgga acgacaccct gaacaagatc gtgatcaagc tgcgcgagca gttcggcaac    2460
```

-continued

```
aagaccatcg tgttcaagca cagcagcggc ggcgaccccg agatcgtgac ccacagcttc    2520
aactgcggcg gcgaattctt ctactgcaac agcacccagc tgtttaattc cacatggaac    2580
gtgaccgagg agagcaacaa caccgtggag aacaacacca tcaccctgcc ctgccgcatc    2640
aagcagatca tcaacatgtg gcaggaggtg ggccgcgcca tgtacgcccc ccccatccgc    2700
ggccagatcc gctgcagcag caacatcacc ggcctgctgc tgacccgcga cggcggcccc    2760
gaggacaaca gaccgaggt gttccgccct ggcggcggcg acatgcgcga caactggcgc    2820
agcgagctgt acaagtacaa ggtggtgaag atcgagcccc tgggcgtggc ccccaccaag    2880
gccaagctta ccgtccaggc ccgcctgctg ctgagcggca tcgtgcagca gcagaacaac    2940
ctgctgcgcg ccatcgaggc ccagcagcac ctgctgcagc tgaccgtgtg gggcatcaag    3000
cagctgcagg cccgcgtgct ggccgtggag cgctacctgc gcgaccagca gctcctcaag    3060
atctgggaca acatgacctg gatcgagtgg gaccgcgaga tcaacaacta caccagcatc    3120
atctacagcc tgatcgagga gagccagaac cagcaggaga gaacgagca ggagctgctg    3180 gagctggaca agtgggccag cctgtggaac tggttcgaca tcaccaagtg gctgtggtac    3240
atcaagatct tcatcatgat cgtgggcggc ctgatcggcc tgcgcatcgt gttcagcgtg    3300
ctgagcatct gaggatccag atctgctgtg ccttctagtt gccagccatc tgttgtttgc    3360 ccctccccg tgccttcctt gaccctggaa ggtgccactc ccactgtcct ttcctaataa    3420
aatgaggaaa ttgcatcgca ttgtctgagt aggtgtcatt ctattctggg gggtggggtg    3480
gggcaggaca gcaaggggga ggattgggaa gacaatagca ggcatgctgg ggatgcggtg    3540
ggctctatgg gtacccaggt gctgaagaat tgacccggtt cctcctgggc cagaaagaag    3600
caggcacatc cccttctctg tgacacaccc tgtccacgcc cctggttctt agttccagcc    3660
ccactcatag gacactcata gctcaggagg gctccgcctt caatcccacc cgctaaagta    3720
cttggagcgg tctctccctc cctcatcagc ccaccaaacc aaacctagcc tccaagagtg    3780
ggaagaaatt aaagcaagat aggctattaa gtgcagaggg agagaaaatg cctccaacat    3840
gtgaggaagt aatgagagaa atcatagaat tttaaggcca tcatggcctt aatcttccgc    3900
ttcctcgctc actgactcgc tgcgctcggt cgttcggctg cggcgagcgg tatcagctca    3960
ctcaaaggcg gtaatacggt tatccacaga atcaggggat aacgcaggaa agaacatgtg    4020
agcaaaaggc cagcaaaagg ccaggaaccg taaaaaggcc gcgttgctgg cgttttccca    4080
taggctccgc cccctgacg agcatcacaa aaatcgacgc tcaagtcaga ggtggcgaaa    4140
cccgacagga ctataaagat accaggcgtt tccccctgga agctccctcg tgcgctctcc    4200
tgttccgacc ctgccgctta ccggatacct gtccgccttt ctcccttcgg aagcgtggc    4260 gctttctcat agctcacgct gtaggtatct cagttcggtg taggtcgttc gctccaagct    4320
gggctgtgtg cacgaacccc ccgttcagcc cgaccgctgc gccttatccg gtaactatcg    4380
tcttgagtcc aacccggtaa gacacgactt atcgccactg gcagcagcca ctggtaacag    4440
gattagcaga gcgaggtatg taggcggtgc tacagagttc ttgaagtggt ggcctaacta    4500
cggctacact agaagaacag tatttggtat ctgcgctctg ctgaagccag ttaccttcgg    4560
aaaaagagtt ggtagctctt gatccggcaa acaaaccacc gctggtagcg tggtttttt    4620 tgtttgcaag cagcagatta cgcgcagaaa aaaaggatct caagaagatc ctttgatctt    4680
ttctacgggg tctgacgctc agtggaacga aaactcacgt taagggattt tggtcatgag    4740
attatcaaaa aggatcttca cctagatcct tttaaattaa aaatgaagtt ttaaatcaat    4800
ctaaagtata tatgagtaaa cttggtctga cagttaccaa tgcttaatca gtgaggcacc    4860
```

```
tatctcagcg atctgtctat ttcgttcatc catagttgcc tgactcgggg ggggggggcg    4920
ctgaggtctg cctcgtgaag aaggtgttgc tgactcatac caggcctgaa tcgcccatc     4980 atccagccag aaagtgaggg agccacggtt gatgagagct tgttgtagg tggaccagtt    5040 ggtgattttg aacttttgct tgccacggaa acggtctgcg ttgtcgggaa gatgcgtgat    5100
ctgatccttc aactcagcaa agttcgatt tattcaacaa agccgccgtc ccgtcaagtc    5160
agcgtaatgc tctgccagtg ttacaaccaa ttaaccaatt ctgattagaa aaactcatcg    5220
agcatcaaat gaaactgcaa tttattcata tcaggattat caataccata tttttgaaaa    5280
agccgtttct gtaatgaagg agaaaactca ccgaggcagt tccataggat ggcaagatcc    5340
tggtatcggt ctgcgattcc gactcgtcca acatcaatac aacctattaa tttcccctcg    5400
tcaaaaataa ggttatcaag tgagaaatca ccatgagtga cgactgaatc cggtgagaat    5460
ggcaaaagct tatgcatttc tttccagact tgttcaacag gccagccatt acgctcgtca    5520
tcaaaatcac tcgcatcaac caaccgtta ttcattcgtg attgcgcctg agcgagacga    5580
aatacgcgat cgctgttaaa aggacaatta caaacaggaa tcgaatgcaa ccggcgcagg    5640
aacactgcca gcgcatcaac aatattttca cctgaatcag gatattcttc taatacctgg    5700
aatgctgttt tcccggggat cgcagtggtg agtaaccatg catcatcagg agtacggata    5760
aaatgcttga tggtcggaag aggcataaat tccgtcagcc agtttagtct gaccatctca    5820
tctgtaacat cattggcaac gctacctttg ccatgtttca gaaacaactc tggcgcatcg    5880
ggcttcccat acaatcgata gattgtcgca cctgattgcc cgacattatc gcgagcccat    5940
ttatacccat ataaatcagc atccatgttg gaatttaatc gcggcctcga gcaagacgtt    6000
tcccgttgaa tatggctcat aacacccctt gtattactgt ttatgtaagc agacagtttt    6060
attgttcatg atgatatatt tttatcttgt gcaatgtaac atcagagatt ttgagacaca    6120
acgtggcttt ccccccccccc ccattattga agcatttatc agggttattg tctcatgagc    6180
ggatacatat ttgaatgtat ttagaaaaat aaacaaatag gggttccgcg cacatttccc    6240
cgaaaagtgc cacctgacgt ctaagaaacc attattatca tgacattaac ctataaaaat    6300
aggcgtatca cgaggccctt tcgtc                                          6325
```

<210> SEQ ID NO 9
<211> LENGTH: 6298
<212> TYPE: DNA
<213> ORGANISM: Artificial Sequence
<220> FEATURE:
<223> OTHER INFORMATION: plasmid CMV/R-gp145dCFI(BBCB)

<400> SEQUENCE: 9

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaatagga cttttccattg acgtcaatgg gtggagtatt tacggtaaac    540
tgcccacttg gcagtacatc aagtgtatca tatgccaagt acgccccta ttgacgtcaa    600
```

```
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccttacct gaggccgcca tccacgccgg ttgagtcgcg ttctgccgcc tcccgcctgt   1080
ggtgcctcct gaactacgtc cgccgtctag gtaagtttag agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatgcgcg tgaaggagaa gtaccagcac ctgtggcgct ggggctggcg ctggggcacc   1440
atgctgctgg gcatcctgat gatctgcaac gccgaggaga agctgtgggt gaccgtgtac   1500 tacgcgtgc ccgtgtggaa ggaggccacc accaccctgt tctgcgccag cgaccgcaag   1560
gcctacgaca ccgaggtgca caacgtgtgg gccacccacg cctgcgtgcc caccgacccc   1620 aaccccagg aggtggagct gaagaacgtg accgagaact tcaacatgtg gaagaacaac   1680
atggtggagc agatgcacga ggacatcatc agcctgtggg accagagcct gaagccctgc   1740
gtgaagctga ccccccctgtg cgtgaccctg aactgcaccg acctgcgcaa cgccaccaac   1800
ggaaacgaca caaacacaac aagcagcagc agaggaatgg tgggaggagg cgagatgaag   1860
aactgcagct tcaacatcac caccaacatc cgcggcaagg tgcagaagga gtacgccctg   1920
ttctacaagc tggacatcgc ccccatcgac aacaactcca caacagata tagactgatt   1980 agctgcaaca ccagcgtgat cacccaggcc tgccccaagg tgagcttcga gcccatcccc   2040
atccactact gcgcccccgc cggcttcgcc atcctgaagt gcaaggacaa gaagttcaac   2100
ggcaagggcc cctgcaccaa cgtgagcacc gtgcagtgca cccacggcat ccgccccgtg   2160
gtgagcaccc agctgctgct gaacggtagc ctggccgagg aggaggtggt gatccgcagc   2220
gctaacttcg ccgacaacgc caaggtgatc atcgtgcagc tgaacgagag cgtggagatc   2280
aactgcaccc gccccaacaa caacacccgc aagagcatcc acatcggccc cggccgcgcc   2340
ttctacacca ccggcgagat catcggcgac atccgccagg cccactgcaa cctgagccgc   2400
gccaagtgga cgacaccct gaacaagatc gtgatcaagc tgcgcgagca gttcggcaac   2460
aagaccatcg tgttcaagca cagcagcggc ggcgaccccg agatcgtgac ccacagcttc   2520
aactgcggcg cgaattctt ctactgcaac accacccgtc tgttcaacaa caacgctacc   2580
gaagacgaaa ccatcacccct gccgtgccgt atcaaacaga tcatcaacat gtggcagggt   2640
gttggtcgtg ctatgtacgc tccgccgatc gctggtaaca tcacctgcaa atccaacatc   2700
accggtctgc tgctggttcg tgacggtggt gaagacaaca aaaccgaaga aatcttccgt   2760
ccgggtggtg gtaacatgaa agacaactgg cgttccgaac tgtacaaata caaagttatc   2820
gaactgaaac cgctgggtat cgctccgacc ggtgctaagc ttaccgtcca ggcccgcctg   2880
ctgctgagcg catcgtgca gcagcagaac aacctgctgc gcgccatcga ggcccagcag   2940
cacctgctgc agctgaccgt gtggggcatc aagcagctgc aggcccgcgt gctggccgtg   3000
```

```
gagcgctacc tgcgcgacca gcagctcctc aagatctggg acaacatgac ctggatcgag  3060
tgggaccgcg agatcaacaa ctacaccagc atcatctaca gcctgatcga ggagagccag  3120
aaccagcagg agaagaacga gcaggagctg ctggagctgg acaagtgggc cagcctgtgg  3180
aactggttcg acatcaccaa gtggctgtgg tacatcaaga tcttcatcat gatcgtgggc  3240
ggcctgatcg gcctgcgcat cgtgttcagc gtgctgagca tctgaggatc cagatctgct  3300
gtgccttcta gttgccagcc atctgttgtt tgcccctccc ccgtgccttc cttgaccctg  3360
gaaggtgcca ctcccactgt ccttttcctaa taaaatgagg aaattgcatc gcattgtctg  3420
agtaggtgtc attctattct ggggggtggg gtggggcagg acagcaaggg ggaggattgg  3480
gaagacaata gcaggcatgc tggggatgcg gtgggctcta gggtaccca ggtgctgaag  3540 aattgacccg gttcctcctg ggccagaaag aagcaggcac atccccttct ctgtgacaca  3600
ccctgtccac gccctggtt cttagttcca gccccactca taggacactc atagctcagg  3660
agggctccgc cttcaatccc acccgctaaa gtacttggag cggtctctcc ctccctcatc  3720
agcccaccaa accaaaccta gcctccaaga gtgggaagaa attaaagcaa gataggctat  3780
taagtgcaga gggagagaaa atgcctccaa catgtgagga agtaatgaga gaaatcatag  3840
aattttaagg ccatcatggc cttaatcttc cgcttcctcg ctcactgact cgctgcgctc  3900
ggtcgttcgg ctgcggcgag cggtatcagc tcactcaaag gcggtaatac ggttatccac  3960
agaatcaggg gataacgcag gaaagaacat gtgagcaaaa ggccagcaaa aggccaggaa  4020
ccgtaaaaag gccgcgttgc tggcgttttt ccataggctc cgcccccctg acgagcatca  4080
caaaaatcga cgctcaagtc agaggtggcg aaacccgaca ggactataaa gataccaggc  4140
gtttccccct ggaagctccc tcgtgcgctc tcctgttccg accctgccgc ttaccggata  4200
cctgtccgcc tttctccctt cgggaagcgt ggcgctttct catagctcac gctgtaggta  4260
tctcagttcg gtgtaggtcg ttcgctccaa gctgggctgt gtgcacgaac cccccgttca  4320
gcccgaccgc tgcgccttat ccggtaacta tcgtcttgag tccaacccgg taagacacga  4380
cttatcgcca ctggcagcag ccactggtaa caggattagc agagcgaggt atgtaggcgg  4440
tgctacagag ttcttgaagt ggtggcctaa ctacggctac actagaagaa cagtatttgg  4500
tatctgcgct ctgctgaagc cagttacctt cggaaaaaga gttggtagct cttgatccgg  4560
caaacaaacc accgctggta gcggtggttt ttttgtttgc aagcagcaga ttacgcgcag  4620
aaaaaaagga tctcaagaag atcctttgat cttttctacg gggtctgacg ctcagtggaa  4680
cgaaaactca cgttaaggga ttttggtcat gagattatca aaaaggatct tcacctagat  4740
ccttttaaat taaaaatgaa gttttaaatc aatctaaagt atatatgagt aaacttggtc  4800
tgacagttac caatgcttaa tcagtgaggc acctatctca gcgatctgtc tatttcgttc  4860
atccatagtt gcctgactcg ggggggggg gcgctgaggt ctgcctcgtg aagaaggtgt  4920
tgctgactca taccaggcct gaatcgcccc atcatccagc cagaaagtga gggagccacg  4980
gttgatgaga gctttgttgt aggtggacca gttggtgatt ttgaactttt gctttgccac  5040
ggaacggtct gcgttgtcgg aagatgcgt gatctgatcc ttcaactcag caaaagttcg  5100
atttattcaa caaagccgcc gtcccgtcaa gtcagcgtaa tgctctgcca gtgttacaac  5160
caattaacca attctgatta gaaaactca tcgagcatca aatgaaactg caatttattc  5220
atatcaggat tatcaatacc atattttga aaaagccgtt tctgtaatga aggagaaaac  5280
tcaccgaggc agttccatag gatggcaaga tcctggtatc ggtctgcgat tccgactcgt  5340
ccaacatcaa tacaacctat taatttcccc tcgtcaaaaa taaggttatc aagtgagaaa  5400
```

```
tcaccatgag tgacgactga atccggtgag aatggcaaaa gcttatgcat ttctttccag   5460
acttgttcaa caggccagcc attacgctcg tcatcaaaat cactcgcatc aaccaaaccg   5520
ttattcattc gtgattgcgc ctgagcgaga cgaaatacgc gatcgctgtt aaaaggacaa   5580
ttacaaacag gaatcgaatg caaccggcgc aggaacactg ccagcgcatc aacaatattt   5640
tcacctgaat caggatattc ttctaatacc tggaatgctg ttttcccggg gatcgcagtg   5700
gtgagtaacc atgcatcatc aggagtacgg ataaaatgct tgatggtcgg aagaggcata   5760
aattccgtca gccagtttag tctgaccatc tcatctgtaa catcattggc aacgctacct   5820
ttgccatgtt tcagaaacaa ctctggcgca tcgggcttcc catacaatcg atagattgtc   5880
gcacctgatt gcccgacatt atcgcgagcc catttatacc catataaatc agcatccatg   5940
ttggaattta atcgcggcct cgagcaagac gtttcccgtt gaatatggct cataacaccc   6000
cttgtattac tgtttatgta agcagacagt tttattgttc atgatgatat attttttatct   6060
tgtgcaatgt aacatcagag attttgagac acaacgtggc tttccccccc ccccccattat   6120
tgaagcattt atcagggtta ttgtctcatg agcggataca tatttgaatg tatttagaaa   6180
aataaacaaa taggggttcc gcgcacattt ccccgaaaag tgccacctga cgtctaagaa   6240
accattatta tcatgacatt aacctataaa aataggcgta tcacgaggcc ctttcgtc    6298

<210> SEQ ID NO 10
<211> LENGTH: 6328
<212> TYPE: DNA
<213> ORGANISM: Artificial Sequence
<220> FEATURE:
<223> OTHER INFORMATION: plasmid CMV/R-gp145dCFI(BCBB)

<400> SEQUENCE: 10
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggA ctttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt tgacctcca   960
tagaagacac cgggaccgat ccagcctcca tcggctcgca tctctccttc acgcgcccgc  1020
cgccttacct gaggccgcca tccacgccgg ttgagtcgcg ttctgccgcc tcccgcctgt  1080
ggtgcctcct gaactacgtc gcgcgtctag gtaagtttag agctcaggtc gagaccgggc  1140
ctttgtccgg cgctcccttg gagcctacct agactcagcc ggctctccac gctttgcctg  1200
```

```
accctgcttg ctcaactcta gttaacggtg gagggcagtg tagtctgagc agtactcgtt      1260
gctgccgcgc gcgccaccag acataatagc tgacagacta acagactgtt cctttccatg      1320
ggtcttttct gcagtcaccg tcgtcgacac gtgtgatcag atatcgcggc cgctctagac      1380
accatgcgcg tgaaggagaa gtaccagcac ctgtggcgct ggggctggcg ctggggcacc      1440
atgctgctgg gcatcctgat gatctgcaac gccgaggaga agctgtgggt gaccgtgtac      1500
tacggcgtgc ccgtgtggaa ggaggccacc accaccctgt tctgcgccag cgaccgcaag      1560
gcctacgaca ccgaggtgca caacgtgtgg gccacccacg cctgcgtgcc caccgacccc      1620 aaccccagg aggtggagct gaagaacgtg accgagaact tcaacatgtg gaagaacaac      1680
atggtggagc agatgcacga ggacatcatc agcctgtggg accagagcct gaagccctgc      1740
gtgaagctga ccccctgtg cgtgaccctg aactgcaccg acctgcgcaa cgccaccaac      1800
ggaaacgaca caaacacaac aagcagcagc agaggaatgg tgggaggagg cgagatgaag      1860
aactgcagct tcaacatcac caccaacatc cgcggcaagg tgcagaagga gtacgccctg      1920
ttctacaagc tggacatcgc ccccatcgac aacaactcca acaacagata tagactgatt      1980
agctgcaacg cttccaccat cacccaggct tgcccgaaag ttaacttcga cccgatcccg      2040
atccactact gcgctccggc tggttacgct atcctgaaat gcaacaacaa accttctcc      2100 ggtaaaggtc cgtgcaacaa cgtttccacc gttcagtgca cccatggtat caaaccggtt      2160
gtttccaccc agctgctgct gaacggttcc ctggctgaaa agaaatcat catccgttcc      2220 gaaaacctga ccgacaacgt taaaaccatc atcgttcacc tgaacaaatc cgttgaaatc      2280
gtttgcaccc gtccgaacaa caacacccgt aaatccatgc gtatcggtcc gggtcagacc      2340
ttctacgcta ccggtgacat catcggtgac atccgtcagg cttactgcaa catctccggt      2400
tccaaatgga acgaaaccct gaaacgtgtt aaagaaaaac tgcaggaaaa ctacaacaac      2460
aacaaaacca tcaaattcgc tccgtcctcc ggtggtgacc tggaaatcac cacccactcc      2520
ttcaactgcc gtggtgaatt cttctactgc aacagcaccc agctgtttaa ttccacatgg      2580
aacgtgaccg aggagagcaa caacaccgtg gagaacaaca ccatcaccct gccctgccgc      2640
atcaagcaga tcatcaacat gtggcaggag gtgggccgcg ccatgtacgc ccccccatc      2700 cgcggccaga tccgctgcag cagcaacatc accggcctgc tgctgacccg cgacggcggc      2760
cccgaggaca caagaccga ggtgttccgc cctggcggcg gcgacatgcg cgacaactgg      2820
cgcagcgagc tgtacaagta caaggtggtg aagatcgagc ccctgggcgt ggcccccacc      2880
aaggccaagc ttaccgtcca ggcccgcctg ctgctgagcg catcgtgca gcagcagaac      2940 aacctgctgc gcgccatcga ggcccagcag cacctgctgc agctgaccgt gtggggcatc      3000
aagcagctgc aggcccgcgt gctggccgtg gagcgctacc tgcgcgacca gcagctcctc      3060
aagatctggg acaacatgac ctggatcgag tgggaccgcg agatcaacaa ctacaccagc      3120
atcatctaca gcctgatcga ggagagccag aaccagcagg agaagaacga gcaggagctg      3180
ctggagctgg acaagtgggc cagcctgtgg aactggttcg acatcaccaa gtggctgtgg      3240
tacatcaaga tcttcatcat gatcgtgggc ggcctgatcg gcctgcgcat cgtgttcagc      3300
gtgctgagca tctgaggatc cagatctgct gtgccttcta gttgccagcc atctgttgtt      3360
tgcccctccc ccgtgccttc cttgaccctg gaaggtgcca ctcccactgt cctttcctaa      3420
taaaatgagg aaattgcatc gcattgtctg agtaggtgtc attctattct ggggggtggg      3480
gtggggcagg acagcaaggg ggaggattgg gaagacaata gcaggcatgc tggggatgcg      3540
gtgggctcta tgggtaccca ggtgctgaag aattgacccg gttcctcctg ggccagaaag      3600
```

```
aagcaggcac atcccottct ctgtgacaca ccctgtccac gcccctggtt cttagttcca   3660
gccccactca taggacactc atagctcagg agggctccgc cttcaatccc acccgctaaa   3720
gtacttggag cggtctctcc ctccctcatc agcccaccaa accaaaccta gcctccaaga   3780
gtgggaagaa attaaagcaa gataggctat taagtgcaga gggagagaaa atgcctccaa   3840
catgtgagga agtaatgaga gaaatcatag aattttaagg ccatcatggc cttaatcttc   3900
cgcttcctcg ctcactgact cgctgcgctc ggtcgttcgg ctgcggcgag cggtatcagc   3960
tcactcaaag gcggtaatac ggttatccac agaatcaggg gataacgcag gaaagaacat   4020
gtgagcaaaa ggccagcaaa aggccaggaa ccgtaaaaag gccgcgttgc tggcgttttt   4080
ccataggctc cgcccccctg acgagcatca caaaaatcga cgctcaagtc agaggtggcg   4140
aaacccgaca ggactataaa gataccaggc gtttccccct ggaagctccc tcgtgcgctc   4200
tcctgttccg accctgccgc ttaccggata cctgtccgcc tttctccctt cgggaagcgt   4260
ggcgctttct catagctcac gctgtaggta tctcagttcg gtgtaggtcg ttcgctccaa   4320
gctgggctgt gtgcacgaac cccccgttca gcccgaccgc tgcgccttat ccggtaacta   4380
tcgtcttgag tccaacccgg taagacacga cttatcgcca ctggcagcag ccactggtaa   4440
caggattagc agagcgaggt atgtaggcgg tgctacagag ttcttgaagt ggtggcctaa   4500
ctacggctac actagaagaa cagtatttgg tatctgcgct ctgctgaagc cagttacctt   4560
cggaaaaaga gttggtagct cttgatccgg caaacaaacc accgctggta gcggtggttt   4620
ttttgtttgc aagcagcaga ttacgcgcag aaaaaaagga tctcaagaag atcctttgat   4680
cttttctacg gggtctgacg ctcagtggaa cgaaaactca cgttaaggga ttttggtcat   4740
gagattatca aaaaggatct tcacctagat ccttttaaat taaaaatgaa gttttaaatc   4800
aatctaaagt atatatgagt aaacttggtc tgacagttac caatgcttaa tcagtgaggc   4860
acctatctca gcgatctgtc tatttcgttc atccatagtt gcctgactcg ggggggggg   4920
gcgctgaggt ctgcctcgtg aagaaggtgt tgctgactca taccaggcct gaatcgcccc   4980
atcatccagc cagaaagtga gggagccacg gttgatgaga gctttgttgt aggtggacca   5040
gttggtgatt ttgaactttt gctttgccac ggaacggtct gcgttgtcgg gaagatgcgt   5100
gatctgatcc ttcaactcag caaaagttcg atttattcaa caaagccgcc gtcccgtcaa   5160
gtcagcgtaa tgctctgcca gtgttacaac caattaacca attctgatta gaaaaactca   5220
tcgagcatca aatgaaactg caatttattc atatcaggat tatcaatacc atattttga   5280
aaaagccgtt tctgtaatga aggagaaaac tcaccgaggc agttccatag gatgcaaga   5340
tcctggtatc ggtctgcgat tccgactcgt ccaacatcaa tacaacctat taatttcccc   5400
tcgtcaaaaa taaggttatc aagtgagaaa tcaccatgag tgacgactga atccggtgag   5460
aatggcaaaa gcttatgcat ttcttccag acttgttcaa caggccagcc attacgctcg   5520
tcatcaaaat cactcgcatc aaccaaaccg ttattcattc gtgattgcgc ctgagcgaga   5580
cgaaatacgc gatcgctgtt aaaaggacaa ttacaaacag gaatcgaatg caaccggcgc   5640
aggaacactg ccagcgcatc aacaatattt tcacctgaat caggatattc ttctaatacc   5700
tggaatgctg ttttcccggg gatcgcagtg gtgagtaacc atgcatcatc aggagtacgg   5760
ataaaatgct tgatggtcgg aagaggcata aattccgtca gccagtttag tctgaccatc   5820
tcatctgtaa catcattggc aacgctacct ttgccatgtt tcagaaacaa ctctggcgca   5880
tcgggcttcc catacaatcg atagattgtc gcacctgatt gcccgacatt atcgcgagcc   5940
catttatacc catataaatc agcatccatg ttggaattta atcgcggcct cgagcaagac   6000
```

| | | | | |
|---|---|---|---|---|
| gtttcccgtt | gaatatggct | cataacaccc | cttgtattac | tgtttatgta agcagacagt | 6060 |
| tttattgttc | atgatgatat | atttttatct | tgtgcaatgt | aacatcagag attttgagac | 6120 |
| acaacgtggc | tttcccccc | cccccattat | tgaagcattt | atcagggtta ttgtctcatg | 6180 |
| agcggataca | tatttgaatg | tatttagaaa | aataaacaaa | taggggttcc gcgcacattt | 6240 |
| ccccgaaaag | tgccacctga | cgtctaagaa | accattatta | tcatgacatt aacctataaa | 6300 |
| aataggcgta | tcacgaggcc | ctttcgtc | | | 6328 |

```
<210> SEQ ID NO 11
<211> LENGTH: 6311
<212> TYPE: DNA
<213> ORGANISM: Artificial Sequence
<220> FEATURE:
<223> OTHER INFORMATION: plasmid CMV/R-gp145dCFI(BCCC)

<400> SEQUENCE: 11
```

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcagattgg | 240 |
| ctattggcca | ttgcatacgt | tgtatccata | tcataatatg | tacatttata ttggctcatg | 300 |
| tccaacatta | ccgccatgtt | gacattgatt | attgactagt | tattaatagt aatcaattac | 360 |
| ggggtcatta | gttcatagcc | catatatgga | gttccgcgtt | acataactta cggtaaatgg | 420 |
| cccgcctggc | tgaccgccca | acgacccccg | cccattgacg | tcaataatga cgtatgttcc | 480 |
| catagtaacg | ccaataggga | ctttccattg | acgtcaatgg | gtggagtatt tacggtaaac | 540 |
| tgcccacttg | gcagtacatc | aagtgtatca | tatgccaagt | acgcccccta ttgacgtcaa | 600 |
| tgacggtaaa | tggcccgcct | ggcattatgc | ccagtacatg | accttatggg actttcctac | 660 |
| ttggcagtac | atctacgtat | tagtcatcgc | tattaccatg | gtgatgcggt tttggcagta | 720 |
| catcaatggg | cgtggatagc | ggtttgactc | acggggattt | ccaagtctcc accccattga | 780 |
| cgtcaatggg | agtttgtttt | ggcaccaaaa | tcaacgggac | tttccaaaat gtcgtaacaa | 840 |
| ctccgcccca | ttgacgcaaa | tgggcggtag | gcgtgtacgg | tgggaggtct atataagcag | 900 |
| agctcgttta | gtgaaccgtc | agatcgcctg | gagacgccat | ccacgctgtt ttgacctcca | 960 |
| tagaagacac | cgggaccgat | ccagcctcca | tcggctcgca | tctctccttc acgcgcccgc | 1020 |
| cgccctacct | gaggccgcca | tccacgccgg | ttgagtcgcg | ttctgccgcc tcccgcctgt | 1080 |
| ggtgcctcct | gaactgcgtc | cgccgtctag | gtaagtttaa | agctcaggtc gagaccgggc | 1140 |
| ctttgtccgg | cgctcccttg | gagcctacct | agactcagcc | ggctctccac gctttgcctg | 1200 |
| accctgcttg | ctcaactcta | gttaacggtg | agggcagtg | tagtctgagc agtactcgtt | 1260 |
| gctgccgcgc | gcgccaccag | acataatagc | tgacagacta | acagactgtt cctttccatg | 1320 |
| ggtcttttct | gcagtcaccg | tcgtcgacac | gtgtgatcag | atatcgcggc cgctctagac | 1380 |
| accatgcgcg | tgaaggagaa | gtaccagcac | ctgtggcgct | ggggctggcg ctggggcacc | 1440 |
| atgctgctgg | gcatcctgat | gatctgcaac | gccgaggaga | gctgtgggt gaccgtgtac | 1500 |
| tacggcgtgc | ccgtgtggaa | ggaggccacc | accaccctgt | tctgcgccag cgaccgcaag | 1560 |
| gcctacgaca | ccgaggtgca | caacgtgtgg | gccacccacg | cctgcgtgcc caccgacccc | 1620 |
| aaccccagg | aggtggagct | gaagaacgtg | accgagaact | tcaacatgtg gaagaacaac | 1680 |
| atggtggagc | agatgcacga | ggacatcatc | agcctgtggg | accagagcct gaagccctgc | 1740 |

-continued

```
gtgaagctga cccccctgtg cgtgaccctg aactgcaccg acctgcgcaa cgccaccaac    1800
ggaaacgaca caaacacaac aagcagcagc agaggaatgg tgggaggagg cgagatgaag    1860
aactgcagct tcaacatcac caccaacatc cgcggcaagg tgcagaagga gtacgccctg    1920
ttctacaagc tggacatcgc ccccatcgac aacaactcca acaacagata tagactgatt    1980
agctgcaacg cttccaccat cacccaggct tgcccgaaag ttaacttcga cccgatcccg    2040
atccactact gcgctccggc tggttacgct atcctgaaat gcaacaacaa aaccttctcc    2100
ggtaaaggtc cgtgcaacaa cgtttccacc gttcagtgca cccatggtat caaaccggtt    2160
gtttccaccc agctgctgct gaacggttcc ctggctgaaa agaaatcat catccgttcc    2220
gaaaacctga ccgacaacgt taaaaccatc atcgttcacc tgaacaaatc cgttgaaatc    2280
gtttgcaccc gtccgaacaa caacacccgt aaatccatgc gtatcggtcc gggtcagacc    2340
ttctacgcta ccggtgacat catcggtgac atccgtcagg cttactgcaa catctccggt    2400
tccaaatgga cgaaaccct gaaacgtgtt aagaaaaac tgcaggaaaa ctacaacaac    2460
aacaaaacca tcaaattcgc tccgtcctcc ggtggtgacc tggaaatcac cacccactcc    2520
ttcaactgcc gtggtgaatt cttctactgc aacaccaccc gtctgttcaa caacaacgct    2580
accgaagacg aaaccatcac cctgccgtgc cgtatcaaac agatcatcaa catgtggcag    2640
ggtgttggtc gtgctatgta cgctccgccg atcgctggta acatcacctg caaatccaac    2700
atcaccggtc tgctgctggt tcgtgacggt ggtgaagaca caaaaccga gaaatcttc    2760
cgtccgggtg gtggtaacat gaaagacaac tggcgttccg aactgtacaa atacaaagtt    2820
atcgaactga accgctggg tatcgctccg accggtgcta agcttaccgt tcaggctcgt    2880
cagctgctgt cctccatcgt tcagcagcag tccaacctgc tgcgtgctat cgaagctcag    2940
cagcacatgc tgcagctgac cgtttggggt atcaaacagc tgcagacccg tgttctggct    3000
atcgaacgtt acctgaaaga ccagcagctc gagatctgga caacatgac ctggatggaa    3060
tgggaccgtg aaatctccaa ctacaccgac accatctacc gtctgctgga agactcccag    3120
acccagcagg aaaaaacga aaagacctg ctggctctgg actcctggaa aaacctgtgg    3180
tcctggttcg acatctccaa ctggctgtgg tacatcaaaa tcttcatcat gatcgttggt    3240
ggtctgatcg gtctgcgtat catcttcgct gttctgtcca tctgaggatc cagatctgct    3300
gtgccttcta gttgccagcc atctgttgtt tgccctccc ccgtgccttc cttgaccctg    3360
gaaggtgcca ctcccactgt cctttcctaa taaaatgagg aaattgcatc gcattgtctg    3420
agtaggtgtc attctattct gggggtggg gtggggcagg acagcaaggg ggaggattgg    3480
gaagacaata gcaggcatgc tggggatgcg gtgggctcta tgggtaccca ggtgctgaag    3540
aattgacccg gttcctcctg gccagaaag aagcaggcac atccccttct ctgtgacaca    3600
ccctgtccac gcccctggtt cttagttcca gccccactca taggacactc atagctcagg    3660
agggctccgc cttcaatccc acccgctaaa gtacttggag cggtctctcc ctccctcatc    3720
agcccaccaa accaaaccta gcctccaaga gtgggaagaa attaaagcaa gataggctat    3780
taagtgcaga gggagagaaa atgcctccaa catgtgagga agtaatgaga gaaatcatag    3840
aattttaagg ccatgattta aggccatcat ggccttaatc ttccgcttcc tcgctcactg    3900
actcgctgcg ctcggtcgtt cggctgcggc gagcggtatc agctcactca aaggcggtaa    3960
tacggttatc cacagaatca ggggataacg caggaaagaa catgtgagca aaaggccagc    4020
aaaaggccag gaaccgtaaa aaggccgcgt tgctggcgtt ttttccatagg ctccgccccc    4080
ctgacgagca tcacaaaaat cgacgctcaa gtcagaggtg cgaaacccg acaggactat    4140
```

```
aaagatacca ggcgtttccc cctggaagct ccctcgtgcg ctctcctgtt ccgaccctgc    4200
cgcttaccgg atacctgtcc gccttttctcc cttcggaag cgtggcgctt tctcatagct    4260
cacgctgtag gtatctcagt tcggtgtagg tcgttcgctc caagctgggc tgtgtgcacg    4320
aaccccccgt tcagcccgac cgctgcgcct tatccggtaa ctatcgtctt gagtccaacc    4380
cggtaagaca cgacttatcg ccactggcag cagccactgg taacaggatt agcagagcga    4440
ggtatgtagg cggtgctaca gagttcttga agtggtggcc taactacggc tacactagaa    4500
gaacagtatt tggtatctgc gctctgctga agccagttac cttcggaaaa agagttggta    4560
gctcttgatc cggcaaacaa accaccgctg gtagcggtgg tttttttgtt tgcaagcagc    4620
agattacgcg cagaaaaaaa ggatctcaag aagatccttt gatcttttct acggggtctg    4680
acgctcagtg gaacgaaaac tcacgttaag ggattttggt catgagatta tcaaaaagga    4740
tcttcaccta gatcctttta aattaaaaat gaagttttaa atcaatctaa agtatatatg    4800
agtaaacttg gtctgacagt taccaatgct taatcagtga ggcacctatc tcagcgatct    4860
gtctatttcg ttcatccata gttgcctgac tcggggggg ggggcgctga ggtctgcctc    4920
gtgaagaagg tgttgctgac tcataccagg cctgaatcgc cccatcatcc agccagaaag    4980
tgagggagcc acggttgatg agagctttgt tgtaggtgga ccagttggtg attttgaact    5040
tttgctttgc cacggaacgg tctgcgttgt cgggaagatg cgtgatctga tccttcaact    5100 cagcaaagt tcgatttatt caacaaagcc gccgtcccgt caagtcagcg taatgctctg    5160
ccagtgttac aaccaattaa ccaattctga ttagaaaaac tcatcgagca tcaaatgaaa    5220
ctgcaattta ttcatatcag gattatcaat accatatttt tgaaaagcc gtttctgtaa    5280 tgaaggagaa aactcaccga ggcagttcca taggatggca agatcctggt atcggtctgc    5340
gattccgact cgtccaacat caatacaacc tattaatttc ccctcgtcaa aaataaggtt    5400
atcaagtgag aaatcaccat gagtgacgac tgaatccggt gagaatggca aaagcttatg    5460
catttctttc cagacttgtt caacaggcca gccattacgc tcgtcatcaa aatcactcgc    5520
atcaaccaaa ccgttattca ttcgtgattg cgcctgagcg agacgaaata cgcgatcgct    5580
gttaaaagga caattacaaa caggaatcga atgcaaccgg cgcaggaaca ctgccagcgc    5640
atcaacaata ttttcacctg aatcaggata ttcttctaat acctggaatg ctgttttccc    5700
ggggatcgca gtggtgagta accatgcatc atcaggagta cggataaaat gcttgatggt    5760
cggaagaggc ataaattccg tcagccagtt tagtctgacc atctcatctg taacatcatt    5820
ggcaacgcta cctttgccat gtttcagaaa caactctggc gcatcgggct tcccatacaa    5880
tcgatagatt gtcgcacctg attgcccgac attatcgcga gcccatttat acccatataa    5940
atcagcatcc atgttggaat ttaatcgcgg cctcgagcaa gacgtttccc gttgaatatg    6000
gctcataaca ccccttgtat tactgtttat gtaagcagac agttttattg ttcatgatga    6060
tatattttta tcttgtgcaa tgtaacatca gagattttga gacacaacgt ggctttcccc    6120 cccccccat tattgaagca tttatcaggg ttattgtctc atgagcggat acatatttga    6180
atgtatttag aaaaataaac aaataggggt tccgcgcaca tttccccgaa aagtgccacc    6240
tgacgtctaa gaaaccatta ttatcatgac attaacctat aaaaataggc gtatcacgag    6300
gccctttcgt c                                                         6311
```

<210> SEQ ID NO 12
<211> LENGTH: 6312
<212> TYPE: DNA
<213> ORGANISM: Artificial Sequence
<220> FEATURE:

<223> OTHER INFORMATION: plasmid CMV/R-gp145dCFI(CBBB)

<400> SEQUENCE: 12

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccg cccattgacg tcaataatga cgtatgttcc      480
catagtaacg ccaatagggc ctttccattg acgtcaatgg gtggagtatt tacggtaaac     540
tgcccacttg gcagtacatc aagtgtatca tatgccaagt acgccccta ttgacgtcaa      600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagag    1380
atatcgccac catgcgtgtt cgtggtatcc cgcgtaactg gccgcagtgg tggatgtggg    1440
gtatcctggg tttctggatg atcatcatct gccgtgttgt tggtaacatg tgggttaccg    1500
tttactacgg tgttccggtt tggaccgacg ctaaaaccac cctgttctgc gcttccgaca    1560
ccaaagccta cgaccgtgaa gttcacaacg tttgggctac ccacgcttgc gttccgaccg    1620
acccgaaccc gcaggaaatc gttctggaaa acgttaccga aaacttcaac atgtggaaaa    1680
acgacatggt tgaccagatg cacgaagaca tcatctccct gtgggaccag tccctgaaac    1740
cgtgcgttaa actgaccccg ctgtgcgtta ccctgcactg caccaacgct accttcaaaa    1800
acaacgttac caacgacatg aacaaagaaa tccgtaactg ctccttcaac accaccaccg    1860
aaatccgtga caaaaaacag cagggttacg ctctgttcta ccgtccggac atcgttctgc    1920
tgaaagaaaa ccgtaacaac tccaacaact ccgaatacat cctgatcaat tgcaacacca    1980
gcgtgatcac ccaggcctgc cccaaggtga gcttcgagcc catccccatc cactactgcg    2040
cccccgccgg cttcgccatc ctgaagtgca aggacaagaa gttcaacggc aagggcccct    2100
gcaccaacgt gagcaccgtg cagtgcaccc acggcatccg cccgtggtg agcacccagc     2160
tgctgctgaa cggtagcctg gccgaggagg aggtggtgat ccgcagcgct aacttcgccg    2220
acaacgccaa ggtgatcatc gtgcagctga acgagagcgt ggagatcaac tgcacccgcc    2280
```

```
ccaacaacaa cacccgcaag agcatccaca tcggccccgg ccgcgccttc tacaccaccg   2340
gcgagatcat cggcgacatc cgccaggccc actgcaacct gagccgcgcc aagtggaacg   2400
acaccctgaa caagatcgtg atcaagctgc gcgagcagtt cggcaacaag accatcgtgt   2460
tcaagcacag cagcggcggc gaccccgaga tcgtgaccca cagcttcaac tgcggcggcg   2520
aattcttcta ctgcaacagc acccagctgt taattccac atggaacgtg accgaggaga    2580
gcaacaacac cgtggagaac aacaccatca ccctgccctg ccgcatcaag cagatcatca   2640
acatgtggca ggaggtgggc cgcgccatgt acgccccccc catccgcggc cagatccgct   2700
gcagcagcaa catcaccggc ctgctgctga cccgcgacgg cggccccgag gacaacaaga   2760
ccgaggtgtt ccgccctggc ggcggcgaca tgcgcgacaa ctggcgcagc gagctgtaca   2820
agtacaaggt ggtgaagatc gagccccctgg gcgtggcccc caccaaggcc aagcttaccg   2880
tccaggcccg cctgctgctg agcggcatcg tgcagcagca gaacaacctg ctgcgcgcca   2940
tcgaggccca gcagcacctg ctgcagctga ccgtgtgggg catcaagcag ctgcaggccc   3000
gcgtgctggc cgtggagcgc tacctgcgcg accagcagct cctcaagatc tgggacaaca   3060
tgacctggat cgagtgggac cgcgagatca caaactacac cagcatcatc tacagcctga   3120
tcgaggagag ccagaaccag caggagaaga cgagcagga gctgctggag ctggacaagt    3180
gggccagcct gtggaactgg ttcgacatca ccaagtggct gtggtacatc aagatcttca   3240
tcatgatcgt gggcggcctg atcggcctgc gcatcgtgtt cagcgtgctg agcatctgag   3300
gatccagatc tgctgtgcct tctagttgcc agccatctgt tgtttgcccc tcccccgtgc   3360
cttccttgac cctggaaggt gccactccca ctgtcctttc taataaaat gaggaaattg    3420
catcgcattg tctgagtagg tgtcattcta ttctgggggg tggggtgggg caggacagca   3480
agggggagga ttgggaagac aatagcaggc atgctgggga tgcggtgggc tctatgggta   3540
cccaggtgct gaagaattga cccggttcct cctgggccag aaagaagcag gcacatcccc   3600
ttctctgtga cacaccctgt ccacgcccct ggttcttagt tccagcccca ctcataggac   3660
actcatagct caggagggct ccgccttcaa tcccacccgc taaagtactt ggagcggtct   3720
ctccctcccct catcagccca ccaaaccaaa cctagcctcc aagagtggga agaaattaaa   3780
gcaagatagg ctattaagtg cagagggaga gaaaatgcct ccaacatgtg aggaagtaat   3840
gagagaaatc atagaatttt aaggccatca tggccttaat cttccgcttc ctcgctcact   3900
gactcgctgc gctcggtcgt tcggctgcgg cgagcggtat cagctcactc aaaggcggta   3960
atacggttat ccacagaatc aggggataac gcaggaaaga acatgtgagc aaaaggccag   4020
caaaaggcca ggaaccgtaa aaaggccgcg ttgctggcgt ttttccatag gctccgcccc   4080
cctgacgagc atcacaaaaa tcgacgctca agtcagaggt ggcgaaaccc gacaggacta   4140
taaagatacc aggcgtttcc ccctggaagc tccctcgtgc gctctcctgt tccgaccctg   4200
ccgcttaccg gatacctgtc cgcctttctc ccttcgggaa gcgtggcgct ttctcatagc   4260
tcacgctgta ggtatctcag ttcggtgtag gtcgttcgct ccaagctggg ctgtgtgcac   4320
gaaccccccg ttcagcccga ccgctgcgcc ttatccggta actatcgtct tgagtccaac   4380
ccggtaagac acgacttatc gccactggca gcagccactg gtaacaggat tagcagagcg   4440
aggtatgtag gcggtgctac agagttcttg aagtggtggc ctaactacgg ctacactaga   4500
agaacagtat ttggtatctg cgctctgctg aagccagtta ccttcggaaa aagagttggt   4560
agctcttgat ccggcaaaca aaccaccgct ggtagcggtg gtttttttgt ttgcaagcag   4620
cagattacgc gcagaaaaaa aggatctcaa gaagatcctt tgatcttttc tacggggtct   4680
```

-continued

```
gacgctcagt ggaacgaaaa ctcacgttaa gggattttgg tcatgagatt atcaaaaagg      4740
atcttcacct agatcctttt aaattaaaaa tgaagtttta aatcaatcta aagtatatat      4800
gagtaaactt ggtctgacag ttaccaatgc ttaatcagtg aggcacctat ctcagcgatc      4860
tgtctatttc gttcatccat agttgcctga ctcggggggg ggggcgctg aggtctgcct       4920 cgtgaagaag gtgttgctga ctcataccag gcctgaatcg ccccatcatc agccagaaa       4980 gtgagggagc cacggttgat gagagctttg ttgtaggtgg accagttggt gattttgaac      5040
ttttgctttg ccacggaacg gtctgcgttg tcgggaagat gcgtgatctg atccttcaac      5100
tcagcaaaag ttcgatttat tcaacaaagc cgccgtcccg tcaagtcagc gtaatgctct      5160
gccagtgtta caaccaatta accaattctg attagaaaaa ctcatcgagc atcaaatgaa      5220
actgcaattt attcatatca ggattatcaa taccatattt ttgaaaaagc cgtttctgta      5280
atgaaggaga aaactcaccg aggcagttcc ataggatggc aagatcctgg tatcggtctg      5340
cgattccgac tcgtccaaca tcaatacaac ctattaattt cccctcgtca aaaataaggt      5400
tatcaagtga gaaatcacca tgagtgacga ctgaatccgg tgagaatggc aaaagcttat      5460
gcatttcttt ccagacttgt tcaacaggcc agccattacg ctcgtcatca aaatcactcg      5520
catcaaccaa accgttattc attcgtgatt gcgcctgagc gagacgaaat acgcgatcgc      5580
tgttaaaagg acaattacaa acaggaatcg aatgcaaccg gcgcaggaac actgccagcg      5640
catcaacaat attttcacct gaatcaggat attcttctaa tacctggaat gctgttttcc      5700
cggggatcgc agtggtgagt aaccatgcat catcaggagt acggataaaa tgcttgatgg      5760
tcggaagagg cataaattcc gtcagccagt ttagtctgac catctcatct gtaacatcat      5820
tggcaacgct acctttgcca tgtttcagaa acaactctgg cgcatcgggc ttcccataca      5880
atcgatagat tgtcgcacct gattgcccga cattatcgcg agcccattta ccccatata       5940 aatcagcatc catgttggaa tttaatcgcg gcctcgagca agacgtttcc cgttgaatat      6000
ggctcataac ccccttgta ttactgttta tgtaagcaga cagttttatt gttcatgatg       6060 atatatttt atcttgtgca atgtaacatc agagattttg agacacaacg tggctttccc      6120 cccccccca ttattgaagc atttatcagg gttattgtct catgagcgga tacatatttg      6180
aatgtattta gaaaaataaa caaatagggg ttccgcgcac atttccccga aaagtgccac      6240
ctgacgtcta agaaaccatt attatcatga cattaaccta taaaaatagg cgtatcacga      6300
ggccctttcg tc                                                         6312
```

<210> SEQ ID NO 13
<211> LENGTH: 6295
<212> TYPE: DNA
<213> ORGANISM: Artificial Sequence
<220> FEATURE:
<223> OTHER INFORMATION: plasmid CMV/R-gp145dCFI(CBCC)

<400> SEQUENCE: 13

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg       120 ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
```

```
cccgcctggc tgaccgccca acgacccccg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgccccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagag   1380
atatcgccac catgcgtgtt cgtggtatcc cgcgtaactg gccgcagtgg tggatgtggg   1440
gtatcctggg tttctggatg atcatcatct gccgtgttgt tggtaacatg tgggttaccg   1500
tttactacgg tgttccggtt tggaccgacg ctaaaaccac cctgttctgc gcttccgaca   1560
ccaaagccta cgaccgtgaa gttcacaacg tttgggctac ccacgcttgc gttccgaccg   1620
acccgaaccc gcaggaaatc gttctggaaa acgttaccga aaacttcaac atgtggaaaa   1680
acgacatggt tgaccagatg cacgaagaca tcatctccct gtgggaccag tccctgaaac   1740
cgtgcgttaa actgaccccg ctgtgcgtta ccctgcactg caccaacgct accttcaaaa   1800
acaacgttac caacgacatg aacaaagaaa tccgtaactg ctccttcaac accaccaccg   1860
aaatccgtga caaaaaacag cagggttacg ctctgttcta ccgtccggac atcgttctgc   1920
tgaaagaaaa ccgtaacaac tccaacaact ccgaatacat cctgatcaat tgcaacacca   1980
gcgtgatcac ccaggcctgc cccaaggtga gcttcgagcc catccccatc cactactgcg   2040
cccccgccgg cttcgccatc ctgaagtgca ggacaagaa gttcaacggc aagggcccct   2100
gcaccaacgt gagcaccgtg cagtgcaccc acggcatccg ccccgtggtg agcacccagc   2160
tgctgctgaa cggtagcctg gccgaggagg aggtggtgat ccgcagcgct aacttcgccg   2220
acaacgccaa ggtgatcatc gtgcagctga acgagagcgt ggagatcaac tgcacccgcc   2280
ccaacaacaa cacccgcaag agcatccaca tcggccccgg ccgcgccttc tacaccaccg   2340
gcgagatcat cggcgacatc cgccaggccc actgcaacct gagccgcgcc aagtggaacg   2400
acaccctgaa caagatcgtg atcaagctgc gcgagcagtt cggcaacaag accatcgtgt   2460
tcaagcacag cagcggcggc gaccccgaga tcgtgaccca cagcttcaac tgcggcggcg   2520
aattcttcta ctgcaacacc acccgtctgt tcaacaacaa cgctaccgaa gacgaaacca   2580
tcaccctgcc gtgccgtatc aaacagatca tcaacatgtg gcagggtgtt ggtcgtgcta   2640
tgtacgctcc gccgatcgct ggtaacatca cctgcaaatc caacatcacc ggtctgctgc   2700
tggttcgtga cggtggtgaa gacaacaaaa ccgaagaaat cttccgtccg ggtggtggta   2760
acatgaaaga caactggcgt tccgaactgt acaaatacaa agttatcgaa ctgaaaccgc   2820
```

-continued

```
tgggtatcgc tccgaccggt gctaagctta ccgttcaggc tcgtcagctg ctgtcctcca   2880
tcgttcagca gcagtccaac ctgctgcgtg ctatcgaagc tcagcagcac atgctgcagc   2940
tgaccgtttg gggtatcaaa cagctgcaga cccgtgttct ggctatcgaa cgttacctga   3000
aagaccagca gctcgagatc tggaacaaca tgacctggat ggaatgggac cgtgaaatct   3060
ccaactacac cgacaccatc taccgtctgc tggaagactc ccagacccag caggaaaaaa   3120
acgaaaaaga cctgctggct ctggactcct ggaaaaacct gtggtcctgg ttcgacatct   3180
ccaactggct gtggtacatc aaaatcttca tcatgatcgt tggtggtctg atcggtctgc   3240
gtatcatctt cgctgttctg tccatctgag gatccagatc tgctgtgcct tctagttgcc   3300
agccatctgt tgtttgcccc tccccgtgc cttccttgac cctggaaggt gccactccca   3360
ctgtcctttc ctaataaaat gaggaaattg catcgcattg tctgagtagg tgtcattcta   3420
ttctgggggg tggggtgggg caggacagca agggggagga ttgggaagac aatagcaggc   3480
atgctgggga tgcggtgggc tctatgggta cccaggtgct gaagaattga cccggttcct   3540
cctgggccag aaagaagcag gcacatcccc ttctctgtga cacaccctgt ccacgcccct   3600
ggttcttagt tccagcccca ctcataggac actcatagct caggagggct ccgccttcaa   3660
tcccacccgc taaagtactt ggagcggtct ctccctccct catcagccca ccaaaccaaa   3720
cctagcctcc aagagtggga agaaattaaa gcaagatagg ctattaagtg cagagggaga   3780
gaaaatgcct ccaacatgtg aggaagtaat gagagaaatc atagaatttt aaggccatga   3840
tttaaggcca tcatggcctt aatcttccgc ttcctcgctc actgactcgc tgcgctcggt   3900
cgttcggctg cggcgagcgg tatcagctca ctcaaaggcg gtaatacggt tatccacaga   3960
atcaggggat aacgcaggaa agaacatgtg agcaaaaggc cagcaaaagg ccaggaaccg   4020
taaaaaggcc gcgttgctgg cgttttttcca taggctccgc ccccctgacg agcatcacaa   4080
aaatcgacgc tcaagtcaga ggtggcgaaa cccgacagga ctataaagat accaggcgtt   4140
tccccctgga agctccctcg tgcgctctcc tgttccgacc ctgccgctta ccggatacct   4200
gtccgccttt ctcccttcgg gaagcgtggc gctttctcat agctcacgct gtaggtatct   4260
cagttcggtg taggtcgttc gctccaagct gggctgtgtg cacgaacccc ccgttcagcc   4320
cgaccgctgc gccttatccg gtaactatcg tcttgagtcc aacccggtaa gacacgactt   4380
atcgccactg gcagcagcca ctggtaacag gattagcaga gcgaggtatg taggcggtgc   4440
tacagagttc ttgaagtggt ggcctaacta cggctacact agaagaacag tatttggtat   4500
ctgcgctctg ctgaagccag ttaccttcgg aaaaagagtt ggtagctctt gatccggcaa   4560
acaaaccacc gctggtagcg gtggtttttt tgtttgcaag cagcagatta cgcgcagaaa   4620
aaaaggatct caagaagatc ctttgatctt ttctacgggg tctgacgctc agtggaacga   4680
aaactcacgt taagggattt tggtcatgag attatcaaaa aggatcttca cctagatcct   4740
tttaaattaa aaatgaagtt ttaaatcaat ctaaagtata tatgagtaaa cttggtctga   4800
cagttaccaa tgcttaatca gtgaggcacc tatctcagcg atctgtctat ttcgttcatc   4860
catagttgcc tgactcgggg ggggggggcg ctgaggtctg cctcgtgaag aaggtgttgc   4920
tgactcatac caggcctgaa tcgccccatc atccagccag aaagtgaggg agccacggtt   4980
gatgagagct tgttgtagg tggaccagtt ggtgattttg aacttttgct ttgccacgga   5040
acggtctgcg ttgtcgggaa gatgcgtgat ctgatccttc aactcagcaa aagttcgatt   5100
tattcaacaa agccgccgtc ccgtcaagtc agcgtaatgc tctgccagtg ttacaaccaa   5160
ttaaccaatt ctgattagaa aaactcatcg agcatcaaat gaaactgcaa tttattcata   5220
```

-continued

| | |
|---|---|
| tcaggattat caataccata tttttgaaaa agccgtttct gtaatgaagg agaaaactca | 5280 |
| ccgaggcagt tccataggat ggcaagatcc tggtatcggt ctgcgattcc gactcgtcca | 5340 |
| acatcaatac aacctattaa tttccctcg tcaaaaataa ggttatcaag tgagaaatca | 5400 |
| ccatgagtga cgactgaatc cggtgagaat ggcaaaagct tatgcatttc tttccagact | 5460 |
| tgttcaacag gccagccatt acgctcgtca tcaaaatcac tcgcatcaac caaaccgtta | 5520 |
| ttcattcgtg attgcgcctg agcgagacga aatacgcgat cgctgttaaa aggacaatta | 5580 |
| caaacaggaa tcgaatgcaa ccggcgcagg aacactgcca gcgcatcaac aatattttca | 5640 |
| cctgaatcag gatattcttc taatacctgg aatgctgttt tcccggggat cgcagtggtg | 5700 |
| agtaaccatg catcatcagg agtacggata aaatgcttga tggtcggaag aggcataaat | 5760 |
| tccgtcagcc agtttagtct gaccatctca tctgtaacat cattggcaac gctacctttg | 5820 |
| ccatgtttca gaaacaactc tggcgcatcg gcttcccat acaatcgata gattgtcgca | 5880 |
| cctgattgcc cgacattatc gcgagccat ttataccat ataaatcagc atccatgttg | 5940 |
| gaatttaatc gcggcctcga gcaagacgtt tcccgttgaa tatggctcat aacacccctt | 6000 |
| gtattactgt ttatgtaagc agacagtttt attgttcatg atgatatatt tttatcttgt | 6060 |
| gcaatgtaac atcagagatt ttgagacaca acgtggcttt ccccccccc ccattattga | 6120 |
| agcatttatc agggttattg tctcatgagc ggatacatat ttgaatgtat ttagaaaaat | 6180 |
| aaacaaatag gggttccgcg cacatttccc cgaaaagtgc cacctgacgt ctaagaaacc | 6240 |
| attattatca tgacattaac ctataaaaat aggcgtatca cgaggccctt tcgtc | 6295 |

<210> SEQ ID NO 14
<211> LENGTH: 6325
<212> TYPE: DNA
<213> ORGANISM: Artificial Sequence
<220> FEATURE:
<223> OTHER INFORMATION: plasmid CMV/R-gp145dCFI(CCBC)

<400> SEQUENCE: 14

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |

-continued

```
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagag    1380
atatcgccac catgcgtgtt cgtggtatcc cgcgtaactg gccgcagtgg tggatgtggg    1440
gtatcctggg tttctggatg atcatcatct gccgtgttgt tggtaacatg tgggttaccg    1500
tttactacgg tgttccggtt tggaccgacg ctaaaaccac cctgttctgc gcttccgaca    1560
ccaaagccta cgaccgtgaa gttcacaacg tttgggctac ccacgcttgc gttccgaccg    1620
acccgaaccc gcaggaaatc gttctggaaa acgttaccga aaacttcaac atgtggaaaa    1680
acgacatggt tgaccagatg cacgaagaca tcatctccct gtgggaccag tccctgaaac    1740
cgtgcgttaa actgaccccg ctgtgcgtta ccctgcactg caccaacgct accttcaaaa    1800
acaacgttac caacgacatg aacaaagaaa tccgtaactg ctccttcaac accaccaccg    1860
aaatccgtga caaaaaacag cagggttacg ctctgttcta ccgtccggac atcgttctgc    1920
tgaaagaaaa ccgtaacaac tccaacaact ccgaatacat cctgatcaat tgcaacgctt    1980
ccaccatcac ccaggcttgc ccgaaagtta acttcgaccc gatcccgatc cactactgcg    2040
ctccggctgg ttacgctatc ctgaaatgca acaacaaaac cttctccggt aaaggtccgt    2100
gcaacaacgt ttccaccgtt cagtgcaccc atggtatcaa accggttgtt ccacccagc    2160
tgctgctgaa cggttccctg gctgaaaaag aaatcatcat ccgttccgaa acctgaccg    2220
acaacgttaa aaccatcatc gttcacctga caaatccgt tgaaatcgtt tgcacccgtc    2280
cgaacaacaa cacccgtaaa tccatgcgta tcggtccggg tcagaccttc tacgctaccg    2340
gtgacatcat cggtgacatc cgtcaggctt actgcaacat ctccggttcc aaatggaacg    2400
aaaccctgaa acgtgttaaa gaaaaactgc aggaaaacta caacaacaac aaaaccatca    2460
aattcgctcc gtcctccggt ggtgacctgg aaatcaccac ccactccttc aactgccgtg    2520
gtgaattctt ctactgcaac agcacccagc tgtttaattc cacatggaac gtgaccgagg    2580
agagcaacaa caccgtggag aacaacacca tcacccctgcc ctgccgcatc aagcagatca    2640
tcaacatgtg gcaggaggtg ggccgcgcca tgtacgcccc cccatccgc ggccagatcc    2700
gctgcagcag caacatcacc ggcctgctgc tgacccgcga cggcggcccc gaggacaaca    2760
agaccgaggt gttccgccct ggcggcggcg acatgcgcga caactggcgc agcgagctgt    2820
acaagtacaa ggtggtgaag atcgagcccc tgggcgtggc ccccaccaag gccaagctta    2880
ccgttcaggc tcgtcagctg ctgtcctcca tcgttcagca gcagtccaac ctgctgcgtg    2940
ctatcgaagc tcagcagcac atgctgcagc tgaccgtttg gggtatcaaa cagctgcaga    3000
cccgtgttct ggctatcgaa cgttacctga agaccagca gctcgagatc tggaacaaca    3060
tgacctggat ggaatgggac cgtgaaatct ccaactacac cgacaccatc taccgtctgc    3120
tggaagactc ccagacccag caggaaaaaa acgaaaaaga cctgctggct ctggactcct    3180
ggaaaaacct gtggtcctgg ttcgacatct ccaactggct gtggtacatc aaaatcttca    3240
tcatgatcgt tggtggtctg atcggtctgc gtatcatctt cgctgttctg tccatctgag    3300
gatccagatc tgctgtgcct tctagttgcc agccatctgt tgtttgcccc tcccccgtgc    3360
cttccttgac cctggaaggt gccactccca ctgtcctttc ctaataaaat gaggaaattg    3420
```

```
catcgcattg tctgagtagg tgtcattcta ttctgggggg tggggtgggg caggacagca    3480
agggggagga ttgggaagac aatagcaggc atgctgggga tgcggtgggc tctatgggta    3540
cccaggtgct gaagaattga cccggttcct cctgggccag aaagaagcag gcacatcccc    3600
ttctctgtga cacaccctgt ccacgcccct ggttcttagt tccagcccca ctcataggac    3660
actcatagct caggagggct ccgccttcaa tcccacccgc taaagtactt ggagcggtct    3720
ctccctccct catcagccca ccaaaccaaa cctagcctcc aagagtggga agaaattaaa    3780
gcaagatagg ctattaagtg cagagggaga gaaaatgcct ccaacatgtg aggaagtaat    3840
gagagaaatc atagaatttt aaggccatga tttaaggcca tcatggcctt aatcttccgc    3900
ttcctcgctc actgactcgc tgcgctcggt cgttcggctg cggcgagcgg tatcagctca    3960
ctcaaaggcg gtaatacggt tatccacaga atcaggggat aacgcaggaa agaacatgtg    4020
agcaaaaggc cagcaaaagg ccaggaaccg taaaaaggcc gcgttgctgg cgttttttcca   4080
taggctccgc cccctgacg agcatcacaa aaatcgacgc tcaagtcaga ggtggcgaaa    4140
cccgacagga ctataaagat accaggcgtt ccccctgga agctccctcg tgcgctctcc    4200
tgttccgacc ctgccgctta ccggatacct gtccgccttt ctcccttcgg gaagcgtggc    4260
gctttctcat agctcacgct gtaggtatct cagttcggtg taggtcgttc gctccaagct    4320
gggctgtgtg cacgaaccc ccgttcagcc cgaccgctgc gccttatccg gtaactatcg    4380
tcttgagtcc aacccggtaa gacacgactt atcgccactg gcagcagcca ctggtaacag    4440
gattagcaga gcgaggtatg taggcggtgc tacagagttc ttgaagtggt ggcctaacta    4500
cggctacact agaagaacag tatttggtat ctgcgctctg ctgaagccag ttaccttcgg    4560
aaaaagagtt ggtagctctt gatccggcaa acaaaccacc gctggtagcg gtggtttttt    4620
tgtttgcaag cagcagatta cgcgcagaaa aaaaggatct caagaagatc ctttgatctt    4680
ttctacgggg tctgacgctc agtggaacga aaactcacgt taagggattt tggtcatgag    4740
attatcaaaa aggatcttca cctagatcct tttaaattaa aaatgaagtt ttaaatcaat    4800
ctaaagtata tatgagtaaa cttggtctga cagttaccaa tgcttaatca gtgaggcacc    4860
tatctcagcg atctgtctat ttcgttcatc catagttgcc tgactcgggg ggggggggcg    4920
ctgaggtctg cctcgtgaag aaggtgttgc tgactcatac caggcctgaa tcgccccatc    4980
atccagccag aaagtgaggg agccacggtt gatgagagct ttgttgtagg tggaccagtt    5040
ggtgattttg aacttttgct ttgccacgga acggtctgcg ttgtcgggaa gatgcgtgat    5100
ctgatccttc aactcagcaa aagttcgatt tattcaacaa agccgccgtc ccgtcaagtc    5160
agcgtaatgc tctgccagtg ttacaaccaa ttaaccaatt ctgattagaa aaactcatcg    5220
agcatcaaat gaaactgcaa tttattcata tcaggattat caataccata tttttgaaaa    5280
agccgtttct gtaatgaagg agaaaactca ccgaggcagt tccataggat ggcaagatcc    5340
tggtatcggt ctgcgattcc gactcgtcca acatcaatac aacctattaa tttccctcg    5400
tcaaaaataa ggttatcaag tgagaaatca ccatgagtga cgactgaatc cggtgagaat    5460
ggcaaaagct tatgcatttc tttccagact tgttcaacag gccagccatt acgctcgtca    5520
tcaaaatcac tcgcatcaac caaaccgtta ttcattcgtg attgcgcctg agcgagacga    5580
aatacgcgat cgctgttaaa aggacaatta caaacaggaa tcgaatgcaa ccggcgcagg    5640
aacactgcca gcgcatcaac aatatttttca cctgaatcag gatattcttc taatacctgg    5700
aatgctgttt tccggggat cgcagtggtg agtaaccatg catcatcagg agtacggata    5760
aaatgcttga tggtcggaag aggcataaat tccgtcagcc agtttagtct gaccatctca    5820
```

```
tctgtaacat cattggcaac gctacctttg ccatgtttca gaaacaactc tggcgcatcg    5880
ggcttcccat acaatcgata gattgtcgca cctgattgcc cgacattatc gcgagcccat    5940
ttatacccat ataaatcagc atccatgttg gaatttaatc gcggcctcga gcaagacgtt    6000
tcccgttgaa tatggctcat aacaccccett gtattactgt ttatgtaagc agacagtttt    6060
attgttcatg atgatatatt tttatcttgt gcaatgtaac atcagagatt ttgagacaca    6120
acgtggcttt ccccccccc ccattattga agcatttatc agggttattg tctcatgagc    6180
ggatacatat ttgaatgtat ttagaaaaat aaacaaatag gggttccgcg cacatttccc    6240
cgaaaagtgc cacctgacgt ctaagaaacc attattatca tgacattaac ctataaaaat    6300
aggcgtatca cgaggccctt tcgtc                                          6325

<210> SEQ ID NO 15
<211> LENGTH: 6318
<212> TYPE: DNA
<213> ORGANISM: Artificial Sequence
<220> FEATURE:
<223> OTHER INFORMATION: plasmid CMV/Rgp-145dCFI(CN54)

<400> SEQUENCE: 15
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140
ctttgtccgg cgctcccttg gagcctacct agactcagcc ggctctccac gctttgcctg    1200
accctgcttg ctcaactcta gttaacggtg agggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagag    1380
atatcgacac catggacagg gccaagctgc tgctgctgct gctgctgctg ctgctgcccc    1440
aggcccaggc cgtgggcaac ctgtgggtga ccgtgtacta cggcgtgccc gtgtggaagg    1500
gcgccaccac caccctgttc tgcgccagcg acgccaaggc ctacgacacc gaggtgcaca    1560
```

```
acgtgtgggc cacccacgcc tgcgtgcccg ccgaccccaa cccccaggag atggtgctgg    1620
agaacgtgac cgagaacttc aacatgtgga agaacgagat ggtgaaccag atgcaggagg    1680
acgtcatcag cctgtgggac cagagcctga agccctgcgt gaagctgacc ccctgtgcg     1740 tgaccctgga gtgcaggaac gtgagcagca acagcaacga cacctaccac gagacctacc    1800
acgagagcat gaaggagatg aagaactgca gcttcaacgc caccaccgtg gtgagggaca    1860
ggaagcagac cgtgtacgcc ctgttctaca ggctggacat cgtgccctg accaagaaga     1920 actacagcga gaacagcagc gagtactaca ggctgatcaa ctgcaacacc agcgccatca    1980
cccaggcctg ccccaaggtg accttcgacc ccatccccat ccactactgc accccgccg     2040 gctacgccat cctgaagtgc aacgacaaga tcttcaacgg caccggcccc tgccacaacg    2100
tgagcaccgt gcagtgcacc cacggcatca agcccgtggt gagcacccag ctgctgctga    2160
acggcagcct ggccgagggc gagatcatca tcaggagcga gaacctgacc aacaacgtga    2220
aaaccatcat cgtgcacctg aaccagagcg tggagatcgt gtgcaccagg cccggcaaca    2280
acaccaggaa gagcatcagg atcggccccg ccagaccctt ctacgccacc ggcgacatca    2340
tcggcgacat caggcaggcc cactgcaaca tcagcgagga caagtggaac gagaccctgc    2400
agagggtgag caagaagctg gccgagcact tccagaacaa gaccatcaag ttcgccagca    2460
gcagcggcgg cgacctggag gtgaccaccc acagcttcaa ctgcaggggc gagttcttct    2520
actgcaacac cagcggcctg ttcaacggcg cctacacccc caacggcacc aagagcaaca    2580
gcagcagcat catcaccatc ccctgcagga tcaagcagat catcaacatg tggcaggagg    2640
tgggcagggc catgtacgcc cctcccatca agggcaacat cacctgcaag agcaacatca    2700
ccggcctgct gctggtgagg gacggcggca ccgagcccaa cgacaccgag accttcaggc    2760
ccggcggcgg cgacatgagg aacaactgga ggagcgagct gtacaagtac aaggtggtgg    2820
agatcaagcc cctgggcgtg ccccccacca ccaccaagct taccgtgcag gccaggcagc    2880
tgctgagcgg catcgtgcag cagcagagca acctgctgag ggccatcgag gcccagcagc    2940
acctgctgca gctgaccgtg tggggcatca agcagctgca ggaccaggtg ctggccatcg    3000
agaggtacct gaaggaccag cagctcgaga tctgggacaa catgacctgg atgcagtggg    3060
acaaggagat cagcaactac accaacaccg tgtacaggct gctggaggag agccagaacc    3120
agcaggagag gaacgagaag gacctgctgg ccctggacag ctggaagaac ctgtggagct    3180
ggttcgacat caccaactgg ctgtggtaca tcaagatctt catcatcatc gtgggcggcc    3240
tgatcggcct gaggatcatc ttcgccgtgc tgagcatcgt gaacagggtg aggcagggct    3300
actgaggatc cagatctgct gtgccttcta gttgccagcc atctgttgtt tgcccctccc    3360
ccgtgccttc cttgaccctg gaaggtgcca ctcccactgt cctttcctaa taaaatgagg    3420
aaattgcatc gcattgtctg agtaggtgtc attctattct ggggggtggg gtggggcagg    3480
acagcaaggg ggaggattgg gaagacaata gcaggcatgc tggggatgcg gtgggctcta    3540
tgggtaccca ggtgctgaag aattgacccg gttcctcctg ggccagaaag aagcaggcac    3600
atccccttct ctgtgacaca ccctgtccac gcccctggtt cttagttcca gccccactca    3660
taggacactc atagctcagg agggctccgc cttcaatccc acccgctaaa gtacttggag    3720
cggtctctcc ctccctcatc agcccaccaa accaaaccta gcctccaaga gtgggaagaa    3780
attaaagcaa gataggctat taagtgcaga gggagagaaa atgcctccaa catgtgagga    3840
agtaatgaga gaaatcatag aattttaagg ccatcatggc cttaatcttc cgcttcctcg    3900
ctcactgact cgctgcgctc ggtcgttcgg ctgcggcgag cggtatcagc tcactcaaag    3960
```

```
gcggtaatac ggttatccac agaatcaggg gataacgcag gaaagaacat gtgagcaaaa   4020
ggccagcaaa aggccaggaa ccgtaaaaag gccgcgttgc tggcgttttt ccataggctc   4080
cgcccccctg acgagcatca caaaaatcga cgctcaagtc agaggtggcg aaacccgaca   4140
ggactataaa gataccaggc gtttccccct ggaagctccc tcgtgcgctc tcctgttccg   4200
accctgccgc ttaccggata cctgtccgcc tttctccctt cgggaagcgt ggcgctttct   4260
catagctcac gctgtaggta tctcagttcg gtgtaggtcg ttcgctccaa gctgggctgt   4320
gtgcacgaac cccccgttca gcccgaccgc tgcgccttat ccggtaacta tcgtcttgag   4380
tccaacccgg taagacacga cttatcgcca ctggcagcag ccactggtaa caggattagc   4440
agagcgaggt atgtaggcgg tgctacagag ttcttgaagt ggtggcctaa ctacggctac   4500
actagaagaa cagtatttgg tatctgcgct ctgctgaagc cagttacctt cggaaaaaga   4560
gttggtagct cttgatccgg caaacaaacc accgctggta gcggtggttt ttttgtttgc   4620
aagcagcaga ttacgcgcag aaaaaaagga tctcaagaag atcctttgat cttttctacg   4680
gggtctgacg ctcagtggaa cgaaaactca cgttaaggga ttttggtcat gagattatca   4740
aaaaggatct tcacctagat ccttttaaat taaaaatgaa gttttaaatc aatctaaagt   4800
atatatgagt aaacttggtc tgacagttac caatgcttaa tcagtgaggc acctatctca   4860
gcgatctgtc tatttcgttc atccatagtt gcctgactcg ggggggggg gcgctgaggt   4920 ctgcctcgtg aagaaggtgt tgctgactca taccaggcct gaatcgcccc atcatccagc   4980
cagaaagtga gggagccacg gttgatgaga gctttgttgt aggtggacca gttggtgatt   5040
ttgaactttt gctttgccac ggaacggtct gcgttgtcgg gaagatgcgt gatctgatcc   5100
ttcaactcag caaaagttcg atttattcaa caaagccgcc gtcccgtcaa gtcagcgtaa   5160
tgctctgcca gtgttacaac caattaacca attctgatta gaaaaactca tcgagcatca   5220
aatgaaactg caatttattc atatcaggat tatcaatacc atatttttga aaaagccgtt   5280
tctgtaatga aggagaaaac tcaccgaggc agttccatag gatggcaaga tcctggtatc   5340
ggtctgcgat tccgactcgt ccaacatcaa tacaacctat taatttcccc tcgtcaaaaa   5400
taaggttatc aagtgagaaa tcaccatgag tgacgactga atccggtgag aatggcaaaa   5460
gcttatgcat ttctttccag acttgttcaa caggccagcc attacgctcg tcatcaaaat   5520
cactcgcatc aaccaaaccg ttattcattc gtgattgcgc ctgagcgaga cgaaatacgc   5580
gatcgctgtt aaaaggacaa ttacaaacag gaatcgaatg caaccggcgc aggaacactg   5640
ccagcgcatc aacaatattt tcacctgaat caggatattc ttctaatacc tggaatgctg   5700
ttttcccggg gatcgcagtg gtgagtaacc atgcatcatc aggagtacgg ataaaatgct   5760
tgatggtcgg aagaggcata aattccgtca gccagtttag tctgaccatc tcatctgtaa   5820
catcattggc aacgctacct ttgccatgtt tcagaaacaa ctctggcgca tcgggcttcc   5880
catacaatcg atagattgtc gcacctgatt gcccgacatt atcgcgagcc catttatacc   5940
catataaatc agcatccatg ttggaattta atcgcggcct cgagcaagac gtttcccgtt   6000
gaatatggct cataacaccc cttgtattac tgtttatgta agcagacagt tttattgttc   6060
atgatgatat atttttatct tgtgcaatgt aacatcagag attttgagac acaacgtggc   6120
tttccccccc cccccattat tgaagcattt atcagggtta ttgtctcatg agcggataca   6180
tatttgaatg tatttagaaa aataaacaaa taggggttcc gcgcacattt ccccgaaaag   6240
tgccacctga cgtctaagaa accattatta tcatgacatt aacctataaa aataggcgta   6300
tcacgaggcc ctttcgtc                                                  6318
```

<210> SEQ ID NO 16
<211> LENGTH: 36066
<212> TYPE: DNA
<213> ORGANISM: Artificial Sequence
<220> FEATURE:
<223> OTHER INFORMATION: Adenoviral vector Adt.GagPol(B).11D

<400> SEQUENCE: 16

```
catcatcaat aatataccttt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg     180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggcccggga    360
tcggtgatca ccgatccaga catgataaga tacattgatg agtttggaca aaccacaact    420
agaatgcagt gaaaaaaatg ctttatttgt gaaatttgtg atgctattgc tttatttgta    480
accattataa gctgcaataa acaagttccc ggatctttct agctagtcta gaattcctag    540
tcctcgtcct ggcggctggc cacgcagtcg tcgccggcca tctgcttgcc gtagtcgcgg    600
atgatcttgg cctgcggcg gggcaccacc ttgatgtcgc tgttgtcctg gatcaccacg    660
gcgccctcgc ccttccacag cagcttggcg ggcccttcc acacggggtc gcggctgtcg    720
cggtagtaca cgcggaagtt ctggatcttg tgatctgct tctgcagctc cttggtctgg    780
atgtcggtgg cgatgatgtc cacgatgcgc tcgccggcgc tgtagccgcc gatgccgccc    840
ttgcgcttga agttgtggat gaacacggcc atctgcacgg cggtcttcag gtgctcggcc    900
tggtcgcgca cctggccgat gatcttcttc agctccttgt tcatgctctc gatcacgccc    960
tggctctggg ggttgtaggg gatgccgaac tcctgcttga tgccggccca ccagcaggcg   1020
gccttcacgg tggtgctggt gaagttgctg ccgttgtcgg tgtgcacggt cttcacgggc   1080
cagcggccgg ccagcttcag caggaagtag gcggtctcct ggccggtctc ggcggggatc   1140
acctcggcct cgatgtagcc gctggccacg tgcacggcca ccaggatcac cttgccctcc   1200
aggtgggtgc agtccagctg ccagatgccg gggctgcagt ccacctggcc gtgcatggcc   1260
tcgcccttca gctggcactt gtcgcagctg gccacgatct ccttggccac cacgggggc   1320
aggttgaagt cgctggccat ggcgcgccag ttgctgtggt acttctcgtg ctcctcctgg   1380
gccttgtcga tgccgtccag gaacagcacc ttgcggatgc cggcgctcac caggccgtcc   1440
acctgctcgt tgccgccgat gcccttgtgg gcgggcaccc aggccaggta caccttctcc   1500
ttcttgatca gctgctcgat gatctggctc accagctcgc tctcgctctt gtcgggctgg   1560
gcctggatga tgcccagggc gtactggctg tcggtcacga tgttcacctc caggccgctg   1620
tcctgcaggg ccaggtggat ggcctgcagc tcggtcttct ggttggtggt gtcggtcagg   1680
ggcaccacct tctggcggcc gcggtcggtc acgtagccgg ccttgcccag cttggtctcg   1740
cggttggcgg cgccgtccac gtagaaggtc tcggcgccga tgatgggctc cttctccagc   1800
tggtaccaca gcttcaccag gggggggtg ttcacgaact cccactcggg gatccaggtg   1860
gcctgccagt actcggtcca ccaggcctcc caggtctcct tctggatggg cagcttgaac   1920
ttgggggtct tgcccagat cacgatgctc tcggtggcga tcttctgcac ggcctcggtc   1980
agctgcttca cgtcgttggt gtgggcgccc ttcatgcggg cgtacttgcc ggtcttcagg   2040
ttcttgaagg gctcctggta gatctggtag gtccactggc cctggccctg cttctggatc   2100
```

```
tcggcgatca ggtccttgct ggggtcgtag tacacgccgt gcacgggctc cttcaggatc    2160
tcgcggttct cggccagctc cagctcggcc tcctcggtca ggggcaccac ctcggtcagg    2220
gccttggtgc cgcgcagcag cttgcacagc tggcgcacct tgatgccggc gtagatctgg    2280
ctggcccagt tcagcttgcc caccagcttc tggatgtcgt tcacggtcca gctgtccttc    2340
tcgggcagca cgatgggctg cacggtccac ttgtcggggt gcagctcgta gcccatccac    2400
aggaaggggg gctccttctg gtgcttcttg tcggggtgg tgaagcccca cgcagcagg     2460 tgctggcgca gctcctcgat cttggtgcgg tgctggccga tctccaggtc gctgcccacg    2520
tacaggtggt ccatgtactg gtagatcacg atgtcggggt tctgcttgcg gaagggctcc    2580
aggatcttgg tcatgctgca ctggaagatg gcggggctgc ccttccagcc ctggggcagc    2640
acgttgtact ggtagcggat gccggggtc tcgttgttga tgctggggat ggtgaaggcg     2700
gtgtacttgc ggaagtcctt gtccaggggc acgctgaagt aggcgtcgcc cacgtccagc    2760
acggtcacgc tcttcttctg cttcaggccg gcggggtggg gatgcccag ctgcacctcc     2820 cagaagtcct gggtgcgctt gttcagctcg cggaagtcca ccagcttgcg ccacttggtg    2880 ctgtcccttct tcttgatggc gaacacgggg gtgttgtagg ggttctcggg gccgatcttg    2940
ctgatcttgc cctccttctc catctcggtg cagatctcca ccagggcctt gatcttctcc    3000
tcggtcaggg gccactgctt cacccttggg ccgtccatgc cgggcttcag cttcacgggc    3060
acggtctcga tggggctgat ggggaagttc agggtgcagc cgatctgggt cagcaggttg    3120
cggccgatga tgttcacggg ggtgggcc accagcacgg tgccgatggc cttgtggccg      3180
cagatctcga tcaggatctg gtcgtactgg cccaccttga tgaagccgcc gatgccgccg    3240
atcatcttgg gcttccagcg gccgggcagg ttcatctcct ccagcacggt gtcgtcggcg    3300
ccggtgtcta aagggcctc cttcagctgg ccccctatct ttattgtgac gagggtcgc       3360 tgccaaagag tgatctgagg gaagctaaag gatacagttc cttgtctatc ggctcctgct    3420
tctgagaggg agttgttgtc tcttccccaa acctgaagct ctcttctggt ggggctgttg    3480
gctctggtct gctctgaaga aaattccctg gccttccctt gtgggaaggc cagatcttcc    3540
ctattagcct gtcgctcggt gcagtccttc atctggtggc cctccttgcc gcacttccag    3600
cagcccttct tgcggggggc gcggcagttg cgggcggtgt ggccctcctt gccgcagttg    3660
aagcacttca cgatcttgcg ctggttgcgg aagttgccgc gctgcatcat gatggtggcg    3720
ctgttggtca cctggctcat ggcctcggcc agcacgcggg ccttgtggcc ggggccgccc    3780
acgccctggc aggcggtcat catctcctcc agggtggcgg cggggcccag gccttcagg     3840 atggtcttgc agtcggggtt ggcgttctgc accagcaggg tctcggtcat ccagttcttc    3900
acctcctggc tggcctgctc ggcgcgcagg gtcttgtaga gcggtccac gtagtcgcgg     3960 aagggctcct tggggccctg gcggatgtcc aggatgctgg tggggctgta catgcgcacg    4020
atcttgttca ggcccaggat gatccagcgc ttgtagatct cgcccacggg gatggggggg    4080
ttgttggtca tccagccgat ctgctcctgc agggtgctgg tggtgccggc gatgtcgctg    4140
ccgcggggct cgcgcatctg gccggggcg atgggccgg cgtgcacggg gtgcacgcgg      4200
tcccactcgg cggcctcctc gttgatggtc tccttcagca tctgcatggc ggcctggtgg    4260
ccgcccacgg tgttcagcat ggtgttcagg tcctgggggg tggcgccctc gctcagggcg    4320
ctgaacatgg ggatcacctc ggggctgaag gccttctcct ccaccacctt cacccaggcg    4380
ttcagggtgc ggggggctgat ggcctggtgc accatctggc cctggatgtt ctgcacgatg    4440
gggtagttct ggctcacctg gttgctgtgg ccggtgtcgg cggcggcctg ctgggccttc     4500
```

```
ttcttgctct tgttctgctc ctcctcgatc ttgtccaggg cctccttggt gtccttgatc   4560
tcgatgcgct ggtgcacgca gtacagggtg gccacggtgt tgtacaggct gcgcagctcc   4620
tcgctgccgg tctgcaggct gggctgcagc tggcccagga tctggcggca gccctcgctg   4680
gtctccagca ggccggggtt cacgcgaagc gctccagct cgcggctggc ccacacgatg   4740
tgcttcagct tgtacttctt cttgccgccg gggcgcaggc ggatcttctc ccagcggtcc   4800
agctcgccgc cgctcagcac gctggcgcgg gcgcccatgt cgaatcgaat tctgcagtga   4860
tcagggatcc gtatagtgag tcgtattagg taccggctgc agttggacct gggagtggac   4920
acctgtggag agaaaggcaa agtggatgtc attgtcactc aagtgtatgg ccagatctca   4980
agcctgccac acctcaagtg aagccaaggg ggtgggccta tagactctat aggcggtact   5040
tacgtcactc ttggcacggg gaatccgcgt tccaatgcac cgttcccggc cgcggaggct   5100
ggatcggtcc cggtgtcttc tatggaggtc aaaacagcgt ggatggcgtc tccaggcgat   5160
ctgacggttc actaaacgag ctcgtcgacg atctctatca ctgataggga gatctctatc   5220 actgatagg agagctctgc ttatatagac ctcccaccgt acacgcctac cgcccatttg   5280
cgtcaatggg gcggagttgt tacgacattt tggaaagtcc cgttgatttt ggtgccaaaa   5340
caaactccca ttgacgtcaa tggggtggag acttggaaat ccccgtgagt caaaccgcta   5400
tccacgccca ttgatgtact gccaaaaccg catcaccatg gtaatagcga tgactaatac   5460
gtagatgtac tgccaagtag gaaagtccca taaggtcatg tactgggcat aatgccaggc   5520
gggccattta ccgtcattga cgtcaatagg gggcgtactt ggcatatgat acacttgatg   5580
tactgccaag tgggcagttt accgtaaata ctccacccat tgacgtcaat ggaaagtccc   5640
tattggcgtt actatgggaa catacgtcat tattgacgtc aatgggcggg ggtcgttggg   5700
cggtcagcca ggcgggccat ttaccgtaag ttatgtaacg cggaactcca tatatgggct   5760
atgaactaat gaccccgtaa ttgattacta ttaataacta gtactgaaat gtgtgggcgt   5820
ggcttaaggg tgggaaagaa tatataaggt gggggtctta tgtagttttg tatctgtttt   5880
gcagcagccg ccgccgccat gagcaccaac tcgtttgatg gaagcattgt gagctctatt   5940
ttgacaacgc gcatgccccc atgggccggg gtgcgtcaga atgtgatggg ctccagcatt   6000
gatggtcgcc ccgtcctgcc cgcaaactct actaccttga cctacgagac cgtgtctgga   6060
acgccgttgg agactgcagc ctccgccgcc gcttcagccg ctgcagccac cgcccgcggg   6120
attgtgactg actttgcttt cctgagcccg cttgcaagca gtgcagcttc ccgttcatcc   6180
gcccgcgatg acaagttgac ggctcttttg gcacaattgg attctttgac ccgggaactt   6240
aatgtcgttt ctcagcagct gttggatctg cgccagcagg tttctgccct gaaggcttcc   6300 tccccctccca atgcggttta aaacataaat aaaaaaccag actctgtttg gatttggatc   6360
aagcaagtgt cttgctgtct ttatttaggg gttttgcgcg cgcggtaggc ccgggaccag   6420
cggtctcggt cgttgagggt cctgtgtatt ttttccagga cgtggtaaag gtgactctgg   6480
atgttcagat acatgggcat aagcccgtct ctggggtgga ggtagcacca ctgcagagct   6540
tcatgctgcg gggtggtgtt gtagatgatc cagtcgtagc aggagcgctg ggcgtggtgc   6600
ctaaaaatgt ctttcagtag caagctgatt gccaggggca ggcccttggt gtaagtgttt   6660
acaaagcggt taagctggga tgggtgcata cgtggggata tgagatgcat cttgactgt   6720 attttttaggt tggctatgtt cccagccata tccctccggg gattcatgtt gtgcagaacc   6780
accagcacag tgtatccggt gcacttggga aatttgtcat gtagcttaga aggaaatgcg   6840
tggaagaact tggagacgcc cttgtgacct ccaagatttt ccatgcattc gtccataatg   6900
```

```
atggcaatgg gcccacgggc ggcggcctgg gcgaagatat ttctgggatc actaacgtca    6960
tagttgtgtt ccaggatgag atcgtcatag gccattttta caaagcgcgg gcggagggtg    7020
ccagactgcg gtataatggt tccatccggc ccaggggcgt agttaccctc acagatttgc    7080
atttcccacg ctttgagttc agatgggggg atcatgtcta cctgcggggc gatgaagaaa    7140
acggtttccg gggtagggga gatcagctgg gaagaaagca ggttcctgag cagctgcgac    7200
ttaccgcagc cggtgggccc gtaaatcaca cctattaccg ggtgcaactg gtagttaaga    7260
gagctgcagc tgccgtcatc cctgagcagg ggggccactt cgttaagcat gtccctgact    7320
cgcatgtttt ccctgaccaa atccgccaga aggcgctcgc cgcccagcga tagcagttct    7380
tgcaaggaag caaagttttt caacggtttg agaccgtccg ccgtaggcat gcttttgagc    7440
gtttgaccaa gcagttccag gcggtcccac agctcggtca cctgctctac ggcatctcga    7500
tccagcatat ctcctcgttt cgcggggttgg ggcggctttc gctgtacggc agtagtcggt    7560
gctcgtccag acgggccagg gtcatgtctt tccacgggcg cagggtcctc gtcagcgtag    7620
tctgggtcac ggtgaagggg tgcgctccgg gctgcgcgct ggccagggtg cgcttgaggc    7680
tggtcctgct ggtgctgaag cgctgccggt cttcgccctg cgcgtcggcc aggtagcatt    7740
tgaccatggt gtcatagtcc agcccctccg cggcgtggcc cttggcgcgc agcttgccct    7800
tggaggaggc gccgcacgag gggcagtgca gacttttgag ggcgtagagc ttgggcgcga    7860
gaaataccga ttccggggag taggcatccg cgccgcaggc cccgcagacg gtctcgcatt    7920
ccacgagcca ggtgagctct ggccgttcgg ggtcaaaaac caggtttccc ccatgctttt    7980
tgatgcgttt cttacctctg gtttccatga gccggtgtcc acgctcggtg acgaaaaggc    8040
tgtccgtgtc cccgtataca gacttgagag gcctgtcctc gagcggtgtt ccgcggtcct    8100
cctcgtatag aaactcggac cactctgaga caaaggctcg cgtccaggcc agcacgaagg    8160
aggctaagtg ggaggggtag cggtcgttgt ccactagggg gtccactcgc tccagggtgt    8220
gaagacacat gtcgccctct tcggcatcaa ggaaggtgat tggtttgtag gtgtaggcca    8280
cgtgaccggg tgttcctgaa gggggggctat aaaaggggggt ggggggcgcgt tcgtcctcac    8340 tctcttccgc atcgctgtct gcgagggcca gctgttgggg tgagtactcc ctctgaaaag    8400
cgggcatgac ttctgcgcta agattgtcag tttccaaaaa cgaggaggat ttgatattca    8460
cctggcccgc ggtgatgcct ttgagggtgg ccgcatccat ctggtcagaa aagacaatct    8520
ttttgttgtc aagcttggtg gcaaacgacc cgtagagggc gttggacagc aacttggcga    8580
tggagcgcag ggtttggttt ttgtcgcgat cggcgcgctc cttggccgcg atgtttagct    8640
gcacgtattc gcgcgcaacg caccgccatt cgggaaagac ggtggtgcgc tcgtcgggca    8700
ccaggtgcac gcgccaaccg cggttgtgca gggtgacaag gtcaacgctg gtggctacct    8760
ctccgcgtag gcgctcgttg gtccagcaga ggcggccgcc cttgcgcgag cagaatggcg    8820 gtaggggtc tagctgcgtc tcgtccgggg gtctgcgtc cacggtaaag accccgggca    8880
gcaggcgcgc gtcgaagtag tctatcttgc atccttgcaa gtctagcgcc tgctgccatg    8940
cgcgggcggc aagcgcgcgc tcgtatgggt tgagtggggg accccatggc atgggtgggg    9000
tgagcgcgga ggcgtacatg ccgcaaatgt cgtaaacgta gagggctct ctgagtattc    9060 caagatatgt agggtagcat cttccaccgc ggatgctggc gcgcacgtaa tcgtatagtt    9120
cgtgcgaggg agcgaggagg tcgggaccga ggttgctacg ggcgggctgc tctgctcgga    9180
agactatctg cctgaagatg gcatgtgagt tggatgatat ggttggacgc tggaagacgt    9240
tgaagctggc gtctgtgaga cctaccgcgt cacgcacgaa ggaggcgtag gagtcgcgca    9300
```

-continued

```
gcttgttgac cagctcggcg gtgacctgca cgtctagggc gcagtagtcc agggtttcct    9360
tgatgatgtc atacttatcc tgtcccttt ttttccacag ctcgcggttg aggacaaact    9420
cttcgcggtc tttccagtac tcttggatcg gaaacccgtc ggcctccgaa cggtaagagc    9480
ctagcatgta gaactggttg acggcctggt aggcgcagca tccctttctct acgggtagcg    9540 cgtatgcctg cgcggccttc cggagcgagg tgtgggtgag cgcaaaggtg tccctgacca    9600
tgactttgag gtactggtat ttgaagtcag tgtcgtcgca tccgccctgc tcccagagca    9660
aaaagtccgt gcgcttttg gaacgcggat ttggcagggc gaaggtgaca tcgttgaaga    9720
gtatctttcc cgcgcgaggc ataaagttgc gtgtgatgcg gaagggtccc ggcacctcgg    9780
aacggttgtt aattacctgg gcggcgagca cgatctcgtc aaagccgttg atgttgtggc    9840
ccacaatgta aagttccaag aagcgcggga tgcccttgat ggaaggcaat tttttaagtt    9900
cctcgtaggt gagctcttca ggggagctga gcccgtgctc tgaaagggcc cagtctgcaa    9960 gatgagggt ggaagcgacg aatgagctcc acaggtcacg ggccattagc atttgcaggt    10020
ggtcgcgaaa ggtcctaaac tggcgaccta tggccatttt ttctggggtg atgcagtaga    10080
aggtaagcgg gtcttgttcc cagcggtccc atccaaggtt cgcggctagg tctcgcgcgg    10140
cagtcactag aggctcatct ccgccgaact tcatgaccag catgaagggc acgagctgct    10200
tcccaaaggc ccccatccaa gtataggtct ctacatcgta ggtgacaaag agacgctcgg    10260
tgcgaggatg cgagccgatc gggaagaact ggatctcccg ccaccaattg gaggagtggc    10320
tattgatgtg gtgaaagtag aagtccctgc gacgggccga acactcgtgc tggcttttgt    10380
aaaaacgtgc gcagtactgg cagcggtgca cgggctgtac atcctgcacg aggttgacct    10440
gacgaccgcg cacaaggaag cagagtggga atttgagccc ctcgcctggc gggtttggct    10500
ggtggtcttc tacttcggct gcttgtcctt gaccgtctgg ctgctcgagg ggagttacgg    10560
tggatcggac caccacgccg cgcgagccca aagtccagat gtccgcgcgc ggcggtcgga    10620
gcttgatgac aacatcgcgc agatgggagc tgtccatggt ctggagctcc cgcggcgtca    10680
ggtcaggcgg gagctcctgc aggtttacct cgcatagacg ggtcagggcg cgggctagat    10740
ccaggtgata cctaatttcc aggggctggt tggtggcggc gtcgatggct tgcaagaggc    10800
cgcatccccg cggcgcgact acggtaccgc gcggcgggcg gtgggccgcg ggggtgtcct    10860
tggatgatgc atctaaaagc ggtgacgcgg gcgagccccc ggaggtaggg ggggctccgg    10920
acccgccggg agaggggca ggggcacgtc ggcgccgcgc gcgggcagga gctggtgctg    10980
cgcgcgtagg ttgctggcga acgcgacgac gcggcgttg atctcctgaa tctggcgcct    11040
ctgcgtgaag acgacgggcc cggtgagctt gaacctgaaa gagagttcga cagaatcaat    11100
ttcggtgtcg ttgacggcgg cctggcgcaa aatctcctgc acgtctcctg agttgtcttg    11160
ataggcgatc tcggccatga actgctcgat ctcttcctcc tggagatctc cgcgtccggc    11220
tcgctccacg gtgcggcga ggtcgttgga aatgcgggcc atgagctgcg agaaggcgtt    11280
gaggcctccc tcgttccaga cgcggctgta gaccacgccc ccttcggcat cgcgggcgcg    11340
catgaccacc tgcgcgagat tgagctccac gtgccgggcg aagacggcgt agtttcgcag    11400
gcgctgaaag aggtagttga gggtggtggc ggtgtgttct gccacgaaga agtacataac    11460
ccagcgtcgc aacgtggatt cgttgatatc ccccaaggcc tcaaggcgct ccatggcctc    11520
gtagaagtcc acggcgaagt tgaaaaactg ggagttgcgc gccgacacgg ttaactcctc    11580
ctccagaaga cggatgagct cggcgacagt gtcgcgcacc tcgcgctcaa aggctacagg    11640
ggcctcttct tcttcttcaa tctcctcttc cataagggcc tccccttctt cttcttctgg    11700
```

-continued

```
cggcggtggg ggaggggggga cacggcggcg acgacggcgc accgggaggc ggtcgacaaa    11760
gcgctcgatc atctccccgc ggcgacggcg catggtctcg gtgacggcgc ggccgttctc    11820 gcggggggcgc agttggaaga cgccgcccgt catgtcccgg ttatgggttg gcgggggggct   11880 gccatgcggc agggatacgg cgctaacgat gcatctcaac aattgttgtg taggtactcc    11940
gccgccgagg gacctgagcg agtccgcatc gaccggatcg gaaaacctct cgagaaaggc    12000
gtctaaccag tcacagtcgc aaggtaggct gagcaccgtg gcgggcggca gcgggcggcg    12060
gtcggggttg tttctggcgg aggtgctgct gatgatgtaa ttaaagtagg cggtcttgag    12120
acggcggatg gtcgacagaa gcaccatgtc cttgggtccg gcctgctgaa tgcgcaggcg   12180
gtcggccatg ccccaggctt cgttttgaca tcggcgcagg tctttgtagt agtcttgcat    12240
gagcctttct accggcactt cttcttctcc ttcctcttgt cctgcatctc ttgcatctat    12300
cgctgcggcg gcggcggagt ttggccgtag gtggcgccct cttcctccca tgcgtgtgac    12360
cccgaagccc ctcatcggct gaagcagggc taggtcggcg acaacgcgct cggctaatat    12420
ggcctgctgc acctgcgtga gggtagactg gaagtcatcc atgtccacaa agcggtggta    12480
tgcgcccgtg ttgatggtgt aagtgcagtt ggccataacg gaccagttaa cggtctggtg    12540
acccggctgc gagagctcgg tgtacctgag acgcgagtaa gccctcgagt caaatacgta    12600
gtcgttgcaa gtccgcacca ggtactggta tcccaccaaa aagtgcggcg gcggctggcg    12660
gtagaggggc cagcgtaggg tggccggggc tccggggggcg agatcttcca acataaggcg    12720
atgatatccg tagatgtacc tggacatcca ggtgatgccg gcggcggtgg tggaggcgcg    12780
cggaaagtcg cggacgcggt tccagatgtt gcgcagcggc aaaaagtgct ccatggtcgg    12840
gacgctctgg ccggtcaggc gcgcgcaatc gttgacgctc tagcgtgcaa aggagagcc    12900 tgtaagcggg cactcttccg tggtctggtg gataaattcg caagggtatc atggcggacg    12960
accggggttc gagccccgta tccggccgtc cgccgtgatc catgcggtta ccgcccgcgt    13020
gtcgaaccca ggtgtgcgac gtcagacaac gggggagtgc tccttttggc ttccttccag    13080
gcgcggcggc tgctgcgcta gcttttttgg ccactggccg cgcgcagcgt aagcggttag    13140
gctgaaaagc gaaagcatta agtggctcgc tccctgtagc cggagggtta ttttccaagg    13200
gttgagtcgc gggaccccccg gttcgagtct cggaccggcc ggactgcggc gaacgggggt    13260
ttgcctcccc gtcatgcaag accccgcttg caaattcctc cggaaacagg gacgagcccc    13320
ttttttgctt ttcccagatg catccggtgc tgcggcagat gcgcccccct cctcagcagc    13380
ggcaagagca agagcagcgg cagacatgca gggcacccctc ccctcctcct accgcgtcag    13440
gaggggcgac atccgcggtt gacgcggcag cagatggtga ttacgaaccc ccgcggcgcc    13500
gggcccggca ctacctggac ttggaggagg gcgagggcct ggcgcggcta ggagcgcct    13560 ctcctgagcg gcacccaagg gtgcagctga agcgtgatac gcgtgaggcg tacgtgccgc    13620
ggcagaacct gtttcgcgac cgcgagggag aggagcccga ggagatgcgg gatcgaaagt    13680
tccacgcagg gcgcgagctg cggcatggcc tgaatcgcga gcggttgctg cgcgaggagg    13740
actttgagcc cgacgcgcga accgggatta gtcccgcgcg cgcacacgtg gcggccgccg    13800
acctggtaac cgcatacgag cagacggtga accaggagat taactttcaa aaaagcttta    13860
acaaccacgt gcgtacgctt gtggcgcgcg aggaggtggc tataggactg atgcatctgt    13920
gggactttgt aagcgcgctg gagcaaaacc caaatagcaa gccgctcatg gcgcagctgt    13980
tccttatagt gcagcacagc agggacaacg aggcattcag ggatgcgctg ctaaacatag    14040
tagagcccga gggccgctgg ctgctcgatt tgataaacat cctgcagagc atagtggtgc    14100
```

```
aggagcgcag cttgagcctg gctgacaagg tggccgccat caactattcc atgcttagcc   14160
tgggcaagtt ttacgcccgc aagatatacc ataccccta cgttcccata gacaaggagg   14220
taaagatcga ggggttctac atgcgcatgg cgctgaaggt gcttaccttg agcgacgacc   14280
tgggcgttta tcgcaacgag cgcatccaca aggccgtgag cgtgagccgg cggcgcgagc   14340
tcagcgaccg cgagctgatg cacagcctgc aaagggccct ggctggcacg ggcagcggcg   14400
atagagaggc cgagtcctac tttgacgcgg gcgctgacct gcgctgggcc caagccgac    14460
gcgccctgga ggcagctggg gccggacctg ggctggcggt ggcacccgcg cgcgctggca   14520
acgtcggcgg cgtggaggaa tatgacgagg acgatgagta cgagccagag acggcgagt    14580
actaagcggt gatgtttctg atcagatgat gcaagacgca acggaccgg cggtgcgggc    14640
ggcgctgcag agccagccgt ccggccttaa ctccacggac gactggcgcc aggtcatgga   14700
ccgcatcatg tcgctgactg cgcgcaatcc tgacgcgttc cggcagcagc cgcaggccaa   14760
ccggctctcc gcaattctgg aagcggtggt cccggcgcgc gcaaaccca cgcacgagaa    14820
ggtgctggcg atcgtaaacg cgctggccga aaacagggcc atccggcccg acgaggccgg   14880
cctggtctac gacgcgctgc ttcagcgcgt ggctcgttac aacagcggca acgtgcagac   14940
caacctggac cggctggtgg gggatgtgcg cgaggccgtg gcgcagcgtg agcgcgcgca   15000
gcagcaggga aacctgggct ccatggttgc actaaacgcc ttcctgagta cacagcccgc   15060
caacgtgccg cggggacagg aggactacac caactttgtg agcgcactgc ggctaatggt   15120
gactgagaca ccgcaaagtg aggtgtacca gtctgggcca gactatttt tccagaccag    15180
tagacaaggc ctgcagaccg taaacctgag ccaggctttc aaaaacttgc aggggctgtg   15240
ggggggtgcgg gctcccacag gcgaccgcgc gaccgtgtct agcttgctga cgcccaactc   15300
gcgcctgttg ctgctgctaa tagcgcccct cacggacagt ggcagcgtgt cccgggacac   15360
atacctaggt cacttgctga cactgtaccg cgaggccata ggtcaggcgc atgtggacga   15420
gcatactttc caggagatta caagtgtcag ccgcgcgctg gggcaggagg acacgggcag   15480
cctggaggca accctaaact acctgctgac caaccggcgg cagaagatcc cctcgttgca   15540
cagtttaaac agcgaggagg agcgcatttt gcgctacgtg cagcagagcg tgagccttaa   15600
cctgatgcgc gacggggtaa cgcccagcgt ggcgctggac atgaccgcgc gcaacatgga   15660
accgggcatg tatgcctcaa accggccgtt tatcaaccgc ctaatggact acttgcatcg   15720
cgcggccgcc gtgaaccccg agtatttcac caatgccatc ttgaaccgc actggctacc    15780
gcccctggt ttctacaccg ggggattcga ggtgcccgag ggtaacgatg gattcctctg    15840
ggacgacata gacgacagcg tgttttcccc gcaaccgcag accctgctag agttgcaaca   15900
gcgcgagcag cagaggcgg cgctgcgaaa ggaaagcttc cgcaggccaa gcagcttgtc    15960
cgatctaggc gctgcggccc cgcggtcaga tgctagtagc ccatttccaa gcttgatagg   16020
gtctcttacc agcactcgca ccacccgccc gcgcctgctg ggcgaggagg agtacctaaa   16080
caactcgctg ctgcagccgc agcgcgaaaa aaacctgcct ccggcatttc caacaacgg    16140
gatagagagc ctagtggaca agatgagtag atggaagacg tacgcgcagg agcacaggga   16200
cgtgccaggc ccgcgcccgc ccacccgtcg tcaaaggcac gaccgtcagc ggggtctggt   16260
gtgggaggac gatgactcgg cagacgacag cagcgtcctg gatttgggag ggagtggcaa   16320
cccgtttgcg caccttcgcc ccaggctggg gagaatgttt taaaaaaaaa aaagcatga    16380
tgcaaaataa aaaactcacc aaggccatgg caccgagcgt tggttttctt gtattcccct   16440
tagtatgcgg cgcgcggcga tgtatgagga aggtcctcct ccctcctacg agagtgtggt   16500
```

```
gagcgcggcg ccagtggcgg cggcgctggg ttctcccttc gatgctcccc tggacccgcc    16560
gtttgtgcct ccgcggtacc tgcggcctac cgggggggaga aacagcatcc gttactctga    16620
gttggcaccc ctattcgaca ccacccgtgt gtacctggtg gacaacaagt caacggatgt    16680
ggcatccctg aactaccaga acgaccacag caactttctg accacggtca ttcaaaacaa    16740
tgactacagc ccggggggagg caagcacaca gaccatcaat cttgacgacc ggtcgcactg    16800
gggcggcgac ctgaaaacca tcctgcatac caacatgcca aatgtgaacg agttcatgtt    16860
taccaataag tttaaggcgc gggtgatggt gtcgcgcttg cctactaagg acaatcaggt    16920
ggagctgaaa tacgagtggg tggagttcac gctgcccgag ggcaactact ccgagaccat    16980
gaccatagac cttatgaaca acgcgatcgt ggagcactac ttgaaagtgg gcagacagaa    17040
cggggttctg gaaagcgaca tcggggtaaa gtttgacacc cgcaacttca gactggggtt    17100 tgacccccgtc actggtcttg tcatgcctgg ggtatataca aacgaagcct tccatccaga    17160
catcattttg ctgccaggat gcggggtgga cttcacccac agccgcctga gcaacttgtt    17220
gggcatccgc aagcggcaac ccttccagga gggctttagg atcacctacg atgatctgga    17280
gggtggtaac attcccgcac tgttggatgt ggacgcctac caggcgagct tgaaagatga    17340
caccgaacag ggcgggggtg gcgcaggcgg cagcaacagc agtggcagcg gcgcggaaga    17400
gaactccaac gcggcagccg cggcaatgca gccggtggag gacatgaacg atcatgccat    17460
tcgcggcgac accttttgcca cacgggctga ggagaagcgc gctgaggccg aagcagcggc    17520
cgaagctgcc gcccccgctg cgcaacccga ggtcgagaag cctcagaaga aaccggtgat    17580 caaaccctg acagaggaca gcaagaaacg cagttacaac ctaataagca atgacagcac    17640
cttcacccag taccgcagct ggtaccttgc atacaactac ggcgaccctc agaccggaat    17700
ccgctcatgg accctgcttt gcactcctga cgtaacctgc ggctcggagc aggtctactg    17760
gtcgttgcca gacatgatgc aagaccccgt gaccttccgc tccacgcgcc agatcagcaa    17820 cttttccggtg gtgggcgccg agctgttgcc cgtgcactcc aagagcttct acaacgacca    17880
ggccgtctac tcccaactca tccgccagtt tacctctctg acccacgtgt tcaatcgctt    17940 tccccgagaac cagattttgg cgcgcccgcc agccccccacc atcaccaccg tcagtgaaaa    18000
cgttcctgct ctcacagatc acgggacgct accgctgcgc aacagcatcg gaggagtcca    18060
gcgagtgacc attactgacg ccagacgcg cacctgcccc tacgtttaca aggccctggg    18120
catagtctcg ccgcgcgtcc tatcgagccg cacttttttga gcaagcatgt ccatccttat    18180
atcgcccagc aataacacag gctggggcct gcgcttccca agcaagatgt ttggcgggggc    18240 caagaagcgc tccgaccaac acccagtgcg cgtgcgcggg cactaccgcg cgccctgggg    18300
cgcgcacaaa cgcggccgca ctgggcgcac caccgtcgat gacgccatcg acgcggtggt    18360
ggaggaggcg cgcaactaca cgcccacgcc gccaccagtg tccacagtgg acgcggccat    18420
tcagaccgtg gtgcgcggag cccggcgcta tgctaaaatg aagagacggc ggaggcgcgt    18480
agcacgtcgc caccgccgcc gacccggcac tgccgcccaa cgcgcggcgg cggccctgct    18540
taaccgcgca cgtcgcaccg gccgacgggc ggccatgcgg gccgctcgaa ggctggccgc    18600
gggtattgtc actgtgcccc ccaggtccag gcgacgagcg gccgccgcag cagccgcggc    18660
cattagtgct atgactcagg gtcgcagggg caacgtgtat tgggtgcgcg actcggttag    18720
cggcctgcgc gtgcccgtgc gcacccgccc cccgcgcaac tagattgcaa gaaaaaacta    18780
cttagactcg tactgttgta tgtatccagc ggcggcggcg cgcaacgaag ctatgtccaa    18840
gcgcaaaatc aaagaagaga tgctccaggt catcgcgccg gagatctatg gccccccgaa    18900
```

```
gaaggaagag caggattaca agccccgaaa gctaaagcgg gtcaaaaaga aaaagaaaga   18960
tgatgatgat gaacttgacg acgaggtgga actgctgcac gctaccgcgc ccaggcgacg   19020
ggtacagtgg aaaggtcgac gcgtaaaacg tgttttgcga cccggcacca ccgtagtctt   19080
tacgcccggt gagcgctcca cccgcaccta caagcgcgtg tatgatgagg tgtacggcga   19140
cgaggacctg cttgagcagg ccaacgagcg cctcggggag tttgcctacg gaaagcggca   19200
taaggacatg ctggcgttgc cgctggacga gggcaaccca acacctagcc taaagcccgt   19260
aacactgcag caggtgctgc ccgcgcttgc accgtccgaa gaaaagcgcg gcctaaagcg   19320
cgagtctggt gacttggcac ccaccgtgca gctgatggta cccaagcgcc agcgactgga   19380
agatgtcttg gaaaaaatga ccgtggaacc tgggctggag cccgaggtcc gcgtgcggcc   19440
aatcaagcag gtggcgccgg gactgggcgt gcagaccgtg gacgttcaga tacccactac   19500
cagtagcacc agtattgcca ccgccacaga gggcatggag acacaaacgt ccccggttgc   19560
ctcagcggtg gcggatgccg cggtgcaggc ggtcgctgcg gccgcgtcca agacctctac   19620
ggaggtgcaa acggacccgt ggatgtttcg cgtttcagcc ccccggcgcc cgcgccgttc   19680
gaggaagtac ggcgccgcca gcgcgctact gcccgaatat gccctacatc cttccattgc   19740
gcctaccccc ggctatcgtg gctacaccta ccgccccaga agacgagcaa ctacccgacg   19800
ccgaaccacc actggaaccc gccgccgccg tcgccgtcgc cagcccgtgc tggccccgat   19860
ttccgtgcgc agggtggctc gcgaaggagg caggaccctg gtgctgccaa cagcgcgcta   19920
ccaccccagc atcgtttaaa agccggtctt tgtggttctt gcagatatgg ccctcacctg   19980
ccgcctccgt ttcccggtgc cgggattccg aggaagaatg caccgtagga ggggcatggc   20040
cggccacggc ctgacgggcg gcatgcgtcg tgcgcaccac cggcggcggc gcgcgtcgca   20100
ccgtcgcatg cgcggcggta tcctgccccct ccttattcca ctgatcgccg cggcgattgg   20160
cgccgtgccc ggaattgcat ccgtggcctt gcaggcgcag agacactgat taaaaacaag   20220
ttgcatgtgg aaaaatcaaa ataaaaagtc tggactctca cgctcgcttg gtcctgtaac   20280
tattttgtag aatggaagac atcaactttg cgtctctggc cccgcgacac ggctcgcgcc   20340
cgttcatggg aaactggcaa gatatcggca ccagcaatat gagcggtggc gccttcagct   20400
ggggctcgct gtggagcggc attaaaaatt tcggttccac cgttaagaac tatggcagca   20460
aggcctggaa cagcagcaca ggccagatgc tgagggataa gttgaaagag caaaatttcc   20520
aacaaaaggt ggtagatggc ctggcctctg gcattagcgg ggtggtggac ctggccaacc   20580
aggcagtgca aaataagatt aacagtaagc ttgatccccg ccctcccgta gaggagcctc   20640
caccggccgt ggagacagtg tctccagagg ggcgtggcga aaagcgtccg cgccccgaca   20700
gggaagaaac tctggtgacg caaatagacg agcctccctc gtacgaggag gcactaaagc   20760
aaggcctgcc caccacccgt cccatcgcgc ccatggctac cggagtgctg ggccagcaca   20820
cacccgtaac gctggacctg cctccccccg ccgacaccca gcagaaacct gtgctgccag   20880
gcccgaccgc cgttgttgta acccgtccta gccgcgcgtc cctgcgccgc gccgccagcg   20940
gtccgcgatc gttgcggccc gtagccagtg caactggcaa aagcacactg aacagcatcg   21000
tgggtctggg ggtgcaatcc ctgaagcgcc gacgatgctt ctgatagcta acgtgtcgta   21060
tgtgtgtcat gtatgcgtcc atgtcgccgc cagaggagct gctgagccgc cgcgcgcccc   21120
ctttccaaga tggctacccc ttcgatgatg ccgcagtggt cttacatgca catctcgggc   21180
caggacgcct cggagtacct gagccccggg ctggtgcagt ttgcccgcgc caccgagacg   21240
tacttcagcc tgaataacaa gtttagaaac cccacggtgg cgcctacgca cgacgtgacc   21300
```

```
acagaccggt cccagcgttt gacgctgcgg ttcatccctg tggaccgtga ggatactgcg    21360
tactcgtaca aggcgcggtt caccctagct gtgggtgata accgtgtgct ggacatggct    21420
tccacgtact ttgacatccg cggcgtgctg gacaggggcc ctacttttaa gccctactct    21480
ggcactgcct acaacgccct ggctcccaag ggtgccccaa atccttgcga atgggatgaa    21540
gctgctactg ctcttgaaat aaacctagaa gaagaggacg atgacaacga agacgaagta    21600
gacgagcaag ctgagcagca aaaaactcac gtatttgggc aggcgcctta ttctggtata    21660
aatattacaa aggagggtat tcaaataggt gtcgaaggtc aaacacctaa atatgccgat    21720
aaaacatttc aacctgaacc tcaaatagga gaatctcagt ggtacgaaac agaaattaat    21780
catgcagctg ggagagtcct aaaaaagact accccaatga aaccatgtta cggttcatat    21840
gcaaaaccca caaatgaaaa tggagggcaa ggcattcttg taaagcaaca aaatggaaag    21900
ctagaaagtc aagtggaaat gcaatttttc tcaactactg aggcagccgc aggcaatggt    21960
gataacttga ctcctaaagt ggtattgtac agtgaagatg tagatataga accccagac    22020 actcatattt cttacatgcc cactattaag gaaggtaact cacgagaact aatgggccaa    22080
caatctatgc ccaacaggcc taattacatt gcttttaggg acaattttat tggtctaatg    22140
tattacaaca gcacgggtaa tatgggtgtt ctggcgggcc aagcatcgca gttgaatgct    22200
gttgtagatt tgcaagacag aaacacagag ctttcatacc agcttttgct tgattccatt    22260
ggtgatagaa ccaggtactt ttctatgtgg aatcaggctg ttgacagcta tgatccagat    22320
gttagaatta ttgaaaatca tggaactgaa gatgaacttc caaattactg ctttccactg    22380
ggaggtgtga ttaatacaga gactcttacc aaggtaaaac ctaaacagg tcaggaaaat    22440 ggatgggaaa aagatgctac agaattttca gataaaaatg aaataagagt tggaaataat    22500
tttgccatgg aaatcaatct aaatgccaac ctgtggagaa atttcctgta ctccaacata    22560
gcgctgtatt tgcccgacaa gctaaagtac agtccttcca acgtaaaaat ttctgataac    22620
ccaaacacct acgactacat gaacaagcga gtggtggctc ccgggctagt ggactgctac    22680
attaaccttg gagcacgctg gtcccttgac tatatggaca acgtcaaccc atttaaccac    22740
caccgcaatg ctggcctgcg ctaccgctca atgttgctgg gcaatggtcg ctatgtgccc    22800
ttccacatcc aggtgcctca gaagttcttt gccattaaaa acctccttct cctgccgggc    22860
tcatacacct acgagtggaa cttcaggaag gatgttaaca tggttctgca gagctcccta    22920
ggaaatgacc taagggttga cggagccagc attaagtttg atagcatttg cctttacgcc    22980
accttcttcc ccatggccca caacaccgcc tccacgcttg aggccatgct agaaacgac    23040 accaacgacc agtcctttaa cgactatctc tccgccgcca acatgctcta ccctataccc    23100
gccaacgcta ccaacgtgcc catatccatc ccctcccgca actgggcggc tttccgcggc    23160
tgggccttca cgcgccttaa gactaaggaa accccatcac tgggctcggg ctacgaccct    23220
tattacacct actctggctc tataccctac ctagatggaa cctttttacct caaccacacc    23280 tttaagaagg tggccattac cttttgactct tctgtcagct ggcctggcaa tgaccgcctg    23340 cttacccca acgagtttga aattaagcgc tcagttgacg gggagggtta caacgttgcc    23400
cagtgtaaca tgaccaaaga ctggttcctg gtacaaatgc tagctaacta taacattggc    23460
taccagggct tctatatccc agagagctac aaggaccgca tgtactcctt ctttagaaac    23520
ttccagccca tgagccgtca ggtggtggat gatactaaat acaaggacta ccaacaggtg    23580
ggcatcctac accaacacaa caactctgga tttgttggct accttgcccc caccatgcgc    23640
gaaggacagg cctaccctgc taacttcccc tatccgctta taggcaagac cgcagttgac    23700
```

```
agcattaccc agaaaaagtt tctttgcgat cgcacccttt ggcgcatccc attctccagt  23760
aactttatgt ccatgggcgc actcacagac ctgggccaaa accttctcta cgccaactcc  23820
gcccacgcgc tagacatgac ttttgaggtg gatcccatgg acgagcccac ccttctttat  23880
gttttgtttg aagtctttga cgtggtccgt gtgcaccagc cgcaccgcgg cgtcatcgaa  23940
accgtgtacc tgcgcacgcc cttctcggcc ggcaacgcca caacataaag aagcaagcaa  24000
catcaacaac agctgccgcc atgggctcca gtgagcagga actgaaagcc attgtcaaag  24060
atcttggttg tgggccatat ttttttgggca cctatgacaa gcgctttcca ggctttgttt  24120
ctccacacaa gctcgcctgc gccatagtca atacggccgg tcgcgagact gggggcgtac  24180
actggatggc ctttgcctgg aacccgcact caaaaacatg ctacctcttt gagccctttg  24240
gcttttctga ccagcgactc aagcaggttt accagtttga gtacgagtca ctcctgcgcc  24300
gtagcgccat tgcttcttcc cccgaccgct gtataacgct ggaaaagtcc acccaaagcg  24360
tacaggggcc caactcggcc gcctgtggac tattctgctg catgtttctc cacgcctttg  24420
ccaactggcc ccaaactccc atggatcaca accccaccat gaaccttatt accggggtac  24480
ccaactccat gctcaacagt ccccaggtac agcccaccct gcgtcgcaac caggaacagc  24540
tctacagctt cctggagcgc cactcgccct acttccgcag ccacagtgcg cagattagga  24600
gcgccacttc tttttgtcac ttgaaaaaca tgtaaaaata atgtactaga gacactttca  24660
ataaaggcaa atgcttttat ttgtacactc tcgggtgatt atttaccccc acccttgccg  24720
tctgcgccgt ttaaaaatca aaggggttct gccgcgcatc gctatgcgcc actggcaggg  24780
acacgttgcg atactggtgt ttagtgctcc acttaaactc aggcacaacc atccgcggca  24840
gctcggtgaa gttttcactc cacaggctgc gcaccatcac caacgcgttt agcaggtcgg  24900
gcgccgatat cttgaagtcg cagttggggc ctccgccctg cgcgcgcgag ttgcgataca  24960
cagggttgca gcactggaac actatcagcg ccgggtggtg cacgctggcc agcacgctct  25020
tgtcggagat cagatccgcg tccaggtcct ccgcgttgct cagggcgaac ggagtcaact  25080
ttggtagctg ccttcccaaa aagggcgcgt gcccaggctt tgagttgcac tcgcaccgta  25140
gtggcatcaa aaggtgaccg tgcccggtct gggcgttagg atacagcgcc tgcataaaag  25200
ccttgatctg cttaaaagcc acctgagcct ttgcgccttc agagaagaac atgccgcaag  25260
acttgccgga aaactgattg gccggacagg ccgcgtcgtg cacgcagcac cttgcgtcgg  25320
tgttggagat ctgcaccaca tttcggcccc accggttctt cacgatcttg gccttgctag  25380
actgctcctt cagcgcgcgc tgcccgtttt cgctcgtcac atccatttca atcacgtgct  25440
ccttatttat cataatgctt ccgtgtagac acttaagctc gccttcgatc tcagcgcagc  25500
ggtgcagcca caacgcgcag cccgtgggct cgtgatgctt gtaggtcacc tctgcaaacg  25560
actgcaggta cgcctgcagg aatcgcccca tcatcgtcac aaaggtcttg ttgctggtga  25620
aggtcagctg caacccgcgg tgctcctcgt tcagccaggt cttgcatacg gccgccagag  25680
cttccacttg gtcaggcagt agtttgaagt tcgcctttag atcgttatcc acgtggtact  25740
tgtccatcag cgcgcgcgca gcctccatgc ccttctccca cgcagacacg atcggcacac  25800
tcagcgggtt catcaccgta atttcacttt ccgcttcgct gggctcttcc tcttcctctt  25860
gcgtccgcat accacgcgcc actgggtcgt cttcattcag ccgccgcact gtgcgcttac  25920
ctcctttgcc atgcttgatt agcaccggtg ggttgctgaa acccaccatt tgtagcgcca  25980
catcttctct ttcttcctcg ctgtccacga ttacctctgg tgatggcggg cgctcgggct  26040
tgggagaagg gcgcttcttt ttcttcttgg gcgcaatggc caaatccgcc gccgaggtcg  26100
```

```
atggccgcgg gctgggtgtg cgcggcacca gcgcgtcttg tgatgagtct tcctcgtcct   26160
cggactcgat acgccgcctc atccgctttt ttggggggcgc ccggggaggc ggcggcgacg   26220
gggacgggga cgacacgtcc tccatggttg ggggacgtcg cgccgcaccg cgtccgcgct   26280
cgggggtggt ttcgcgctgc tcctcttccc gactggccat ttccttctcc tataggcaga   26340
aaagatcat  ggagtcagtc gagaagaagg acagcctaac cgcccctct  gagttcgcca   26400
ccaccgcctc caccgatgcc gccaacgcgc ctaccacctt ccccgtcgag gcaccccgc    26460
ttgaggagga ggaagtgatt atcgagcagg acccaggttt tgtaagcgaa gacgacgagg   26520
accgctcagt accaacagag gataaaaagc aagaccagga caacgcagag gcaaacgagg   26580
aacaagtcgg gcgggggggac gaaaggcatg gcgactacct agatgtggga gacgacgtgc   26640
tgttgaagca tctgcagcgc cagtgcgcca ttatctgcga cgcgttgcaa gagcgcagcg   26700
atgtgcccct cgccatagcg gatgtcagcc ttgcctacga acgccaccta ttctcaccgc   26760
gcgtaccccc caaacgccaa gaaaacggca catgcgagcc caacccgcgc ctcaacttct   26820
accccgtatt tgccgtgcca gaggtgcttg ccacctatca catcttttc  caaaactgca   26880
agatacccct atcctgccgt gccaaccgca gccgagcgga caagcagctg gccttgcggc   26940
agggcgctgt catacctgat atcgcctcgc tcaacgaagt gccaaaaatc tttgagggtc   27000
ttggacgcga cgagaagcgc gcggcaaacg ctctgcaaca ggaaaacagc gaaaatgaaa   27060
gtcactctgg agtgttggtg gaactcgagg gtgacaacgc gcgcctagcc gtactaaaac   27120
gcagcatcga ggtcacccac tttgcctacc cggcacttaa cctaccccc  aaggtcatga   27180
gcacagtcat gagtgagctg atcgtgcgcc gtgcgcagcc cctggagagg gatgcaaatt   27240
tgcaagaaca aacagaggag ggcctacccg cagttggcga cgagcagcta gcgcgctggc   27300
ttcaaacgcg cgagcctgcc gacttggagg agcgacgcaa actaatgatg gccgcagtgc   27360
tcgttaccgt ggagcttgag tgcatgcagc ggttctttgc tgaccccgag atgcagcgca   27420
agctagagga aacattgcac tacacctttc gacagggcta cgtacgccag gcctgcaaga   27480
tctccaacgt ggagctctgc aacctggtct cctaccttgg aattttgcac gaaaaccgcc   27540
ttgggcaaaa cgtgcttcat tccacgctca agggcgaggc gcgccgcgac tacgtccgcg   27600
actgcgttta cttatttcta tgctacacct ggcagacggc catgggcgtt tggcagcagt   27660
gcttggagga gtgcaacctc aaggagctgc agaaactgct aaagcaaaac ttgaaggacc   27720
tatggacggc cttcaacgag cgctccgtgg ccgcgcacct ggcggacatc attttccccg   27780
aacgcctgct taaaaccctg caacagggtc tgccagactt caccagtcaa agcatgttgc   27840
agaactttag gaactttatc ctagagcgct caggaatctt gcccgccacc tgctgtgcac   27900
ttcctagcga ctttgtgccc attaagtacc gcgaatgccc tccgccgctt tggggccact   27960
gctaccttct gcagctagcc aactaccttg cctaccactc tgacataatg gaagacgtga   28020
gcggtgacgg tctactggag tgtcactgtc gctgcaacct atgcaccccg caccgctccc   28080
tggtttgcaa ttcgcagctg cttaacgaaa gtcaaattat cggtacccttt gagctgcagg   28140
gtccctcgcc tgacgaaaag tccgcggctc cggggttgaa actcactccg gggctgtgga   28200
cgtcggctta ccttcgcaaa tttgtacctg aggactacca cgcccacgag attaggttct   28260
acgaagacca atcccgcccg cctaatgcgg agcttaccgc ctgcgtcatt acccagggcc   28320
acattcttgg ccaattgcaa gccatcaaca agcccgcca  agagtttctg ctacgaaagg   28380
gacgggggt  ttacttggac ccccagtccg gcgaggagct caacccaatc cccccgccgc   28440
cgcagcccta tcagcagcag ccgcggggccc ttgcttccca ggatggcacc caaaaagaag   28500
```

```
ctgcagctgc cgccgccacc cacggacgag gaggaatact gggacagtca ggcagaggag   28560
gttttggacg aggaggagga ggacatgatg gaagactggg agagcctaga cgaggaagct   28620
tccgaggtcg aagaggtgtc agacgaaaca ccgtcaccct cggtcgcatt ccctcgccg    28680 gcgcccaga aatcggcaac cggttccagc atggctacaa cctccgctcc tcaggcgccg   28740
ccggcactgc ccgttcgccg acccaaccgt agatgggaca ccactggaac cagggccggt   28800
aagtccaagc agccgccgcc gttagcccaa gagcaacaac agcgccaagg ctaccgctca   28860
tggcgcgggc acaagaacgc catagttgct tgcttgcaag actgtggggg caacatctcc   28920
ttcgcccgcc gctttcttct ctaccatcac ggcgtggcct tcccccgtaa catcctgcat   28980
tactaccgtc atctctacag cccatactgc accggcggca gcggcagcaa cagcagcggc   29040
cacacagaag caaaggcgac cggatagcaa gactctgaca aagcccaaga aatccacagc   29100
ggcggcagca gcaggaggag gagcgctgcg tctggcgccc aacgaacccg tatcgacccg   29160
cgagcttaga aacaggattt ttcccactct gtatgctata tttcaacaga gcaggggcca   29220
agaacaagag ctgaaaataa aaaacaggtc tctgcgatcc ctcacccgca gctgcctgta   29280
tcacaaaagc gaagatcagc ttcggcgcac gctggaagac gcggaggctc tcttcagtaa   29340
atactgcgcg ctgactctta aggactagtt tcgcgccctt tctcaaattt aagcgcgaaa   29400
actacgtcat ctccagcggc cacacccggc gccagcacct gttgtcagcg ccattatgag   29460
caaggaaatt cccacgccct acatgtggag ttaccagcca caaatgggac ttgcggctgg   29520
agctgcccaa gactactcaa cccgaataaa ctacatgagc gcgggacccc acatgatatc   29580
ccgggtcaac ggaatacgcg cccaccgaaa ccgaattctc ctggaacagg cggctattac   29640
caccacacct cgtaataacc ttaatccccg tagttggccc gctgccctgg tgtaccagga   29700
aagtcccgct cccaccactg tggtacttcc cagagacgcc caggccgaag ttcagatgac   29760
taactcaggg gcgcagcttg cgggcggctt tcgtcacagg gtgcggtcgc ccgggcaggg   29820
tataactcac ctgacaatca gagggcgagg tattcagctc aacgacgagt cggtgagctc   29880
ctcgcttggt ctccgtccgg acgggacatt tcagatcggc ggcgccggcc gctcttcatt   29940
cacgcctcgt caggcaatcc taactctgca gacctcgtcc tctgagccgc gctctggagg   30000
cattggaact ctgcaattta ttgaggagtt tgtgccatcg gtctacttta accccttctc   30060
gggacctccc ggccactatc cggatcaatt tattcctaac tttgacgcgg taaaggactc   30120
ggcggacggc tacgactgaa tgttaagtgg agaggcagag caactgcgcc tgaaacacct   30180
ggtccactgt cgccgccaca agtgctttgc ccgcgactcc ggtgagtttt gctactttga   30240
attgcccgag gatcatatcg agggcccggc gcacggcgtc cggcttaccg cccagggaga   30300
gcttgcccgt agcctgattc gggagtttac ccagcgcccc ctgctagttg agcgggacag   30360
gggaccctgt gttctcactg tgatttgcaa ctgtcctaac cctggattac atcaagatct   30420
ttgttgccat ctctgtgctg agtataataa atacagaaat taaatatac tggggctcct   30480 atcgccatcc tgtaaacgcc accgtcttca cccgcccaag caaaccaagg cgaaccttac   30540
ctggtacttt taacatctct ccctctgtga tttacaacag tttcaaccca gacgagtga   30600 gtctacgaga gaacctctcc gagctcagct actccatcag aaaaacacc accctcctta    30660 cctgccggga acgtacgagt gcgtcaccgg ccgctgcacc acacctaccg cctgaccgta   30720
aaccagactt tttccggaca gacctcaata actctgttta ccagaacagg aggtgagctt   30780
agaaaaccct tagggtatta ggccaaaggc gcagctactg tggggtttat gaacaattca   30840
agcaactcta cgggctattc taattcaggt ttctctagaa atggacggaa ttattacaga   30900
```

```
gcagcgcctg ctagaaagac gcagggcagc ggccgagcaa cagcgcatga atcaagagct   30960
ccaagacatg gttaacttgc accagtgcaa aaggggtatc ttttgtctgg taaagcaggc   31020
caaagtcacc tacgacagta ataccaccgg acaccgcctt agctacaagt tgccaaccaa   31080
gcgtcagaaa ttggtggtca tggtgggaga aaagcccatt accataactc agcactcggt   31140
agaaaccgaa ggctgcattc actcaccttg tcaaggacct gaggatctct gcacccttat   31200
taagaccctg tgcggtctca aagatcttat tccctttaac taataaaaaa aaataataaa   31260
gcatcactta cttaaaatca gttagcaaat ttctgtccag tttattcagc agcacctcct   31320
tgccctcctc ccagctctgg tattgcagct tcctcctggc tgcaaacttt ctccacaatc   31380
taaatggaat gtcagtttcc tcctgttcct gtccatccgc acccactatc ttcatgttgt   31440
tgcagatgaa gcgcgcaaga ccgtctgaag ataccttcaa ccccgtgtat ccatatgaca   31500
cggaaaccgg tcctccaact gtgccttttc ttactcctcc ctttgtatcc cccaatgggt   31560
ttcaagagag tcccccctggg gtactctctt tgcgcctatc cgaacctcta gttacctcca   31620
atggcatgct tgcgctcaaa atgggcaacg gcctctctct ggacgaggcc ggcaacctta   31680
cctcccaaaa tgtaaccact gtgagcccac ctctcaaaaa aaccaagtca aacataaacc   31740
tggaaatatc tgcacccctc acagttacct cagaagccct aactgtggct gccgccgcac   31800
ctctaatggt cgcgggcaac acactccacca tgcaatcaca ggccccgcta accgtgcacg   31860
actccaaact tagcattgcc acccaaggac ccctcacagt gtcagaagga aagctagccc   31920
tgcaaacatc aggccccctc accaccaccg atagcagtac ccttactatc actgcctcac   31980
cccctctaac tactgccact ggtagcttgg gcattgactt gaaagagccc atttatacac   32040
aaaatggaaa actaggacta aagtacgggg ctccttttgca tgtaacagac gacctaaaca   32100 cttttgaccgt agcaactggt ccaggtgtga ctattaataa tacttccttg caaactaaag   32160
ttactggagc cttgggtttt gattcacaag gcaatatgca acttaatgta gcaggaggac   32220
taaggattga ttctcaaaac agacgcctta tacttgatgt tagttatccg tttgatgctc   32280
aaaaccaact aaatctaaga ctaggacagg gccctctttt tataaactca gcccacaact   32340
tggatattaa ctacaacaaa ggcctttact tgtttacagc ttcaaacaat tccaaaaagc   32400
ttgaggttaa cctaagcact gccaaggggt tgatgtttga cgctacagcc atagccatta   32460
atgcaggaga tgggcttgaa tttggttcac ctaatgcacc aaacacaaat cccctcaaaa   32520
caaaaattgg ccatggccta gaatttgatt caaacaaggc tatggttcct aaaactaggaa   32580 ctggcccttag ttttgacagc acaggtgcca ttacagtagg aaacaaaaat aatgataagc   32640
taactttgtg gaccacacca gctccatctc ctaactgtag actaaatgca gagaaagatg   32700
ctaaactcac tttggtctta acaaaatgtg gcagtcaaat acttgctaca gtttcagttt   32760
tggctgttaa aggcagtttg gctccaatat ctggaacagt tcaaagtgct catcttatta   32820
taagatttga cgaaaatgga gtgctactaa acaattcctt cctggaccca gaatattgga   32880
actttagaaa tggagatctt actgaaggca cagcctatac aaacgctgtt ggatttatgc   32940
ctaacctatc agcttatcca aaatctcacg gtaaaactgc caaagtaac attgtcagtc   33000 aagtttactt aaacggagac aaaactaaac ctgtaacact aaccattaca ctaaacggta   33060
cacaggaaac aggagacaca actccaagtg catactctat gtcatttca tgggactggt   33120 ctggccacaa ctacattaat gaaatatttg ccacatcctc ttacactttt tcatacattg   33180
cccaagaata aagaatcgtt tgtgttatgt ttcaacgtgt ttattttca attgcccggg   33240 atcggtgatc accgatccag acatgataag atacattgat gagtttggac aaaccacaac   33300
```

```
tagaatgcag tgaaaaaaat gctttatttg tgaaatttgt gatgctattg ctttatttgt   33360
aaccattata agctgcaata aacaagttcc cggatcgcga tccggcccga ggctgtagcc   33420
gacgatggtg cgccaggaga gttgttgatt cattgtttgc ctccctgctg cggttttttca  33480
ccgaagttca tgccagtcca gcgttttttgc agcagaaaag ccgccgactt cggtttgcgg   33540
tcgcgagtga agatcccttt cttgttaccg ccaacgcgca atatgccttg cgaggtcgca   33600
aaatcggcga aattccatac ctgttcaccg acgacgcgc tgacgcgatc aaagacgcgg    33660
tgatacatat ccagccatgc acactgatac tcttcactcc acatgtcggt gtacattgag   33720
tgcagcccgg ctaacgtatc cacgccgtat tcggtgatga taatcggctg atgcagtttc   33780
tcctgccagg ccagaagttc ttttttccagt accttctctg ccgtttccaa atcgccgctt   33840
tggacatacc atccgtaata acggttcagg cacagcacat caaagagatc gctgatggta   33900
tcggtgtgag cgtcgcagaa cattacattg acgcaggtga tcggacgcgt cgggtcgagt   33960
ttacgcgttg cttccgccag tggcgcgaaa tattcccgtg caccttgcgg acgggtatcc   34020
ggttcgttgg caatactcca catcaccacg cttgggtggt ttttgtcacg cgctatcagc   34080
tctttaatcg cctgtaagtg cgcttgctga gttttccccgt tgactgcctc ttcgctgtac   34140
agttctttcg gcttgttgcc cgcttcgaaa ccaatgccta agagaggtt aaagccgaca    34200
gcagcagttt catcaatcac cacgatgcca tgttcatctg cccagtcgag catctcttca   34260
gcgtaagggt aatgcgaggt acggtaggag ttggccccaa tccagtccat taatgcgtgg   34320
tcgtgcacca tcagcacgtt atcgaatcct ttgccacgca agtccgcatc ttcatgacga   34380
ccaaagccag taaagtagaa cggtttgtgg ttaatcagga actgttcgcc cttcactgcc   34440
actgaccgga tgccgacgcg aagcgggtag atatcacact ctgtctggct tttggctgtg   34500
acgcacagtt catagagata accttcaccc ggttgccaga ggtgcggatt caccacttgc   34560
aaagtcccgc tagtgccttg tccagttgca accacctgtt gatccgcatc acgcagttca   34620
acgctgacat caccattggc caccacctgc cagtcaacag acgcgtggtt acagtcttgc   34680
gcgacatgcg tcaccacggt gatatcgtcc acccaggtgt tcggcgtggt gtagagcatt   34740
acgctgcgat ggattccggc atagttaaag aaatcatgga agtaagactg cttttttcttg   34800
ccgttttcgt cggtaatcac cattcccggc gggatagtct gccagttcag ttcgttgttc   34860
acacaaacgg tgatacgtac acttttccccg gcaataacat acggcgtgac atcggcttca   34920
aatggcgtat agccgccctg atgctccatc acttcctgat tattgaccca cactttgccg   34980
taatgagtga ccgcatcgaa acgcagcacg atacgctggc ctgcccaacc tttcggtata   35040
aagacttcgc gctgatacca gacgttgccc gcataattac gaatatctgc atcggcgaac   35100
tgatcgttaa aactgcctgg cacagcaatt gcccggcttt cttgtaacgc gctttcccac   35160
caacgctgat caattccaca gttttcgcga tccagactga atgcccacag gccgtcgagt   35220
tttttgattt cacgggttgg ggtttctaca ggacggacca tgcgttcgac cttctcttc    35280
tttttttgggc ccatgatggc agatccgtat agtgagtcgt attagctggt tctttccgcc   35340
tcagaagcca tagagcccac cgcatcccca gcatgcctgc tattgtcttc caatcctcc    35400
cccttgctgt cctgccccac cccaccccccc agaatagaat gacacctact cagacaatgc   35460
gatgcaattt cctcattta ttaggaaagg acagtgggag tggcaccttc cagggtcaag     35520
gaaggcacgg gggaggggca aacaacagat ggctggcaac tagaaggcac agtcgaggct   35580
gatcagcgag ctctagatgc atgctcgagc ggccgccagt gtgatggata tctgcagaat   35640
tccagcacac tggcggccgt tactagtgga tccgagctcg gtaccggcc gttataacac    35700
```

-continued

| | |
|---|---|
| cactcgacac ggcaccagct caatcagtca cagtgtaaaa aagggccaag tgcagagcga | 35760 |
| gtatatatag gactaaaaaa tgacgtaacg gttaaagtcc acaaaaaaca cccagaaaac | 35820 |
| cgcacgcgaa cctacgccca gaaacgaaag ccaaaaaacc cacaacttcc tcaaatcgtc | 35880 |
| acttccgttt tcccacgtta cgtcacttcc cattttaaga aaactacaat tcccaacaca | 35940 |
| tacaagttac tccgccctaa aacctacgtc acccgccccg ttcccacgcc ccgcgccacg | 36000 |
| tcacaaactc cacccccctca ttatcatatt ggcttcaatc caaaataagg tatattattg | 36060 |
| atgatg | 36066 |

<210> SEQ ID NO 17
<211> LENGTH: 33583
<212> TYPE: DNA
<213> ORGANISM: Artificial Sequence
<220> FEATURE:
<223> OTHER INFORMATION: Adenoviral vector Adgp140(A).11D

<400> SEQUENCE: 17

| | |
|---|---|
| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggcccggga | 360 |
| tcggtgatca ccgatccaga catgataaga tacattgatg agtttggaca aaccacaact | 420 |
| agaatgcagt gaaaaaaatg ctttatttgt gaaatttgtg atgctattgc tttatttgta | 480 |
| accattataa gctgcaataa acaagttccc ggatctttct agctagtcta gactagctag | 540 |
| actcgagagc ggccgcaatc gataagcttg atgatcccac gtgttcacca cagccagcgg | 600 |
| ctgatgtcga accagttcca caggctggcc cacttgtcca gggccagcag gtcctgctcg | 660 |
| ttcttctcct gctggttctg gctctcctcg atcaggttgt agatgatctg ggtgtagttg | 720 |
| ctgatctcct tgtcccactg cagccaggtc atgttgtccc agatctcgag ctgctggtcc | 780 |
| ttcaggtagc gctccacggc cagcacgcgg gcctgcagct gcttgatgcc ccacacggtc | 840 |
| agcttcagca tgtgctgctg ggcctcgatg gcgcgcagca ggttgctctg ctgctgcacg | 900 |
| atgccgctca gcagctggcg ggcctgggcg gtaagcttgg cgcggctggg ggccacgccc | 960 |
| aggggctcga tcttcaccac cttgtacttg tacagctcgc tgcgccagtt gtcgcgcatg | 1020 |
| ttgccgccgc cggggcggaa gatctcgttg gtgctgttgt tgccgccgtc gcgggtcagc | 1080 |
| agcaggccgt gatgttgct ctcgcagcgg atcacgccct ggatggggg ggtacatg | 1140 |
| gcctggccca ccttctgcca catgttgatg atctgcttga tgcggcaggt cagggtgatg | 1200 |
| gtgtcgttgc tggtggtgtt gttgctctcg gtgctgttgc tctcccaggt gctgttgaac | 1260 |
| aggccgctgg tgttgcagta gaagaactcg ccgccgcaga tgaagctgtg ggtggtgatc | 1320 |
| tcgatgtcgc cgccgctgct cttctcgaag atgatggtct tgttcttgaa gtgctcgcgc | 1380 |
| agcttcttgg ccacgccgcg cagggtgtcg ttccacttgg cgcggctcac gtggcagtgg | 1440 |
| gcctggcgga tgtcgccgat gatgccgccg gtggcgtaga aggcctggcc ggggccgatg | 1500 |
| cgcacgccct tgcgggtgtt gttgttgggg cgggtgcagt tgatcttcac ggccttatcc | 1560 |
| agctgcacga tgatggtctt ggcgttgttg gtgatgttct cgctgcggat ctggatgccc | 1620 |
| tcctcggcca ggctgccgtt cagcagcagc tgggtgctga tcaccggtcg gatgccgtgg | 1680 |

```
gtgcactgca cggtgctcac gttcttgcag gggccggtac cgttgaactc ggtgtccttg    1740
cacttcagga tggcgaagcc ggcggggcg cagtagtgga tggggatggg ctcgaagctc     1800
accttggggc aggcctgggt gatggcgctg gtgttgcagt tgatcaggcg gtacttgtcg    1860
gtctcgttct tctcgttgat ctgcaccacg tccagcttgt agaacaggct gtacacctgc    1920
tgcttcttgt ccttcagctc ggtggtgatg ttgaagctac agttgcgcat ctcgttggtc    1980
acgttgctgg cggtggcgtt gcagtccagg gtcacgcaca gggggtcag cttcacgcag     2040 ggcttcaggc tctggtccca caggctgatg atgtcggtgt gcatctgctc caccatgttg    2100
ttgcgccaca tgttgaagtc ctcggtcacg ttctccaggt ggatctcctg ggggttgggg    2160
tcggtgggca cgcaggcgtg ggtctcccac acgttgtgca cctcggtgtc gtaggccttg    2220
gcgtcgctgg cgcagaacag ggtggtctcg gcgtccttcc acacgggcac gccgtagtac    2280
acggccaccc acaggttctc ggcggcgctg tagatcacca gcatgcccag gatcatggtg    2340
ccccagcgcc acaggttctg ccagctggtc tggatgccgc gcacgcgcat ggtggcgata    2400
tctctagatc gaattctgca gtgatcaggg atcccagatc cgtatagtga gtcgtattag    2460
gtaccggctg cagttggacc tgggagtgga cacctgtgga gagaaaggca aagtggatgt    2520
cattgtcact caagtgtatg ccagatctc aagcctgcca cacctcaagt gaagccaagg     2580
gggtgggcct atagactcta taggcggtac ttacgtcact cttggcacgg gaatccgcg     2640 ttccaatgca ccgttcccgg ccgcggaggc tggatcggtc ccggtgtctt ctatggaggt    2700
caaaacagcg tggatggcgt ctccaggcga tctgacggtt cactaaacga gctctgctta    2760
tatagacctc ccaccgtaca cgcctaccgc ccatttgcgt caatggggcg gagttgttac    2820
gacattttgg aaagtcccgt tgattttggt gccaaaacaa actcccattg acgtcaatgg    2880
ggtggagact tggaaatccc cgtgagtcaa accgctatcc acgcccattg atgtactgcc    2940
aaaaccgcat caccatggta atagcgatga ctaatacgta gatgtactgc caagtaggaa    3000
agtcccataa ggtcatgtac tgggcataat gccaggcggg ccatttaccg tcattgacgt    3060 caatagggg cgtacttggc atatgataca cttgatgtac tgccaagtgg gcagtttacc     3120
gtaaatactc cacccattga cgtcaatgga aagtccctat tggcgttact atgggaacat    3180
acgtcattat tgacgtcaat gggcgggggt cgttgggcgg tcagccaggc gggccattta    3240
ccgtaagtta tgtaacgcgg aactccatat atgggctatg aactaatgac cccgtaattg    3300
attactatta ataactagta ctgaaatgtg tgggcgtggc ttaagggtgg gaaagaatat    3360
ataaggtggg ggtcttatgt agttttgtat ctgttttgca gcagccgccg ccgccatgag    3420
caccaactcg tttgatggaa gcattgtgag ctcatatttg acaacgcgca tgcccccatg    3480
ggccggggtg cgtcagaatg tgatgggctc cagcattgat ggtcgccccg tcctgcccgc    3540
aaactctact accttgacct acgagaccgt gtctggaacg ccgttggaga ctgcagcctc    3600
cgccgccgct tcagccgctg cagccaccgc ccgcggatt tgactgact ttgctttcct     3660 gagcccgctt gcaagcagtg cagcttcccg ttcatccgcc cgcgatgaca agttgacggc    3720
tcttttggca caattggatt ctttgacccg gaacttaat gtcgtttctc agcagctgtt     3780
ggatctgcgc cagcaggttt ctgccctgaa ggcttcctcc cctcccaatg cggtttaaaa    3840
cataaataaa aaaccagact ctgtttggat ttggatcaag caagtgtctt gctgtctta     3900 tttagggggtt ttgcgcgcgc ggtaggcccg ggaccagcgg tctcggtcgt tgagggtcct   3960
gtgtattttt tccaggacgt ggtaaaggtg actctggatg ttcagataca tgggcataag   4020
cccgtctctg gggtggaggt agcaccactg cagagcttca tgctgcgggg tggtgttgta   4080
```

```
gatgatccag tcgtagcagg agcgctgggc gtggtgccta aaaatgtctt tcagtagcaa    4140
gctgattgcc aggggcaggc ccttggtgta agtgtttaca aagcggttaa gctgggatgg    4200
gtgcatacgt ggggatatga gatgcatctt ggactgtatt tttaggttgg ctatgttccc    4260
agccatatcc ctccggggat tcatgttgtg cagaaccacc agcacagtgt atccggtgca    4320
cttgggaaat ttgtcatgta gcttagaagg aaatgcgtgg aagaacttgg agacgccctt    4380
gtgacctcca agattttcca tgcattcgtc cataatgatg gcaatgggcc cacgggcggc    4440
ggcctgggcg aagatatttc tgggatcact aacgtcatag ttgtgttcca ggatgagatc    4500
gtcataggcc atttttacaa agcgcggggcg gagggtgcca gactgcggta taatggttcc    4560
atccggccca ggggcgtagt taccctcaca gatttgcatt tcccacgctt tgagttcaga    4620 tgggggatc atgtctacct gcgggcgat gaagaaaacg gtttccgggg taggggagat    4680
cagctgggaa gaaagcaggt tcctgagcag ctgcgactta ccgcagccgg tgggcccgta    4740
aatcacacct attaccggct gcaactggta gttaagagag ctgcagctgc cgtcatccct    4800
gagcaggggg gccacttcgt taagcatgtc cctgactcgc atgttttccc tgaccaaatc    4860
cgccagaagg cgctcgccgc ccagcgatag cagttcttgc aaggaagcaa agttttcaa    4920 cggtttgaga ccgtccgccg taggcatgct tttgagcgtt tgaccaagca gttccaggcg    4980
gtcccacagc tcggtcacct gctctacggc atctcgatcc agcatatctc ctcgtttcgc    5040
gggttggggc ggctttcgct gtacggcagt agtcggtgct cgtccagacg ggccagggtc    5100
atgtctttcc acgggcgcag ggtcctcgtc agcgtagtct gggtcacggt gaagggtgc    5160 gctccgggct gcgcgctggc cagggtgcgc ttgaggctgg tcctgctggt gctgaagcgc    5220
tgccggtctt cgccctgcgc gtcggccagg tagcatttga ccatggtgtc atagtccagc    5280
ccctccgcgg cgtggcccctt ggcgcgcagc ttgcccttgg aggaggcgcc gcacgagggg    5340
cagtgcagac ttttgagggc gtagagcttg ggcgcgagaa ataccgattc cggggagtag    5400
gcatccgcgc cgcaggcccc gcagacgtc tcgcattcca cgagccaggt gagctctggc    5460
cgttcggggt caaaaaccag gtttccccca tgctttttga tgcgtttctt acctctggtt    5520
tccatgagcc ggtgtccacg ctcggtgacg aaaaggctgt ccgtgtcccc gtatacagac    5580
ttgagaggcc tgtcctcgag cggtgttccg cggtcctcct cgtatagaaa ctcggaccac    5640
tctgagacaa aggctcgcgt ccaggccagc acgaaggagg ctaagtggga ggggtagcgg    5700
tcgttgtcca ctaggggtc cactcgctcc agggtgtgaa gacacatgtc gccctcttcg    5760
gcatcaagga aggtgattgg tttgtaggtg taggccacgt gaccgggtgt tcctgaaggg    5820
gggctataaa aggggtggg ggcgcgttcg tcctcactct cttccgcatc gctgtctgcg    5880
agggccagct gttggggtga gtactccctc tgaaaagcgg gcatgacttc tgcgctaaga    5940
ttgtcagttt ccaaaaacga ggaggatttg atattcacct ggcccgcggt gatgcctttg    6000
agggtggccg catccatctg gtcagaaaag acaatctttt tgttgtcaag cttggtggca    6060
aacgacccgt agagggcgtt ggacagcaac ttggcgatgg agcgcagggt ttggtttttg    6120
tcgcgatcgc cgcgctcctt ggccgcgatg tttagctgca cgtattcgcg cgcaacgcac    6180
cgccattcgg gaaagacggt ggtgcgctcg tcgggcacca ggtgcacgcg ccaaccgcgg    6240
ttgtgcaggg tgacaaggtc aacgctggtg gctacctctc cgcgtaggcg ctcgttggtc    6300
cagcagaggc ggccgcccctt gcgcgagcag aatggcggta gggggtctag ctgcgtctcg    6360
tccggggggt ctgcgtccac ggtaaagacc ccgggcagca ggcgcgcgtc gaagtagtct    6420
atcttgcatc cttgcaagtc tagcgcctgc tgccatgcgc gggcggcaag cgcgcgctcg    6480
```

```
tatgggttga gtgggggacc ccatggcatg gggtgggtga gcgcggaggc gtacatgccg    6540
caaatgtcgt aaacgtagag gggctctctg agtattccaa gatatgtagg gtagcatctt    6600
ccaccgcgga tgctggcgcg cacgtaatcg tatagttcgt gcgagggagc gaggaggtcg    6660
ggaccgaggt tgctacgggc gggctgctct gctcggaaga ctatctgcct gaagatggca    6720
tgtgagttgg atgatatggt tggacgctgg aagacgttga agctggcgtc tgtgagacct    6780
accgcgtcac gcacgaagga ggcgtaggag tcgcgcagct tgttgaccag ctcggcggtg    6840
acctgcacgt ctagggcgca gtagtccagg gtttccttga tgatgtcata cttatcctgt    6900 ccctttttt tccacagctc gcggttgagg acaaactctt cgcggtcttt ccagtactct    6960
tggatcggaa acccgtcggc ctccgaacgg taagagccta gcatgtagaa ctggttgacg    7020
gcctggtagg cgcagcatcc cttttctacg ggtagcgcgt atgcctgcgc ggccttccgg    7080
agcgaggtgt gggtgagcgc aaaggtgtcc ctgaccatga ctttgaggta ctggtatttg    7140
aagtcagtgt cgtcgcatcc gccctgctcc cagagcaaaa agtccgtgcg ctttttggaa    7200
cgcggatttg gcagggcgaa ggtgacatcg ttgaagagta tctttcccgc gcgaggcata    7260
aagttgcgtg tgatgcggaa gggtcccggc acctcggaac ggttgttaat tacctgggcg    7320
gcgagcacga tctcgtcaaa gccgttgatg ttgtggccca caatgtaaag ttccaagaag    7380
cgcgggatgc ccttgatgga aggcaatttt ttaagttcct cgtaggtgag ctcttcaggg    7440
gagctgagcc cgtgctctga aagggcccag tctgcaagat gagggttgga agcgacgaat    7500
gagctccaca ggtcacgggc cattagcatt tgcaggtggt cgcgaaaggt cctaaactgg    7560
cgacctatgg ccatttttc tggggtgatg cagtagaagg taagcgggtc ttgttcccag    7620
cggtcccatc caaggttcgc ggctaggtct cgcgcggcag tcactagagg ctcatctccg    7680
ccgaacttca tgaccagcat gaagggcacg agctgcttcc caaaggcccc catccaagta    7740
taggtctcta catcgtaggt gacaaagaga cgctcggtgc gaggatgcga gccgatcggg    7800
aagaactgga tctcccgcca ccaattggag gagtggctat tgatgtggtg aaagtagaag    7860
tccctgcgac gggccgaaca ctcgtgctgg ctttttgtaaa aacgtgcgca gtactggcag    7920
cggtgcacgg gctgtacatc ctgcacgagg ttgacctgac gaccgcgcac aaggaagcag    7980
agtgggaatt tgagcccctc gcctggcggg tttggctggt ggtcttctac ttcggctgct    8040
tgtccttgac cgtctggctg ctcgagggga gttacggtgg atcggaccac cacgccgcgc    8100
gagcccaaag tccagatgtc cgcgcgcggc ggtcggagct tgatgacaac atcgcgcaga    8160
tgggagctgt ccatggtctg gagctcccgc ggcgtcaggt caggcgggag ctcctgcagg    8220
tttacctcgc atagacgggt cagggcgcgg gctagatcca ggtgatacct aatttccagg    8280
ggctggttgg tggcggcgtc gatggcttgc aagaggccgc atccccgcgg cgcgactacg    8340
gtaccgcgcg gcgggcggtg ggccgcgggg gtgtccttgg atgatgcatc taaaagcggt    8400
gacgcgggcg agcccccgga ggtagggggg gctccggacc cgccgggaga gggggcaggg    8460
gcacgtcggc gccgcgcgcg ggcaggagct ggtgctgcgc gcgtaggttg ctggcgaacg    8520
cgacgacgcg gcggttgatc tcctgaatct ggcgcctctg cgtgaagacg acgggcccgg    8580
tgagcttgaa cctgaaagag agttcgacag aatcaatttc ggtgtcgttg acggcggcct    8640
ggcgcaaaat ctcctgcacg tctcctgagt tgtcttgata ggcgatctcg gccatgaact    8700
gctcgatctc ttcctcctgg agatctccgc gtccggctcg ctccacggtg gcggcgaggt    8760
cgttggaaat gcgggccatg agctgcgaga aggcgttgag gcctccctcg ttccagacgc    8820
ggctgtagac cacgccccct tcggcatcgc gggcgcgcat gaccacctgc gcgagattga    8880
```

```
gctccacgtg ccgggcgaag acggcgtagt ttcgcaggcg ctgaaagagg tagttgaggg     8940
tggtggcggt gtgttctgcc acgaagaagt acataaccca gcgtcgcaac gtggattcgt     9000
tgatatcccc caaggcctca aggcgctcca tggcctcgta gaagtccacg gcgaagttga     9060
aaaactggga gttgcgcgcc gacacggtta actcctcctc cagaagacgg atgagctcgg     9120
cgacagtgtc gcgcacctcg cgctcaaagg ctacaggggc ctcttcttct tcttcaatct     9180
cctcttccat aagggcctcc ccttcttctt cttctggcgg cggtggggga gggggacac     9240
ggcggcgacg acggcgcacc gggaggcggt cgacaaagcg ctcgatcatc tccccgcggc     9300
gacggcgcat ggtctcggtg acggcgcggc cgttctcgcg ggggcgcagt ggaagacgc     9360
cgcccgtcat gtcccggtta tgggttggcg gggggctgcc atgcggcagg gatacggcgc     9420
taacgatgca tctcaacaat tgttgtgtag gtactccgcc gccagggac ctgagcgagt     9480
ccgcatcgac cggatcggaa aacctctcga gaaaggcgtc taaccagtca cagtcgcaag     9540
gtaggctgag caccgtggcg ggcggcagcg ggcggcggtc ggggttgttt ctggcggagg     9600
tgctgctgat gatgtaatta aagtaggcgg tcttgagacg gcggatggtc gacagaagca     9660
ccatgtcctt gggtccggcc tgctgaatgc gcaggcggtc ggccatgccc caggcttcgt     9720
tttgacatcg gcgcaggtct ttgtagtagt cttgcatgag cctttctacc ggcacttctt     9780
cttctccttc ctcttgtcct gcatctcttg catctatcgc tgcggcggcg gcggagtttg     9840
gccgtaggtg gcgccctctt cctcccatgc gtgtgacccc gaagcccctc atcggctgaa     9900
gcagggctag gtcggcgaca acgcgctcgg ctaatatggc ctgctgcacc tgcgtgaggg     9960
tagactggaa gtcatccatg tccacaaagc ggtggtatgc gcccgtgttg atggtgtaag    10020
tgcagttggc cataacggac cagttaacgg tctggtgacc cggctgcgag agctcggtgt    10080
acctgagacg cgagtaagcc ctcgagtcaa atacgtagtc gttgcaagtc cgcaccaggt    10140
actggtatcc caccaaaaag tgcggcggcg gctggcggta gaggggccag cgtagggtgg    10200
ccgggctcc gggggcgaga tcttccaaca taagggatg atatccgtag atgtacctgg    10260
acatccaggt gatgccggcg gcggtggtgg aggcgcgcgg aaagtcgcgg acgcggttcc    10320
agatgttgcg cagcggcaaa aagtgctcca tggtcgggac gctctggccg gtcaggcgcg    10380
cgcaatcgtt gacgctctag cgtgcaaaag gagagcctgt aagcgggcac tcttccgtgg    10440
tctggtggat aaattcgcaa gggtatcatg gcggacgacc ggggttcgag ccccgtatcc    10500
ggccgtccgc cgtgatccat gcggttaccg cccgcgtgtc gaacccaggt gtgcgacgtc    10560
agacaacggg ggagtgctcc ttttggcttc cttccaggcg cggcggctgc tgcgctagct    10620
tttttggcca ctggccgcgc gcagcgtaag cggttaggct ggaaagcgaa agcattaagt    10680
ggctcgctcc ctgtagccgg agggttattt tccaagggtt gagtcgcggg accccggtt    10740
cgagtctcgg accggccgga ctgcggcgaa cgggggtttg cctccccgtc atgcaagacc    10800
ccgcttgcaa attcctccgg aaacaggagc gagccccttt tttgcttttc ccagatgcat    10860
ccggtgctgc ggcagatgcg cccccctcct cagcagcggc aagagcaaga gcagcggcag    10920
acatgcaggg caccctcccc tcctcctacc gcgtcaggag gggcgacatc cgcggttgac    10980
gcggcagcag atggtgatta cgaaccccg cggcgccggg cccggcacta cctggacttg    11040
gaggagggcg agggcctggc gcggctagga gcgccctctc ctgagcggca cccaagggtg    11100
cagctgaagc gtgatacgcg tgaggcgtac gtgccgcggc agaacctgtt tcgcgaccgc    11160
gagggagagg agcccgagga gatgcgggat cgaaagttcc acgcagggcg cgagctgcgg    11220
catggcctga atcgcgagcg gttgctgcgc gaggaggact ttgagcccga cgcgcgaacc    11280
```

```
gggattagtc ccgcgcgcgc acacgtggcg gccgccgacc tggtaaccgc atacgagcag    11340
acggtgaacc aggagattaa cttccaaaaa agctttaaca accacgtgcg tacgcttgtg    11400
gcgcgcgagg aggtggctat aggactgatg catctgtggg actttgtaag cgcgctggag    11460
caaaacccaa atagcaagcc gctcatggcg cagctgttcc ttatagtgca gcacagcagg    11520
gacaacgagg cattcaggga tgcgctgcta aacatagtag agcccgaggg ccgctggctg    11580
ctcgatttga taaacatcct gcagagcata gtggtgcagg agcgcagctt gagcctggct    11640
gacaaggtgg ccgccatcaa ctattccatg cttagcctgg gcaagtttta cgcccgcaag    11700
atataccata ccccttacgt tcccatagac aaggaggtaa agatcgaggg gttctacatg    11760
cgcatggcgc tgaaggtgct taccttgagc gacgacctgg gcgtttatcg caacgagcgc    11820
atccacaagg ccgtgagcgt gagccggcgg cgcgagctca gcgaccgcga gctgatgcac    11880
agcctgcaaa gggccctggc tggcacgggc agcggcgata gagaggccga gtcctacttt    11940
gacgcgggcg ctgacctgcg ctgggcccca agccgacgcg ccctggaggc agctggggcc    12000
ggacctgggc tggcggtggc acccgcgcgc gctggcaacg tcggcggcgt ggaggaatat    12060
gacgaggacg atgagtacga gccagaggac ggcgagtact aagcggtgat gtttctgatc    12120
agatgatgca agacgcaacg gacccggcgg tgcgggcggc gctgcagagc cagccgtccg    12180
gccttaactc cacggacgac tggcgccagg tcatgaccg catcatgtcg ctgactgcgc    12240
gcaatcctga cgcgttccgg cagcagccgc aggccaaccg gctctccgca attctggaag    12300
cggtggtccc ggcgcgcgca aaccccacgc acgagaaggt gctggcgatc gtaaacgcgc    12360
tggccgaaaa cagggccatc cggcccgacg aggccggcct ggtctacgac gcgctgcttc    12420
agcgcgtggc tcgttacaac agcggcaacg tgcagaccaa cctggaccgg ctggtgggg     12480 atgtgcgcga ggccgtggcg cagcgtgagc gcgcgcagca gcagggcaac ctgggctcca    12540
tggttgcact aaacgccttc ctgagtacac agcccgccaa cgtgccgcgg ggacaggagg    12600
actacaccaa ctttgtgagc gcactgcggc taatggtgac tgagacaccg caaagtgagg    12660
tgtaccagtc tgggccagac tatttttcc agaccagtag acaaggcctg cagaccgtaa     12720
acctgagcca ggctttcaaa aacttgcagg ggctgtgggg ggtgcgggct cccacaggcg    12780
accgcgcgac cgtgtctagc ttgctgacgc ccaactcgcg cctgttgctg ctgctaatag    12840
cgcccttcac ggacagtggc agcgtgtccc gggacacata cctaggtcac ttgctgacac    12900
tgtaccgcga ggccataggt caggcgcatg tggacgagca tactttccag gagattacaa    12960
gtgtcagccg cgcgctgggg caggaggaca cgggcagcct ggaggcaacc ctaaactacc    13020
tgctgaccaa ccggcggcag aagatcccct cgttgcacag tttaaacagc gaggaggagc    13080
gcattttgcg ctacgtgcag cagagcgtga gccttaacct gatgcgcgac ggggtaacgc    13140
ccagcgtggc gctggacatg accgcgcgca acatggaacc gggcatgtat gcctcaaacc    13200
ggccgtttat caaccgccta atggactact gcatcgcgc ggccgccgtg aaccccgagt     13260
atttcaccaa tgccatcttg aacccgcact ggctaccgcc ccctggtttc tacaccgggg    13320
gattcgaggt gcccgagggt aacgatggat tcctctggga cgacatagac gacagcgtgt    13380
tttccccgca accgcagacc ctgctagagt tgcaacagcg cgagcaggca gaggcggcgc    13440
tgcgaaagga aagcttccgc aggccaagca gcttgtccga tctaggcgct gcggccccgc    13500
ggtcagatgc tagtagccca tttccaagct tgataggtc tcttaccagc actcgcacca     13560
cccgcccgcg cctgctgggc gaggaggagt acctaaacaa ctcgctgctg cagccgcagc    13620
gcgaaaaaaa cctgcctccg gcatttccca acaacgggat agagagccta gtggacaaga    13680
```

```
tgagtagatg gaagacgtac gcgcaggagc acagggacgt gccaggcccg cgcccgccca   13740
cccgtcgtca aaggcacgac cgtcagcggg gtctggtgtg ggaggacgat gactcggcag   13800
acgacagcag cgtcctggat ttgggaggga gtggcaaccc gtttgcgcac cttcgcccca   13860
ggctggggag aatgttttaa aaaaaaaaaa agcatgatgc aaaataaaaa actcaccaag   13920
gccatggcac cgagcgttgg ttttcttgta ttccccttag tatgcggcgc gcggcgatgt   13980
atgaggaagg tcctcctccc tcctacgaga gtgtggtgag cgcggcgcca gtggcggcgg   14040
cgctgggttc tcccttcgat gctcccctgg accgccgtt tgtgcctccg cggtacctgc    14100
ggcctaccgg ggggagaaac agcatccgtt actctgagtt ggcacccta ttcgacacca    14160 cccgtgtgta cctggtggac aacaagtcaa cggatgtggc atccctgaac taccagaacg   14220
accacagcaa ctttctgacc acggtcattc aaaacaatga ctacagcccg ggggaggcaa   14280
gcacacagac catcaatctt gacgaccggt cgcactgggg cggcgacctg aaaaccatcc   14340
tgcataccaa catgccaaat gtgaacgagt tcatgtttac caataagttt aaggcgcggg   14400
tgatggtgtc gcgcttgcct actaaggaca atcaggtgga gctgaaatac gagtgggtgg   14460
agttcacgct gcccgagggc aactactccg agaccatgac catagacctt atgaacaacg   14520
cgatcgtgga gcactacttg aaagtgggca gacagaacgg ggttctggaa agcgacatcg   14580
gggtaaagtt tgacacccgc aacttcagac tggggtttga ccccgtcact ggtcttgtca   14640
tgcctggggt atatacaaac gaagccttcc atccagacat cattttgctg ccaggatgcg   14700
gggtggactt cacccacagc cgcctgagca acttgttggg catccgcaag cggcaaccct   14760
tccaggaggg ctttaggatc acctacgatg atctggaggg tggtaacatt cccgcactgt   14820
tggatgtgga cgcctaccag gcgagcttga aagatgacac cgaacagggc gggggtggcg   14880
caggcggcag caacagcagt ggcagcggcg cggaagagaa ctccaacgcg gcagccgcgg   14940
caatgcagcc ggtggaggac atgaacgatc atgccattcg cggcgacacc tttgccacac   15000
gggctgagga gaagcgcgct gaggccgaag cagcggccga agctgccgcc cccgctgcgc   15060
aacccgaggt cgagaagcct cagaagaaac cggtgatcaa accctgaca gaggacagca    15120 agaaacgcag ttacaaccta ataagcaatg acagcacctt cacccagtac cgcagctggt   15180
accttgcata caactacggc gaccctcaga ccggaatccg ctcatggacc ctgctttgca   15240
ctcctgacgt aacctgcggc tcggagcagg tctactggtc gttgccagac atgatgcaag   15300
accccgtgac cttccgctcc acgcgccaga tcagcaactt tccggtggtg ggcgccgagc   15360
tgttgcccgt gcactccaag agcttctaca acgaccaggc cgtctactcc caactcatcc   15420
gccagtttac ctctctgacc cacgtgttca atcgcttttcc cgagaaccag attttggcgc   15480
gcccgccagc ccccaccatc accaccgtca gtgaaaacgt tcctgctctc acagatcacg   15540
ggacgctacc gctgcgcaac agcatcggag gagtccagcg agtgaccatt actgacgcca   15600
gacgccgcac ctgcccctac gtttacaagg ccctgggcat agtctcgccg cgcgtcctat   15660
cgagccgcac tttttgagca agcatgtcca tccttatatc gcccagcaat aacacaggct   15720
ggggcctgcg cttcccaagc aagatgtttg gcggggccaa gaagcgctcc gaccaacacc   15780
cagtgcgcgt gcgcgggcac taccgcgcgc cctggggcgc gcacaaacgc ggccgcactg   15840
ggcgcaccac cgtcgatgac gccatcgacg cggtggtgga ggaggcgcgc aactacacgc   15900
ccacgccgcc accagtgtcc acagtggacg cggccattca gaccgtggtg cgcggagccc   15960
ggcgctatgc taaaatgaag agacggcgga ggcgcgtagc acgtcgccac cgccgccgac   16020
ccggcactgc cgcccaacgc gcggcggcgg ccctgcttaa ccgcgcacgt cgcaccggcc   16080
```

```
gacgggcggc catgcgggcc gctcgaaggc tggccgcggg tattgtcact gtgcccccca    16140
ggtccaggcg acgagcggcc gccgcagcag ccgcggccat tagtgctatg actcagggtc    16200 gcagggcaa  cgtgtattgg gtgcgcgact cggttagcgg cctgcgcgtg cccgtgcgca    16260 cccgccccc  gcgcaactag attgcaagaa aaaactactt agactcgtac tgttgtatgt    16320
atccagcggc ggcggcgcgc aacgaagcta tgtccaagcg caaaatcaaa gaagagatgc    16380
tccaggtcat cgcgccggag atctatggcc ccccgaagaa ggaagagcag gattacaagc    16440
cccgaaagct aaagcgggtc aaaaagaaaa agaaagatga tgatgatgaa cttgacgacg    16500
aggtggaact gctgcacgct accgcgccca ggcgacgggt acagtggaaa ggtcgacgcg    16560
taaaacgtgt tttgcgaccc ggcaccaccg tagtctttac gcccggtgag cgctccaccc    16620
gcacctacaa gcgcgtgtat gatgaggtgt acgcgacga  ggacctgctt gagcaggcca    16680
acgagcgcct cggggagttt gcctacgaa  agcggcataa ggacatgctg gcgttgccgc    16740
tggacgaggg caacccaaca cctagcctaa agcccgtaac actgcagcag gtgctgcccg    16800
cgcttgcacc gtccgaagaa agcgcggcc  taaagcgcga gtctggtgac ttggcaccca    16860
ccgtgcagct gatggtaccc aagcgccagc gactggaaga tgtcttggaa aaaatgaccg    16920
tggaacctgg gctggagccc gaggtccgcg tgcggccaat caagcaggtg gcgccgggac    16980
tgggcgtgca gaccgtggac gttcagatac ccactaccag tagcaccagt attgccaccg    17040
ccacagaggg catggagaca caaacgtccc cggttgcctc agcggtggcg gatgccgcgg    17100
tgcaggcggt cgctgcggcc gcgtccaaga cctctacgga ggtgcaaacg gacccgtgga    17160
tgtttcgcgt ttcagccccc cggcgccgc  gccgttcgag gaagtacggc gccgccagcg    17220
cgctactgcc cgaatatgcc ctacatcctt ccattgcgcc taccccggc  tatcgtggct    17280 acacctaccg ccccagaaga cgagcaacta cccgacgccg aaccaccact ggaacccgcc    17340
gccgccgtcg ccgtcgccag cccgtgctgg ccccgatttc cgtgcgcagg gtggctcgcg    17400
aaggaggcag gaccctggtg ctgccaacag cgcgctacca ccccagcatc gtttaaaagc    17460
cggtctttgt ggttcttgca gatatggcc  tcacctgccg cctccgtttc ccggtgccgg    17520
gattccgagg aagaatgcac cgtaggaggg gcatggccgg ccacgccctg acgggcggca    17580
tgcgtcgtgc gcaccaccgg cggcggcgcg cgtcgcaccg tcgcatgcgc ggcggtatcc    17640
tgcccctcct tattccactg atccgccgcg cgattggcgc cgtgcccgga attgcatccg    17700
tggccttgca ggcgcagaga cactgattaa aaacaagttg catgtggaaa aatcaaaata    17760
aaaagtctgg actctcacgc tcgcttggtc ctgtaactat tttgtagaat ggaagacatc    17820
aactttgcgt ctctggcccc gcgacacggc tcgcgcccgt tcatgggaaa ctggcaagat    17880
atcggcacca gcaatatgag cggtggcgcc ttcagctggg gctcgctgtg gagcggcatt    17940
aaaaatttcg gttccaccgt taagaactat ggcagcaagg cctggaacag cagcacaggc    18000
cagatgctga gggataagtt gaaagagcaa aatttccaac aaaaggtggt agatggcctg    18060
gcctctggca ttagcggggt ggtggacctg gccaaccagg cagtgcaaaa taagattaac    18120
agtaagcttg atccccgccc tcccgtagag gagcctccac cggccgtgga cacagtgtct    18180
ccagaggggc gtggcgaaaa gcgtccgcgc cccgacaggg aagaaactct ggtgacgcaa    18240
atagacgagc ctccctcgta cgaggaggca ctaaagcaag gcctgcccac cacccgtccc    18300
atcgcgccca tggctaccgg agtgctgggc cagcacacac ccgtaacgct ggacctgcct    18360
ccccccgccg acacccagca gaaacctgtg ctgccaggcc cgaccgccgt tgttgtaacc    18420
cgtcctagcc gcgcgtccct gcgccgcgcc gccagcggtc cgcgatcgtt gcggcccgta    18480
```

```
gccagtggca actggcaaag cacactgaac agcatcgtgg gtctgggggt gcaatccctg   18540
aagcgccgac gatgcttctg atagctaacg tgtcgtatgt gtgtcatgta tgcgtccatg   18600
tcgccgccag aggagctgct gagccgccgc gcgcccgctt ccaagatggg ctaccccttc   18660
gatgatgccg cagtggtctt acatgcacat ctcgggccag gacgcctcgg agtacctgag   18720
ccccgggctg gtgcagtttg cccgcgccac cgagacgtac ttcagcctga ataacaagtt   18780
tagaaacccc acggtggcgc ctacgcacga cgtgaccaca gaccggtccc agcgtttgac   18840
gctgcggttc atccctgtgg accgtgagga tactgcgtac tcgtacaagg cgcggttcac   18900
cctagctgtg ggtgataacc gtgtgctgga catggcttcc acgtactttg acatccgcgg   18960
cgtgctggac aggggcccta cttttaagcc ctactctggc actgcctaca acgccctggc   19020
tcccaagggt gccccaaatc cttgcgaatg ggatgaagct gctactgctc ttgaaataaa   19080
cctagaagaa gaggacgatg acaacgaaga cgaagtagac gagcaagctg agcagcaaaa   19140
aactcacgta tttgggcagg cgccttattc tggtataaat attacaaagg agggtattca   19200
aataggtgtc gaaggtcaaa cacctaaata tgccgataaa acatttcaac ctgaacctca   19260
aataggagaa tctcagtggt acgaaacaga aattaatcat gcagctggga gagtcctaaa   19320
aaagactacc ccaatgaaac catgttacgg ttcatatgca aaacccacaa atgaaaatgg   19380
agggcaaggc attcttgtaa agcaacaaaa tggaaagcta gaaagtcaag tggaaatgca   19440 attttttctca actactgagg cagccgcagg caatggtgat aacttgactc ctaaagtggt   19500
attgtacagt gaagatgtag atatagaaac cccagacact catatttctt acatgcccac   19560
tattaaggaa ggtaactcac gagaactaat gggccaacaa tctatgccca acaggcctaa   19620
ttacattgct tttagggaca atttattgg tctaatgtat tacaacagca cgggtaatat   19680
gggtgttctg gcgggccaag catcgcagtt gaatgctgtt gtagatttgc aagacagaaa   19740
cacagagctt tcataccagc ttttgcttga ttccattggt gatagaacca ggtacttttc   19800
tatgtggaat caggctgttg acagctatga tccagatgtt agaattattg aaaatcatgg   19860
aactgaagat gaacttccaa attactgctt tccactggga ggtgtgatta atacagagac   19920
tcttaccaag gtaaaaccta aaacaggtca ggaaaatgga tgggaaaaag atgctacaga   19980
attttcagat aaaaatgaaa taagagttgg aaataatttt gccatggaaa tcaatctaaa   20040
tgccaacctg tggagaaatt tcctgtactc caacatagcg ctgtatttgc ccgacaagct   20100
aaagtacagt ccttccaacg taaaaatttc tgataaccca aacacctacg actacatgaa   20160
caagcgagtg gtggctcccg ggctagtgga ctgctacatt aaccttggag cacgctggtc   20220
ccttgactat atggacaacg tcaacccatt taaccaccac cgcaatgctg gcctgcgcta   20280
ccgctcaatg ttgctgggca atggtcgcta tgtgcccttc cacatccagg tgcctcagaa   20340
gttctttgcc attaaaaacc tccttctcct gccgggctca tacacctacg agtggaactt   20400
caggaaggat gttaacatgg ttctgcagag ctccctagga aatgacctaa gggttgacgg   20460
agccagcatt aagtttgata gcatttgcct ttacgccacc ttcttcccca tggcccacaa   20520
caccgcctcc acgcttgagg ccatgcttag aaacgacacc aacgaccagt cctttaacga   20580
ctatctctcc gccgccaaca tgctctaccc tataccgcc aacgctacca acgtgcccat   20640
atccatcccc tcccgcaact gggcggcttt ccgcggctgg gccttcacgc gccttaagac   20700
taaggaaacc ccatcactgg gctcgggcta cgacccttat tacacctact ctggctctat   20760
accctaccta gatggaacct tttacctcaa ccacaccttt aagaaggtgg ccattaccctt   20820 tgactcttct gtcagctggc ctggcaatga ccgcctgctt accccaacg agtttgaaat   20880
```

```
taagcgctca gttgacgggg agggttacaa cgttgcccag tgtaacatga ccaaagactg    20940
gttcctggta caaatgctag ctaactataa cattggctac cagggcttct atatcccaga    21000
gagctacaag gaccgcatgt actccttctt tagaaacttc cagcccatga gccgtcaggt    21060
ggtggatgat actaaataca aggactacca acaggtgggc atcctacacc aacacaacaa    21120
ctctggattt gttggctacc ttgccccac catgcgcgaa ggacaggcct accctgctaa     21180
cttcccctat ccgcttatag gcaagaccgc agttgacagc attacccaga aaaagtttct    21240
ttgcgatcgc acccttggc gcatcccatt ctccagtaac tttatgtcca tgggcgcact     21300
cacagacctg ggccaaaacc ttctctacgc caactccgcc cacgcgctag acatgacttt    21360
tgaggtggat cccatggacg agcccaccct tctttatgtt ttgtttgaag tctttgacgt    21420
ggtccgtgtg caccagccgc accgcggcgt catcgaaacc gtgtacctgc gcacgccctt    21480
ctcggccggc aacgccacaa cataaagaag caagcaacat caacaacagc tgccgccatg    21540
ggctccagtg agcaggaact gaaagccatt gtcaaagatc ttggttgtgg gccatatttt    21600
ttgggcacct atgacaagcg ctttccaggc tttgtttctc cacacaagct cgcctgcgcc    21660
atagtcaata cggccggtcg cgagactggg ggcgtacact ggatggcctt tgcctggaac    21720
ccgcactcaa aaacatgcta cctctttgag ccctttggct tttctgacca gcgactcaag    21780
caggtttacc agtttgagta cgagtcactc ctgcgccgta cgccattgc ttcttccccc     21840
gaccgctgta taacgctgga aaagtccacc caaagcgtac aggggcccaa ctcggccgcc    21900
tgtggactat tctgctgcat gtttctccac gcctttgcca actggcccca aactcccatg    21960
gatcacaacc ccaccatgaa ccttattacc ggggtaccca actccatgct caacagtccc    22020
caggtacagc ccaccctgcg tcgcaaccag gaacagctct acagcttcct ggagcgccac    22080
tcgcccctact tccgcagcca cagtgcgcag attaggagcg ccacttcttt ttgtcacttg    22140
aaaaacatgt aaaataatg tactagagac actttcaata aaggcaaatg cttttatttg     22200
tacactctcg ggtgattatt taccccccacc cttgccgtct gcgccgttta aaaatcaaag    22260
gggttctgcc gcgcatcgct atgcgccact ggcagggaca cgttgcgata ctggtgttta    22320
gtgctccact taaactcagg cacaaccatc cgcggcagct cggtgaagtt ttcactccac    22380
aggctgcgca ccatcaccaa cgcgtttagc aggtcgggcg ccgatatctt gaagtcgcag    22440
ttggggcctc cgccctgcgc gcgcgagttg cgatacacag ggttgcagca ctggaacact    22500
atcagcgccg ggtggtgcac gctggccagc acgctcttgt cggagatcag atccgcgtcc    22560
aggtcctccg cgttgctcag ggcgaacgga gtcaactttg gtagctgcct tcccaaaaag    22620
ggcgcgtgcc caggctttga gttgcactcg caccgtagtg gcatcaaaag gtgaccgtgc    22680
ccggtctggg cgttaggata cagcgcctgc ataaagcct tgatctgctt aaaagccacc     22740
tgagcctttg cgccttcaga gaagaacatg ccgcaagact gccggaaaa ctgattggcc     22800
ggacaggccg cgtcgtgcac gcagcacctt cgtcggtgt tggagatctg caccacatt     22860
cggccccacc ggttcttcac gatcttggcc ttgctagact gctccttcag cgcgcgctgc    22920
ccgttttcgc tcgtcacatc catttcaatc acgtgctcct tatttatcat aatgcttccg    22980
tgtagacact taagctcgcc ttcgatctca gcgcagcggt gcagccacaa cgcgcagccc    23040
gtgggctcgt gatgcttgta ggtcacctct gcaaacgact gcaggtacgc ctgcaggaat    23100
cgccccatca tcgtcacaaa ggtcttgttg ctggtgaagg tcagctgcaa cccgcggtgc    23160
tcctcgttca gccaggtctt gcatacggcc gccagagctt ccacttggtc aggcagtagt    23220
ttgaagttcg cctttagatc gttatccacg tggtacttgt ccatcagcgc gcgcgcagcc    23280
```

```
tccatgccct tctcccacgc agacacgatc ggcacactca gcgggttcat caccgtaatt    23340
tcactttccg cttcgctggg ctcttcctct tcctcttgcg tccgcatacc acgcgccact    23400
gggtcgtctt cattcagccg ccgcactgtg cgcttacctc ctttgccatg cttgattagc    23460
accggtgggt tgctgaaacc caccatttgt agcgccacat cttctctttc ttcctcgctg    23520
tccacgatta cctctggtga tggcgggcgc tcgggcttgg gagaagggcg cttctttttc    23580
ttcttgggcg caatggccaa atccgccgcc gaggtcgatg gccgcgggct gggtgtgcgc    23640
ggcaccagcg cgtcttgtga tgagtcttcc tcgtcctcgg actcgatacg ccgcctcatc    23700
cgcttttttg ggggcgcccg gggaggcggc ggcgacgggg acggggacga cacgtcctcc    23760
atggttgggg gacgtcgcgc cgcaccgcgt ccgcgctcgg gggtggtttc gcgctgctcc    23820
tcttcccgac tggccatttc cttctcctat aggcagaaaa agatcatgga gtcagtcgag    23880
aagaaggaca gcctaaccgc cccctctgag ttcgccacca ccgcctccac cgatgccgcc    23940
aacgcgccta ccaccttccc cgtcgaggca ccccgcttg aggaggagga agtgattatc    24000
gagcaggacc caggttttgt aagcgaagac gacgaggacc gctcagtacc aacagaggat    24060
aaaaagcaag accaggacaa cgcagaggca acgaggaac aagtcgggcg ggggacgaa    24120 aggcatggcg actacctaga tgtgggagac gacgtgctgt tgaagcatct gcagcgccag    24180
tgcgccatta tctgcgacgc gttgcaagag cgcagcgatg tgccctcgc catagcggat    24240 gtcagccttg cctacgaacg ccacctattc tcaccgcgcg tacccccaa acgccaagaa    24300 aacggcacat gcgagcccaa cccgcgcctc aacttctacc ccgtatttgc cgtgccagag    24360
gtgcttgcca cctatcacat cttttttccaa aactgcaaga taccccctatc ctgccgtgcc    24420 aaccgcagcc gagcggacaa gcagctggcc ttgcggcagg gcgctgtcat acctgatatc    24480
gcctcgctca acgaagtgcc aaaaatcttt gagggtcttg gacgcgacga gaagcgcgcg    24540
gcaaacgctc tgcaacagga aaacagcgaa aatgaaagtc actctggagt gttggtggaa    24600
ctcgagggtg acaacgcgcg cctagccgta ctaaaacgca gcatcgaggt cacccactt    24660 gcctacccgg cacttaacct acccccaag gtcatgagca cagtcatgag tgagctgatc    24720
gtgcgccgtg cgcagcccct ggagagggat gcaaatttgc aagaacaaac agaggaggcc    24780
ctacccgcag ttggcgacga gcagctagcg cgctggcttc aaacgcgcga gcctgccgac    24840
ttggaggagc gacgcaaact aatgatggcc gcagtgctcg ttaccgtgga gcttgagtgc    24900
atgcagcggt tctttgctga cccggagatg cagcgcaagc tagaggaaac attgcactac    24960
acctttcgac agggctacgt acgccaggcc tgcaagatct ccaacgtgga gctctgcaac    25020
ctggtctcct accttggaat tttgcacgaa aaccgccttg ggcaaaacgt gcttcattcc    25080
acgctcaagg gcgaggcgcg ccgcgactac gtccgcgact gcgtttactt atttctatgc    25140
tacacctggc agacggccat gggcgtttgg cagcagtgct tggaggagtg caacctcaag    25200
gagctgcaga aactgctaaa gcaaaacttg aaggacctat ggacggcctt caacgagcgc    25260
tccgtggccg cgcacctggc ggacatcatt ttccccgaac gcctgcttaa aaccctgcaa    25320
cagggtctgc cagacttcac cagtcaaagc atgttgcaga actttaggaa ctttatccta    25380
gagcgctcag gaatcttgcc cgccacctgc tgtgcacttc ctagcgactt tgtgcccatt    25440
aagtaccgcg aatgccctcc gccgctttgg ggccactgct accttctgca gctagccaac    25500
taccttgcct accactctga cataatggaa gacgtgagcg gtgacggtct actggagtgt    25560
cactgtcgct gcaaccctat gcaccccgcac cgctccctgg tttgcaattc gcagctgctt    25620
aacgaaagtc aaattatcgg taccctttgag ctgcagggtc cctcgcctga cgaaaagtcc    25680
```

```
gcggctccgg ggttgaaact cactccgggg ctgtggacgt cggcttacct tcgcaaattt   25740
gtacctgagg actaccacgc ccacgagatt aggttctacg aagaccaatc ccgcccgcct   25800
aatgcggagc ttaccgcctg cgtcattacc cagggccaca ttcttggcca attgcaagcc   25860
atcaacaaag cccgccaaga gtttctgcta cgaaagggac gggggggttta cttggacccc   25920 cagtccggcg aggagctcaa cccaatcccc ccgccgccgc agccctatca gcagcagccg   25980
cgggcccttg cttcccagga tggcacccaa aaagaagctg cagctgccgc cgccacccac   26040
ggacgaggag gaatactggg acagtcaggc agaggaggtt ttggacgagg aggaggagga   26100
catgatggaa gactgggaga gcctagacga ggaagcttcc gaggtcgaag aggtgtcaga   26160
cgaaacaccg tcaccctcgg tcgcattccc ctcgccggcg ccccagaaat cggcaaccgg   26220
ttccagcatg gctacaacct ccgctcctca ggcgccgccg gcactgcccg ttcgccgacc   26280
caaccgtaga tgggacacca ctggaaccag ggccggtaag tccaagcagc cgccgccgtt   26340
agcccaagag caacaacagc gccaaggcta ccgctcatgg cgcgggcaca gaacgccat    26400 agttgcttgc ttgcaagact gtgggggcaa catctccttc gcccgccgct ttcttctcta   26460
ccatcacggc gtggccttcc cccgtaacat cctgcattac taccgtcatc tctacagccc   26520
atactgcacc ggcggcagcg gcagcaacag cagcggccac acagaagcaa aggcgaccgg   26580
atagcaagac tctgacaaag cccaagaaat ccacagcggc ggcagcagca ggaggaggag   26640
cgctgcgtct ggcgcccaac gaacccgtat cgacccgcga gcttagaaac aggatttttc   26700
ccactctgta tgctatattt caacagagca ggggccaaga acaagagctg aaaataaaaa   26760
acaggtctct gcgatccctc acccgcagct gcctgtatca caaaagcgaa gatcagcttc   26820
ggcgcacgct ggaagacgcg gaggctctct tcagtaaata ctgcgcgctg actcttaagg   26880
actagtttcg cgccctttct caaatttaag cgcgaaaact acgtcatctc cagcggccac   26940
acccggcgcc agcacctgtt gtcagcgcca ttatgagcaa ggaaattccc acgccctaca   27000
tgtggagtta ccagccacaa atgggacttg cggctggagc tgcccaagac tactcaaccc   27060
gaataaacta catgagcgcg ggaccccaca tgatatcccg ggtcaacgga atacgcgccc   27120
accgaaaccg aattctcctg gaacaggcgg ctattaccac cacacctcgt aataacctta   27180
atccccgtag ttggcccgct gccctggtgt accaggaaag tcccgctccc accactgtgg   27240
tacttcccag agacgcccag gccgaagttc agatgactaa ctcaggggcg cagcttgcgg   27300
gcggctttcg tcacagggtg cggtcgcccg ggcagggtat aactcacctg acaatcagag   27360
ggcgaggtat tcagctcaac gacgagtcgg tgagctcctc gcttggtctc cgtccggacg   27420
ggacatttca gatcggcggc gccggccgct cttcattcac gcctcgtcag gcaatcctaa   27480
ctctgcagac ctcgtcctct gagccgcgct ctggaggcat tggaactctg caatttattg   27540
aggagtttgt gccatcggtc tactttaacc ccttctcggg acctcccggc cactatccgg   27600
atcaatttat tcctaacttt gacgcggtaa aggactcggc ggacggctac gactgaatgt   27660
taagtggaga ggcagagcaa ctgcgcctga acacctggt ccactgtcgc cgccacaagt    27720
gctttgcccg cgactccggt gagttttgct actttgaatt gcccgaggat catatcgagg   27780
gcccggcgca cggcgtccgg cttaccgccc agggagagct tgcccgtagc ctgattcggg   27840
agtttaccca gcgcccctg ctagttgagc gggacagggg accctgtgtt ctcactgtga    27900
tttgcaactg tcctaaccct ggattacatc aagatctttg ttgccatctc tgtgctgagt   27960
ataataaata cagaaattaa aatatactgg ggctcctatc gccatcctgt aaacgccacc   28020
gtcttcaccc gcccaagcaa accaaggcga accttacctg gtacttttaa catctctccc   28080
```

```
tctgtgattt acaacagttt caacccagac ggagtgagtc tacgagagaa cctctccgag   28140
ctcagctact ccatcagaaa aaacaccacc ctccttacct gccgggaacg tacgagtgcg   28200
tcaccggccg ctgcaccaca cctaccgcct gaccgtaaac cagacttttt ccggacagac   28260
ctcaataact ctgtttacca gaacaggagg tgagcttaga aaacccttag ggtattaggc   28320
caaaggcgca gctactgtgg ggtttatgaa caattcaagc aactctacgg gctattctaa   28380
ttcaggtttc tctagaaatg gacggaatta ttacagagca gcgcctgcta gaaagacgca   28440
gggcagcggc cgagcaacag cgcatgaatc aagagctcca agacatggtt aacttgcacc   28500
agtgcaaaag gggtatcttt tgtctggtaa agcaggccaa agtcacctac gacagtaata   28560
ccaccggaca ccgccttagc tacaagttgc caaccaagcg tcagaaattg gtggtcatgg   28620
tgggagaaaa gcccattacc ataactcagc actcggtaga aaccgaaggc tgcattcact   28680
caccttgtca aggacctgag gatctctgca cccttattaa gaccctgtgc ggtctcaaag   28740
atcttattcc ctttaactaa taaaaaaaaa taataaagca tcacttactt aaaatcagtt   28800
agcaaatttc tgtccagttt attcagcagc acctccttgc cctcctccca gctctggtat   28860
tgcagcttcc tcctggctgc aaactttctc cacaatctaa atggaatgtc agtttcctcc   28920
tgttcctgtc catccgcacc cactatcttc atgttgttgc agatgaagcg cgcaagaccg   28980
tctgaagata ccttcaaccc cgtgtatcca tatgacacgg aaaccggtcc tccaactgtg   29040
cctttttctta ctcctccctt tgtatccccc aatgggtttc aagagagtcc ccctggggta   29100
ctctctttgc gcctatccga acctctagtt acctccaatg gcatgcttgc gctcaaaatg   29160
ggcaacggcc tctctctgga cgaggccggc aaccttacct cccaaaatgt aaccactgtg   29220
agcccacctc tcaaaaaaac caagtcaaac ataaacctgg aaatatctgc acccctcaca   29280
gttacctcag aagccctaac tgtggctgcc gccgcacctc taatggtcgc gggcaacaca   29340
ctcaccatgc aatcacaggc cccgctaacc gtgcacgact ccaaacttag cattgccacc   29400
caaggacccc tcacagtgtc agaaggaaag ctagccctgc aaacatcagg cccccctcacc   29460
accaccgata gcagtaccct tactatcact gcctcacccc ctctaactac tgccactggt   29520
agcttgggca ttgacttgaa agagcccatt tatacacaaa atggaaaact aggactaaag   29580
tacgggctc ctttgcatgt aacagacgac ctaaacactt tgaccgtagc aactggtcca   29640
ggtgtgacta ttaataatac ttccttgcaa actaaagtta ctggagcctt gggttttgat   29700
tcacaaggca atatgcaact taatgtagca ggaggactaa ggattgattc tcaaaacaga   29760
cgccttatac ttgatgttag ttatccgttt gatgctcaaa accaactaaa tctaagacta   29820
ggacagggcc ctctttttat aaactcagcc cacaacttgg atattaacta caacaaaggc   29880
ctttacttgt ttacagcttc aaacaattcc aaaaagcttg aggttaacct aagcactgcc   29940
aaggggttga tgtttgacgc tacagccata gccattaatg caggagatgg gcttgaattt   30000
ggttcaccta atgcaccaaa cacaaatccc ctcaaaacaa aaattggcca tggcctagaa   30060
tttgattcaa acaaggctat ggttcctaaa ctaggaactg gccttagttt tgacagcaca   30120
ggtgccatta cagtaggaaa caaaaataat gataagctaa cttttgtggac cacaccagct   30180
ccatctccta actgtagact aaatgcagag aaagatgcta aactcacttt ggtcttaaca   30240
aaatgtggca gtcaaatact tgctacagtt tcagttttgg ctgttaaagg cagtttggct   30300
ccaatatctg gaacagttca aagtgctcat cttattataa gatttgacga aaatggagtg   30360
ctactaaaca attccttcct ggacccagaa tattggaact ttagaaatgg agatcttact   30420
gaaggcacag cctatacaaa cgctgttgga tttatgccta acctatcagc ttatccaaaa   30480
```

```
tctcacggta aaactgccaa aagtaacatt gtcagtcaag tttacttaaa cggagacaaa   30540
actaaacctg taacactaac cattacacta aacggtacac aggaaacagg agacacaact   30600
ccaagtgcat actctatgtc attttcatgg gactggtctg gccacaacta cattaatgaa   30660
atatttgcca catcctctta cacttttttca tacattgccc aagaataaag aatcgtttgt   30720
gttatgtttc aacgtgttta ttttttcaatt gcccgggatc ggtgatcacc gatccagaca   30780
tgataagata cattgatgag tttggacaaa ccacaactag aatgcagtga aaaaaatgct   30840
ttatttgtga aatttgtgat gctattgctt tatttgtaac cattataagc tgcaataaac   30900
aagttcccgg atcgcgatcc ggcccgaggc tgtagccgac gatggtgcgc caggagagtt   30960
gttgattcat tgtttgcctc cctgctgcgg ttttttcaccg aagttcatgc cagtccagcg   31020
tttttgcagc agaaaagccg ccgacttcgg tttgcggtcg cgagtgaaga tcccttttctt   31080 gttaccgcca acgcgcaata tgccttgcga ggtcgcaaaa tcggcgaaat tccatacctg   31140
ttcaccgacg acgcgctga cgcgatcaaa gacgcggtga tacatatcca gccatgcaca   31200
ctgatactct tcactccaca tgtcggtgta cattgagtgc agcccggcta acgtatccac   31260
gccgtattcg gtgatgataa tcggctgatg cagtttctcc tgccaggcca gaagttcttt   31320
ttccagtacc ttctctgccg tttccaaatc gccgctttgg acataccatc cgtaataacg   31380
gttcaggcac agcacatcaa agagatcgct gatggtatcg gtgtgagcgt cgcagaacat   31440
tacattgacg caggtgatcg gacgcgtcgg gtcgagttta cgcgttgctt ccgccagtgg   31500
cgcgaaatat tcccgtgcac cttgcggacg ggtatccggt tcgttggcaa tactccacat   31560
caccacgctt gggtggtttt tgtcacgcgc tatcagctct ttaatcgcct gtaagtgcgc   31620
ttgctgagtt tccccgttga ctgcctcttc gctgtacagt tctttcggct tgttgcccgc   31680
ttcgaaacca atgcctaaag agaggttaaa gccgacagca gcagtttcat caatcaccac   31740
gatgccatgt tcatctgccc agtcgagcat ctcttcagcg taagggtaat gcgaggtacg   31800
gtaggagttg gccccaatcc agtccattaa tgcgtggtcg tgcaccatca gcacgttatc   31860
gaatcctttg ccacgcaagt ccgcatcttc atgacgacca aagccagtaa agtagaacgg   31920
tttgtggtta atcaggaact gttcgccctt cactgccact gaccggatgc cgacgcgaag   31980
cgggtagata tcacactctg tctggctttt ggctgtgacg cacagttcat agagataacc   32040
ttcacccggt tgcagaggt gcggattcac cacttgcaaa gtcccgctag tgccttgtcc   32100
agttgcaacc acctgttgat ccgcatcacg cagttcaacg ctgacatcac cattggccac   32160
cacctgccag tcaacagacg cgtggttaca gtcttgcgcg acatgcgtca ccacggtgat   32220
atcgtccacc caggtgttcg gcgtggtgta gagcattacg ctgcgatgga ttccggcata   32280
gttaaagaaa tcatggaagt aagactgctt tttcttgccg ttttcgtcgg taatcaccat   32340
tcccggcggg atagtctgcc agttcagttc gttgttcaca caaacggtga tacgtacact   32400
tttcccggca ataacatacg gcgtgacatc ggcttcaaat ggcgtatagc cgccctgatg   32460
ctccatcact tcctgattat tgacccacac tttgccgtaa tgagtgaccg catcgaaacg   32520
cagcacgata cgctggcctg cccaaccttt cggtataaag acttcgcgct gataccagac   32580
gttgcccgca taattacgaa tatctgcatc ggcgaactga tcgttaaaac tgcctggcac   32640
agcaattgcc cggcttttctt gtaacgcgct ttcccaccaa cgctgatcaa ttccacagtt   32700
ttcgcgatcc agactgaatg cccacaggcc gtcgagtttt ttgatttcac gggttgggt   32760 ttctacagga cggaccatgc gttcgacctt tctcttctt tttgggccca tgatggcaga   32820
tccgtatagt gagtcgtatt agctggttct ttccgcctca gaagccatag agcccaccgc   32880
```

-continued

```
atccccagca tgcctgctat tgtcttccca atcctccccc ttgctgtcct gccccacccc      32940
accccccaga atagaatgac acctactcag acaatgcgat gcaatttcct cattttatta      33000
ggaaaggaca gtgggagtgg caccttccag ggtcaaggaa ggcacggggg aggggcaaac      33060
aacagatggc tggcaactag aaggcacagt cgaggctgat cagcgagctc tagatgcatg      33120
ctcgagcggc cgccagtgtg atggatatct gcagaattcc agcacactgg cggccgttac      33180
tagtggatcc gagctcggta cccggccgtt ataacaccac tcgacacggc accagctcaa      33240
tcagtcacag tgtaaaaaag ggccaagtgc agagcgagta tatataggac taaaaaatga      33300
cgtaacggtt aaagtccaca aaaacaccc agaaaaccgc acgcgaacct acgcccagaa       33360
acgaaagcca aaaacccac aacttcctca aatcgtcact tccgttttcc cacgttacgt       33420
cacttcccat tttaagaaaa ctacaattcc caacacatac aagttactcc gccctaaaac      33480
ctacgtcacc cgccccgttc ccacgccccg cgccacgtca caaactccac cccctcatta      33540
tcatattggc ttcaatccaa aataaggtat attattgatg atg                       33583
```

```
<210> SEQ ID NO 18
<211> LENGTH: 33476
<212> TYPE: DNA
<213> ORGANISM: Artificial Sequence
<220> FEATURE:
<223> OTHER INFORMATION: denoviral vector Adt.gp140dv12(B).11D

<400> SEQUENCE: 18
```

```
catcatcaat aatataccttt attttggatt gaagccaata tgataatgag ggggtggagt       60
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgtttttg      180
gtgtgcgccg gtgtacacag gaagtgacaa ttttcgcgcg gttttaggcg gatgttgtag      240
taaatttggg cgtaaccgag taagatttgg ccatttttcgc gggaaaactg aataagagga      300
agtgaaatct gaataatttt gtgttactca tagcgcgtaa tatttgtcta gggcccggga      360
tcggtgatca ccgatccaga catgataaga tacattgatg agtttggaca aaccacaact      420
agaatgcagt gaaaaaatg ctttatttgt gaaatttgtg atgctattgc tttatttgta       480
accattataa gctgcaataa acaagttccc ggatctttct agctagtcta gactagctag      540
actcgagagc ggccgcaatc gataagcttg atatcgaatt ctgcagtgat cagggatcct      600
caccacagcc agttggtgat gttgaaccag ttccacaggc tggcccactt gtccagctcc      660
agcagctcct gctcgttctt ctcgtgctgg ttctggctct cctcgatcag gctgtggatc      720
aggctggtgt agttgttgat ctcgcggtcc cactccatcc aggtggtgtg gttccagatc      780
tgctcgagca gctgctggtc cttcaggtag cgctccacgg ccagggtgcg ggcctgcagc      840
tgcttgatgc cccacacggt cagctgcagc aggtgctgct gggcctcgat ggcgcgcagc      900
aggttgttct gctgctgcac gatgccgctc agcagctggc gggcctggac ggtaagcttg      960
gccttggtgg gggccacgcc cagggcctcg atcttcacca ccttgtactt gtacagctcg     1020
ctgcgccagt tgtcgcgcat gtcgccgccg cccaggcgga agatctcgct ctcgttgttg     1080
ctgttgccgc cgtcgcgggt cagcagcagg ccggtgatgt tgctgctgca gcggatctgg     1140
ccgctgatgg ggggggcgta catggccttg cccacccttct gccacatgtt gatgatctgc     1200
ttgatgcggc agggcagggt gatggtgtcg ctgccctcgg tgttgttgct gccctcggtg     1260
ctccaggtgt gttgaaccca ggtgctgttg aacagctggg tgctgttgca gtagaagaac     1320
tcgccgccgc agttgaagct gtgggtcacg atctcggggt cgccgccgct gctgtgcttg     1380
```

```
aacacgatgg tcttgttgcc gaactgctcg cgcagcttga tcacgatctt gttcagggtg      1440
tcgttccact tggcgcggct caggttgcag tgggcctggc ggatgtcgcc gatgatctcg      1500
ccggtggtgt agaaggcgcg gccggggccg atgtggatgc tcttgcgggt gttgttgttg      1560
gggcgggtgc agttgatctc cacgctctcg ttcagctgca cgatgatcac cttggcgttg      1620
tcggcgaagt tagcgctgcg gatcaccacc tcctcctcgg ccaggttacc cgtaaccagc      1680
agctgggtgc tcaccacggg gcggatgccg tgggtgcact gcacggtgct cacgttggtg      1740
caggggccct tgccgttgaa cttcttgtcc ttgcacttca ggatggcgaa gccggcgggg      1800
gcgcagtagt ggttggggat gggctcgaag ctcaccttgg ggcaggcctg ggtgatcacg      1860
ctggtgttgc agctggtgct agcgtcggtg cacttcaggc tcacgcacag ggggtcagc      1920 ttcacgcagg gcttcaggct ctggtcccac aggctgatga tgtcctcgtg catctgctcc      1980
accatgtcgt tcttccacat gtcgaagttc tcggtcacgt tcaccagcac cacctcctgg      2040 gggttgggt cggtgggcac gcaggcgtgg gtggcccaca cgttgtgcac ctcggtgtcg      2100
taggccttgg cgtcgctggc gcagagcagg gtggtggtgg cctccttcca cacgggcacg      2160
ccgtagtaca cggtcaccca cagcttctcg gtggcgctgc agatcatcag catgcccagc      2220
agcatggtgc cccagcgcca gccccagcgc cacaggtgct ggtacttctc cttcacgcgc      2280
atggtgtcta gagcggccgc gatcggctgc agttggacct gggagtggac acctgtggag      2340
agaaaggcaa agtggatgtc attgtcactc aagtgtatgg ccagatctca agcctgccac      2400
acctcaagtg aagccaaggg ggtgggccta tagactctat aggcggtact tacgtcactc      2460
ttggcacggg gaatccgcgt tccaatgcac cgttcccggc cgcggaggct ggatcggtcc      2520
cggtgtcttc tatggaggtc aaaacagcgt ggatggcgtc tccaggcgat ctgacggttc      2580
actaaacgag ctcgtcgacg atctctatca ctgatagggga gatctctatc actgataggg      2640
agagctctgc ttatatagac ctcccaccgt acacgcctac cgcccatttg cgtcaatggg      2700
gcggagttgt tacgacattt tggaaagtcc cgttgatttt ggtgccaaaa caaactccca      2760
ttgacgtcaa tggggtggag acttggaaat ccccgtgagt caaaccgcta tccacgccca      2820
ttgatgtact gccaaaaccg catcaccatg gtaatagcga tgactaatac gtagatgtac      2880
tgccaagtag gaaagtccca taaggtcatg tactgggcat aatgccaggc gggccattta      2940
ccgtcattga cgtcaatagg gggcgtactt ggcatatgat acacttgatg tactgccaag      3000
tgggcagttt accgtaaata ctccacccat tgacgtcaat ggaaagtccc tattggcgtt      3060
actatgggaa catacgtcat tattgacgtc aatgggcggg ggtcgttggg cggtcagcca      3120
ggcgggccat ttaccgtaag ttatgtaacg cggaactcca tatatgggct atgaactaat      3180
gaccccgtaa ttgattacta ttaataacta gtactgaaat gtgtgggcgt ggcttaaggg      3240
tgggaaagaa tatataaggt ggggggtctta tgtagttttg tatctgtttt gcagcagccg      3300
ccgccgccat gagcaccaac tcgtttgatg gaagcattgt gagctcatat ttgacaacgc      3360
gcatgccccc atgggccggg gtgcgtcaga atgtgatggg ctccagcatt gatggtcgcc      3420
ccgtcctgcc cgcaaactct actaccttga cctacgagac cgtgtctgga acgccgttgg      3480
agactgcagc ctccgccgcc gcttcagccg ctgcagccac cgcccgcggg attgtgactg      3540
actttgcttt cctgagcccg cttgcaagca gtgcagcttc ccgttcatcc gcccgcgatg      3600
acaagttgac ggctctttg gcacaattgg attctttgac ccgggaactt aatgtcgttt      3660
ctcagcagct gttggatctg cgccagcagg tttctgccct gaaggcttcc tcccctccca      3720
atgcggttta aaacataaat aaaaaaccag actctgtttg gatttggatc aagcaagtgt      3780
```

```
cttgctgtct ttatttaggg gttttgcgcg cgcggtaggc ccgggaccag cggtctcggt    3840
cgttgagggt cctgtgtatt ttttccagga cgtggtaaag gtgactctgg atgttcagat    3900
acatgggcat aagcccgtct ctggggtgga ggtagcacca ctgcagagct tcatgctgcg    3960
gggtggtgtt gtagatgatc cagtcgtagc aggagcgctg ggcgtggtgc ctaaaaatgt    4020
ctttcagtag caagctgatt gccaggggca ggcccttggt gtaagtgttt acaaagcggt    4080
taagctggga tgggtgcata cgtggggata tgagatgcat cttggactgt attttaggt     4140
tggctatgtt cccagccata tccctccggg gattcatgtt gtgcagaacc accagcacag    4200
tgtatccggt gcacttggga aatttgtcat gtagcttaga aggaaatgcg tggaagaact    4260
tggagacgcc cttgtgacct ccaagatttt ccatgcattc gtccataatg atggcaatgg    4320
gcccacgggc ggcggcctgg gcgaagatat ttctgggatc actaacgtca tagttgtgtt    4380
ccaggatgag atcgtcatag gccattttta caaagcgcgg gcggagggtg ccagactgcg    4440
gtataatggt tccatccggc ccaggggcgt agttaccctc acagatttgc atttcccacg    4500
ctttgagttc agatgggggg atcatgtcta cctgcggggc gatgaagaaa acggtttccg    4560
gggtagggga gatcagctgg gaagaaagca ggttcctgag cagctgcgac ttaccgcagc    4620
cggtgggccc gtaaatcaca cctattaccg gctgcaactg gtagttaaga gagctgcagc    4680
tgccgtcatc cctgagcagg ggggccactt cgttaagcat gtccctgact cgcatgtttt    4740
ccctgaccaa atccgccaga aggcgctcgc cgcccagcga tagcagttct tgcaaggaag    4800
caaagttttt caacggtttg agaccgtccg ccgtaggcat gcttttgagc gtttgaccaa    4860
gcagttccag gcggtcccac agctcggtca cctgctctac ggcatctcga tccagcatat    4920
ctcctcgttt cgcggggttgg ggcggctttc gctgtacggc agtagtcggt gctcgtccag    4980
acgggccagg gtcatgtctt tccacgggcg cagggtcctc gtcagcgtag tctgggtcac    5040
ggtgaagggg tgcgctccgg gctgcgcgct ggccagggtg cgcttgaggc tggtcctgct    5100
ggtgctgaag cgctgccggt cttcgccctg cgcgtcggcc aggtagcatt tgaccatggt    5160
gtcatagtcc agcccctccg cggcgtggcc cttggcgcgc agcttgccct tggaggaggc    5220
gccgcacgag gggcagtgca gacttttgag ggcgtagagc ttgggcgcga gaataccga     5280
ttccggggag taggcatccg cgccgcaggc cccgcagacg gtctcgcatt ccacgagcca    5340
ggtgagctct ggccgttcgg ggtcaaaaac caggtttccc ccatgctttt tgatgcgttt    5400
cttacctctg gtttccatga gccggtgtcc acgctcggtg acgaaaaggc tgtccgtgtc    5460
cccgtataca gacttgagag gcctgtcctc gagcggtgtt ccgcggtcct cctcgtatag    5520
aaactcggac cactctgaga caaaggctcg cgtccaggcc agcacgaagg aggctaagtg    5580
ggaggggtag cggtcgttgt ccactagggg gtccactcgc tccagggtgt gaagacacat    5640
gtcgccctct tcggcatcaa ggaaggtgat tggtttgtag gtgtaggcca cgtgaccggg    5700
tgttcctgaa gggggctat aaaagggggt ggggcgcgt cgtcctcac tctcttccgc       5760
atcgctgtct gcgagggcca gctgttgggg tgagtactcc ctctgaaaag cgggcatgac    5820
ttctgcgcta agattgtcag tttccaaaaa cgaggaggat ttgatattca cctgcccgc     5880
ggtgatgcct ttgagggtgg ccgcatccat ctggtcagaa aagacaatct ttttgttgtc    5940
aagcttggtg gcaaacgacc cgtagagggc gttggacagc aacttggcga tggagcgcag    6000
ggtttggttt ttgtcgcgat cggcgcgctc cttggccgcg atgtttagct gcacgtattc    6060
gcgcgcaacg caccgccatt cgggaaagac ggtggtgcgc tcgtcgggca ccaggtcac    6120
gcgccaaccg cggttgtgca gggtgacaag gtcaacgctg gtggctacct ctccgcgtag   6180
```

-continued

```
gcgctcgttg gtccagcaga ggcggccgcc cttgcgcgag cagaatggcg gtaggggggtc      6240 tagctgcgtc tcgtccgggg ggtctgcgtc cacggtaaag accccgggca gcaggcgcgc      6300
gtcgaagtag tctatcttgc atccttgcaa gtctagcgcc tgctgccatg cgcgggcggc      6360
aagcgcgcgc tcgtatgggt tgagtggggg accccatggc atgggtggg tgagcgcgga      6420 ggcgtacatg ccgcaaatgt cgtaaacgta gaggggctct ctgagtattc aagatatgt      6480 agggtagcat cttccaccgc ggatgctggc gcgcacgtaa tcgtatagtt cgtgcgaggg      6540
agcgaggagg tcgggaccga ggttgctacg ggcgggctgc tctgctcgga agactatctg      6600
cctgaagatg gcatgtgagt tggatgatat ggttggacgc tggaagacgt tgaagctggc      6660
gtctgtgaga cctaccgcgt cacgcacgaa ggaggcgtag gagtcgcgca gcttgttgac      6720
cagctcggcg gtgacctgca cgtctagggc gcagtagtcc agggtttcct tgatgatgtc      6780
atacttatcc tgtcccttt ttttccacag ctcgcggttg aggacaaact cttcgcggtc      6840
tttccagtac tcttggatcg gaaacccgtc ggcctccgaa cggtaagagc ctagcatgta      6900
gaactggttg acggcctggt aggcgcagca tccctttct acgggtagcg cgtatgcctg      6960
cgcggccttc cggagcgagg tgtgggtgag cgcaaaggtg tccctgacca tgactttgag      7020
gtactggtat ttgaagtcag tgtcgtcgca tccgccctgc tcccagagca aaaagtccgt      7080 gcgcttttg gaacgcggat ttggcagggc gaaggtgaca tcgttgaaga gtatcttttcc      7140 cgcgcgaggc ataaagttgc gtgtgatgcg gaagggtccc ggcacctcgg aacggttgtt      7200
aattacctgg gcggcgagca cgatctcgtc aaagccgttg atgttgtggc ccacaatgta      7260
aagttccaag aagcgcggga tgcccttgat ggaaggcaat ttttaagtt cctcgtaggt      7320 gagctcttca ggggagctga gcccgtgctc tgaaagggcc cagtctgcaa gatgagggtt      7380
ggaagcgacg aatgagctcc acaggtcacg ggccattagc atttgcaggt ggtcgcgaaa      7440
ggtcctaaac tggcgaccta tggccatttt ttctggggtg atgcagtaga aggtaagcgg      7500
gtcttgttcc cagcggtccc atccaaggtt cgcggctagg tctcgcgcgg cagtcactag      7560
aggctcatct ccgccgaact tcatgaccag catgaagggc acgagctgct tcccaaaggc      7620
ccccatccaa gtataggtct ctacatcgta ggtgacaaag agacgctcgg tgcgaggatg      7680
cgagccgatc gggaagaact ggatctcccg ccaccaattg gaggagtggc tattgatgtg      7740
gtgaaagtag aagtccctgc gacgggccga acactcgtgc tggcttttgt aaaaacgtgc      7800
gcagtactgg cagcggtgca cgggctgtac atcctgcacg aggttgacct gacgaccgcg      7860
cacaaggaag cagagtggga atttgagccc ctcgcctggc gggtttggct ggtggtcttc      7920
tacttcggct gcttgtcctt gaccgtctgg ctgctcgagg ggagttacgg tggatcggac      7980
caccacgccg cgcgagccca agtccagat gtccgcgcgc ggcggtcgga gcttgatgac      8040
aacatcgcgc agatgggagc tgtccatggt ctggagctcc cgcggcgtca ggtcaggcgg      8100
gagctcctgc aggtttacct cgcatagacg ggtcagggcg cgggctagat ccaggtgata      8160
cctaatttcc aggggctggt tggtggcggc gtcgatggct tgcaagaggc cgcatccccg      8220
cggcgcgact acggtaccgc gcggcgggcg gtgggccgcg ggggtgtcct tggatgatgc      8280
atctaaaagc ggtgacgcgg gcgagccccc ggaggtaggg ggggctccgg acccgccggg      8340 agaggggggca ggggcacgtc ggcgccgcgc gcgggcagga gctggtgctg cgcgcgtagg      8400
ttgctggcga acgcgacgac gcggcggttg atctcctgaa tctggcgcct ctgcgtgaag      8460
acgacgggcc cggtgagctt gaacctgaaa gagagttcga cagaatcaat ttcggtgtcg      8520
ttgacggcgg cctggcgcaa aatctcctgc acgtctcctg agttgtcttg ataggcgatc      8580
```

```
tcggccatga actgctcgat ctcttcctcc tggagatctc cgcgtccggc tcgctccacg   8640
gtggcggcga ggtcgttgga aatgcgggcc atgagctgcg agaaggcgtt gaggcctccc   8700
tcgttccaga cgcggctgta gaccacgccc ccttcggcat cgcgggcgcg catgaccacc   8760
tgcgcgagat tgagctccac gtgccgggcg aagacgcgcg agtttcgcag cgcgctgaaag  8820 aggtagttga gggtggtggc ggtgtgttct gccacgaaga agtacataac ccagcgtcgc   8880
aacgtggatt cgttgatatc ccccaaggcc tcaaggcgct ccatggcctc gtagaagtcc   8940
acggcgaagt tgaaaaactg ggagttgcgc gccgacacgg ttaactcctc ctccagaaga   9000
cggatgagct cggcgacagt gtcgcgcacc tcgcgctcaa aggctacagg ggcctcttct   9060
tcttcttcaa tctcctcttc cataaggggcc tccccttctt cttcttctgg cggcggtggg   9120
ggagggggga cacggcggcg acgacggcgc accgggaggc ggtcgacaaa gcgctcgatc   9180
atctccccgc ggcgacggcg catggtctcg gtgacggcgc ggccgttctc gcgggggcgc   9240
agttggaaga cgccgcccgt catgtcccgg ttatgggttg gcgggggggct gccatgcggc   9300 agggatacgg cgctaacgat gcatctcaac aattgttgtg taggtactcc gccgccgagg   9360
gacctgagcg agtccgcatc gaccggatcg gaaaacctct cgagaaaggc gtctaaccag   9420
tcacagtcgc aaggtaggct gagcaccgtg gcgggcggca gcgggcggcg gtcggggttg   9480
tttctggcgg aggtgctgct gatgatgtaa ttaaagtagg cggtcttgag acggcggatg   9540
gtcgacagaa gcaccatgtc cttgggtccg gcctgctgaa tgcgcaggcg gtcggccatg   9600
ccccaggctt cgttttgaca tcggcgcagg tctttgtagt agtcttgcat gagcctttct   9660
accggcactt cttcttctcc ttcctcttgt cctgcatctc ttgcatctat cgctgcggcg   9720
gcggcggagt ttggccgtag gtggcgccct cttcctccca tgcgtgtgac cccgaagccc   9780
ctcatcggct gaagcagggc taggtcggcg acaacgcgct cggctaatat ggcctgctgc   9840
acctgcgtga gggtagactg gaagtcatcc atgtccacaa agcggtggta tgcgcccgtg   9900
ttgatggtgt aagtgcagtt ggccataacg gaccagttaa cggtctggtg acccggctgc   9960
gagagctcgg tgtacctgag acgcgagtaa gccctcgagt caaatacgta gtcgttgcaa  10020
gtccgcacca ggtactggta tcccaccaaa aagtgcggcg gcggctggcg gtagagggcg  10080
cagcgtaggg tggccggggc tccggggggcg agatcttcca acataaggcg atgatatccg  10140
tagatgtacc tggacatcca ggtgatgccg cggcggtgg tggaggcgcg cggaaagtcg  10200
cggacgcggt tccagatgtt gcgcagcggc aaaaagtgct ccatggtcgg gacgctctgg  10260
ccggtcaggc gcgcgcaatc gttgacgctc tagcgtgcaa aaggagagcc tgtaagcggg  10320
cactcttccg tggtctggtg gataaattcg caagggtatc atggcggacg accgggttc   10380 gagcccgta tccggccgtc cgccgtgatc catgcgggta ccgccgcgt gtcgaaccca   10440 ggtgtgcgac gtcagacaac ggggagtgc tccttttggc ttccttccag gcgcggcggc   10500
tgctgcgcta gctttttgg ccactggccg cgcgcagcgt aagcggttag gctgaaaagc   10560
gaaagcatta agtggctcgc tccctgtagc cggagggtta ttttccaagg gttgagtcgc   10620 gggaccccccg gttcgagtct cggaccggcc ggactgcggc gaacggggt ttgcctcccc   10680 gtcatgcaag accccgcttg caaattcctc cggaaacagg gacgagcccc tttttttgctt  10740 ttcccagatg catccggtgc tgcggcagat gcgcccccct cctcagcagc ggcaagagca   10800
agagcagcgg cagacatgca gggcaccctc ccctcctcct accgcgtcag gagggcgac   10860 atccgcggtt gacgcggcag cagatggtga ttacgaaccc ccgcggcgcc gggcccggca   10920
ctacctggac ttggaggagg gcgagggcct ggcgcggcta ggagcgccct ctcctgagcg   10980
```

```
gcacccaagg gtgcagctga agcgtgatac gcgtgaggcg tacgtgccgc ggcagaacct    11040
gtttcgcgac cgcgagggag aggagcccga ggagatgcgg gatcgaaagt tccacgcagg    11100
gcgcgagctg cggcatggcc tgaatcgcga gcggttgctg cgcgaggagg actttgagcc    11160
cgacgcgcga accgggatta gtcccgcgcg cgcacacgtg gcggccgccg acctggtaac    11220
cgcatacgag cagacggtga accaggagat taactttcaa aaaagcttta caaccacgt    11280 gcgtacgctt gtggcgcgcg aggaggtggc tataggactg atgcatctgt gggactttgt    11340
aagcgcgctg gagcaaaacc caaatagcaa gccgctcatg gcgcagctgt tccttatagt    11400
gcagcacagc agggacaacg aggcattcag ggatgcgctg ctaaacatag tagagcccga    11460
gggccgctgg ctgctcgatt tgataaacat cctgcagagc atagtggtgc aggagcgcag    11520
cttgagcctg gctgacaagg tggccgccat caactattcc atgcttagcc tgggcaagtt    11580
ttacgcccgc aagatatacc ataccccctta cgttcccata gacaaggagg taaagatcga    11640
ggggttctac atgcgcatgg cgctgaaggt gcttaccttg agcgacgacc tgggcgttta    11700
tcgcaacgag cgcatccaca aggccgtgag cgtgagccgg cggcgcgagc tcagcgaccg    11760
cgagctgatg cacagcctgc aaagggccct ggctggcacg ggcagcggcg atagagaggc    11820
cgagtcctac tttgacgcgg gcgctgacct gcgctgggcc ccaagccgac gcgccctgga    11880
ggcagctggg gccggacctg ggctggcggt ggcaccgcg cgcgctggca acgtcggcgg    11940
cgtggaggaa tatgacgagg acgatgagta cgagccagag gacggcgagt actaagcggt    12000
gatgtttctg atcagatgat gcaagacgca acggacccgg cggtgcgggc ggcgctgcag    12060
agccagccgt ccggccttaa ctccacggac gactggcgcc aggtcatgga ccgcatcatg    12120
tcgctgactg cgcgcaatcc tgacgcgttc cggcagcagc cgcaggccaa ccggctctcc    12180
gcaattctgg aagcggtggt cccggcgcgc gcaaacccca cgcacgagaa ggtgctggcg    12240
atcgtaaacg cgctggccga aaacagggcc atccggcccg acgaggccgg cctggtctac    12300
gacgcgctgc ttcagcgcgt ggctcgttac aacagcggca acgtgcagac caacctggac    12360
cggctggtgg gggatgtgcg cgaggccgtg gcgcagcgtg agcgcgcgca gcagcagggc    12420
aacctgggct ccatggttgc actaaacgcc ttcctgagta cacagcccgc caacgtgccg    12480
cggggacagg aggactacac caactttgtg agcgcactgc ggctaatggt gactgagaca    12540
ccgcaaagtg aggtgtacca gtctgggcca gactatttt tccagaccag tagacaaggc    12600
ctgcagaccg taaacctgag ccaggctttc aaaaacttgc aggggctgtg gggggtgcgg    12660
gctcccacag gcgaccgcgc gaccgtgtct agcttgctga cgcccaactc gcgcctgttg    12720
ctgctgctaa tagcgcccttt cacggacagt ggcagcgtgt cccgggacac ataccctaggt    12780 cacttgctga cactgtaccg cgaggccata ggtcaggcgc atgtggacga gcatactttc    12840
caggagatta caagtgtcag ccgcgcgctg gggcaggagg acacgggcag cctggaggca    12900 acccctaaact acctgctgac caaccggcgg cagaagatcc cctcgttgca cagttttaaac    12960 agcgaggagg agcgcatttt gcgctacgtg cagcagagcg tgagccttaa cctgatgcgc    13020 gacgggtaa cgcccagcgt ggcgctggac atgaccgcgc gcaacatgga accgggcatg    13080
tatgcctcaa accggccgtt tatcaaccgc ctaatggact acttgcatcg cgcggccgcc    13140
gtgaaccccg agtatttcac caatgccatc ttgaaccccc actggctacc gcccctggt    13200 ttctacaccg ggggattcga ggtgcccgag ggtaacgatg gattcctctg ggacgacata    13260
gacgacagcg tgtttttcccc gcaaccgcag accctgctag agttgcaaca gcgcgagcag    13320
gcagaggcgg cgctgcgaaa ggaaagcttc cgcaggccaa gcagcttgtc cgatctaggc    13380
```

```
gctgcggccc cgcggtcaga tgctagtagc ccatttccaa gcttgatagg gtctcttacc   13440
agcactcgca ccacccgccc gcgcctgctg ggcgaggagg agtacctaaa caactcgctg   13500
ctgcagccgc agcgcgaaaa aaacctgcct ccggcatttc ccaacaacgg gatagagagc   13560
ctagtggaca agatgagtag atggaagacg tacgcgcagg agcacaggga cgtgccaggc   13620
ccgcgcccgc ccacccgtcg tcaaaggcac gaccgtcagc ggggtctggt gtgggaggac   13680
gatgactcgg cagacgacag cagcgtcctg gatttgggag ggagtggcaa cccgtttgcg   13740
caccttcgcc ccaggctggg gagaatgttt taaaaaaaaa aaaagcatga tgcaaaataa   13800
aaaactcacc aaggccatgg caccgagcgt tggttttctt gtattcccct tagtatgcgg   13860
cgcgcggcga tgtatgagga aggtcctcct ccctcctacg agagtgtggt gagcgcggcg   13920 ccagtgcgg cggcgctggg ttctcccttc gatgctcccc tggacccgcc gtttgtgcct   13980
ccgcggtacc tgcggcctac cgggggggaga acagcatcc gttactctga gttggcaccc   14040
ctattcgaca ccacccgtgt gtacctggtg gacaacaagt caacggatgt ggcatccctg   14100
aactaccaga acgaccacag caactttctg accacggtca ttcaaaacaa tgactacagc   14160 ccggggggagg caagcacaca gaccatcaat cttgacgacc ggtcgcactg gggcggcgac   14220
ctgaaaacca tcctgcatac caacatgcca aatgtgaacg agttcatgtt taccaataag   14280
tttaaggcgc gggtgatggt gtcgcgcttg cctactaagg acaatcaggt ggagctgaaa   14340
tacgagtggg tggagttcac gctgcccgag ggcaactact ccgagaccat gaccatagac   14400
cttatgaaca acgcgatcgt ggagcactac ttgaaagtgg gcagacagaa cggggttctg   14460
gaaagcgaca tcggggtaaa gtttgacacc cgcaacttca gactggggtt tgaccccgtc   14520
actggtcttg tcatgcctgg ggtatataca aacgaagcct tccatccaga catcattttg   14580
ctgccaggat gcggggtgga cttcacccac agccgcctga gcaacttgtt gggcatccgc   14640
aagcggcaac ccttccagga gggctttagg atcacctacg atgatctgga gggtggtaac   14700
attcccgcac tgttggatgt ggacgcctac caggcgagct gaaagatga caccgaacag   14760 ggcgggggtg gcgcaggcgg cagcaacagc agtggcagcg gcgcggaaga gaactccaac   14820
gcggcagccg cggcaatgca gccggtggag gacatgaaca atcatgccat cgcggcgac   14880 acctttgcca cacgggctga ggagaagcgc gctgaggccg aagcagcggc cgaagctgcc   14940
gcccccgctg cgcaacccga ggtcgagaag cctcagaaga aaccggtgat caaaccctg   15000 acagaggaca gcaagaaacg cagttacaac ctaataagca atgacagcac cttcacccag   15060
taccgcagct ggtaccttgc atacaactac ggcgaccctc agaccggaat ccgctcatgg   15120
accctgcttt gcactcctga cgtaacctgc ggctcggagc aggtctactg gtcgttgcca   15180
gacatgatgc aagacccccgt gaccttccgc tccacgcgcc agatcagcaa ctttccggtg   15240
gtgggcgccg agctgttgcc cgtgcactcc aagagcttct acaacgacca ggccgtctac   15300
tcccaactca tccgccagtt tacctctctg acccacgtgt tcaatcgctt tcccgagaac   15360
cagattttgg cgcgcccgcc agcccccacc atcaccaccg tcagtgaaaa cgttcctgct   15420
ctcacagatc acgggacgct accgctcgcg aacagcatcg gaggagtcca gcgagtgacc   15480
attactgacg ccagacgccg cacctgcccc tacgtttaca aggccctggg catagtctcg   15540
ccgcgcgtcc tatcgagccg cacttttga gcaagcatgt ccatcctat atcgcccagc   15600 aataacacag gctgggggcct gcgcttccca agcaagatgt ttggcggggc caagaagcgc   15660
tccgaccaac acccagtgcg cgtgcgcggg cactaccgcg cgccctgggg cgcgcacaaa   15720
cgcggccgca ctgggcgcac caccgtcgat gacgccatcg acgcggtggt ggaggaggcg   15780
```

```
cgcaactaca cgcccacgcc gccaccagtg tccacagtgg acgcggccat tcagaccgtg   15840
gtgcgcggag cccggcgcta tgctaaaatg aagagacggc ggaggcgcgt agcacgtcgc   15900
caccgccgcc gacccggcac tgccgcccaa cgcgcggcgg cggccctgct taaccgcgca   15960
cgtcgcaccg gccgacgggc ggccatgcgg gccgctcgaa ggctggccgc gggtattgtc   16020
actgtgcccc ccaggtccag gcgacgagcg gccgccgcag cagccgcggc cattagtgct   16080
atgactcagg gtcgcagggg caacgtgtat tgggtgcgcg actcggttag cggcctgcgc   16140
gtgcccgtgc gcacccgccc cccgcgcaac tagattgcaa gaaaaaacta cttagactcg   16200
tactgttgta tgtatccagc ggcggcggcg cgcaacgaag ctatgtccaa gcgcaaaatc   16260
aaagaagaga tgctccaggt catcgcgccg gagatctatg ccccccgaa gaaggaagag    16320 caggattaca agccccgaaa gctaaagcgg gtcaaaaaga aaagaaaga tgatgatgat    16380 gaacttgacg acgaggtgga actgctgcac gctaccgcgc ccaggcgacg ggtacagtgg   16440
aaaggtcgac gcgtaaaacg tgttttgcga cccggcacca ccgtagtctt tacgcccggt   16500
gagcgctcca cccgcaccta caagcgcgtg tatgatgagg tgtacggcga cgaggacctg   16560
cttgagcagg ccaacgagcg cctcggggag tttgcctacg gaaagcggca taaggacatg   16620
ctggcgttgc cgctggacga gggcaaccca acacctagcc taaagcccgt aacactgcag   16680
caggtgctgc ccgcgcttgc accgtccgaa gaaaagcgcg gcctaaagcg cgagtctggt   16740
gacttggcac ccaccgtgca gctgatggta cccaagcgcc agcgactgga agatgtcttg   16800
gaaaaaatga ccgtggaacc tgggctggag cccgaggtcc gcgtgcggcc aatcaagcag   16860
gtggcgccgg gactgggcgt gcagaccgtg gacgttcaga tacccactac cagtagcacc   16920
agtattgcca ccgccacaga gggcatggag acacaaacgt ccccggttgc ctcagcggtg   16980
gcggatgccg cggtgcaggc ggtcgctgcg gccgcgtcca agacctctac ggaggtgcaa   17040
acggacccgt ggatgtttcg cgtttcagcc ccccggcgcc cgcgccgttc gaggaagtac   17100
ggcgccgcca gcgcgctact gccgaatat gccctacatc cttccattgc gcctaccccc   17160
ggctatcgtg gctacaccta ccgccccaga agacgagcaa ctacccgacg ccgaaccacc   17220
actgaacccc gccgccgccg tcgccgtcgc cagcccgtgc tggccccgat ttccgtgcgc   17280
agggtggctc gcgaaggagg caggaccctg gtgctgccaa cagcgcgcta ccaccccagc   17340
atcgtttaaa agccggtctt tgtggttctt gcagatatgg ccctcacctg ccgcctccgt   17400
ttcccggtgc cgggattccg aggaagaatg caccgtagga ggggcatggc cggccacggc   17460
ctgacgggcg gcatgcgtcg tgcgcaccac cggcggcggc gcgcgtcgca ccgtcgcatg   17520
cgcggcggta tcctgcccct ccttattcca ctgatcgccg cggcgattgg cgccgtgccc   17580
ggaattgcat ccgtggcctt gcaggcgcag agacactgat taaaacaag ttgcatgtgg    17640 aaaaatcaaa ataaaagtc tggactctca cgctcgcttg gtcctgtaac tatttgtag    17700 aatgaaagac atcaactttg cgtctctggc cccgcgacac ggctcgcgcc cgttcatggg   17760
aaactggcaa gatatcggca ccagcaatat gagcggtggc gccttcagct ggggctcgct   17820
gtggagcgga attaaaaatt tcggttccac cgttaagaac tatggcagca aggcctggaa   17880
cagcagcaca ggccagatgc tgagggataa gttgaaagag caaaatttcc aacaaaaggt   17940
ggtagatggc ctggcctctg gcattagcgg ggtggtggac ctggccaacc aggcagtgca   18000
aaataagatt aacagtaagc ttgatccccg ccctcccgta gaggagcctc caccggccgt   18060
ggagacagtg tctccagagg ggcgtggcga aaagcgtccg cgcccgacca gggagaaac    18120 tctggtgacg caaatagacg agcctccctc gtacgaggag gcactaaagc aaggcctgcc   18180
```

```
caccacccgt cccatcgcgc ccatggctac cggagtgctg ggccagcaca cacccgtaac   18240
gctggacctg cctcccccg  ccgacaccca gcagaaacct gtgctgccag gcccgaccgc   18300
cgttgttgta acccgtccta gccgcgcgtc cctgcgccgc gccgccagcg gtccgcgatc   18360
gttgcggccc gtagccagtg gcaactggca aagcacactg aacagcatcg tgggtctggg   18420
ggtgcaatcc ctgaagcgcc gacgatgctt ctgatagcta acgtgtcgta tgtgtgtcat   18480
gtatgcgtca atgtcgccgc cagaggagct gctgagccgc cgcgcgcccg ctttccaaga   18540
tggctacccc ttcgatgatg ccgcagtggt cttacatgca catctcgggc caggacgcct   18600
cggagtacct gagccccggg ctggtgcagt ttgcccgcgc caccgagacg tacttcagcc   18660
tgaataacaa gtttagaaac cccacggtgg cgcctacgca cgacgtgacc acagaccggt   18720
cccagcgttt gacgctgcgg ttcatccctg tggaccgtga ggatactgcg tactcgtaca   18780
aggcgcggtt caccctagct gtgggtgata accgtgtgct ggacatggct tccacgtact   18840
ttgacatccg cggcgtgctg gacagggggcc ctacttttaa gccctactct ggcactgcct   18900
acaacgccct ggctcccaag ggtgccccaa atccttgcga atgggatgaa gctgctactg   18960
ctcttgaaat aaacctagaa gaagaggacg atgacaacga agacgaagta gacgagcaag   19020
ctgagcagca aaaaactcac gtatttgggc aggcgcctta ttctggtata aatattacaa   19080
aggagggtat tcaaataggt gtcgaaggtc aaacacctaa atatgccgat aaaacatttc   19140
aacctgaacc tcaaatagga gaatctcagt ggtacgaaac agaaattaat catgcagctg   19200
ggagagtcct aaaaaagact accccaatga aaccatgtta cggttcatat gcaaaaccca   19260
caaatgaaaa tggagggcaa ggcattcttg taaagcaaca aaatggaaag ctagaaagtc   19320
aagtggaaat gcaattttc  tcaactactg aggcagccgc aggcaatggt gataacttga   19380
ctcctaaagt ggtattgtac agtgaagatg tagatataga aaccccagac actcatattt   19440
cttacatgcc cactattaag gaaggtaact cacgagaact aatgggccaa caatctatgc   19500
ccaacaggcc taattacatt gcttttaggg acaattttat tggtctaatg tattacaaca   19560
gcacgggtaa tatgggtgtt ctggcgggcc aagcatcgca gttgaatgct gttgtagatt   19620
tgcaagacag aaacacagag ctttcatacc agcttttgct tgattccatt ggtgatagaa   19680
ccaggtactt ttctatgtgg aatcaggctg ttgacagcta tgatccagat gttagaatta   19740
ttgaaaatca tggaactgaa gatgaacttc caaattactg ctttccactg ggaggtgtga   19800
ttaatacaga gactcttacc aaggtaaaac ctaaaacagg tcaggaaaat ggatgggaaa   19860
aagatgctac agaattttca gataaaaatg aaataagagt tggaaataat ttgccatgg   19920 aaatcaatct aaatgccaac ctgtggagaa atttcctgta ctccaacata gcgctgtatt   19980
tgcccgacaa gctaaagtac agtccttcca acgtaaaaat ttctgataac caaacacctt   20040
acgactacat gaacaagcga gtggtggctc ccgggctagt ggactgctac attaaccttg   20100
gagcacgctg gtcccttgac tatatggaca acgtcaaccc atttaaccac caccgcaatg   20160
ctggcctgcg ctaccgctca atgttgctgg gcaatggtcg ctatgtgccc ttccacatcc   20220
aggtgcctca gaagttcttt gccattaaaa acctccttct cctgccgggc tcatacacct   20280
acgagtggaa cttcaggaag gatgttaaca tggttctgca gagctcccta ggaaatgacc   20340
taagggttga cggagccagc attaagtttg atagcatttg cctttacgcc accttcttcc   20400
ccatggccca caacaccgcc tccacgcttg aggccatgct tagaaacgac accaacgacc   20460
agtcctttaa cgactatctc tccgccgcca acatgctcta ccctatacccc gccaacgcta   20520 ccaacgtgcc catatccatc ccctcccgca actgggcggc tttccgcggc tgggccttca   20580
```

```
cgcgccttaa gactaaggaa acccccatcac tgggctcggg ctacgaccct tattacacct   20640
actctggctc tataccctac ctagatggaa ccttttacct caaccacacc tttaagaagg   20700
tggccattac ctttgactct tctgtcagct ggcctggcaa tgaccgcctg cttacccca    20760 acgagtttga aattaagcgc tcagttgacg gggagggtta caacgttgcc cagtgtaaca   20820
tgaccaaaga ctggttcctg gtacaaatgc tagctaacta taacattggc taccagggct   20880
tctatatccc agagagctac aaggaccgca tgtactcctt ctttagaaac ttccagccca   20940
tgagccgtca ggtggtggat gatactaaat acaaggacta ccaacaggtg ggcatcctac   21000
accaacacaa caactctgga tttgttggct accttgcccc caccatgcgc gaaggacagg   21060
cctaccctgc taacttcccc tatccgctta taggcaagac cgcagttgac agcattaccc   21120
agaaaaagtt tctttgcgat cgcacccttt ggcgcatccc attctccagt aactttatgt   21180
ccatgggcgc actcacagac ctgggccaaa accttctcta cgccaactcc gcccacgcgc   21240
tagacatgac ttttgaggtg gatcccatgg acgagcccac ccttctttat gttttgtttg   21300
aagtctttga cgtggtccgt gtgcaccagc cgcaccgcgg cgtcatcgaa accgtgtacc   21360
tgcgcacgcc cttctcggcc ggcaacgcca aacataaag aagcaagcaa catcaacaac    21420
agctgccgcc atgggctcca gtgagcagga actgaaagcc attgtcaaag atcttggttg   21480
tgggccatat ttttttgggca cctatgacaa gcgctttcca ggctttgttt ctccacacaa   21540
gctcgcctgc gccatagtca atacggccgg tcgcgagact gggggcgtac actggatggc   21600
ctttgcctgg aacccgcact caaaaacatg ctacctctttt gagccctttg gcttttctga   21660
ccagcgactc aagcaggttt accagtttga gtacgagtca ctcctgcgcc gtagcgccat   21720
tgcttcttcc cccgaccgct gtataacgct ggaaaagtcc acccaaagcg tacaggggcc   21780
caactcggcc gcctgtggac tattctgctg catgtttctc cacgcctttg ccaactggcc   21840
ccaaactccc atggatcaca accccaccat gaaccttatt accggggtac ccaactccat   21900
gctcaacagt ccccaggtac agcccaccct gcgtcgcaac caggaacagc tctacagctt   21960
cctggagcgc cactcgcccct acttccgcag ccacagtgcg cagattagga gcgccacttc   22020 ttttttgtcac ttgaaaaaca tgtaaaaata atgtactaga cacactttca ataaaggcaa   22080
atgcttttat ttgtacactc tcgggtgatt atttacccccc acccttgccg tctgcgccgt   22140
ttaaaaatca aggggttct gccgcgcatc gctatgcgcc actggcaggg acacgttgcg   22200
atactggtgt ttagtgctcc acttaaactc aggcacaacc atccgcggca gctcggtgaa   22260
gttttcactc cacaggctgc gcaccatcac caacgcgttt agcaggtcgg gcgccgatat   22320
cttgaagtcg cagttggggc ctccgccctg cgcgcgcgag ttgcgataca cagggttgca   22380
gcactggaac actatcagcg ccgggtggtg cacgctggcc agcacgctct tgtcggagat   22440
cagatccgcg tccaggtcct ccgcgttgct cagggcgaac ggagtcaact ttggtagctg   22500
ccttcccaaa aagggcgcgt gcccaggctt tgagttgcac tcgcaccgta gtggcatcaa   22560
aaggtgaccg tgcccggtct gggcgttagg atacagcgcc tgcataaaag ccttgatctg   22620
cttaaaagcc acctgagcct ttgcgccttc agagaagaac atgccgcaag acttgccgga   22680
aaactgattg gccggacagg ccgcgtcgtg cacgcagcac cttgcgtcgg tgttggagat   22740
ctgcaccaca tttcggcccc accggttctt cacgatcttg ccttgctag actgctcctt   22800 cagcgcgcgc tgcccgtttt cgctcgtcac atccatttca atcacgtgct ccttatttat   22860
cataatgctt ccgtgtagac acttaagctc gccttcgatc tcagcgcagc ggtgcagcca   22920
caacgcgcag cccgtgggct cgtgatgctt gtaggtcacc tctgcaaacg actgcaggta   22980
```

```
cgcctgcagg aatcgcccca tcatcgtcac aaaggtcttg ttgctggtga aggtcagctg   23040
caacccgcgg tgctcctcgt tcagccaggt cttgcatacg gccgccagag cttccacttg   23100
gtcaggcagt agtttgaagt tcgcctttag atcgttatcc acgtggtact tgtccatcag   23160
cgcgcgcgca gcctccatgc ccttctccca cgcagacacg atcggcacac tcagcgggtt   23220
catcaccgta atttcacttt ccgcttcgct gggctcttcc tcttcctctt gcgtccgcat   23280
accacgcgcc actgggtcgt cttcattcag ccgccgcact gtgcgcttac ctccttgcc    23340 atgcttgatt agcaccggtg ggttgctgaa acccaccatt tgtagcgcca catcttctct   23400
ttcttcctcg ctgtccacga ttacctctgg tgatggcggg cgctcgggct tgggagaagg   23460
gcgcttcttt ttcttcttgg gcgcaatggc caaatccgcc gccgaggtcg atggccgcgg   23520
gctgggtgtg cgcggcacca gcgcgtcttg tgatgagtct tcctcgtcct cggactcgat   23580
acgccgcctc atccgctttt ttgggggcgc ccggggaggc ggcggcgacg gggacgggga   23640
cgacacgtcc tccatggttg ggggacgtcg cgccgcaccg cgtccgcgct cggggggtggt   23700 ttcgcgctgc tcctcttccc gactggccat ttccttctcc tataggcaga aaagatcat    23760 ggagtcagtc gagaagaagg acagcctaac cgccccctct gagttcgcca ccaccgcctc   23820
caccgatgcc gccaacgcgc ctaccacctt ccccgtcgag gcaccccgc ttgaggagga    23880 ggaagtgatt atcgagcagg acccaggttt tgtaagcgaa gacgacgagg accgctcagt   23940
accaacagag gataaaaagc aagaccagga caacgcagag gcaaacgagg aacaagtcgg   24000 gcgggggac gaaaggcatg gcgactacct agatgtggga gacgacgtgc tgttgaagca    24060
tctgcagcgc cagtgcgcca ttatctgcga cgcgttgcaa gagcgcagcg atgtgcccct   24120
cgccatagcg gatgtcagcc ttgcctacga acgccaccta ttctcaccgc gcgtaccccc   24180
caaacgccaa gaaaacggca catgcgagcc caacccgcgc ctcaacttct accccgtatt   24240
tgccgtgcca gaggtgcttg ccacctatca catcttttc caaaactgca agatacccct    24300
atcctgccgt gccaaccgca gccgagcgga caagcagctg gccttgcggc agggcgctgt   24360
catacctgat atcgcctcgc tcaacgaagt gccaaaaatc tttgagggtc ttggacgcga   24420
cgagaagcgc gcggcaaacg ctctgcaaca ggaaaacagc gaaaatgaaa gtcactctgg   24480
agtgttggtg gaactcgagg gtgacaacgc gcgcctagcc gtactaaaac gcagcatcga   24540
ggtcacccac tttgcctacc cggcacttaa cctaccccc aaggtcatga gcacagtcat    24600
gagtgagctg atcgtgcgcc gtgcgcagcc cctggagagg gatgcaaatt gcaagaaca    24660 aacagaggag ggcctacccg cagttggcga cgagcagcta gcgcgctggc ttcaaacgcg   24720
cgagcctgcc gacttggagg agcgacgcaa actaatgatg gccgcagtgc tcgttaccgt   24780
ggagcttgag tgcatgcagc ggttctttgc tgacccggag atgcagcgca agctagagga   24840
aacattgcac tacacctttc gacagggcta cgtacgccag gcctgcaaga tctccaacgt   24900
ggagctctgc aacctggtct cctaccttgg aattttgcac gaaaaccgcc ttgggcaaaa   24960
cgtgcttcat tccacgctca agggcgaggc gcgccgcgac tacgtccgcg actgcgttta   25020
cttatttcta tgctacacct ggcagacggc catgggcgtt tggcagcagt gcttggagga   25080
gtgcaacctc aaggagctgc agaaactgct aaagcaaaac ttgaaggacc tatggacggc   25140
cttcaacgag cgctccgtgg ccgcgcacct ggcggacatc attttcccg aacgcctgct    25200 taaaaccctg caacagggtc tgccagactt caccagtcaa agcatgttgc agaactttag   25260
gaactttatc ctagagcgct caggaatctt gcccgccacc tgctgtgcac ttcctagcga   25320 cttttgtgccc attaagtacc gcgaatgccc tccgccgctt gggcgccact gctaccttct   25380
```

```
gcagctagcc aactaccttg cctaccactc tgacataatg gaagacgtga gcggtgacgg   25440
tctactggag tgtcactgtc gctgcaacct atgcaccccg caccgctccc tggtttgcaa   25500
ttcgcagctg cttaacgaaa gtcaaattat cggtaccttt gagctgcagg gtccctcgcc   25560
tgacgaaaag tccgcggctc cggggttgaa actcactccg gggctgtgga cgtcggctta   25620
ccttcgcaaa tttgtacctg aggactacca cgcccacgag attaggttct acgaagacca   25680
atcccgcccg cctaatgcgg agcttaccgc ctgcgtcatt acccagggcc acattcttgg   25740
ccaattgcaa gccatcaaca aagcccgcca agagtttctg ctacgaaagg acgggggt    25800 ttacttggac ccccagtccg gcgaggagct caacccaatc cccccgccgc cgcagcccta   25860
tcagcagcag ccgcgggccc ttgcttccca ggatggcacc caaaaagaag ctgcagctgc   25920
cgccgccacc cacggacgag gaggaatact gggacagtca ggcagaggag gttttggacg   25980
aggaggagga ggacatgatg gaagactggg agagcctaga cgaggaagct tccgaggtcg   26040
aagaggtgtc agacgaaaca ccgtcaccct cggtcgcatt cccctcgccg cgcccccaga   26100
aatcggcaac cggttccagc atggctacaa cctccgctcc tcaggcgccg ccggcactgc   26160
ccgttcgccg acccaaccgt agatgggaca ccactggaac cagggccggt aagtccaagc   26220
agccgccgcc gttagcccaa gagcaacaac agcgccaagg ctaccgctca tggcgcgggc   26280
acaagaacgc catagttgct tgcttgcaag actgtggggg caacatctcc ttcgcccgcc   26340
gctttcttct ctaccatcac ggcgtggcct tcccccgtaa catcctgcat tactaccgtc   26400
atctctacag cccatactgc accgcgcgca gcggcagcaa cagcagcggc cacacagaag   26460
caaaggcgac cggatagcaa gactctgaca aagcccaaga aatccacagc ggcggcagca   26520
gcaggaggag gagcgctgcg tctggcgccc aacgaacccg tatcgacccg cgagcttaga   26580
aacaggattt ttcccactct gtatgctata tttcaacaga gcaggggcca agaacaagag   26640
ctgaaaataa aaaacaggtc tctgcgatcc ctcacccgca gctgcctgta tcacaaaagc   26700
gaagatcagc ttcggcgcac gctggaagac gcggaggctc tcttcagtaa atactgcgcg   26760
ctgactctta aggactagtt tcgcgcccct tctcaaattt aagcgcgaaa actacgtcat   26820
ctccagcggc cacacccggc gccagcacct gttgtcagcg ccattatgag caaggaaatt   26880
cccacgccct acatgtggag ttaccagcca caaatgggac ttgcggctgg agctgcccaa   26940
gactactcaa cccgaataaa ctacatgagc gcgggacccc acatgatatc ccgggtcaac   27000
ggaatacgcg cccaccgaaa ccgaattctc ctggaacagg cggctattac caccacacct   27060
cgtaataacc ttaatccccg tagttggccc gctgccctgg tgtaccagga aagtcccgct   27120
cccaccactg tggtacttcc cagagacgcc caggccgaag ttcagatgac taactcaggg   27180
gcgcagcttg cgggcggctt tcgtcacagg gtgcggtcgc ccgggcaggg tataactcac   27240
ctgacaatca gagggcgagg tattcagctc aacgacgagt cggtgagctc ctcgcttggt   27300
ctccgtccgg acgggacatt tcagatcggg gcgccggcc gctcttcatt cacgcctcgt   27360
caggcaatcc taactctgca gacctcgtcc tctgagccgc gctctggagg cattggaact   27420
ctgcaattta ttgaggagtt tgtgccatcg gtctacttta accccttctc gggacctccc   27480
ggccactatc cggatcaatt tattcctaac tttgacgcgg taaaggactc ggcggacggc   27540
tacgactgaa tgttaagtgg agaggcagag caactgcgcc tgaaacacct ggtccactgt   27600
cgccgccaca agtgctttgc ccgcgactcc ggtgagtttt gctactttga attgcccgag   27660
gatcatatcg agggcccggc gcacggcgtc cggcttaccg cccagggaga gcttgcccgt   27720
agcctgattc gggagtttac ccagcgcccc ctgctagttg agcgggacag gggaccctgt   27780
```

```
gttctcactg tgatttgcaa ctgtcctaac cctggattac atcaagatct tgttgccat   27840 ctctgtgctg agtataataa atacagaaat taaaatatac tggggctcct atcgccatcc   27900
tgtaaacgcc accgtcttca cccgcccaag caaaccaagg cgaaccttac ctggtacttt   27960
taacatctct ccctctgtga tttacaacag tttcaaccca gacggagtga gtctacgaga   28020
gaacctctcc gagctcagct actccatcag aaaaaacacc accctcctta cctgccggga   28080
acgtacgagt gcgtcaccgg ccgctgcacc acacctaccg cctgaccgta aaccagactt   28140
tttccggaca gacctcaata actctgttta ccagaacagg aggtgagctt agaaaaccct   28200
tagggtatta ggccaaaggc gcagctactg tggggtttat gaacaattca agcaactcta   28260
cgggctattc taattcaggt ttctctagaa atggacggaa ttattacaga gcagcgcctg   28320
ctagaaagac gcagggcagc ggccgagcaa cagcgcatga atcaagagct ccaagacatg   28380
gttaacttgc accagtgcaa aagggggtatc ttttgtctgg taaagcaggc caaagtcacc   28440
tacgacagta ataccaccgg acaccgcctt agctacaagt tgccaaccaa gcgtcagaaa   28500
ttggtggtca tggtgggaga aaagcccatt accataactc agcactcggt agaaaccgaa   28560
ggctgcattc actcaccttg tcaaggacct gaggatctct gcacccttat taagaccctg   28620
tgcggtctca aagatcttat tccctttaac taataaaaaa aataataaa gcatcactta   28680 cttaaaatca gttagcaaat ttctgtccag tttattcagc agcacctcct tgccctcctc   28740
ccagctctgg tattgcagct tcctcctggc tgcaaacttt ctccacaatc taaatggaat   28800 gtcagttttcc tcctgttcct gtccatccgc acccactatc ttcatgttgt tgcagatgaa   28860
gcgcgcaaga ccgtctgaag ataccttcaa ccccgtgtat ccatatgaca cggaaaccgg   28920
tcctccaact gtgccttttc ttactcctcc ctttgtatcc cccaatgggt ttcaagagag   28980
tccccctggg gtactctctt tgcgcctatc cgaacctcta gttacctcca atggcatgct   29040
tgcgctcaaa atgggcaacg gcctctctct ggacgaggcc ggcaacctta cctcccaaaa   29100
tgtaaccact gtgagcccac ctctcaaaaa aaccaagtca aacataaacc tggaaatatc   29160
tgcacccctc acagttacct cagaagccct aactgtggct gccgccgcac ctctaatggt   29220
cgcgggcaac acactcacca tgcaatcaca ggccccgcta accgtgcacg actccaaact   29280
tagcattgcc acccaaggac ccctcacagt gtcagaagga aagctagccc tgcaaacatc   29340 aggcccctc accaccaccg atagcagtac ccttactatc actgcctcac cccctctaac   29400
tactgccact ggtagcttgg gcattgactt gaaagagccc atttatacac aaaatggaaa   29460
actaggacta aagtacgggg ctcctttgca tgtaacagac gacctaaaca ctttgaccgt   29520
agcaactggt ccaggtgtga ctattaataa tacttccttg caaactaaag ttactggagc   29580
cttgggtttt gattcacaag gcaatatgca acttaatgta gcaggaggac taaggattga   29640
ttctcaaaac agacgcctta tacttgatgt tagttatccg tttgatgctc aaaaccaact   29700
aaatctaaga ctaggacagg gccctctttt tataaactca gcccacaact tggatattaa   29760
ctacaacaaa ggcctttact tgtttacagc ttcaaacaat tccaaaaagc ttgaggttaa   29820
cctaagcact gccaagggggt tgatgtttga cgctacagcc atagccatta atgcaggaga   29880
tgggcttgaa tttggttcac ctaatgcacc aaacacaaat cccctcaaaa caaaaattgg   29940
ccatggccta gaatttgatt caaacaaggc tatggttcct aaactaggaa ctggcctag   30000 ttttgacagc acaggtgcca ttacagtagg aaacaaaaat aatgataagc taactttgtg   30060
gaccacacca gctccatctc ctaactgtag actaaatgca gagaaagatg ctaaactcac   30120
tttggtctta acaaaatgtg gcagtcaaat acttgctaca gtttcagttt tggctgttaa   30180
```

```
aggcagtttg gctccaatat ctggaacagt tcaaagtgct catcttatta taagatttga    30240
cgaaaatgga gtgctactaa acaattcctt cctggaccca gaatattgga actttagaaa    30300
tggagatctt actgaaggca cagcctatac aaacgctgtt ggatttatgc ctaacctatc    30360
agcttatcca aaatctcacg gtaaaactgc caaaagtaac attgtcagtc aagtttactt    30420
aaacggagac aaaactaaac ctgtaacact aaccattaca ctaaacggta cacaggaaac    30480
aggagacaca actccaagtg catactctat gtcattttca tgggactggt ctggccacaa    30540
ctacattaat gaaatatttg ccacatcctc ttacactttt tcatacattg cccaagaata    30600
aagaatcgtt tgtgttatgt ttcaacgtgt ttattttcca attgcccggg atcggtgatc    30660
accgatccag acatgataag atacattgat gagtttggac aaaccacaac tagaatgcag    30720
tgaaaaaaat gctttatttg tgaaatttgt gatgctattg ctttatttgt aaccattata    30780
agctgcaata acaagttcc cggatcgcga tccggcccga ggctgtagcc gacgatggtg    30840
cgccaggaga gttgttgatt cattgtttgc ctccctgctg cggttttta ccgaagttca    30900 tgccagtcca gcgttttgc agcagaaaag ccgccgactt cggtttgcgg tcgcgagtga    30960
agatcccttt cttgttaccg ccaacgcgca atatgccttg cgaggtcgca aaatcggcga    31020
aattccatac ctgttcaccg acgacggcgc tgacgcgatc aaagacgcgg tgatacatat    31080
ccagccatgc acactgatac tcttcactcc acatgtcggt gtacattgag tgcagcccgg    31140
ctaacgtatc cacgccgtat tcggtgatga taatcggctg atgcagtttc tcctgccagg    31200
ccagaagttc ttttccagt accttctctg ccgtttccaa atcgccgctt tggacatacc    31260
atccgtaata acggttcagg cacagcacat caaagagatc gctgatggta tcggtgtgag    31320
cgtcgcagaa cattcattg acgcaggtga tcggacgcgt cgggtcgagt ttacgcgttg    31380
cttccgccag tggcgcgaaa tattcccgtg caccttgcgg acgggtatcc ggttcgttgg    31440
caatactcca catcaccacg cttgggtggt ttttgtcacg cgctatcagc tcttaatcg    31500 cctgtaagtg cgcttgctga gtttccccgt tgactgcctc ttcgctgtac agttctttcg    31560
gcttgttgcc cgcttcgaaa ccaatgccta aagagaggtt aaagccgaca gcagcagttt    31620
catcaatcac cacgatgcca tgttcatctg cccagtcgag catctcttca gcgtaagggt    31680
aatgcgaggt acggtaggag ttggccccaa tccagtccat taatgcgtgg tcgtgcacca    31740
tcagcacgtt atcgaatcct ttgccacgca agtccgcatc ttcatgacga ccaaagccag    31800
taaagtagaa cggtttgtgg ttaatcagga actgttcgcc cttcactgcc actgaccgga    31860
tgccgacgcg aagcgggtag atatcacact ctgtctggct tttggctgtg acgcacagtt    31920
catagagata accttcaccc ggttgccaga ggtgcggatt caccacttgc aaagtcccgc    31980
tagtgccttg tccagttgca accacctgtt gatccgcatc acgcagttca acgctgacat    32040
caccattggc caccacctgc cagtcaacag acgcgtggtt acagtcttgc gcgacatgcg    32100
tcaccacggt gatatcgtcc acccaggtgt tcggcgtggt gtagagcatt acgctgcgat    32160
ggattccggc atagttaaag aaatcatgga agtaagactg cttttcttg ccgttttcgt    32220 cggtaatcac cattcccggc gggatagtct gccagttcag ttcgttgttc acacaaacgg    32280
tgatacgtac acttttcccg gcaataacat acggcgtgac atcggcttca aatggcgtat    32340
agccgccctg atgctccatc acttcctgat tattgaccca cactttgccg taatgagtga    32400
ccgcatcgaa acgcagcacg atacgctggc ctgcccaacc tttcggtata aagacttcgc    32460
gctgatacca gacgttgccc gcataattac gaatatctgc atcggcgaac tgatcgttaa    32520
aactgcctgg cacagcaatt gcccggcttt cttgtaacgc gctttcccac caacgctgat    32580
```

| | | | | |
|---|---|---|---|---|
| caattccaca | gttttcgcga | tccagactga | atgcccacag | gccgtcgagt | tttttgattt | 32640 |
| cacgggttgg | ggtttctaca | ggacggacca | tgcgttcgac | ctttctcttc | ttttttgggc | 32700 |
| ccatgatggc | agatccgtat | agtgagtcgt | attagctggt | tctttccgcc | tcagaagcca | 32760 |
| tagagcccac | cgcatcccca | gcatgcctgc | tattgtcttc | ccaatcctcc | cccttgctgt | 32820 |
| cctgccccac | cccaccccCC | agaatagaat | gacacctact | cagacaatgc | gatgcaattt | 32880 |
| cctcatttta | ttaggaaagg | acagtgggag | tggcaccttc | cagggtcaag | gaaggcacgg | 32940 |
| gggaggggca | aacaacagat | ggctggcaac | tagaaggcac | agtcgaggct | gatcagcgag | 33000 |
| ctctagatgc | atgctcgagc | ggccgccagt | gtgatggata | tctgcagaat | tccagcacac | 33060 |
| tggcggccgt | tactagtgga | tccgagctcg | gtacccggcc | gttataacac | cactcgacac | 33120 |
| ggcaccagct | caatcagtca | cagtgtaaaa | aagggccaag | tgcagagcga | gtatatatag | 33180 |
| gactaaaaaa | tgacgtaacg | gttaaagtcc | acaaaaaaca | cccagaaaac | cgcacgcgaa | 33240 |
| cctacgccca | gaaacgaaag | ccaaaaaacc | cacaacttcc | tcaaatcgtc | acttccgttt | 33300 |
| tcccacgtta | cgtcacttcc | cattttaaga | aaactacaat | tcccaacaca | tacaagttac | 33360 |
| tccgccctaa | aacctacgtc | acccgccccg | ttcccacgcc | ccgcgccacg | tcacaaactc | 33420 |
| cacccctca | ttatcatatt | ggcttcaatc | caaataagg | tatattattg | atgatg | 33476 |

<210> SEQ ID NO 19
<211> LENGTH: 33589
<212> TYPE: DNA
<213> ORGANISM: Artificial Sequence
<220> FEATURE:
<223> OTHER INFORMATION: Adenoviral vector Adgp140(C).11D

<400> SEQUENCE: 19

| | | | | |
|---|---|---|---|---|
| catcatcaat | aatataccTT | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttTTTg | 180 |
| gtgtgcgccg | gtgtacacag | gaagtgcaa | ttttcgcgcg | gttttaggcg | gatgttgtag | 240 |
| taaatttggg | cgtaaccgag | taagatttgg | ccatttTCGC | gggaaaactg | aataagagga | 300 |
| agtgaaatct | gaataatttt | gtgttactca | tagcgcgtaa | tatttgtcta | gggcccggga | 360 |
| tcggtgatca | ccgatccaga | catgataaga | tacattgatg | agtttggaca | aaccacaact | 420 |
| agaatgcagt | gaaaaaaatg | ctttatttgt | gaaatttgtg | atgctattgc | tttatttgta | 480 |
| accattataa | gctgcaataa | acaagttccc | ggatctttct | agctagtcta | gactagctag | 540 |
| actcgagagc | ggccgcaatc | gataagcttg | atctagagat | gatcctcacc | acagccagtt | 600 |
| ggagatgtcg | aaccaggacc | acaggttttt | ccaggagtcc | agagccagca | ggtctttttc | 660 |
| gtttttTTcc | tgctgggtct | gggagtcttc | cagcagacgg | tagatggtgt | cggtgtagtt | 720 |
| ggagatttca | cggtcccatt | ccatccaggt | catgttgttc | cagatctcga | gctgctggtc | 780 |
| tttcaggtaa | cgttcgatag | ccagaacacg | gtctgcagc | tgtttgatac | cccaaacggt | 840 |
| cagctgcagc | atgtgctgct | gagcttcgat | agcacgcagc | aggttggact | gctgctgaac | 900 |
| gatggaggac | agcagctgac | gagcctgaac | ggtaagctta | gcaccggtcg | gagcgatacc | 960 |
| cagcggtttc | agttcgataa | ctttgtattt | gtacagttcg | gaacgccagt | tgtctttcat | 1020 |
| gttaccacca | cccggacgga | agatttcttc | ggttttgttg | tcttcaccac | cgtcacgaac | 1080 |
| cagcagcaga | ccggtgatgt | tggatttgca | ggtgatgtta | ccagcgatcg | gcggagcgta | 1140 |
| catagcacga | ccaacaccct | gccacatgtt | gatgatctgt | ttgatacggc | acggcagggt | 1200 |

```
gatggtttcg tcttcggtag cgttgttgtt gaacagacgg gtggtgttgc agtagaagaa    1260
ttcaccacgg cagttgaagg agtgggtggt gatttccagg tcaccaccgg aggacggagc    1320
gaatttgatg gttttgttgt tgttgtagtt ttcctgcagt ttttctttaa cacgtttcag    1380
ggtttcgttc catttggaac cggagatgtt gcagtaagcc tgacggatgt caccgatgat    1440
gtcaccggta gcgtagaagg tctgacccgg accgatacgc atggatttac gggtgttgtt    1500
gttcggacgg gtgcaaacga tttcaacgga tttgttcagg tgaacgatga tggttttaac    1560
gttgtcggtc aggttttcgg aacggatgat gatttctttt tcagccaggg aaccgttcag    1620
cagcagctgg gtggaaacaa ccggtttgat accatgggtg cactgaacgg tggaaacgtt    1680
gttgcacgga cctttaccgg agaaggtttt gttgttgcat ttcaggatag cgtaaccagc    1740
cggagcgcag tagtggatcg ggatcgggtc gaagttaact ttcgggcaag cctgggtgat    1800
ggtggaagcg ttgcagttga tcaggatgta ttcggagttg ttggagttgt tacggttttc    1860
tttcagcaga acgatgtccg gacgtagaaa cagagcgtaa ccctgctgtt ttttgtcacg    1920
gatttcggtg gtggtgttga aggagcagtt acggatttct tgttcatgt cgttggtaac     1980 gttgttttg aaggtagcgt tggtgcagtg cagggtaacg cacagcgggg tcagtttaac     2040
gcacggtttc agggactggt cccacaggga gatgatgtct tcgtgcatct ggtcaaccat    2100 gtcgttttc cacatgttga agttttcggt aacgttttcc agaacgattt cctgcgggtt     2160
cgggtcggtc ggaacgcaag cgtgggtagc ccaaacgttg tgaacttcac ggtcgtaggc    2220
tttggtgtcg gaagcgcaga acagggtggt tttagcgtcg gtccaaaccg gaacaccgta    2280
gtaaacggta acccacatgt taccaacaac acggcagatg atgatcatcc agaaacccag    2340 gatacccccac atccaccact gcggccagtt acgcgggata ccacgaacac gcatggtggc    2400
gatatctcta gtcatcgaat tctgcagtga tcagggatcc cagatccgta tagtgagtcg    2460
tattaggtac cggctgcagt tggacctggg agtggacacc tgtggagaga aaggcaaagt    2520
ggatgtcatt gtcactcaag tgtatggcca gatctcaagc ctgccacacc tcaagtgaag    2580 ccaaggggt gggcctatag actctatagg cggtacttac gtcactcttg cacggggaa      2640 tccgcgttcc aatgcaccgt tcccggccgc ggaggctgga tcggtcccgg tgtcttctat    2700
ggaggtcaaa acagcgtgga tggcgtctcc aggcgatctg acggttcact aaacgagctc    2760
tgcttatata gacctcccac cgtacacgcc taccgcccat ttgcgtcaat ggggcggagt    2820
tgttacgaca ttttggaaag tcccgttgat tttggtgcca aaacaaactc ccattgacgt    2880
caatggggtg gagacttgga atccccgtg agtcaaaccg ctatccacgc ccattgatgt     2940
actgccaaaa ccgcatcacc atggtaatag cgatgactaa tacgtagatg tactgccaag    3000
taggaaagtc cctaaggtc atgtactggg cataatgcca ggcgggccat ttaccgtcat     3060
tgacgtcaat agggggcgta cttggcatat gatacacttg atgtactgcc aagtgggcag    3120
tttaccgtaa atactccacc cattgacgtc aatggaaagt ccctattggc gttactatgg    3180
gaacatacgt cattattgac gtcaatgggc ggggtcgtt gggcggtcag ccaggcgggc      3240
catttaccgt aagttatgta acgcggaact ccatatatgg gctatgaact aatgaccccg    3300
taattgatta ctattaataa ctagtactga aatgtgtggg cgtggcttaa gggtgggaaa    3360
gaatatataa ggtgggggtc ttatgtagtt ttgtatctgt tttgcagcag ccgccgccgc    3420
catgagcacc aactcgtttg atggaagcat tgtgagctca tatttgacaa cgcgcatgcc    3480
cccatgggcc ggggtgcgtc agaatgtgat gggctccagc attgatggtc gccccgtcct    3540
gcccgcaaac tctactacct tgacctacga gaccgtgtct ggaacgccgt tggagactgc    3600
```

-continued

```
agcctccgcc gccgcttcag ccgctgcagc caccgcccgc gggattgtga ctgactttgc    3660
tttcctgagc ccgcttgcaa gcagtgcagc ttcccgttca tccgcccgcg atgacaagtt    3720
gacggctctt ttggcacaat tggattcttt gacccgggaa cttaatgtcg tttctcagca    3780
gctgttggat ctgcgccagc aggtttctgc cctgaaggct tcctcccctc caatgcggt     3840
ttaaaacata aataaaaaac cagactctgt ttggatttgg atcaagcaag tgtcttgctg    3900
tctttattta ggggttttgc gcgcgcggta ggcccgggac cagcggtctc ggtcgttgag    3960
ggtcctgtgt attttttcca ggacgtggta aaggtgactc tggatgttca gatacatggg    4020
cataagcccg tctctggggt ggaggtagca ccactgcaga gcttcatgct gcggggtggt    4080
gttgtagatg atccagtcgt agcaggagcg ctgggcgtgg tgcctaaaaa tgtctttcag    4140
tagcaagctg attgccaggg gcaggcccct tggtgtaagtg tttacaaagc ggttaagctg   4200
ggatgggtgc atacgtgggg atatgagatg catcttggac tgtattttta ggttggctat    4260
gttcccagcc atatccctcc gggattcat gttgtgcaga accaccagca cagtgtatcc     4320
ggtgcacttg ggaaatttgt catgtagctt agaaggaaat gcgtggaaga acttggagac    4380
gcccttgtga cctccaagat tttccatgca ttcgtccata atgatggcaa tgggcccacg    4440
ggcggcggcc tgggcgaaga tatttctggg atcactaacg tcatagttgt gttccaggat    4500
gagatcgtca taggccattt ttacaaagcg cgggcggagg gtgccagact gcggtataat    4560
ggttccatcc ggcccagggg cgtagttacc ctcacagatt tgcatttccc acgctttgag    4620
ttcagatggg gggatcatgt ctacctgcgg ggcgatgaag aaaacggttt ccggggtagg    4680
ggagatcagc tgggaagaaa gcaggttcct gagcagctgc gacttaccgc agccggtggg    4740
cccgtaaatc acacctatta ccggctgcaa ctggtagtta agagagctgc agctgccgtc    4800
atccctgagc agggggggcca cttcgttaag catgtccctg actcgcatgt tttccctgac    4860
caaatccgcc agaaggcgct cgccgcccag cgatagcagt tcttgcaagg aagcaaagtt    4920
tttcaacggt ttgagaccgt ccgccgtagg catgcttttg agcgtttgac caagcagttc    4980
caggcggtcc cacagctcgg tcacctgctc tacggcatct cgatccagca tatctcctcg    5040
tttcgcgggt tggggcggct ttcgctgtac ggcagtagtc ggtgctcgtc cagacgggcc    5100
agggtcatgt cttttccacgg gcgcagggtc ctcgtcagcg tagtctgggt cacggtgaag    5160
gggtgcgctc cgggctgcgc gctggccagg gtgcgcttga ggctggtcct gctggtgctg    5220
aagcgctgcc ggtcttcgcc ctgcgcgtcg gccaggtagc atttgaccat ggtgtcatag    5280
tccagccccct ccgcggcgtg gcccttggcg cgcagcttgc ccttggagga ggcgccgcac   5340
gaggggcagt gcagactttt gagggcgtag agcttgggcg cgagaaatac cgattccggg    5400
gagtaggcat ccgcgccgca ggcccgcag acggtctcgc attccacgag ccaggtgagc     5460
tctggccgtt cggggtcaaa aaccaggttt cccccatgct ttttgatgcg tttcttacct    5520
ctggtttcca tgagccggtg tccacgctcg gtgacgaaaa ggctgtccgt gtccccgtat    5580
acagacttga gaggcctgtc ctcgagcggt gttccgcggt cctcctcgta tagaaactcg    5640
gaccactctg agacaaaggc tcgcgtccag gccagcacga aggaggctaa gtgggagggg    5700
tagcggtcgt tgtccactag ggggtccact cgctccaggg tgtgaagaca catgtcgccc    5760
tcttcggcat caaggaaggt gattggtttg taggtgtagg ccacgtgacc gggtgttcct    5820
gaagggggc tataaaggg ggtgggggcg cgttcgtcct cactctcttc cgcatcgctg       5880
tctgcgaggg ccagctgttg gggtgagtac tccctctgaa aagcgggcat gacttctgcg    5940
ctaagattgt cagtttccaa aaacgaggag gatttgatat tcacctggcc cgcggtgatg    6000
```

```
cctttgaggg tggccgcatc catctggtca gaaaagacaa tctttttgtt gtcaagcttg   6060
gtggcaaacg acccgtagag ggcgttggac agcaacttgg cgatggagcg cagggtttgg   6120
tttttgtcgc gatcggcgcg ctccttggcc gcgatgttta gctgcacgta ttcgcgcgca   6180
acgcaccgcc attcgggaaa gacggtggtg cgctcgtcgg gcaccaggtg cacgcgccaa   6240
ccgcggttgt gcagggtgac aaggtcaacg ctggtggcta cctctccgcg taggcgctcg   6300
ttggtccagc agaggcggcc gcccttgcgc gagcagaatg gcggtagggg gtctagctgc   6360
gtctcgtccg gggggtctgc gtccacggta aagaccccgg gcagcaggcg cgcgtcgaag   6420
tagtctatct tgcatccttg caagtctagc gcctgctgcc atgcgcgggc ggcaagcgcg   6480
cgctcgtatg ggttgagtgg gggaccccat ggcatggggt gggtgagcgc ggaggcgtac   6540
atgccgcaaa tgtcgtaaac gtagaggggc tctctgagta ttccaagata tgtagggtag   6600
catcttccac cgcggatgct ggcgcgcacg taatcgtata gttcgtgcga gggagcgagg   6660
aggtcgggac cgaggttgct acgggcgggc tgctctgctc ggaagactat ctgcctgaag   6720
atggcatgtg agttggatga tatggttgga cgctggaaga cgttgaagct ggcgtctgtg   6780
agacctaccg cgtcacgcac gaaggaggcg taggagtcgc gcagcttgtt gaccagctcg   6840
gcggtgacct gcacgtctag ggcgcagtag tccagggttt ccttgatgat gtcatactta   6900
tcctgtccct ttttttttcca cagctcgcgg ttgaggacaa actcttcgcg gtctttccag   6960
tactcttgga tcggaaaccc gtcggcctcc gaacggtaag agcctagcat gtagaactgg   7020
ttgacggcct ggtaggcgca gcatcccttt tctacgggta gcgcgtatgc ctgcgcggcc   7080
ttccggagcg aggtgtgggt gagcgcaaag gtgtccctga ccatgacttt gaggtactgg   7140
tatttgaagt cagtgtcgtc gcatccgccc tgctcccaga gcaaaaagtc cgtgcgcttt   7200
ttggaacgcg gatttggcag ggcgaaggtg acatcgttga agagtatctt tcccgcgcga   7260
ggcataaagt tgcgtgtgat gcggaagggt cccggcacct cggaacggtt gttaattacc   7320
tgggcggcga gcacgatctc gtcaaagccg ttgatgttgt ggcccacaat gtaaagttcc   7380
aagaagcgcg ggatgccctt gatgaaaggc aattttttaa gttcctcgta ggtgagctct   7440
tcaggggagc tgagcccgtg ctctgaaagg gcccagtctg caagatgagg gttggaagcg   7500
acgaatgagc tccacaggtc acgggccatt agcatttgca ggtggtcgcg aaaggtccta   7560
aactggcgac ctatggccat ttttttctggg gtgatgcagt agaaggtaag cgggtcttgt   7620
tcccagcggt cccatccaag gttcgcggct aggtctcgcg cggcagtcac tagaggctca   7680
tctccgccga acttcatgac cagcatgaag ggcacgagct gcttcccaaa ggcccccatc   7740
caagtatagg tctctacatc gtaggtgaca aagagacgct cggtgcgagg atgcgagccg   7800
atcgggaaga actggatctc ccgccaccaa ttggaggagt ggctattgat gtggtgaaag   7860
tagaagtccc tgcgacgggc cgaacactcg tgctggcttt tgtaaaaacg tgcgcagtac   7920
tggcagcggt gcacgggctg tacatcctgc acgaggttga cctgacgacc gcgcacaagg   7980
aagcagagtg ggaatttgag cccctcgcct ggcgggtttg gctggtggtc ttctacttcg   8040
gctgcttgtc cttgaccgtc tggctgctcg agggagagtta cggtggatcg gaccaccacg   8100
ccgcgcgagc ccaaagtcca gatgtccgcg cgcggcggtc ggagcttgat gacaacatcg   8160
cgcagatggg agctgtccat ggtctggagc tcccgcggcg tcaggtcagg cgggagctcc   8220
tgcaggttta cctcgcatag acgggtcagg gcgcgggcta gatccaggtg atacctaatt   8280
tccaggggct ggttggtggc ggcgtcgatg gcttgcaaga ggccgcatcc ccgcggcgcg   8340
actacggtac cgcgcggcgg gcggtgggcc gcggggggtgt ccttggatga tgcatctaaa   8400
```

```
agcggtgacg cgggcgagcc cccggaggta ggggggggctc cggacccgcc gggagagggg    8460
gcaggggcac gtcggcgccg cgcgcgggca ggagctggtg ctgcgcgcgt aggttgctgg    8520
cgaacgcgac gacgcggcgg ttgatctcct gaatctggcg cctctgcgtg aagacgacgg    8580
gcccggtgag cttgaacctg aaagagagtt cgacagaatc aatttcggtg tcgttgacgg    8640
cggcctggcg caaaatctcc tgcacgtctc ctgagttgtc ttgataggcg atctcggcca    8700
tgaactgctc gatctcttcc tcctggagat ctccgcgtcc ggctcgctcc acggtggcgg    8760
cgaggtcgtt ggaaatgcgg gccatgagct gcgagaaggc gttgaggcct ccctcgttcc    8820
agacgcggct gtagaccacg ccccttcgg catcgcgggc gcgcatgacc acctgcgcga    8880
gattgagctc cacgtgccgg gcgaagacgg cgtagtttcg caggcgctga agaggtagt    8940 tgagggtggt ggcggtgtgt tctgccacga agaagtacat aacccagcgt cgcaacgtgg    9000
attcgttgat atccccccaag gcctcaaggc gctccatggc ctcgtagaag tccacggcga    9060
agttgaaaaa ctgggagttg cgcgccgaca cggttaactc ctcctccaga agacggatga    9120
gctcggcgac agtgtcgcgc acctcgcgct caaaggctac aggggcctct tcttcttctt    9180
caatctcctc ttccataagg gcctcccctt cttcttcttc tggcggcggt ggggagggg    9240 ggacacggcg gcgacgacgg cgcaccggga ggcggtcgac aaagcgctcg atcatctccc    9300
cgcggcgacg gcgcatggtc tcggtgacgg cgcggccgtt ctcgcggggg cgcagttgga    9360
agacgccgcc cgtcatgtcc cggttatggg ttggcggggg gctgccatgc ggcagggata    9420
cggcgctaac gatgcatctc aacaattgtt gtgtaggtac tccgccgccg agggacctga    9480
gcgagtccgc atcgaccgga tcggaaaacc tctcgagaaa ggcgtctaac cagtcacagt    9540
cgcaaggtag gctgagcacc gtggcggggcg gcagcgggcg gcggtcgggg ttgtttctgg    9600
cggaggtgct gctgatgatg taattaaagt aggcggtctt gagacggcgg atggtcgaca    9660
gaagcaccat gtccttgggt ccggcctgct gaatgcgcag gcggtcggcc atgcccagg    9720 cttcgttttg acatcggcgc aggtctttgt agtagtcttg catgagcctt tctaccggca    9780
cttcttcttc tccttcctct tgtcctgcat ctcttgcatc tatcgctgcg gcggcggcgg    9840
agtttggccg taggtggcgc cctcttcctc ccatgcgtgt gaccccgaag ccctcatcg    9900 gctgaagcag ggctaggtcg gcgacaacgc gctcggctaa tatggcctgc tgcacctgcg    9960
tgagggtaga ctggaagtca tccatgtcca caaagcggtg gtatgcgccc gtgttgatgg   10020
tgtaagtgca gttggccata acggaccagt taacggtctg gtgacccggc tgcgagagct   10080
cggtgtacct gagacgcgag taagccctcg agtcaaatac gtagtcgttg caagtccgca   10140
ccaggtactg gtatcccacc aaaaagtgcg gcggcggctg gcggtagagg ggccagcgta   10200
gggtggccgg ggctccgggg gcgagatctt ccaacataag gcgatgatat ccgtagatgt   10260
acctggacat ccaggtgatg ccggcggcgg tggtggaggc gcgcggaaag tcgcggacgc   10320
ggttccagat gttgcgcagc ggcaaaaagt gctccatggt cgggacgctc tggccggtca   10380
ggcgcgcgca atcgttgacg ctctagcgtg caaaaggaga gcctgtaagc gggcactctt   10440
ccgtggtctg gtggataaat tcgcaagggt atcatggcgg acgaccgggg ttcgagcccc   10500
gtatccggcc gtccgccgtg atccatgcgg ttaccgcccg cgtgtcgaac ccaggtgtgc   10560
gacgtcagac aacgggggag tgctcctttt ggcttccttc caggcgcggc ggctgctgcg   10620
ctagcttttt tggccactgg ccgcgcgcag cgtaagcggt taggctggaa agcgaaagca   10680
ttaagtggct cgctccctgt agccggaggg ttattttcca agggttgagt cgcgggaccc   10740
ccggttcgag tctcggaccg gccggactgc ggcgaacggg ggtttgcctc cccgtcatgc   10800
```

```
aagaccccgc ttgcaaattc ctccggaaac agggacgagc ccctttttg cttttcccag    10860 atgcatccgg tgctgcggca gatgcgcccc cctcctcagc agcggcaaga gcaagagcag    10920
cggcagacat gcagggcacc ctcccctcct cctaccgcgt caggaggggc gacatccgcg    10980
gttgacgcgg cagcagatgg tgattacgaa ccccgcggc gccgggcccg gcactacctg    11040
gacttggagg agggcgaggg cctggcgcgg ctaggagcgc cctctcctga gcggcaccca    11100
agggtgcagc tgaagcgtga tacgcgtgag gcgtacgtgc cgcggcagaa cctgtttcgc    11160
gaccgcgagg gagaggagcc cgaggagatg cgggatcgaa agttccacgc agggcgcgag    11220
ctgcggcatg gcctgaatcg cgagcggttg ctgcgcgagg aggactttga gcccgacgcg    11280
cgaaccggga ttagtcccgc gcgcgcacac gtggcggccg ccgacctggt aaccgcatac    11340
gagcagacgg tgaaccagga gattaacttt caaaaaagct ttaacaacca cgtgcgtacg    11400
cttgtggcgc gcgaggaggt ggctatagga ctgatgcatc tgtgggactt tgtaagcgcg    11460
ctggagcaaa acccaaatag caagccgctc atggcgcagc tgttccttat agtgcagcac    11520
agcagggaca acgaggcatt cagggatgcg ctgctaaaca tagtagagcc cgagggccgc    11580
tggctgctcg atttgataaa catcctgcag agcatagtgg tgcaggagcg cagcttgagc    11640
ctggctgaca aggtggccgc catcaactat tccatgctta gcctgggcaa gttttacgcc    11700
cgcaagatat accatacccc ttacgttccc atagacaagg aggtaaagat cgaggggttc    11760
tacatgcgca tggcgctgaa ggtgcttacc ttgagcgacg acctgggcgt ttatcgcaac    11820
gagcgcatcc acaaggccgt gagcgtgagc cggcggcgcg agctcagcga ccgcgagctg    11880
atgcacagcc tgcaaagggc cctggctggc acgggcagcg gcgatagaga ggccgagtcc    11940
tactttgacg cgggcgctga cctgcgctgg gccccaagcc gacgcgccct ggaggcagct    12000
ggggccggac ctgggctggc ggtggcaccc gcgcgcgctg gcaacgtcgg cggcgtggag    12060
gaatatgacg aggacgatga gtacgagcca gaggacggcg agtactaagc ggtgatgttt    12120
ctgatcagat gatgcaagac gcaacggacc cggcggtgcg ggcggcgctg cagagccagc    12180
cgtccggcct taactccacg gacgactggc gccaggtcat ggaccgcatc atgtcgctga    12240
ctgcgcgcaa tcctgacgcg ttccggcagc agccgcaggc caaccggctc tccgcaattc    12300
tggaagcggt ggtcccggcg cgcgcaaacc ccacgcacga aaggtgctg gcgatcgtaa    12360 acgcgctggc cgaaaacagg gccatccggc ccgacgaggc cggcctggtc tacgacgcgc    12420
tgcttcagcg cgtggctcgt tacaacagcg gcaacgtgca gaccaacctg gaccggctgg    12480 tggggatgt gcgcgaggcc gtggcgcagc gtgagcgcgc gcagcagcag ggcaacctgg    12540
gctccatggt tgcactaaac gccttcctga gtacacagcc cgccaacgtg ccgcggggac    12600
aggaggacta caccaacttt gtgagcgcac tgcggctaat ggtgactgag acaccgcaaa    12660
gtgaggtgta ccagtctggg ccagactatt ttttccagac cagtagacaa ggcctgcaga    12720
ccgtaaacct gagccaggct ttcaaaaact gcagggggct gtgggggtg cgggctccca    12780 caggcgaccg cgcgaccgtg tctagcttgc tgacgcccaa ctcgcgcctg ttgctgctgc    12840
taatagcgcc cttcacggac agtggcagcg tgtcccggga cacataccta ggtcacttgc    12900
tgacactgta ccgcgaggcc ataggtcagg cgcatgtgga cgagcatact ttccaggaga    12960
ttacaagtgt cagccgcgcg ctggggcagg aggacgggg cagcctggag caaccctaa    13020 actacctgct gaccaaccgg cggcagaaga tcccctcgtt gcacagttta aacagcgagg    13080
aggagcgcat tttgcgctac gtgcagcaga gcgtgagcct taacctgatg cgcgacgggg    13140
taacgcccag cgtggcgctg gacatgaccg cgcgcaacat ggaaccgggc atgtatgcct    13200
```

```
caaaccggcc gtttatcaac cgcctaatgg actacttgca tcgcgcggcc gccgtgaacc   13260
ccgagtattt caccaatgcc atcttgaacc cgcactggct accgcccct ggtttctaca    13320 ccggggatt cgaggtgccc gagggtaacg atggattcct ctgggacgac atagacgaca    13380
gcgtgttttc cccgcaaccg cagaccctgc tagagttgca acagcgcgag caggcagagg   13440
cggcgctgcg aaaggaaagc ttccgcaggc caagcagctt gtccgatcta ggcgctgcgg   13500
ccccgcggtc agatgctagt agcccatttc caagcttgat agggtctctt accagcactc   13560
gcaccacccg cccgcgcctg ctgggcgagg aggagtacct aaacaactcg ctgctgcagc   13620
cgcagcgcga aaaaaacctg cctccggcat ttcccaacaa cgggatagag agcctagtgg   13680
acaagatgag tagatggaag acgtacgcgc aggagcacag ggacgtgcca ggcccgcgcc   13740
cgcccacccg tcgtcaaagg cacgaccgtc agcgggtct ggtgtgggag gacgatgact     13800
cggcagacga cagcagcgtc ctggatttgg gagggagtgg caacccgttt gcgcaccttc   13860
gccccaggct ggggagaatg ttttaaaaaa aaaaaagca tgatgcaaaa taaaaaactc    13920
accaaggcca tggcaccgag cgttggtttt cttgtattcc ccttagtatg cggcgcgcgg   13980
cgatgtatga ggaaggtcct cctccctcct acgagagtgt ggtgagcgcg cgccagtgg    14040 cggcggcgct gggttctccc ttcgatgctc ccctggaccc gccgtttgtg cctccgcggt   14100
acctgcggcc taccggggg agaaacagca tccgttactc tgagttggca ccctattcg     14160 acaccacccg tgtgtacctg gtggacaaca agtcaacgga tgtggcatcc ctgaactacc   14220
agaacgacca cagcaacttt ctgaccacgg tcattcaaaa caatgactac agcccggggg   14280
aggcaagcac acagaccatc aatcttgacg accggtcgca ctggggcggc gacctgaaaa   14340
ccatcctgca taccaacatg ccaaatgtga acgagttcat gtttaccaat aagtttaagg   14400
cgcgggtgat ggtgtcgcgc ttgcctacta aggacaatca ggtggagctg aaatacgagt   14460
gggtggagtt cacgctgccc gagggcaact actccgagac catgaccata gaccttatga   14520
acaacgcgat cgtggagcac tacttgaaag tgggcagaca gaacgggtt ctggaaagcg    14580 acatcggggt aaagtttgac acccgcaact tcagactggg gtttgacccc gtcactggtc   14640
ttgtcatgcc tggggtatat acaaacgaag ccttccatcc agacatcatt ttgctgccag   14700
gatgcggggt ggacttcacc cacagccgcc tgagcaactt gttgggcatc cgcaagcggc   14760
aacccttcca ggagggcttt aggatcacct acgatgatct ggaggtggt aacattcccg     14820 cactgttgga tgtggacgcc taccaggcga gcttgaaaga tgacaccgaa cagggcgggg   14880
gtggcgcagg cggcagcaac agcagtggca gcggcgcgga agagaactcc aacgcggcag   14940
ccgcggcaat gcagccggtg gaggacatga acgatcatgc cattcgcggc gacacctttg   15000
ccacacgggc tgaggagaag cgcgctgagg ccgaagcagc ggccgaagct gccgcccccg   15060
ctgcgcaacc cgaggtcgag aagcctcaga agaaaccggt gatcaaaccc ctgacagagg   15120
acagcaagaa acgcagttac aacctaataa gcaatgacag caccttcacc cagtaccgca   15180
gctggtacct tgcatacaac tacggcgacc ctcagaccgg aatccgctca tggacccctg   15240
tttgcactcc tgacgtaacc tgcggctcgg agcaggtcta ctggtcgttg ccagacatga   15300
tgcaagaccc cgtgaccttc cgctccacgc gccagatcag caactttccg gtggtgggcg   15360
ccgagctgtt gccccgtgcac tccaagagct tctacaacga ccaggccgtc tactcccaac   15420
tcatccgcca gtttacctct ctgacccacg tgttcaatcg ctttcccgag aaccagattt   15480
tggcgcgccc gccagccccc accatcacca ccgtcagtga aaacgttcct gctctcacag   15540
atcacgggac gctaccgctg cgcaacagca tcggaggagt ccagcgagtg accattactg   15600
```

```
acgccagacg ccgcacctgc ccctacgttt acaaggccct gggcatagtc tcgccgcgcg   15660
tcctatcgag ccgcacttt  tgagcaagca tgtccatcct tatatcgccc agcaataaca   15720
caggctgggg cctgcgcttc ccaagcaaga tgtttggcgg ggccaagaag cgctccgacc   15780
aacacccagt gcgcgtgcgc gggcactacc gcgcgccctg gggcgcgcac aaacgcggcc   15840
gcactgggcg caccaccgtc gatgacgcca tcgacgcggt ggtggaggag gcgcgcaact   15900
acacgcccac gccgccacca gtgtccacag tggacgcggc cattcagacc gtggtgcgcg   15960
gagcccggcg ctatgctaaa atgaagagac ggcggaggcg cgtagcacgt cgccaccgcc   16020
gccgacccgg cactgccgcc caacgcgcgg cggcggccct gcttaaccgc gcacgtcgca   16080
ccggccgacg ggcggccatg cgggccgctc gaaggctggc cgcgggtatt gtcactgtgc   16140
cccccaggtc caggcgacga gcggccgccg cagcagccgc ggccattagt gctatgactc   16200
agggtcgcag gggcaacgtg tattgggtgc gcgactcggt tagcggcctg cgcgtgcccg   16260
tgcgcacccg ccccccgcgc aactagattg caagaaaaaa ctacttagac tcgtactgtt   16320
gtatgtatcc agcggcggcg gcgcgcaacg aagctatgtc caagcgcaaa atcaaagaag   16380
agatgctcca ggtcatcgcg ccggagatct atggcccccc gaagaaggaa gagcaggatt   16440
acaagccccg aaagctaaag cgggtcaaaa agaaaaagaa agatgatgat gatgaacttg   16500
acgacgaggt ggaactgctg cacgctaccg cgcccaggcg acgggtacag tggaaaggtc   16560
gacgcgtaaa acgtgttttg cgacccggca ccaccgtagt ctttacgccc ggtgagcgct   16620
ccacccgcac ctacaagcgc gtgtatgatg aggtgtacgg cgacgaggac ctgcttgagc   16680
aggccaacga gcgcctcggg gagtttgcct acggaaagcg gcataaggac atgctggcgt   16740
tgccgctgga cgagggcaac ccaacaccta gcctaaagcc cgtaacactg cagcaggtgc   16800
tgcccgcgct tgcaccgtcc gaagaaaagc gcggcgagtct ggtgacttgg   16860 cacccaccgt gcagctgatg gtacccaagc gccagcgact ggaagatgtc ttggaaaaaa   16920
tgaccgtgga acctgggctg gagcccgagg tccgcgtgcg gccaatcaag caggtggcgc   16980
cgggactggg cgtgcagacc gtggacgttc agatacccac taccagtagc accagtattg   17040
ccaccgccac agagggcatg gagacacaaa cgtccccggt tgcctcagcg gtggcggatg   17100
ccgcggtgca ggcggtcgct gcggccgcgt ccaagacctc tacggaggtg caaacggacc   17160
cgtggatgtt tcgcgtttca gcccccccggc gcccgcgccg ttcgaggaag tacggcgccg   17220
ccagcgcgct actgcccgaa tatgccctac atccttccat tgcgcctacc cccggctatc   17280
gtggctacac ctaccgcccc agaagacgag caactacccg acgccgaacc accactggaa   17340
cccgccgccg ccgtcgccgt cgccagcccg tgctggcccc gatttccgtg cgcagggtgg   17400
ctcgcgaagg aggcaggacc ctggtgctgc aacagcgcg ctaccacccc agcatcgttt   17460
aaaagccggt cttcgtggtt cttgcagata tggccctcac ctgccgcctc cgtttcccgg   17520
tgccgggatt ccgaggaaga atgcaccgta ggaggggcat ggccggccac ggcctgacgg   17580
gcggcatgcg tcgtgcgcac caccggcggc ggcgcgcgtc gcaccgtcgc atgcgcggcg   17640
gtatcctgcc cctccttatt ccactgatcg ccgcggcgat tggcgccgtg cccggaattg   17700
catccgtggc cttgcaggcg cagagacact gattaaaaac aagttgcatg tggaaaaatc   17760
aaaataaaaa gtctggactc tcacgctcgc ttggtcctgt aactattttg tagaatggaa   17820
gacatcaact ttgcgtctct ggccccgcga cacggctcgc gccgttcat  gggaaactgg   17880 caagatatcg gcaccagcaa tatgagcggt ggcgccttca gctggggctc gctgtgggagc   17940 ggcattaaaa atttcggttc caccgttaag aactatggca gcaaggcctg gaacagcagc   18000
```

```
acaggccaga tgctgaggga taagttgaaa gagcaaaatt tccaacaaaa ggtggtagat    18060
ggcctggcct ctggcattag cggggtggtg gacctggcca accaggcagt gcaaaataag    18120
attaacagta agcttgatcc ccgccctccc gtagaggagc ctccaccggc cgtggagaca    18180
gtgtctccag aggggcgtgg cgaaaagcgt ccgcgcccg acaggaaga aactctggtg     18240 acgcaaatag acgagcctcc ctcgtacgag gaggcactaa agcaaggcct gcccaccacc    18300
cgtcccatcg cgcccatggc taccggagtg ctgggccagc acacaccgt aacgctggac     18360 ctgcctcccc ccgccgacac ccagcagaaa cctgtgctgc caggcccgac cgccgttgtt    18420
gtaacccgtc ctagccgcgc gtccctgcgc gcgccgcca gcggtccgcg atcgttgcgg     18480
cccgtagcca gtggcaactg gcaaagcaca ctgaacagca tcgtgggtct ggggggtgcaa   18540 tccctgaagc gccgacgatg cttctgatag ctaacgtgtc gtatgtgtgt catgtatgcg    18600
tccatgtcgc cgccagagga gctgctgagc cgccgcgcgc ccgcttttcca agatggctac    18660 cccttcgatg atgccgcagt ggtcttacat gcacatctcg ggccaggacg cctcggagta    18720
cctgagcccc gggctggtgc agtttgcccg cgccaccgag acgtacttca gcctgaataa    18780
caagtttaga accccacgg tggcgcctac gcacgacgtg accacagacc ggtcccagcg     18840
tttgacgctg cggttcatcc ctgtggaccg tgaggatact gcgtactcgt acaaggcgcg    18900 gttcaccta gctgtgggtg ataaccgtgt gctggacatg gcttccacgt actttgacat     18960
ccgcggcgtg ctggacaggg gccctacttt taagccctac tctggcactg cctacaacgc    19020
cctggctccc aagggtgccc caaatccttg cgaatgggat gaagctgcta ctgctcttga    19080
aataaaccta gaagaagagg acgatgacaa cgaagacgaa gtagacgagc aagctgagca    19140
gcaaaaaact cacgtatttg ggcaggcgcc ttattctggt ataaatatta caaggaggg    19200 tattcaaata ggtgtcgaag gtcaaacacc taaatatgcc gataaaacat ttcaacctga    19260
acctcaaata ggagaatctc agtggtacga aacagaaatt aatcatgcag ctgggagagt    19320
cctaaaaaag actaccccaa tgaaaccatg ttacggttca tatgcaaaac ccacaaatga    19380
aaatggaggg caaggcattc ttgtaaagca acaaaatgga aagctagaaa gtcaagtgga    19440 aatgcaatttt ttctcaacta ctgaggcagc cgcaggcaat ggtgataact tgactcctaa    19500
agtggtattg tacagtgaag atgtagatat agaaacccca gacactcata tttcttacat    19560
gcccactatt aaggaaggta actcacgaga actaatgggc caacaatcta tgcccaacag    19620
gcctaattac attgctttta gggacaattt tattggtcta atgtattaca acagcacggg    19680
taatatgggt gttctggcgg gccaagcatc gcagttgaat gctgttgtag atttgcaaga    19740
cagaaacaca gagctttcat accagctttt gcttgattcc attggtgata gaaccaggta    19800 ctttttctatg tggaatcagg ctgttgacag ctatgatcca gatgttagaa ttattgaaaa    19860
tcatggaact gaagatgaac ttccaaatta ctgctttcca ctgggaggtg tgattaatac    19920
agagactctt accaaggtaa aacctaaaac aggtcaggaa aatggatggg aaaaagatgc    19980
tacagaattt tcagataaaa atgaaataag agttggaaat aattttgcca tggaaatcaa    20040
tctaaatgcc aacctgtgga gaaatttcct gtactccaac atagcgctgt atttgcccga    20100
caagctaaag tacagtcctt ccaacgtaaa aatttctgat aacccaaaca cctacgacta    20160
catgaacaag cgagtggtgg ctcccggct agtggactgc tacattaacc ttggagcacg    20220 ctggtcccttt gactatatgg acaacgtcaa cccatttaac caccaccgca atgctggcct    20280
gcgctaccgc tcaatgttgc tgggcaatgg tcgctatgtg cccttccaca tccaggtgcc    20340
tcagaagttc tttgccatta aaaacctcct tctcctgccg ggctcataca cctacgagtg    20400
```

```
gaacttcagg aaggatgtta acatggttct gcagagctcc ctaggaaatg acctaagggt    20460
tgacggagcc agcattaagt ttgatagcat ttgcctttac gccaccttct tccccatggc    20520
ccacaacacc gcctccacgc ttgaggccat gcttagaaac gacaccaacg accagtcctt    20580
taacgactat ctctccgccg ccaacatgct ctaccctata cccgccaacg ctaccaacgt    20640
gcccatatcc atccctccc gcaactgggc ggctttccgc ggctgggcct tcacgcgcct     20700
taagactaag gaaaccccat cactgggctc gggctacgac ccttattaca cctactctgg    20760
ctctataccc tacctagatg gaacctttta cctcaaccac acctttaaga aggtggccat    20820
tacctttgac tcttctgtca gctggcctgg caatgaccgc ctgcttaccc ccaacgagtt    20880
tgaaattaag cgctcagttg acggggaggg ttacaacgtt gcccagtgta acatgaccaa    20940
agactggttc ctggtacaaa tgctagctaa ctataacatt ggctaccagg gcttctatat    21000
cccagagagc tacaaggacc gcatgtactc cttctttaga aacttccagc ccatgagccg    21060
tcaggtggtg gatgatacta aatcaaagga ctaccaacag gtgggcatcc tacaccaaca    21120
caacaactct ggatttgttg gctaccttgc ccccaccatg cgcgaaggac aggcctaccc    21180
tgctaacttc ccctatccgc ttataggcaa gaccgcagtt gacagcatta cccagaaaaa    21240
gtttctttgc gatcgcaccc tttggcgcat cccattctcc agtaactttt tgtccatggg    21300
cgcactcaca gacctgggcc aaaaccttct ctacgccaac tccgcccacg cgctagacat    21360
gacttttgag gtggatccca tggacgagcc caccttctt tatgttttgt ttgaagtctt    21420
tgacgtggtc cgtgtgcacc agccgcaccg cggcgtcatc gaaaccgtgt acctgcgcac    21480
gcccttctcg gccggcaacg ccacaacata agaagcaag caacatcaac aacagctgcc    21540
gccatgggct ccagtgagca ggaactgaaa gccattgtca agatcttgg ttgtgggcca     21600 tatttttgg gcacctatga caagcgcttt ccaggctttg tttctccaca caagctcgcc    21660
tgcgccatag tcaatacggc cggtcgcgag actggggggcg tacactggat ggcctttgcc    21720
tggaacccgc actcaaaaac atgctacctc tttgagcct ttggcttttc tgaccagcga     21780
ctcaagcagg tttaccagtt tgagtacgag tcactcctgc gccgtagcgc cattgcttct    21840
tcccccgacc gctgtataac gctggaaaag tccacccaaa gcgtacaggg gcccaactcg    21900
gccgcctgtg gactattctg ctgcatgttt ctccacgcct ttgccaactg gccccaaact    21960
cccatggatc acaaccccac catgaacctt attaccgggg tacccaactc catgctcaac    22020
agtccccagg tacagcccac cctgcgtcgc aaccaggaac agctctacag cttcctggag    22080
cgccactcgc cctacttccg cagccacagt gcgcagatta ggagcgccac ttcttttgt    22140 cacttgaaaa acatgtaaaa ataatgtact agagacactt tcaataaagg caaatgcttt    22200
tatttgtaca ctctcgggtg attatttacc cccaccttg ccgtctgcgc cgtttaaaaa     22260
tcaaaggggt tctgccgcgc atcgctatgc gccactggca gggacacgtt gcgatactgg    22320
tgtttagtgc tccacttaaa ctcaggcaca accatccgcg gcagctcggt gaagttttca    22380
ctccacaggc tgcgcaccat caccaacgcg tttagcaggt cgggcgccga tatcttgaag    22440
tcgcagttgg ggcctccgcc ctgcgcgcgc gagttgcgat acacagggtt gcagcactgg    22500
aacactatca gcgccgggtg gtgcacgctg gccagcacgc tcttgtcgga gatcagatcc    22560
gcgtccaggt cctccgcgtt gctcaggcg aacggagtca actttggtag ctgccttccc     22620
aaaaagggcg cgtgcccagg ctttgagttg cactcgcacc gtagtggcat caaaaggtga    22680
ccgtgcccgg tctgggcgtt aggatacagc gcctgcataa aagcccttgat ctgcttaaaa   22740 gccacctgag cctttgcgcc ttcagagaag aacatgccgc aagacttgcc ggaaaactga    22800
```

```
ttggccggac aggccgcgtc gtgcacgcag caccttgcgt cggtgttgga gatctgcacc   22860
acatttcggc cccaccggtt cttcacgatc ttggccttgc tagactgctc cttcagcgcg   22920
cgctgcccgt tttcgctcgt cacatccatt tcaatcacgt gctccttatt tatcataatg   22980
cttccgtgta gacacttaag ctcgccttcg atctcagcgc agcggtgcag ccacaacgcg   23040
cagcccgtgg gctcgtgatg cttgtaggtc acctctgcaa acgactgcag gtacgcctgc   23100
aggaatcgcc ccatcatcgt cacaaaggtc ttgttgctgg tgaaggtcag ctgcaacccg   23160
cggtgctcct cgttcagcca ggtcttgcat acggccgcca gagcttccac ttggtcaggc   23220
agtagtttga agttcgcctt tagatcgtta tccacgtggt acttgtccat cagcgcgcgc   23280
gcagcctcca tgcccttctc ccacgcagac acgatcggca cactcagcgg gttcatcacc   23340
gtaatttcac tttccgcttc gctgggctct tcctcttcct cttgcgtccg cataccacgc   23400
gccactgggt cgtcttcatt cagccgccgc actgtgcgct tacctccttt gccatgcttg   23460
attagcaccg gtgggttgct gaaacccacc atttgtagcg ccacatcttc tctttcttcc   23520
tcgctgtcca cgattacctc tggtgatggc gggcgctcgg gcttgggaga agggcgcttc   23580
tttttcttct tgggcgcaat ggccaaatcc gccgccgagg tcgatggccg cgggctgggt   23640
gtgcgcggca ccagcgcgtc ttgtgatgag tcttcctcgt cctcggactc gatacgccgc   23700
ctcatccgct tttttggggg cgcccgggga ggcggcggcg acggggacgg ggacgacacg   23760
tcctccatgg ttgggggacg tcgcgccgca ccgcgtccgc gctcgggggt ggtttcgcgc   23820
tgctcctctt cccgactggc catttccttc tcctataggc agaaaaagat catggagtca   23880
gtcgagaaga aggacagcct aaccgccccc tctgagttcg ccaccaccgc ctccaccgat   23940
gccgccaacg cgcctaccac cttccccgtc gaggcacccc cgcttgagga ggaggaagtg   24000
attatcgagc aggacccagg ttttgtaagc gaagacgacg aggaccgctc agtaccaaca   24060
gaggatataaa agcaagacca ggacaacgca gaggcaaacg aggaacaagt cgggcgggggg   24120
gacgaaaggc atggcgacta cctagatgtg ggagacgacg tgctgttgaa gcatctgcag   24180
cgccagtgcg ccattatctg cgacgcgttg caagagcgca gcgatgtgcc cctcgccata   24240
gcggatgtca gccttgccta cgaacgccac ctattctcac cgcgcgtacc ccccaaacgc   24300
caagaaaacg gcacatgcga gcccaacccg cgcctcaact tctacccccgt atttgccgtg   24360
ccagaggtgc ttgccaccta tcacatcttt ttccaaaact gcaagatacc cctatcctgc   24420
cgtgccaacc gcagccgagc ggacaagcag ctggccttgc ggcagggcgc tgtcatacct   24480
gatatcgcct cgctcaacga agtgccaaaa atctttgagg gtcttggacg cgacgagaag   24540
cgcgcggcaa acgctctgca acaggaaaac agcgaaaatg aaagtcactc tggagtgttg   24600
gtggaactcg agggtgacaa cgcgcgccta gccgtactaa aacgcagcat cgaggtcacc   24660
cactttgcct acccggcact taacctaccc cccaaggtca tgagcacagt catgagtgag   24720
ctgatcgtgc gccgtgcgca gcccctggag agggatgcaa atttgcaaga acaaacagag   24780
gagggcctac ccgcagttgg cgacgagcag ctagcgcgct ggcttcaaac gcgcgagcct   24840
gccgacttgg aggagcgacg caaactaatg atggccgcag tgctcgttac cgtggagctt   24900
gagtgcatgc agcggttctt tgctgacccg gagatgcagc gcaagctaga ggaaacattg   24960
cactacacct ttcgacaggg ctacgtacgc caggcctgca gatctccaa cgtggagctc   25020
tgcaacctgg tctcctacct tggaattttg cacgaaaacc gccttgggca aaacgtgctt   25080
cattccacgc tcaagggcga ggcgcgccgc gactacgtcc gcgactgcgt ttacttattt   25140
ctatgctaca cctggcagac ggccatgggc gtttggcagc agtgcttgga ggagtgcaac   25200
```

```
ctcaaggagc tgcagaaact gctaaagcaa aacttgaagg acctatggac ggccttcaac    25260
gagcgctccg tggccgcgca cctggcggac atcattttcc ccgaacgcct gcttaaaacc    25320
ctgcaacagg gtctgccaga cttcaccagt caaagcatgt tgcagaactt taggaacttt    25380
atcctagagc gctcaggaat cttgcccgcc acctgctgtg cacttcctag cgactttgtg    25440
cccattaagt accgcgaatg ccctccgccg ctttggggcc actgctacct tctgcagcta    25500
gccaactacc ttgcctacca ctctgacata atggaagacg tgagcggtga cggtctactg    25560
gagtgtcact gtcgctgcaa cctatgcacc ccgcaccgct ccctggtttg caattcgcag    25620
ctgcttaacg aaagtcaaat tatcggtacc tttgagctgc agggtccctc gcctgacgaa    25680
aagtccgcgg ctccggggtt gaaactcact ccggggctgt ggacgtcggc ttaccttcgc    25740
aaatttgtac ctgaggacta ccacgcccac gagattaggt tctacgaaga ccaatcccgc    25800
ccgcctaatg cggagcttac cgcctgcgtc attacccagg gccacattct tggccaattg    25860
caagccatca acaaagcccg ccaagagttt ctgctacgaa agggacgggg ggtttacttg    25920
gacccccagt ccggcgagga gctcaaccca atccccccgc cgccgcagcc ctatcagcag    25980
cagccgcggg cccttgcttc ccaggatggc acccaaaaag aagctgcagc tgccgccgcc    26040
acccacggac gaggaggaat actgggacag tcaggcagag gaggttttgg acgaggagga    26100
ggaggacatg atggaagact gggagagcct agacgaggaa gcttccgagg tcgaagaggt    26160
gtcagacgaa acaccgtcac cctcggtcgc attcccctcg ccggcgcccc agaaatcggc    26220
aaccggttcc agcatggcta caacctccgc tcctcaggcg ccgccggcac tgcccgttcg    26280
ccgacccaac cgtagatggg acaccactgg aaccagggcc ggtaagtcca agcagccgcc    26340
gccgttagcc caagagcaac aacagcgcca aggctaccgc tcatgcgcg ggcacaagaa    26400
```

```
atccggatca atttattcct aactttgacg cggtaaagga ctcggcggac ggctacgact   27660
gaatgttaag tggagaggca gagcaactgc gcctgaaaca cctggtccac tgtcgccgcc   27720
acaagtgctt tgcccgcgac tccggtgagt tttgctactt tgaattgccc gaggatcata   27780
tcgagggccc ggcgcacggc gtccggctta ccgcccaggg agagcttgcc cgtagcctga   27840
ttcgggagtt tacccagcgc ccctgctag ttgagcggga caggggaccc tgtgttctca   27900
ctgtgatttg caactgtcct aaccctggat tacatcaaga tctttgttgc catctctgtg   27960
ctgagtataa taaatacaga aattaaaata tactggggct cctatcgcca tcctgtaaac   28020
gccaccgtct tcacccgccc aagcaaacca aggcgaacct tacctggtac ttttaacatc   28080
tctccctctg tgatttacaa cagtttcaac ccagacggag tgagtctacg agagaacctc   28140
tccgagctca gctactccat cagaaaaaac accaccctcc ttacctgccg gaacgtacg    28200
agtgcgtcac cggccgctgc accacaccta ccgcctgacc gtaaaccaga cttttccgg    28260
acagacctca ataactctgt ttaccagaac aggaggtgag cttagaaaac ccttagggta   28320
ttaggccaaa ggcgcagcta ctgtggggtt tatgaacaat tcaagcaact ctacgggcta   28380
ttctaattca ggtttctcta gaaatggacg gaattattac agagcagcgc ctgctagaaa   28440
gacgcagggc agcggccgag caacagcgca tgaatcaaga gctccaagac atggttaact   28500
tgcaccagtg caaaggggt atcttttgtc tggtaaagca ggccaaagtc acctacgaca   28560
gtaataccac cggacaccgc cttagctaca agttgccaac caagcgtcag aaattggtgg   28620
tcatggtggg agaaaagccc attaccataa ctcagcactc ggtagaaacc gaaggctgca   28680
ttcactcacc ttgtcaagga cctgaggatc tctgcaccct tattaagacc ctgtgcggtc   28740
tcaaagatct tattcccttt aactaataaa aaaaataat aaagcatcac ttacttaaaa    28800
tcagttagca aatttctgtc cagtttattc agcagcacct ccttgccctc ctcccagctc   28860
tggtattgca gcttcctcct ggctgcaaac tttctccaca atctaaatgg aatgtcagtt   28920
tcctcctgtt cctgtccatc cgcacccact atcttcatgt tgttgcagat gaagcgcgca   28980
agaccgtctg aagataccatt caaccccgtg tatccatatg acacggaaac cggtcctcca   29040
actgtgcctt ttcttactcc tcccttgta tcccccaatg ggtttcaaga gagtcccct    29100
ggggtactct ctttgcgcct atccgaacct ctagttacct ccaatggcat gcttgcgctc   29160
aaaatgggca acggcctctc tctggacgag gccggcaacc ttacctccca aaatgtaacc   29220
actgtgagcc cacctctcaa aaaaccaag tcaaacataa acctggaaat atctgcaccc    29280
ctcacagtta cctcagaagc cctaactgtg gctgccgccg cacctctaat ggtcgcgggc   29340
aacacactca ccatgcaatc acaggccccg ctaaccgtgc acgactccaa acttagcatt   29400
gccacccaag gaccctcac agtgtcagaa ggaaagctag ccctgcaaac atcaggcccc    29460
ctcaccacca ccgatagcag tacccttact atcactgcct cacccctct aactactgcc    29520
actggtagct gggcattga cttgaaagag cccatttata cacaaaatgg aaaactagga   29580
ctaaagtacg gggctccttt gcatgtaaca gacgacctaa acactttgac cgtagcaact   29640
ggtccaggtg tgactattaa taatacttcc ttgcaaacta agttactgg agccttgggt    29700
tttgattcac aaggcaatat gcaacttaat gtagcaggag gactaaggat tgattctcaa   29760
aacagacgcc ttatacttga tgttagttat ccgtttgatg ctcaaaacca actaaatcta   29820
agactaggac agggccctct ttttataaac tcagcccaca acttggatat taactacaac   29880
aaaggccttt acttgtttac agcttcaaac aattccaaaa agcttgaggt taacctaagc   29940
actgccaagg ggttgatgtt tgacgctaca gccatagcca ttaatgcagg agatgggctt   30000
```

```
gaatttggtt cacctaatgc accaaacaca aatcccctca aaacaaaaat tggccatggc   30060
ctagaatttg attcaaacaa ggctatggtt cctaaactag gaactggcct tagttttgac   30120
agcacaggtg ccattacagt aggaaacaaa aataatgata agctaacttt gtggaccaca   30180
ccagctccat ctcctaactg tagactaaat gcagagaaag atgctaaact cactttggtc   30240
ttaacaaaat gtggcagtca aatacttgct acagtttcag ttttggctgt taaaggcagt   30300
ttggctccaa tatctggaac agttcaaagt gctcatctta ttataagatt tgacgaaaat   30360
ggagtgctac taaacaattc cttcctggac ccagaatatt ggaactttag aaatggagat   30420
cttactgaag gcacagccta tacaaacgct gttggattta tgcctaacct atcagcttat   30480
ccaaaatctc acggtaaaac tgccaaaagt aacattgtca gtcaagttta cttaaacgga   30540
gacaaaacta aacctgtaac actaaccatt acactaaacg gtacacagga aacaggagac   30600
acaactccaa gtgcatactc tatgtcattt tcatgggact ggtctggcca caactacatt   30660
aatgaaatat ttgccacatc ctcttacact ttttcataca ttgcccaaga ataaagaatc   30720
gtttgtgtta tgtttcaacg tgtttatttt tcaattgccc gggatcggtg atcaccgatc   30780
cagacatgat aagatacatt gatgagtttg gacaaaccac aactagaatg cagtgaaaaa   30840
aatgctttat ttgtgaaatt tgtgatgcta ttgctttatt tgtaaccatt ataagctgca   30900
ataaacaagt tcccggatcg cgatccggcc cgaggctgta ccgacgatg gtgcgccagg   30960 agagttgttg attcattgtt tgcctccctg ctgcggtttt tcaccgaagt tcatgccagt   31020
ccagcgtttt tgcagcagaa aagccgccga cttcggtttg cggtcgcgag tgaagatccc   31080
tttcttgtta ccgccaacgc gcaatatgcc ttgcgaggtc gcaaaatcgg cgaaattcca   31140
tacctgttca ccgacgacgg cgctgacgcg atcaaagacg cggtgataca tatccagcca   31200
tgcacactga tactcttcac tccacatgtc ggtgtacatt gagtgcagcc cggctaacgt   31260
atccacgccg tattcggtga tgataatcgg ctgatgcagt ttctcctgcc aggccagaag   31320 ttcttttttcc agtaccttct ctgccgtttc caaatcgccg ctttggacat accatccgta   31380
ataacggttc aggcacagca catcaaagag atcgctgatg gtatcggtgt gagcgtcgca   31440
gaacattaca ttgacgcagg tgatcggacg cgtcgggtcg agtttacgcg ttgcttccgc   31500
cagtggcgcg aaatattccc gtgcaccttg cggacgggta tccggttcgt tggcaatact   31560
ccacatcacc acgcttgggt ggttttttgtc acgcgctatc agctctttaa tcgcctgtaa   31620
gtgcgcttgc tgagtttccc cgttgactgc ctcttcgctg tacagttctt tcggcttgtt   31680
gcccgcttcg aaaccaatgc ctaaagagag gttaaagccg acagcagcag tttcatcaat   31740
caccacgatg ccatgttcat ctgcccagtc gagcatctct tcagcgtaag ggtaatgcga   31800
ggtacggtag gagttggccc caatccagtc cattaatgcg tggtcgtgca ccatcagcac   31860
gttatcgaat cctttgccac gcaagtccgc atcttcatga cgaccaaagc cagtaaagta   31920
gaacggtttg tggttaatca ggaactgttc gcccttcact gccactgacc ggatgccgac   31980
gcgaagcggg tagatatcac actctgtctg gcttttggct gtgacgcaca gttcatagag   32040
ataaccttca cccggttgcc agaggtgcgg attcaccact tgcaaagtcc cgctagtgcc   32100
ttgtccagtt gcaaccacct gttgatccgc atcacgcagt tcaacgctga catcaccatt   32160
ggccaccacc tgccagtcaa cagacgcgtg gttacagtct tgcgcgacat gcgtcaccac   32220
ggtgatatcg tccacccagg tgttcggcgt ggtgtagagc attacgctgc gatggattcc   32280
ggcatagtta aagaaatcat ggaagtaaga ctgcttttttc ttgccgtttt cgtcggtaat   32340
caccattccc ggcgggatag tctgccagtt cagttcgttg ttcacacaaa cggtgatacg   32400
```

```
tacacttttc cggcaataa catacggcgt gacatcggct tcaaatggcg tatagccgcc    32460
ctgatgctcc atcacttcct gattattgac ccacactttg ccgtaatgag tgaccgcatc    32520
gaaacgcagc acgatacgct ggcctgccca acctttcggt ataaagactt cgcgctgata    32580
ccagacgttg cccgcataat tacgaatatc tgcatcggcg aactgatcgt taaaactgcc    32640
tggcacagca attgcccggc tttcttgtaa cgcgctttcc caccaacgct gatcaattcc    32700
acagttttcg cgatccagac tgaatgccca caggccgtcg agttttttga tttcacgggt    32760
tggggtttct acaggacgga ccatgcgttc gacctttctc ttctttttg ggcccatgat    32820 ggcagatccg tatagtgagt cgtattagct ggttctttcc gcctcagaag ccatagagcc    32880
caccgcatcc ccagcatgcc tgctattgtc ttcccaatcc tcccccttgc tgtcctgccc    32940 cacccccaccc cccagaatag aatgacacct actcagacaa tgcgatgcaa tttcctcatt    33000
ttattaggaa aggacagtgg gagtggcacc ttccagggtc aaggaaggca cggggagggg    33060
gcaaacaaca gatggctggc aactagaagg cacagtcgag gctgatcagc gagctctaga    33120
tgcatgctcg agcggccgcc agtgtgatgg atatctgcag aattccagca cactggcggc    33180
cgttactagt ggatccgagc tcggtacccg gccgttataa caccactcga cacggcacca    33240
gctcaatcag tcacagtgta aaaaagggcc aagtgcagag cgagtatata taggactaaa    33300
aaatgacgta acggttaaag tccacaaaaa acacccagaa aaccgcacgc gaacctacgc    33360
ccagaaacga aagccaaaaa acccacaact tcctcaaatc gtcacttccg ttttcccacg    33420
ttacgtcact tcccattta agaaaactac aattcccaac acatacaagt tactccgccc    33480
taaaacctac gtcacccgcc ccgttcccac gccccgcgcc acgtcacaaa ctccacccc    33540 tcattatcat attggcttca atccaaaata aggtatatta ttgatgatg                33589
```

<210> SEQ ID NO 20
<211> LENGTH: 500
<212> TYPE: PRT
<213> ORGANISM: Human immunodeficiency virus

<400> SEQUENCE: 20

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175
```

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
        260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
        340                 345                 350

Val Gly Gly Pro Gly His Lys Ala Arg Val Leu Ala Glu Ala Met Ser
    355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
        420                 425                 430

Phe Leu Gly Lys Ile Trp Pro Ser His Lys Gly Arg Pro Gly Asn Phe
    435                 440                 445

Leu Gln Ser Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
            485                 490                 495

Pro Ser Ser Gln
        500

<210> SEQ ID NO 21
<211> LENGTH: 1002
<212> TYPE: PRT
<213> ORGANISM: Human immunodeficiency virus

<400> SEQUENCE: 21

Met Arg Glu Asp Leu Ala Phe Pro Gln Gly Lys Ala Arg Glu Phe Ser
1               5                   10                  15

Ser Glu Gln Thr Arg Ala Asn Ser Pro Thr Arg Arg Glu Leu Gln Val
            20                  25                  30

Trp Gly Arg Asp Asn Asn Ser Leu Ser Glu Ala Gly Ala Asp Arg Gln
        35                  40                  45

```
Gly Thr Val Ser Phe Ser Phe Pro Gln Ile Thr Leu Trp Gln Arg Pro
    50                  55                  60
Leu Val Thr Ile Lys Ile Gly Gly Gln Leu Lys Glu Ala Leu Leu Asp
65                  70                  75                  80
Thr Gly Ala Asp Asp Thr Val Leu Glu Glu Met Asn Leu Pro Gly Arg
                85                  90                  95
Trp Lys Pro Lys Met Ile Gly Gly Ile Gly Gly Phe Ile Lys Val Gly
            100                 105                 110
Gln Tyr Asp Gln Ile Leu Ile Glu Ile Cys Gly His Lys Ala Ile Gly
        115                 120                 125
Thr Val Leu Val Gly Pro Thr Pro Val Asn Ile Ile Gly Arg Asn Leu
    130                 135                 140
Leu Thr Gln Ile Gly Cys Thr Leu Asn Phe Pro Ile Ser Pro Ile Glu
145                 150                 155                 160
Thr Val Pro Val Lys Leu Lys Pro Gly Met Asp Gly Pro Lys Val Lys
                165                 170                 175
Gln Trp Pro Leu Thr Glu Glu Lys Ile Lys Ala Leu Val Glu Ile Cys
            180                 185                 190
Thr Glu Met Glu Lys Glu Gly Lys Ile Ser Lys Ile Gly Pro Glu Asn
        195                 200                 205
Pro Tyr Asn Thr Pro Val Phe Ala Ile Lys Lys Lys Asp Ser Thr Lys
    210                 215                 220
Trp Arg Lys Leu Val Asp Phe Arg Glu Leu Asn Lys Arg Thr Gln Asp
225                 230                 235                 240
Phe Trp Glu Val Gln Leu Gly Ile Pro His Pro Ala Gly Leu Lys Gln
                245                 250                 255
Lys Lys Ser Val Thr Val Leu Asp Val Gly Asp Ala Tyr Phe Ser Val
            260                 265                 270
Pro Leu Asp Lys Asp Phe Arg Lys Tyr Thr Ala Phe Thr Ile Pro Ser
        275                 280                 285
Ile Asn Asn Glu Thr Pro Gly Ile Arg Tyr Gln Tyr Asn Val Leu Pro
    290                 295                 300
Gln Gly Trp Lys Gly Ser Pro Ala Ile Phe Gln Cys Ser Met Thr Lys
305                 310                 315                 320
Ile Leu Glu Pro Phe Arg Lys Gln Asn Pro Asp Ile Val Ile Tyr Gln
                325                 330                 335
Tyr Met Asp His Leu Tyr Val Gly Ser Asp Leu Glu Ile Gly Gln His
            340                 345                 350
Arg Thr Lys Ile Glu Glu Leu Arg Gln His Leu Leu Arg Trp Gly Phe
        355                 360                 365
Thr Thr Pro Asp Lys Lys His Gln Lys Glu Pro Pro Phe Leu Trp Met
    370                 375                 380
Gly Tyr Glu Leu His Pro Asp Lys Trp Thr Val Gln Pro Ile Val Leu
385                 390                 395                 400
Pro Glu Lys Asp Ser Trp Thr Val Asn Asp Ile Gln Lys Leu Val Gly
                405                 410                 415
Lys Leu Asn Trp Ala Ser Gln Ile Tyr Ala Gly Ile Lys Val Arg Gln
            420                 425                 430
Leu Cys Lys Leu Leu Arg Gly Thr Lys Ala Leu Thr Glu Val Val Pro
        435                 440                 445
Leu Thr Glu Glu Ala Glu Leu Glu Leu Ala Glu Asn Arg Glu Ile Leu
    450                 455                 460
Lys Glu Pro Val His Gly Val Tyr Tyr Asp Pro Ser Lys Asp Leu Ile
```

```
                465                 470                 475                 480
Ala Glu Ile Gln Lys Gln Gly Gln Gly Gln Trp Thr Tyr Gln Ile Tyr
                        485                 490                 495

Gln Glu Pro Phe Lys Asn Leu Lys Thr Gly Lys Tyr Ala Arg Met Lys
                500                 505                 510

Gly Ala His Thr Asn Asp Val Lys Gln Leu Thr Glu Ala Val Gln Lys
                515                 520                 525

Ile Ala Thr Glu Ser Ile Val Ile Trp Gly Lys Thr Pro Lys Phe Lys
                530                 535                 540

Leu Pro Ile Gln Lys Glu Thr Trp Glu Ala Trp Trp Thr Glu Tyr Trp
545                 550                 555                 560

Gln Ala Thr Trp Ile Pro Glu Trp Glu Phe Val Asn Thr Pro Pro Leu
                        565                 570                 575

Val Lys Leu Trp Tyr Gln Leu Glu Lys Glu Pro Ile Ile Gly Ala Glu
                    580                 585                 590

Thr Phe Tyr Val Asp Gly Ala Ala Asn Arg Glu Thr Lys Leu Gly Lys
                595                 600                 605

Ala Gly Tyr Val Thr Asp Arg Gly Arg Gln Lys Val Val Pro Leu Thr
                610                 615                 620

Asp Thr Thr Asn Gln Lys Thr Glu Leu Gln Ala Ile His Leu Ala Leu
625                 630                 635                 640

Gln Asp Ser Gly Leu Glu Val Asn Ile Val Thr Asp Ser Gln Tyr Ala
                    645                 650                 655

Leu Gly Ile Ile Gln Ala Gln Pro Asp Lys Ser Glu Ser Glu Leu Val
                660                 665                 670

Ser Gln Ile Ile Glu Gln Leu Ile Lys Lys Glu Lys Val Tyr Leu Ala
                675                 680                 685

Trp Val Pro Ala His Lys Gly Ile Gly Gly Asn Glu Gln Val Asp Gly
                690                 695                 700

Leu Val Ser Ala Gly Ile Arg Lys Val Leu Phe Leu Asp Gly Ile Asp
705                 710                 715                 720

Lys Ala Gln Glu Glu His Glu Lys Tyr His Ser Asn Trp Arg Ala Met
                        725                 730                 735

Ala Ser Asp Phe Asn Leu Pro Pro Val Val Ala Lys Glu Ile Val Ala
                740                 745                 750

Ser Cys Asp Lys Cys Gln Leu Lys Gly Glu Ala Met His Gly Gln Val
                755                 760                 765

Asp Cys Ser Pro Gly Ile Trp Gln Leu Ala Cys Thr His Leu Glu Gly
                770                 775                 780

Lys Val Ile Leu Val Ala Val His Val Ala Ser Gly Tyr Ile Glu Ala
785                 790                 795                 800

Glu Val Ile Pro Ala Glu Thr Gly Gln Glu Thr Ala Tyr Phe Leu Leu
                        805                 810                 815

Lys Leu Ala Gly Arg Trp Pro Val Lys Thr Val His Thr Asp Asn Gly
                820                 825                 830

Ser Asn Phe Thr Ser Thr Thr Val Lys Ala Ala Cys Trp Trp Ala Gly
                835                 840                 845

Ile Lys Gln Glu Phe Gly Ile Pro Tyr Asn Pro Gln Ser Gln Gly Val
                850                 855                 860

Ile Glu Ser Met Asn Lys Glu Leu Lys Lys Ile Ile Gly Gln Val Arg
865                 870                 875                 880

Asp Gln Ala Glu His Leu Lys Thr Ala Val Gln Met Ala Val Phe Ile
                        885                 890                 895
```

-continued

```
His Asn Phe Lys Arg Lys Gly Ile Gly Gly Tyr Ser Ala Gly Glu
            900                 905                 910

Arg Ile Val Asp Ile Ile Ala Thr Asp Ile Gln Thr Lys Glu Leu Gln
915                 920                 925

Lys Gln Ile Thr Lys Ile Gln Asn Phe Arg Val Tyr Tyr Arg Asp Ser
        930                 935                 940

Arg Asp Pro Val Trp Lys Gly Pro Ala Lys Leu Leu Trp Lys Gly Glu
945                 950                 955                 960

Gly Ala Val Val Ile Gln Asp Asn Ser Asp Ile Lys Val Val Pro Arg
                965                 970                 975

Arg Lys Ala Lys Ile Ile Arg Asp Tyr Gly Lys Gln Met Ala Gly Asp
            980                 985                 990

Asp Cys Val Ala Ser Arg Gln Asp  Glu Asp
            995                 1000

<210> SEQ ID NO 22
<211> LENGTH: 204
<212> TYPE: PRT
<213> ORGANISM: Human immunodeficiency virus

<400> SEQUENCE: 22

Met Lys Trp Ser Lys Ser Ser Val Ile Gly Trp Pro Ala Val Arg Glu
1               5                   10                  15

Arg Met Arg Arg Ala Glu Pro Ala Asp Gly Val Gly Ala Val Ser
            20                  25                  30

Arg Asp Leu Glu Lys His Gly Ala Ile Thr Ser Ser Asn Thr Ala Ala
        35                  40                  45

Asn Asn Ala Ala Cys Ala Trp Leu Glu Ala Gln Glu Glu Glu Glu Val
    50                  55                  60

Gly Phe Pro Val Thr Pro Gln Val Pro Leu Arg Pro Met Thr Tyr Lys
65                  70                  75                  80

Ala Ala Val Asp Leu Ser His Phe Leu Lys Lys Gly Gly Leu Glu
                85                  90                  95

Gly Leu Ile His Ser Gln Arg Arg Gln Asp Ile Leu Asp Leu Trp Ile
            100                 105                 110

Tyr His Thr Gln Gly Tyr Phe Pro Asp Trp Gln Asn Tyr Thr Pro Gly
        115                 120                 125

Pro Gly Val Arg Tyr Pro Leu Thr Phe Gly Trp Cys Tyr Lys Leu Val
    130                 135                 140

Pro Val Glu Pro Asp Lys Val Glu Glu Ala Asn Lys Gly Glu Asn Thr
145                 150                 155                 160

Ser Leu Leu His Pro Val Ser Leu His Gly Met Asp Asp Pro Glu Arg
                165                 170                 175

Glu Val Leu Glu Trp Arg Phe Asp Ser Arg Leu Ala Phe His His Val
            180                 185                 190

Ala Arg Glu Leu His Pro Glu Tyr Phe Lys Asn Cys
        195                 200

<210> SEQ ID NO 23
<211> LENGTH: 626
<212> TYPE: PRT
<213> ORGANISM: Human immunodeficiency virus

<400> SEQUENCE: 23

Met Arg Val Arg Gly Ile Gln Thr Ser Trp Gln Asn Leu Trp Arg Trp
1               5                   10                  15

Gly Thr Met Ile Leu Gly Met Leu Val Ile Tyr Ser Ala Ala Glu Asn
```

```
                    20                  25                  30
Leu Trp Val Ala Val Tyr Tyr Gly Val Pro Val Trp Lys Asp Ala Glu
            35                  40                  45
Thr Thr Leu Phe Cys Ala Ser Asp Ala Lys Ala Tyr Asp Thr Glu Val
    50                  55                  60
His Asn Val Trp Glu Thr His Ala Cys Val Pro Thr Asp Pro Asn Pro
 65                 70                  75                  80
Gln Glu Ile His Leu Glu Asn Val Thr Glu Asp Phe Asn Met Trp Arg
                85                  90                  95
Asn Asn Met Val Glu Gln Met His Thr Asp Ile Ile Ser Leu Trp Asp
            100                 105                 110
Gln Ser Leu Lys Pro Cys Val Lys Leu Thr Pro Leu Cys Val Thr Leu
        115                 120                 125
Asp Cys Asn Ala Thr Ala Ser Asn Val Thr Asn Glu Met Arg Asn Cys
    130                 135                 140
Ser Phe Asn Ile Thr Thr Glu Leu Lys Asp Lys Lys Gln Gln Val Tyr
145                 150                 155                 160
Ser Leu Phe Tyr Lys Leu Asp Val Val Gln Ile Asn Glu Lys Asn Glu
                165                 170                 175
Thr Asp Lys Tyr Arg Leu Ile Asn Cys Asn Thr Ser Ala Ile Thr Gln
            180                 185                 190
Ala Cys Pro Lys Val Ser Phe Glu Pro Ile Pro Ile His Tyr Cys Ala
        195                 200                 205
Pro Ala Gly Phe Ala Ile Leu Lys Cys Lys Asp Thr Glu Phe Asn Gly
    210                 215                 220
Thr Gly Pro Cys Lys Asn Val Ser Thr Val Gln Cys Thr His Gly Ile
225                 230                 235                 240
Arg Pro Val Ile Ser Thr Gln Leu Leu Leu Asn Gly Ser Leu Ala Glu
                245                 250                 255
Glu Gly Ile Gln Ile Arg Ser Glu Asn Ile Thr Asn Asn Ala Lys Thr
            260                 265                 270
Ile Ile Val Gln Leu Asp Lys Ala Val Lys Ile Asn Cys Thr Arg Pro
        275                 280                 285
Asn Asn Asn Thr Arg Lys Gly Val Arg Ile Gly Pro Gly Gln Ala Phe
    290                 295                 300
Tyr Ala Thr Gly Gly Ile Gly Asp Ile Arg Gln Ala His Cys His
305                 310                 315                 320
Val Ser Arg Ala Lys Trp Asn Asp Thr Leu Arg Gly Val Ala Lys Lys
                325                 330                 335
Leu Arg Glu His Phe Lys Asn Lys Thr Ile Ile Phe Glu Lys Ser Ser
            340                 345                 350
Gly Gly Asp Ile Glu Ile Thr Thr His Ser Phe Ile Cys Gly Gly Glu
        355                 360                 365
Phe Phe Tyr Cys Asn Thr Ser Gly Leu Phe Asn Ser Thr Trp Glu Ser
    370                 375                 380
Asn Ser Thr Glu Ser Asn Asn Thr Thr Ser Asn Asp Thr Ile Thr Leu
385                 390                 395                 400
Thr Cys Arg Ile Lys Gln Ile Ile Asn Met Trp Gln Lys Val Gly Gln
                405                 410                 415
Ala Met Tyr Pro Pro Ile Gln Gly Val Ile Arg Cys Glu Ser Asn
            420                 425                 430
Ile Thr Gly Leu Leu Leu Thr Arg Asp Gly Gly Asn Asn Ser Thr Asn
        435                 440                 445
```

-continued

```
Glu Ile Phe Arg Pro Gly Gly Gly Asn Met Arg Asp Asn Trp Arg Ser
450                 455                 460

Glu Leu Tyr Lys Tyr Lys Val Val Lys Ile Glu Pro Leu Gly Val Ala
465                 470                 475                 480

Pro Ser Arg Ala Lys Leu Thr Ala Gln Ala Arg Gln Leu Leu Ser Gly
                485                 490                 495

Ile Val Gln Gln Gln Ser Asn Leu Leu Arg Ala Ile Glu Ala Gln Gln
            500                 505                 510

His Met Leu Lys Leu Thr Val Trp Gly Ile Lys Gln Leu Gln Ala Arg
        515                 520                 525

Val Leu Ala Val Glu Arg Tyr Leu Lys Asp Gln Leu Glu Ile Trp
530                 535                 540

Asp Asn Met Thr Trp Leu Gln Trp Asp Lys Glu Ile Ser Asn Tyr Thr
545                 550                 555                 560

Gln Ile Ile Tyr Asn Leu Ile Glu Glu Ser Gln Asn Gln Gln Glu Lys
                565                 570                 575

Asn Glu Gln Asp Leu Leu Ala Leu Asp Lys Trp Ala Ser Leu Trp Asn
            580                 585                 590

Trp Phe Asp Ile Ser Arg Trp Leu Trp Tyr Ile Lys Ile Phe Ile Met
        595                 600                 605

Ile Val Gly Gly Leu Ile Gly Leu Arg Ile Val Phe Ala Val Leu Ser
610                 615                 620

Val Ile
625

<210> SEQ ID NO 24
<211> LENGTH: 642
<212> TYPE: PRT
<213> ORGANISM: Human immunodeficiency virus

<400> SEQUENCE: 24

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Leu Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asp Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Ser
            180                 185                 190
```

```
Leu Thr Ser Cys Asn Thr Ser Val Ile Thr Gln Ala Cys Pro Lys Val
            195                 200                 205

Ser Phe Glu Pro Ile Pro Asn His Tyr Cys Ala Pro Ala Gly Phe Ala
210                 215                 220

Ile Leu Lys Cys Lys Asp Lys Lys Phe Asn Gly Lys Gly Pro Cys Thr
225                 230                 235                 240

Asn Val Ser Thr Val Gln Cys Thr His Gly Ile Arg Pro Val Val Ser
                245                 250                 255

Thr Gln Leu Leu Val Thr Gly Asn Leu Ala Glu Glu Val Val Ile
                260                 265                 270

Arg Ser Ala Asn Phe Ala Asp Asn Ala Lys Val Ile Ile Val Gln Leu
                275                 280                 285

Asn Glu Ser Val Glu Ile Asn Cys Thr Arg Pro Asn Asn Asn Thr Arg
                290                 295                 300

Lys Ser Ile His Ile Gly Pro Gly Arg Ala Phe Tyr Thr Thr Gly Glu
305                 310                 315                 320

Ile Ile Gly Asp Ile Arg Gln Ala His Cys Asn Leu Ser Arg Ala Lys
                325                 330                 335

Trp Asn Asp Thr Leu Asn Lys Ile Val Ile Lys Leu Arg Glu Gln Phe
                340                 345                 350

Gly Asn Lys Thr Ile Val Phe Lys His Ser Ser Gly Gly Asp Pro Glu
                355                 360                 365

Ile Val Thr His Ser Phe Asn Cys Gly Gly Glu Phe Phe Tyr Cys Asn
                370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Ile Ile Asn Met Trp Gln Lys Val Gly Lys Ala Met
                420                 425                 430

Tyr Ala Pro Pro Ile Ser Gly Gln Ile Arg Cys Ser Ser Asn Ile Thr
                435                 440                 445

Gly Leu Leu Leu Thr Arg Asp Gly Gly Asn Ser Asn Asn Glu Ser Glu
450                 455                 460

Ile Phe Arg Leu Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Leu Thr Val Gln Ala Arg Gln Leu Leu Ser Gly Ile
                500                 505                 510

Val Gln Gln Gln Asn Asn Leu Leu Arg Ala Ile Glu Ala Gln Gln His
                515                 520                 525

Leu Leu Gln Leu Thr Val Trp Gly Ile Lys Gln Leu Gln Ala Arg Thr
530                 535                 540

Leu Ala Val Glu Arg Tyr Leu Lys Asp Gln Gln Leu Leu Glu Gln Ile
545                 550                 555                 560

Trp Asn His Thr Thr Trp Met Glu Trp Asp Arg Glu Ile Asn Asn Tyr
                565                 570                 575

Thr Ser Leu Ile His Ser Leu Ile Glu Glu Ser Gln Asn Gln His Glu
                580                 585                 590

Lys Asn Glu Gln Glu Leu Leu Glu Leu Asp Lys Trp Ala Ser Leu Trp
                595                 600                 605

Asn Trp Phe Asn Ile Thr Asn Trp Leu Trp Tyr Ile Lys Leu Phe Ile
                610                 615                 620
```

```
Met Ile Val Gly Gly Leu Val Gly Leu Arg Ile Val Phe Ala Val Leu
625                 630                 635                 640

Ser Ile

<210> SEQ ID NO 25
<211> LENGTH: 626
<212> TYPE: PRT
<213> ORGANISM: Human immunodeficiency virus

<400> SEQUENCE: 25

Met Arg Val Arg Gly Ile Pro Arg Asn Trp Pro Gln Trp Trp Met Trp
1               5                   10                  15

Gly Ile Leu Gly Phe Trp Met Ile Ile Cys Arg Val Val Gly Asn
            20                  25                  30

Met Trp Val Thr Val Tyr Tyr Gly Val Pro Val Trp Thr Asp Ala Lys
            35                  40                  45

Thr Thr Leu Phe Cys Ala Ser Asp Thr Lys Ala Tyr Asp Arg Glu Val
        50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Ala Thr Phe Lys Asn Asn Val Thr Asn Asp Met Asn
130                 135                 140

Lys Glu Ile Arg Asn Cys Ser Phe Asn Thr Thr Thr Glu Ile Arg Asp
145                 150                 155                 160

Lys Lys Gln Gln Gly Tyr Ala Leu Phe Tyr Arg Pro Asp Ile Val Leu
                165                 170                 175

Leu Lys Glu Asn Arg Asn Asn Ser Asn Asn Ser Glu Tyr Ile Leu Ile
            180                 185                 190

Asn Cys Asn Ala Ser Thr Ile Thr Gln Ala Cys Pro Lys Val Asn Phe
        195                 200                 205

Asp Pro Ile Pro Ile His Tyr Cys Ala Pro Ala Gly Tyr Ala Ile Leu
    210                 215                 220

Lys Cys Asn Asn Lys Thr Phe Ser Gly Lys Gly Pro Cys Asn Asn Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Lys Glu Ile Ile Arg Ser
            260                 265                 270

Glu Asn Leu Thr Asp Asn Val Lys Thr Ile Ile Val His Leu Asn Lys
        275                 280                 285

Ser Val Glu Ile Val Cys Thr Arg Pro Asn Asn Asn Thr Arg Lys Ser
    290                 295                 300

Met Arg Ile Gly Pro Gly Gln Thr Phe Tyr Ala Thr Gly Asp Ile Ile
305                 310                 315                 320

Gly Asp Ile Arg Gln Ala Tyr Cys Asn Ile Ser Gly Ser Lys Trp Asn
                325                 330                 335

Glu Thr Leu Lys Arg Val Lys Glu Lys Leu Gln Glu Asn Tyr Asn Asn
            340                 345                 350
```

```
Asn Lys Thr Ile Lys Phe Ala Pro Ser Ser Gly Gly Asp Leu Glu Ile
        355                 360                 365

Thr Thr His Ser Phe Asn Cys Arg Gly Glu Phe Phe Tyr Cys Asn Thr
    370                 375                 380

Thr Arg Leu Phe Asn Asn Asn Ala Thr Glu Asp Glu Thr Ile Thr Leu
385                 390                 395                 400

Pro Cys Arg Ile Lys Gln Ile Ile Asn Met Trp Gln Gly Val Gly Arg
                405                 410                 415

Ala Met Tyr Ala Pro Pro Ile Ala Gly Asn Ile Thr Cys Lys Ser Asn
                420                 425                 430

Ile Thr Gly Leu Leu Leu Val Arg Asp Gly Gly Glu Asp Asn Lys Thr
                435                 440                 445

Glu Glu Ile Phe Arg Pro Gly Gly Gly Asn Met Lys Asp Asn Trp Arg
        450                 455                 460

Ser Glu Leu Tyr Lys Tyr Lys Val Ile Glu Leu Lys Pro Leu Gly Ile
465                 470                 475                 480

Ala Pro Thr Gly Ala Lys Leu Thr Val Gln Ala Arg Gln Leu Leu Ser
                485                 490                 495

Ser Ile Val Gln Gln Gln Ser Asn Leu Leu Arg Ala Ile Glu Ala Gln
                500                 505                 510

Gln His Met Leu Gln Leu Thr Val Trp Gly Ile Lys Gln Leu Gln Thr
            515                 520                 525

Arg Val Leu Ala Ile Glu Arg Tyr Leu Lys Asp Gln Gln Leu Glu Ile
        530                 535                 540

Trp Asn Asn Met Thr Trp Met Glu Trp Asp Arg Glu Ile Ser Asn Tyr
545                 550                 555                 560

Thr Asp Thr Ile Tyr Arg Leu Leu Glu Asp Ser Gln Thr Gln Gln Glu
                565                 570                 575

Lys Asn Glu Lys Asp Leu Leu Ala Leu Asp Ser Trp Lys Asn Leu Trp
                580                 585                 590

Ser Trp Phe Asp Ile Ser Asn Trp Leu Trp Tyr Ile Lys Ile Phe Ile
            595                 600                 605

Met Ile Val Gly Gly Leu Ile Gly Leu Arg Ile Ile Phe Ala Val Leu
        610                 615                 620

Ser Ile
625

<210> SEQ ID NO 26
<211> LENGTH: 973
<212> TYPE: DNA
<213> ORGANISM: Artificial Sequence
<220> FEATURE:
<223> OTHER INFORMATION: CMV/R promoter

<400> SEQUENCE: 26
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacgtta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
```

-continued

```
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc gtcagatcgc ctggagacgc catccacgct gttttgacct ccatagaaga    720
caccgggacc gatccagcct ccatcggctc gcatctctcc ttcacgcgcc cgccgcccta    780
cctgaggccg ccatccacgc cggttgagtc gcgttctgcc gcctcccgcc tgtggtgcct    840
cctgaactgc gtccgccgtc taggtaagtt taaagctcag gtcgagaccg ggcctttgtc    900
cggcgctccc ttggagccta cctagactca gccggctctc cacgctttgc ctgaccctgc    960
ttgctcaact cta                                                       973
```